US008822518B2

(12) United States Patent
Cowan et al.

(10) Patent No.: US 8,822,518 B2
(45) Date of Patent: Sep. 2, 2014

(54) COMPOUNDS AS ANTAGONISTS OR INVERSE AGONISTS OF OPIOID RECEPTORS FOR TREATMENT OF ADDICTION

(71) Applicant: GlaxoSmithKline LLC, Philadelphia, PA (US)

(72) Inventors: David John Cowan, Research Triangle Park, NC (US); Andrew Lamont Larkin, Research Triangle Park, NC (US); Cunyu Zhang, Research Triangle Park, NC (US); David Lee Musso, Research Triangle Park, NC (US); Gary Martin Green, Research Triangle Park, NC (US); Rodolfo Cadilla, Research Triangle Park, NC (US); Paul Kenneth Spearing, Research Triangle Park, NC (US); Michael Joseph Bishop, Research Triangle Park, NC (US); Jason Daniel Speake, Research Triangle Park, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 14/103,893

(22) Filed: Dec. 12, 2013

(65) Prior Publication Data

US 2014/0100255 A1    Apr. 10, 2014

Related U.S. Application Data

(63) Continuation of application No. 12/376,580, filed as application No. PCT/US2007/075422 on Aug. 8, 2007, now Pat. No. 8,633,175.

(60) Provisional application No. 60/821,845, filed on Aug. 9, 2006.

(51) Int. Cl.
    *A61K 31/675*    (2006.01)
    *A61P 25/00*     (2006.01)
    *A61P 25/30*     (2006.01)
    *A61P 25/36*     (2006.01)

(52) U.S. Cl.
    USPC .............. 514/383; 514/93; 514/810; 514/812

(58) Field of Classification Search
    None
    See application file for complete search history.

(56) References Cited

U.S. PATENT DOCUMENTS 5,500,427 A    3/1996  Kubo et al.
8,633,175 B2 *  1/2014  Cowan et al. ................ 514/93

2005/0245543 A1  11/2005  Howard et al.
2006/0014733 A1   1/2006  Howard, Jr. et al.
2006/0173006 A1   8/2006  Sun et al.

FOREIGN PATENT DOCUMENTS

| EP | 0352781 | 1/1990 |
|---|---|---|
| JP | 2003/206280 | 7/2003 |
| WO | 92/22533 | 12/1992 |
| WO | 98/24766 | 6/1998 |
| WO | 00/55161 | 9/2000 |
| WO | 2004/052848 | 6/2004 |
| WO | 2005/012271 | 2/2005 |
| WO | 2006/011043 | 2/2006 |
| WO | 2007/031791 | 3/2007 |
| WO | 2007/087441 | 8/2007 |
| WO | 2007/087442 | 8/2007 |
| WO | 2008/059335 | 5/2008 |
| WO | 2008/106202 | 9/2008 |
| WO | 2009/030962 | 3/2009 |

OTHER PUBLICATIONS

Giuliano et al. 2013 "Attenuation of cocaine and heroin seeking by μ-opioid receptor antagonism" Psychopharmacology 227:137-147.*
Xu and Rothman, Modulation of Guanosine-5'-O-(3-[35S] thio)triphosphate ([35S] GTP-γ-S) Binding by Opioid Agonists and Antagonists, Reviews in Analgesia 7:83-96 (2003)—This reference, herein resubmitted, was provided with GSK Mar. 21, 2012 Response to Office Action dated Dec. 22, 2011.
Emmerson, et al., Na+ modulation, inverse agonism, and anorectic potency of 4-phenylpiperidine opioid antagonists, Eur J Pharmacol 494:121-130 (2004)—This reference, herein resubmitted, was provided with GSK Mar. 21, 2012 Response to Office Action dated Dec. 22, 2011.
Hadcock and Scott, Role of opiates and their receptors in the regulation of food intake and body weight, Drug Discovery Today 2(2):171-175 (2005)—This reference, herein resubmitted, was provided with GSK Mar. 21, 2012 Response to Office Action dated Dec. 22, 2011.
Sadee, et al., Opioid receptor activity, neutral antagonists, and therapeutic opportunities, Life Sciences 76:1427-1437 (2005)—This reference, herein resubmitted, was provided with GSK Mar. 21, 2012 Response to Office Action dated Dec. 22, 2011.
Cunningham and Coop, Therapeutic applications of opioid antagonists, Chemistry Today 24(3):54-58 (2006)—This reference, herein resubmitted, was provided with GSK Mar. 21, 2012 Response to Office Action dated Dec. 22, 2011.
Fichna, et al., [5S] GTPyS binding stimulated by endomorphin-2 and morphiceptin analogs, Biochem & Biophys Res Comm 345;162-168 (2006)—This reference, herein resubmitted, was provided with GSK Mar. 21, 2012 Response to Office Action dated Dec. 22, 2011.
Rennison, et al., Determinants of Opioid Activity in Derivatives of 14-Aminomorphinones: Effects of Changes to the Chain Linking of the C14-Amino Group to the Aryl Ring, J Med Chem 49:6104-6110 (2006)—This reference, herein resubmitted, was provided with GSK Mar. 21, 2012 Response to Office Action dated Dec. 22, 2011.
Thomas, et al., Highly Potent and Selective Phenylmorphan-Based Inverse Agonists of the Opioid δ Receptor, J Med Chem 49:5597-5609 (2006)—This reference, herein resubmitted, was provided with GSK Mar. 21, 2012 Response to Office Action dated Dec. 22, 2011.

(Continued)

Primary Examiner — Gregory S Emch
Assistant Examiner — Adam M Weidner
(74) Attorney, Agent, or Firm — Robert H. Brink

(57) ABSTRACT

Novel compounds which are antagonists or inverse agonists at one or more of the opioid receptors, pharmaceutical compositions containing them, to processes for their preparation.

10 Claims, No Drawings

(56) References Cited

OTHER PUBLICATIONS

Ignar, et al., Regulation of Ingestive Behaviors in the Rat by GSK1521498, a Novel μ-Opioid Receptor-Selective Inverse Agonist, J Pharmacol & Experimental Therapeutics 339(1):24-34 (2011)—This referencsa, herein resubmitted, was provided with GSK Mar. 21, 2012 Response to Office Action dated Dec. 22, 2011.

Nathan, et al., Opioid Receptor Modulation of Hedonic Taste Preference and Food Intake: A Single-Dose Safety, Pharmacokinetic, and Pharmacodynamic Investigation with GSK1521498, a Novel μ-Opioid Receptor Inverse Agonist, J Clin Pharmacol, published online May 24, 2011. http://jcp.sagepub.com/content/early/2011/05/24/009 127001 1399577—This reference, herein resubmitted, was provided with GSK Mar. 21, 2012 Response to Office Action dated Dec. 22, 2011.

Nathan, et al., Multiple-Dose Safety, Pharmacokinetics, and Pharmacodynamics of the μ-Opioid Receptor Inverse Agonist GSK1521498, J Clin Pharmacol, published online Dec. 12, 2011. http://jcp.sagepub.com/content/early/2011/12/07/009 127001 1421785—This reference, herein resubmitted, was provided with GSK Mar. 21, 2012 Response to Office Action dated Dec. 22, 2011.

Rabiner, et al., Pharmacological differentiation of opioid receptor antagonists by molecular and functional imaging of target occupancy and food reward-related brain activation in humans, Molecular Psychiatry 16:826-835 (2011)—This reference, herein resubmitted, was provided with GSK Mar. 21, 2012 Response to Office Action dated Dec. 22, 2011.

Gustafsson, J.A. New insights in oestrogen receptor (ER) research—the ERB. European Journal of Cancer, 2000, (36), Suppl. 4:S16.

Nykjaer, A., et al. P75NTR—live or let die. Current Opinion in Neurobiology, 2005, vol. 15, pp. 49-57.

Bowie, J.W., et al. Deciphering the Message in Protein Sequences: Tolerance to Amino Acid Substitutions. Science, New Series, 1990, vol. 247, No. 4948, pp. 1306-1310.

Zaki, P.A., et al. Agonist-, Antagonist-, and Inverse Agonist-Regulated Trafficing of the—Opiod Receptor Correlated with, but Does Not Require, G Protein Activation. The Journal of Pharmacology and Experimental Therapeutics, 2001, vol. 298, No. 3, pp. 1015-1020.

Burgess, W.H., et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. The Journal of Cell Biology, 1990, Vol. 11, pp. 2129-2138.

Pawson, T., et al, Assembly of Cell Regulatory Systems Through Protein Interaction Domains. Science, 2003, vol. 300, pp. 445,452.

* cited by examiner

COMPOUNDS AS ANTAGONISTS OR INVERSE AGONISTS OF OPIOID RECEPTORS FOR TREATMENT OF ADDICTION

CROSS-REFERENCE TO RELATED APPLICATIONS

This application is filed as a continuation application of U.S. Ser. No. 12/376,580, filed Feb. 6, 2009, which is a National Phase Application of International Application No. PCT/EP2007/075422 filed Aug. 8, 2007, which claims priority from 60/821,845 filed Aug. 9, 2006 in the United States.

FIELD OF THE INVENTION

This invention relates to novel compounds which are antagonists or inverse agonists at one or more of the opioid receptors, to pharmaceutical compositions containing them, to processes for their preparation, and to their use in therapy.

BACKGROUND OF THE INVENTION

Obesity is a medical condition that is reaching epidemic proportions among humans throughout the world. It is a condition that is associated with other diseases or conditions that disrupt life and lifestyles. Obesity is recognized as a serious risk factor for other diseases and/or conditions such as diabetes, hypertension, and arteriosclerosis. It is also known that increased body weight due to obesity can place a burden on joints, such as knee joints, causing arthritis, pain, and stiffness.

Because overeating and obesity have become such a problem, many individuals are interested in weight reduction and/or maintaining a healthy body weight.

The ability to bind antagonistically to opioid receptors has been suggested to be useful for treatment of many other diseases or conditions not related to obesity including drug and/or substance addiction, depression, opiate overdose, irritable bowel syndrome, schizophrenia, compulsive disorders, septic shock, nausea, vomiting, and stroke. This ability may be useful for the treatment of obesity as well. It has been suggested that the opioid receptors may play a role in control of food intake and food selection. (See, for example, Bodnar, R. J., in Peptides, 25, (2004), p. 697.) Antagonists or inverse agonists of the opioid receptors have been shown to reduce body weight in obese rats.

There is, therefore, an ongoing need for new opioid antagonists for the treatment of obesity, diseases and/or conditions associated with obesity, as well as the above-mentioned non-obesity related diseases and/or conditions.

SUMMARY OF THE INVENTION

The present invention provides a compound of Formula I or Formula Ia,

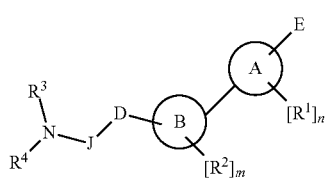

Formula I

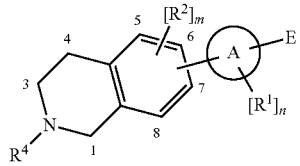

Formula Ia a salt, a solvate, or physiologically functional derivative thereof wherein:

ring A is selected from the group consisting of aryl, 5-membered heteroaryl, and 6-membered heteroaryl, with the proviso that in Formula I when (i) ring A is pyridyl, (ii) ring B is phenyl, and (iii) E is in the meta position relative to the bond joining ring A to ring B, the bond joining D to ring B is in the para position relative to the bond joining ring A to ring B and in Formula Ia, ring A is attached to the tetrahydroisoqinolyl ring at carbon 6 or carbon 7;

ring B is selected from the group consisting of aryl, 5-membered heteroaryl, and 6-membered heteroaryl;

D is —$CH_2$—, —O—, or —$CH(CH_3)$—, with the proviso that D is not attached to ring B at the atom adjacent to the bond joining rings A and B;

E is selected from the group consisting of —$C(O)NH_2$, —$C(O)NHC_{1-3}$alkyl, —$C(O)NH(C_{1-3}$alkyl)aryl, —NHC(O)$C_{1-3}$alkyl, 5-membered heterocycle, 6-membered heterocycle, 5-membered heteroaryl, and 6-membered heteroaryl, with the proviso that in Formula I E is not attached to the atom adjacent to the bond joining rings A and B;

$R^1$ and $R^2$ are selected independently from the group consisting of —F, —Cl, —Br, —OH, —CN, —$C_{1-3}$alkyl, —$OC_{1-3}$alkyl, —$C_{1-3}$fluoroalkyl, —$OC_{1-3}$fluoroalkyl; m and n are each independently 0, 1, or 2;

J is a bond or a $C_{1-4}$alkylene;

$R^3$ is selected from the group consisting of —H, $C_{1-12}$alkyl, $C_{3-10}$cycloalkyl, alkoxycarbonyl, arylalkyl, heterocyclyl, heterocyclylalkyl, heteroarylalkyl, cycloalkenyl, $C_{2-12}$fluoroalkyl, and heteroalkyl;

$R^4$ is selected from the group consisting of $C_{3-12}$alkyl, $C_{3-10}$cycloalkyl, arylalkyl, heterocyclyl, heterocyclylalkyl, heteroarylalkyl, cycloalkenyl, $C_{3-12}$fluoroalkyl, and heteroalkyl; or $R^3$ and $R^4$ may be joined to form a substituted or unsubstituted 5-7 membered ring.

The present invention also provides a pharmaceutical composition comprising a compound of Formula I or Formula Ia, a salt, solvate, or physiologically functional derivative thereof and one or more excipients.

And the present invention further provides a method of treatment comprising the administering to a mammal, particularly a human, a pharmaceutical composition comprising (i) a compound of Formula I or Formula Ia, a pharmaceutically acceptable salt, solvate, or physiologically functional derivative thereof and (ii) at least one excipient or carrier, wherein said treatment is for a disease or condition selected from the group consisting of obesity, diabetes, hypertension, depression, anxiety, drug addiction, substance addiction, or a combination thereof. Preferably the disease or condition is obesity.

There is further provided processes for making compounds of Formula I or Formula Ia, salts, solvates, and physiologically functional derivatives thereof.

DETAILED DESCRIPTION OF THE INVENTION

In Formulae I and Ia, ring A is selected from the group consisting of aryl, 5-membered heteroaryl, and 6-membered heteroaryl, with the proviso that in Formula I when (i) ring A is pyridyl, (ii) ring B is phenyl, and (iii) E is in the meta position relative to the bond joining ring A to ring B, the bond joining D to ring B is in the para position relative to the bond joining ring A to ring B. Preferably in Formulae I and Ia, ring A is selected from the group consisting of phenyl, thiophenyl, furanyl, oxazolyl, and pyridyl. Of these, preferably ring A is phenyl or pyridyl; most preferably ring A is phenyl. In Formula Ia ring A is attached to the tetrahydroisoquinolyl ring either through carbon 6 or carbon 7.

Ring B of Formula I is selected from the group consisting aryl, 5-membered heteroaryl, and 6-membered heteroaryl. Preferably in Formula I, ring B is selected from the group consisting of phenyl, thiophenyl, furanyl, and pyridyl. Of these, preferably ring B is phenyl or pyridyl; most preferably ring B is phenyl.

In one embodiment of Formula I, ring A and ring B are both selected from the group consisting of phenyl and pyridyl. In Formula I, it is further preferred that ring A and ring B both be phenyl. In a preferred embodiment of Formula I, ring A and ring B are both phenyl and ring B is substituted one or two times with a halogen such as fluoro or chloro.

In Formula I, D is —$CH_2$—, —O—, or —$CH(CH_3)$—, with the proviso that D is not attached to ring B at the atom adjacent to the bond that joins ring A to ring B. That is, D is not attached to ring B at the ortho position to the bond that joins ring A to ring B. Preferably in Formula I, D is —$CH_2$— or —O—.

E of Formulae I and Ia is selected from the group consisting of —$C(O)NH_2$, —$C(O)NHC_{1-3}$alkyl, —$C(O)NH(C_{1-3}$alkyl)aryl, —$NHC(O)C_{1-3}$alkyl, 5-membered heterocycle, 6-membered heterocycle, 5-membered heteroaryl, and 6-membered heteroaryl, with the proviso that E is not attached to the carbon atom adjacent (i.e., "ortho" position) to the bond joining rings A and B. Preferably, in Formula I and Formula Ia, E is selected from the group consisting of —$C(O)NH_2$, imidazolidinyl, imidazolidinedionyl, imidazoyl, imidazolinonyl, triazolyl, triazolinonyl, pyridyl and their tautomers. Most preferably in Formula I and Formula Ia, E is $C(O)NH_2$ or triazolyl.

In Formulae I and Ia, $R^1$ and $R^2$ are selected independently from the group consisting of —H, —F, —Cl, —Br, —OH, —CN, —$C_{1-3}$alkyl, —$OC_{1-3}$alkyl, —$C_{1-3}$fluoroalkyl, —$OC_{1-3}$fluoroalkyl. Preferably, $R^1$ and $R^2$ are selected independently from the group consisting of —F, —Cl, —$CH_3$, —$CF_3$, and —$OCH_3$. In $[R^1]_n$ and $[R^2]_m$, m and n are each independently 0, 1, or 2.

J in Formula I is a bond or a $C_{1-4}$alkylene. Preferably, in Formula I, D is —$CH_2$— and J is a bond or $C_{1-2}$alkylene. In one embodiment of Formula I, when D is —$CH_2$— then J is a bond or $C_{1-2}$alkylene. Also, preferably, in Formula I, when D is —O— then J is $C_{2-3}$alkylene.

In Formula I, $R^3$ is selected from the group consisting of —H, $C_{1-12}$alkyl, $C_{3-10}$cycloalkyl, alkoxycarbonyl, arylalkyl, heterocyclyl, heterocycloalkyl, heteroarylalkyl, cycloalkenyl, $C_{2-12}$fluoroalkyl, and heteroalkyl. $R^3$ can be substituted or unsubstituted.

$R^4$ of Formulae I and Ia is selected from the group consisting of $C_{3-12}$alkyl, $C_{3-10}$cycloalkyl, arylalkyl, heterocyclyl, heterocycloalkyl, heteroarylalkyl, cycloalkenyl, $C_{3-12}$fluoroalkyl, and heteroalkyl. $R^4$ can be substituted or unsubstituted. Preferably, in Formula I, $R^3$ is —H. Preferably, in both Formula I and Formula Ia, $R^4$ is selected from the group consisting of arylmethyl, arylethyl, heteroarylmethyl, heteroarylethyl, $C_{4-10}$alkyl, cycloalkyl, cycloalkyl, heterocyclylmethyl, and heterocyclylethyl; such as, but not limited to 3-fluorophenylethyl, 3-fluorobenzyl, 2-trifluoromethylbenzyl, 2-trifluoromethoxybenzyl, 4-trifluoromethylbenzyl, 4-fluorobenzyl, 3-methoxyphenylethyl, 3-thiophenylmethyl, 2-thiophenylethyl, 4,4-dimethylcyclohexyl, 3,3-dimethylcyclohexyl, 2-indanyl, 5-cyano-2-indanyl, 5-methoxy-2-indanyl, 5-fluoro-2-indanyl, 4-fluoro-2-indanyl, 4-methoxy-2-indanyl, 4-methoxy-2-indanyl, 4,8-difluoro-2-indanyl, 5,6-difluoro-2-indanyl, 5,6-dimethoxy-2-indanyl, 2-methyl-2-indanyl, cyclohexylmethyl, cyclohexylethyl, 4,4-difluorocyclohexyl, 1-cyclohexenylmethyl, 1-cyclohexenylethyl, cyclooctyl, cycloheptylmethyl, 3-methylbutyl, adamantyl, morpholinoethyl, piperidinylethyl, 4-tert-butylcyclohexyl, 3,3,5,5-tetramethylcyclohexyl, 3,5-difluorobenzyl, 3,5-difluorophenylethyl, 2-diphenylmethyl, methoxyethyl, dimethylaminoethyl, 3-pyridinylethyl, 3-pyridinylmethyl, and phenyloxyethyl. Of these, preferably $R^4$ is selected from among the group consisting of 2-indanyl, 5-fluoro-2-indanyl, 4,4-dimethylcyclohexyl, cyclohexylethyl, cyclohexylmethyl, 2-thiophenylethyl, 3-fluorophenylethyl, 3-methylbutyl, and 4,4-difluorocyclohexyl.

Or, in Formula I, $R^3$ and $R^4$ may be joined to form a substituted or unsubstituted 5-7 membered ring, including rings such as, but not limited to piperidinyl, piperizinyl, morpholinyl, azepinyl, tetrahydroisoquinolinyl, dihydroindolyl, and pyrrolidinyl.

Particularly preferred compounds of Formula I are selected from the group consisting of 4'-{[(4,4-dimethylcyclohexyl)amino]methyl}-3-biphenylcarboxamide; 4'-[(2,3-dihydro-1H-inden-2-ylamino)methyl]-3-biphenylcarboxamide; N-{[3'-(1H-imidazol-2-yl)-4-biphenylyl]methyl}-2,3-dihydro-1H-inden-2-amine; 4'-{[(4,4-dimethylcyclohexyl)amino]methyl}-2-fluoro-3-biphenylcarboxamide; 4'-{[(4,4-dimethylcyclohexyl)amino]methyl}-2-methyl-3-biphenylcarboxamide; 4'-{[(4,4-dimethylcyclohexyl)amino]methyl}-2'-(trifluoromethyl)-3-biphenylcarboxamide; 3'-fluoro-4'-({[(2S)-5-fluoro-2,3-dihydro-1H-inden-2-yl]amino}methyl)-3-biphenylcarboxamide; 1-{4'-[(2,3-dihydro-1H-inden-2-ylamino)methyl]-3-biphenylyl}-2,4-imidazolidinedione; N-{[3'-(1H-imidazol-2-yl)-4-biphenylyl]methyl}-4,4-dimethylcyclohexanamine; N-{[3,5-difluoro-3'-(1H-imidazol-2-yl)-4-biphenylyl]methyl}-2,3-dihydro-1H-inden-2-amine; N-{[3,5-difluoro-3'-(1H-1,2,4-triazol-3-yl)-4-biphenylyl]methyl}-4,4-dimethylcyclohexanamine; N-{[3,5-difluoro-3'-(1H-1,2,4-triazol-3-yl)-4-biphenylyl]methyl}-2,3-dihydro-1H-inden-2-amine; and 2'-chloro-4'-{[(4,4-dimethylcyclohexyl)amino]methyl}-3-biphenylcarboxamide, including their salts, solvates, and physiologically functional derivatives. The preferred salts of these named compounds are a citrate, phosphate, or hydrochloride salt (mono- and di-). Tautomers of these compounds and their salts are also preferred.

The most preferred compound is N-{[3,5-difluoro-3'-(1H-1,2,4-triazol-3-yl)-4-biphenylyl]methyl}-2,3-dihydro-1H-inden-2-amine or a salt thereof. A citrate, phosphate or mono- or di-hydrochloride salt of N-{[3,5-difluoro-3'-(1H-1,2,4-triazol-3-yl)-4-biphenylyl]methyl}-2,3-dihydro-1H-inden-2-amine is especially preferred.

In Formula Ia ring A is attached to the tetrahydroisoquinolyl ring either through carbon 6 or carbon 7, and E, $R^1$, $R^2$, and $R^4$ are as described for Formula I. The preferred point of attachment of ring A to the tetrahydroisoquinolyl ring is through carbon 6 in Formula Ia.

There is provided a pharmaceutical composition comprising (i) a compound of Formula I or Formula Ia, a pharmaceutically acceptable salt, solvate, or physiologically functional derivative thereof and (ii) at least one carrier (also referred to as an excipient or diluent), preferably a pharmaceutically acceptable carrier.

Further, there is provided a method of treatment (including prophylaxis) comprising the administering to a mammal, especially a human, a pharmaceutical composition comprising (i) a compound of Formula I or Formula Ia, a pharmaceutically acceptable salt, solvate, or physiologically functional derivative thereof and (ii) at least one carrier (excipient or diluent). There also is provided a method of treatment (including prophylaxis) comprising the administering to a mammal, especially a human, a compound of Formula I or Formula Ia, a pharmaceutically acceptable salt, solvate, or physiologically functional derivative thereof.

One aspect of the present invention includes a compound (salt, solvate, or functional derivative thereof) of the present invention for use as an active therapeutic substance.

Another aspect of the present invention includes a compound of Formula I or Formula Ia, a salt, a solvate, or a functional derivative thereof for use in the treatment (including prophylaxis) of obesity, diabetes, hypertension, depression (major and/or bipolar), anxiety, drug addiction, and/or substance addiction. Of these conditions/diseases, obesity is preferred.

Still another aspect of the present invention includes the use of a compound of Formula I or Formula Ia, a salt, a solvate, or a functional derivative thereof in the manufacture of a medicament for use in the treatment (including prophylaxis) of obesity, diabetes, hypertension, depression (major and/or bipolar), anxiety, drug addiction, and/or substance addiction. Of these conditions/diseases, obesity is preferred.

Processes for making the compounds of Formula I or Formula Ia, salts, solvates, and physiologically functional derivatives thereof are also set forth.

Terms are used within their accepted meanings. The following definitions are meant to clarify, but not limit, the terms defined.

As used herein, the term "alkyl" refers to a straight or branched chain alkyl, preferably having from one to twelve carbon atoms, which may be unsubstituted or substituted, with multiple degrees of substitution included within the present invention. Examples of "alkyl" as used herein include, but are not limited to, methyl, ethyl, propyl, isopropyl, isobutyl, n-butyl, t-butyl, isopentyl, n-pentyl, and the like, as well as substituted versions thereof.

As used herein, the term "alkylene" refers to a straight or branched chain divalent alkyl radical, preferably having from one to ten carbon atoms. Alkylene groups as defined herein may be unsubstituted or substituted, with multiple degrees of substitution included within the present invention. Examples of "alkylene" as used herein include, but are not limited to, methylenyl, ethylenyl, n-propylenyl, n-butylenyl, and the like, as well as substituted versions thereof.

As used herein, the term "cycloalkyl" refers to an unsubstituted or substituted mono- or polycyclic non-aromatic saturated ring, which optionally includes an alkylene linker through which the cycloalkyl may be attached. Exemplary "cycloalkyl" groups include, but are not limited to, cyclopropyl, cyclobutyl, cyclopentyl, cyclohexyl, cycloheptyl, and the like, as well as unsubstituted and substituted versions thereof. As used herein, the term "cycloalkyl" includes unsubstituted and substituted fused polycyclic hydrocarbon saturated ring and aromatic ring system, namely polycyclic hydrocarbons with less than maximum number of non-cumulative double bonds, for example where a saturated hydrocarbon ring (such as a cyclopentyl ring) is fused with an aromatic ring (herein "aryl," such as a benzene ring) to form, for example, groups such as indane.

As used herein, the term "cycloalkenyl" refers to unsubstituted and substituted non-aromatic ring containing one or more carbon-to-carbon double bonds which optionally includes an alkylene linker through which the cycloalkenyl may be attached, with multiple degrees of substitution included within the present invention. Exemplary "cycloalkenyl" groups include, but are not limited to, cyclopropenyl, cyclobutenyl, cyclopentenyl, cyclohexenyl, cycloheptenyl, and the like, as well as substituted versions thereof.

As used herein, the term "heterocycle" or "heterocyclyl" refers to unsubstituted and substituted mono- or polycyclic non-aromatic ring system containing one or more heteroatoms. Preferred heteroatoms include N, O, and/or S, including N-oxides, sulfur oxides, and dioxides. Preferably the ring is three to twelve-membered and is either fully saturated or has one or more degrees of unsaturation. Multiple degrees of substitution are included within the present definition. Such rings may be optionally fused to one or more of another "heterocyclic" ring(s) or cycloalkyl ring(s). Examples of "heterocyclic" groups include, but are not limited to, tetrahydrofuranyl, pyranyl, 1,4-dioxanyl, 1,3-dioxanyl, piperidinyl, pyrrolidinyl, morpholinyl, imidazolidinedionyl, imidazolidinonyl, and their various tautomers.

As used herein, the term "heterocyclylalkyl" refers to a heterocycle, as defined herein, bonded to an alkyl group, as defined herein.

As used herein, the term "arylalkyl" refers to an aryl group, as defined herein, bonded to an alkyl group, as defined herein.

As used herein, the term "heteroalkyl" refers to an alkyl group, as defined herein, wherein one or more of the carbon atoms of the alkyl group are replaced by a heteroatom. Preferred heteroatoms include N, O, and/or S, including N-oxides, sulfur oxides, and sulfur dioxides.

As used herein, the term "aryl" refers to unsubstituted and substituted benzene ring. Multiple degrees of substitution are included within the present definition. Examples of "aryl" groups include, but are not limited to, phenyl, benzyl, biphenyl and the like, as well as substituted derivatives thereof.

As used herein, the term "heteroaryl" refers to unsubstituted and substituted monocyclic five to seven membered aromatic ring. These heteroaryl rings contain one or more heteroatoms such as nitrogen, sulfur, and/or oxygen atoms, where N-oxides, sulfur oxides, and dioxides are permissible heteroatom substitutions. Multiple degrees of substitution are included within the present definition. Examples of "heteroaryl" groups used herein include, but should not be limited to, furanyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, and the like, as well as substituted versions thereof.

As used herein, the term "heteroarylalkyl" refers to a heteroaryl as defined herein bonded to an alkyl as defined herein.

As used herein, the term "halogen" refers to fluorine (or fluoro), chlorine (or chloro), bromine (or bromo), or iodine (or iodo). Preferably, each halogen when present is individually either fluorine or chlorine.

As used herein, the term "fluoroalkyl" refers to an alkyl group, as defined herein, that is substituted with at least one fluorine atom. Examples of branched or straight chained "fluoroalkyl" groups useful in the present invention include, but are not limited to, methyl, ethyl, propyl, isopropyl, n-butyl, and t-butyl substituted independently with one or more fluorine. The term "fluoroalkyl" should be interpreted to include such substituents as perfluoroalkyl groups and the like.

As used herein, the term "alkoxy" refers to the group —$OR^a$, where $R^a$ is alkyl as defined above.

As used herein, the term "alkoxycarbonyl" refers to the group —C(O)OR$^a$, where R$^a$ is alkyl as herein defined As used herein, the term "nitro" refers to the group —NO$_2$.

As used herein, the term "cyano" refers to the group —CN.

As used herein, the term "azido" refers to the group —N$_3$.

As used herein, the term "acyl" refers to the group —C(O)R$^b$, where R$^b$ is alkyl, aryl, heteroaryl, or heterocyclyl, as each is defined herein.

As used herein, the term "oxo" refers to the group =O.

The terms "members" (and variants thereof, e.g., "membered") in the context of heterocyclic, heteroaryl, heteroaromatic, aryl, and aromatic groups refers to the total atoms, carbons and heteroatoms (e.g., N, O, and S) which form the ring. Thus, an example of a 6-membered heterocyclic ring is piperidine; an example of a 6-membered heteroaryl is pyridine; and an example of a 6-membered aryl ring is benzene.

As used herein, the term "optionally" means that the subsequently described event(s) may or may not occur, and includes both event(s) that occur and event(s) that do not occur.

Also, as used herein throughout the present specification, the phrase "optionally substituted" or variations thereof denote an optional substitution, including multiple degrees of substitution, with one or more substituent group. The phrase should not be interpreted as duplicative of the substitutions herein described and depicted. Exemplary optional substituent groups include acyl; alkyl; alkylsulfonyl; alkoxy; alkoxycarbonyl; cyano; halogen; haloalkyl; hydroxy; oxo; nitro; aryl, which may be further substituted with acyl, alkoxy, alkyl, alkylsulfonyl, cyano, halogen, haloalkyl, hydroxy, or nitro; heteroaryl, which may be further substituted with acyl, alkoxy, alkyl, alkylsulfonyl, cyano, halogen, haloalkyl, hydroxy, or nitro; or —N(R*)$_2$; where for each occurrence R* is independently selected from hydrogen, alkyl, cycloalkyl, heterocyclyl, aryl, aralkyl, heteroaryl, heteroaralkyl, alkylsulfonyl, arylsulfonyl, or heteroarylsulfonyl, where each occurrence of such aryl or heteroaryl may be substituted with one or more acyl, alkoxy, alkyl, alkenyl, alkylsulfonyl, cyano, halogen, haloalkyl, hydroxy, or nitro, or the two R*s may combine to form a ring, optionally having additional heteroatoms (e.g., N, O, S, etc.), optionally having one or more degrees of unsaturation, and optionally being further substituted with acyl, alkoxy, alkyl, halogen, or haloalkyl.

The compounds of Formula I and Formula Ia may crystallize in more than one form, a characteristic known as polymorphism, and such polymorphic forms ("polymorphs") are within the scope of Formula I and Formula Ia. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain compounds of Formula I and Formula Ia may exist in stereoisomeric forms (e.g., they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by Formula I and Formula Ia as mixtures with isomers thereof in which one or more chiral centers are inverted. Certain compounds of Formula I and Formula Ia may be prepared as regioisomers. The present invention covers both the mixture of regioisomers as well as individual compounds. Likewise, it is understood that compounds of Formula I and Formula Ia may exist in tautomeric forms other than that shown in the formula and these are also included within the scope of the present invention. It is to be understood that the present invention includes all combinations and subsets of the particular groups defined herein above. The scope of the present invention includes mixtures of stereoisomers as well as purified enantiomers or enantiomerically/diastereomerically enriched mixtures. Also included within the scope of the invention are the individual isomers of the compounds represented by Formula I and Formula Ia, as well as any wholly or partially equilibrated mixtures thereof. The present invention also includes the individual isomers of the compounds represented by the formula as well as mixtures with isomers thereof in which one or more chiral centers are inverted.

Typically the salts of compounds of Formula I and Formula Ia of the present invention are pharmaceutically acceptable salts. Salts encompassed within the term "pharmaceutically acceptable salts" refer to non-toxic salts of the compounds of this invention. Salts of the compounds of the present invention may comprise acid addition salts. In general, the salts are formed from pharmaceutically acceptable inorganic and organic acids. More specific examples of suitable acid salts include maleic, hydrochloric, hydrobromic, sulphuric, phosphoric, nitric, perchloric, fumic, acetic, propionic, succinic, glycolic, formic, lactic, aleic, tartaric, citric, palmoic, malonic, hydroxymaleic, phenylacetic, glutamic, benzoic, salicylic, fumaric, toluenesulfonic, methansulfonic (mesylate), naphthaliene-2-sulfonic, benzenesulfonic, hydroxynaphthoic, hydroiodic, malic, teroic, tannic, and the like.

Other representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, oxalate, pamoate (embonate), palmitate, pantothenate, phosphate/diphosphate, polygalacturonate, salicylate, stearate, subacetate, succinate, sulfate, tannate, tartrate, teoclate, tosylate, and valerate salts.

Other salts, which are not pharmaceutically acceptable, may be useful in the preparation of compounds of this invention and these should be considered to form a further aspect of the invention. These salts, such as oxalic and trifluoroacetic, while not in themselves pharmaceutically acceptable, may be useful in the preparation of salts useful as intermediates in obtaining the compounds of the invention and their pharmaceutically acceptable salts.

As used herein, the term "solvate" refers to a complex of variable stoichiometry formed by a solute (in this invention, a compound of Formula I and Formula Ia, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Most preferably the solvent used is water and the solvate is a hydrate.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery, 5th* Edition, Vol 1: Principles and Practice, which is incorporated herein by reference to the extent that it teaches physiologically functional derivatives.

Processes for preparing pharmaceutically acceptable salts, solvates, and physiologically functional derivatives of the compounds of Formula I and Formula Ia are generally known in the art. See, for example, *Burger's Medicinal Chemistry and Drug Discovery, 5th* Edition, Volume 1: Principles and Practice.

As used herein, the term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula I and Formula Ia, as well as salts, solvates, and physiologically functional derivatives thereof, may be administered as the raw chemical. Additionally, the active ingredient may be presented as a pharmaceutical composition.

As used herein, the term "treatment" includes prophylaxis and refers to alleviating the specified condition, eliminating or reducing one or more symptoms of the condition, slowing or eliminating the progression of the condition, and preventing or delaying the reoccurrence of the condition in a previously afflicted or diagnosed patient or subject. Prophylaxis (or prevention or delay of disease onset) is typically accomplished by administering a drug in the same or similar manner as one would to a patient with the developed disease or condition.

Accordingly, the invention further provides pharmaceutical compositions (also referred to herein as "pharmaceutical formulations") that include effective amounts of compounds of the Formula I or Formula Ia, salts, solvates, or physiologically functional derivatives thereof, and one or more pharmaceutically acceptable excipients (including carriers and/or diluents). The compounds of Formula I and Formula Ia, salts, solvates, and physiologically functional derivatives thereof, are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the Formula I or Formula Ia, a salt, solvate, or physiologically functional derivative thereof, with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of Formula I or Formula Ia (salt, solvate, or derivative thereof) for the treatment of humans suffering from frailty, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of Formula I or Formula Ia (salt, solvate, or derivative thereof) per se. Similar dosages should be appropriate for treatment (including prophylaxis) of the other conditions referred to herein.

Pharmaceutical formulations may be presented in unit dose forms containing a predetermined amount of active ingredient per unit dose. Such a unit may contain, as a non-limiting example, 0.5 mg to 1 g of a compound of the Formula I or Formula Ia (alternatively, asalt, solvate, or derivative thereof), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). In the present invention oral routes are preferred.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds may also be coupled with soluble polymers as targetable drug carriers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds of the present invention, their salts, solvates, or physiologically functional derivatives thereof, may be employed alone or in combination with other therapeutic agents. The compound(s) of Formula I or Formula Ia and the other pharmaceutically active agent(s) may be administered together or separately and, when administered separately, administration may occur simultaneously or sequentially, in any order. The amounts of the compound(s) of Formula I or Formula Ia and the other pharmaceutically active agent(s) and the relative timings of administration will be selected in order to achieve the desired combined therapeutic effect. The administration in combination of a compound of Formula I or Formula Ia (salt, solvate, or physiologically functional derivative thereto) with other treatment compounds or agent may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of the present invention may be used in the treatment of a variety of disorders and conditions and, as such, the compounds of the present invention may be used in combination with a variety of other suitable therapeutic agents useful in the treatment (including prophylaxis) of obesity and/or associated diseases, disorders, or conditions. More specifically, the present invention includes the treatment (including prophylaxis) of obesity. Other disorders, conditions, and/or diseases associated with obesity can include diabetes, depression (major and bipolar), anxiety, hypertension, drug and substance addiction, and arteriosclerosis.

One aspect of the present invention comprises a compound of Formula I or Formula Ia (a salt, solvate, or physiologically functional derivative thereof) in combination with at least one other species selected from the group consisting of at least one agent or drug for treating obesity, diabetes, hypertension, and arteriosclerosis. In particular, a compound of Formula I or Formula Ia (a salt, solvate, or physiologically functional derivative thereof) may be combined with at least one species for the treatment of obesity selected from the group of human ciliary neurotropic factor, a CB-1 antagonist or inverse agonist (such as rimonabant), a neurotransmitter reuptake inhibitor (such as sibutramine, bupropion, or bupropion HCl, radafaxine), a lipase inhibitor (such as orlistat), an MC4R agonist, a 5-HT2c agonist, a ghrelin receptor antagonist, a CCK-A receptor agonist, an NPY Y1 antagonist, $PYY_{3-36}$ and a PPAR activator.

The compounds of this invention may be made by a variety of methods, including well-known standard synthetic methods. Illustrative general synthetic methods are set out below and then specific compounds of the invention are prepared in the working examples.

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be affected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

Processes for Preparing Compounds of Formula I and Formula Ia

In each of the following synthetic descriptions protecting groups for sensitive or reactive groups were employed where necessary in accordance with general principles of synthetic chemistry. Protecting groups are manipulated according to standard methods of organic synthesis (T. W. Green and P. G. M. Wuts (1999) *Protecting Groups in Organic Synthesis*, 3rd edition, John Wiley and Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of the compounds of Formula I and Formula Ia.

In all of the synthetic descriptions that follow, the variables ring A, ring B, D, E, J, $R^1$, $R^2$, $R^3$, $R^4$, m and n are as described for Formula I and Formula Ia unless otherwise noted.

General Methods of Synthesizing Compounds of Formula I and Formula Ia

General Method 1: Bond formation between Formula II and Formula III with nucleophilic substitution/displacement of X by N.

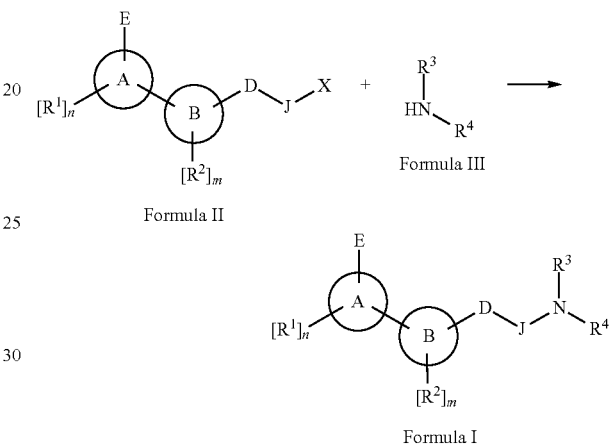

Formula II

Formula III

Formula I

Compounds of Formula I can be prepared by nucleophilic displacement of X from a compound of Formula II with the N of a compound of Formula III. In Formula II, X is a suitable leaving group, for example, a halogen atom (e.g., chloride, bromide or iodide), a triflate, or a tosylate group. The reaction takes place in a suitable organic solvent (e.g., MeOH, EtOH, or acetonitrile) with or without a promoter (e.g. NaI) at a temperature of room temperature to 160° C. using conventional or microwave heating. When $NHR^3R^4$ is a salt (e.g., HCL or trifluoroacetate), a base (e.g., $Et_3N$ or $(iPr)_2NEt$) is added to the reaction mixture. Compounds of Formula III can be obtained commercially from conventional suppliers such as Aldrich, for example, or can be suitably prepared from commercially available starting materials by one skilled in the art of organic chemistry. Compounds of Formula II can be readily prepared through a Suzuki reaction involving compounds of Formula IV with or without additional synthetic manipulation by means known to one skilled in the art of organic chemistry.

General Method 2: Bond Formation between Formula IV and Formula V.

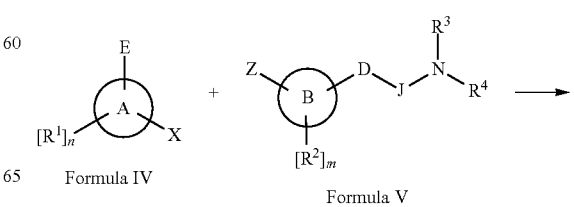

Formula IV

Formula V

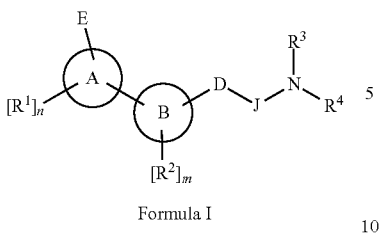

Formula I

Compounds of Formula I can be prepared by reaction of a compound of Formula IV where X is a leaving group (eg. halogen, or triflate) with a compound of Formula V where Z is a boronate, boronic acid, halogen, or triflate, for example, and $R^3$ could be a protecting group which is later removed in a separate step. The reaction occurs under Suzuki reaction conditions in a suitable organic solvent such as acetonitrile, in the presence of a suitable catalyst such as $(Ph_3P)_4Pd$ or $PdCl_2$ (dppf), and in the presence of an inorganic base such as $Na_2CO_3$ with or without the addition of water at a temperature ranging from room temperature to 100° C.

General Method 3: Bond cleavage between N and $R^4$ of Formula VI by deprotection as of a basic amine as last step.

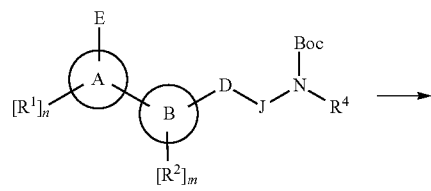

Formula VI

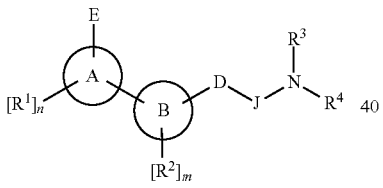

Formula I

Compounds of Formula I can be readily prepared from compounds of Formula VI, which may have been rendered using a similar procedure as described in General Method 2, wherein $R^3$ of Formula V is now a suitable protecting group (ie. Boc). The protecting group is then removed using known literature procedures to produce a compound of Formula I wherein $R^3$ is —H.

General Method 4: Bond formation between Formula VII and a ketone or aldehyde by reductive alkylation of $NHR^3$.

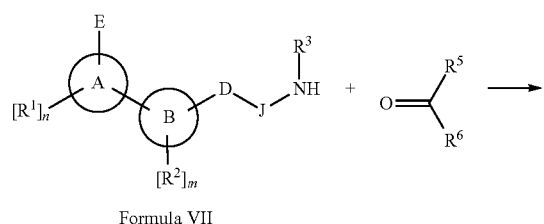

Formula VII

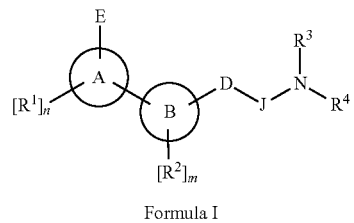

Formula I

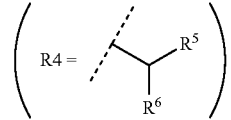

Compounds of Formula I can be prepared from compounds of Formula VII by reductive alkylation with a ketone or aldehyde in a suitable solvent such as MeOH or $CH_2Cl_2$, in the presence of a reducing agent such as sodium cyanoborohydride, sodium (triacetoxy)borohydride or $PS—BH_3CN$, with or without acetic acid, at a temperature from room temperature to 50° C. Sometimes it was found to be advantageous to react compounds of Formula VII where $R^3$ is H, with the ketone or aldehyde in a suitable solvent such as benzene or toluene, at reflux temperature, under Dean-Stark conditions before the addition of the reducing agent. In this procedure $R^5$ and $R^6$ may together form a ketone; or when $R^5$ is hydrogen, $R^5$ and $R^6$ may form an aldehyde.

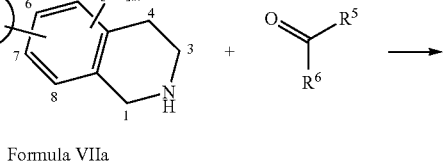

Formula VIIa

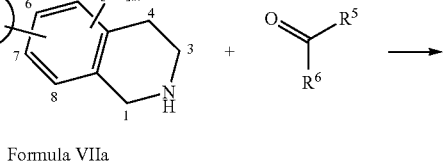

Formula Ia

Compounds of Formula Ia can be prepared in a similar manner using the reductive alkylation conditions described. Compounds of Formula VIIIa can be prepared via Suzuki coupling between a compound of formula IV where X is a leaving group (eg. halogen, or triflate) and an appropriately substituted tetrahydroisoquinoline derivative where Z is a boronate, boronic acid, halogen, or triflate, for example, and $R^3$ could be a protecting group which is later removed in a separate step. The reaction occurs under Suzuki reaction conditions in a suitable organic solvent such as acetonitrile, in the presence of a suitable catalyst such as $(Ph_3P)_4Pd$ or $PdCl_2(dppf)$, and in the presence of an inorganic base such as $Na_2CO_3$ with or without the addition of water at a temperature ranging from room temperature to 100° C.

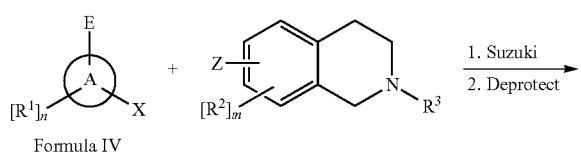

Formula IV

Formula VIIa

General Method 5: Bond formation between Formula IX and Formula III by reductive alkylation

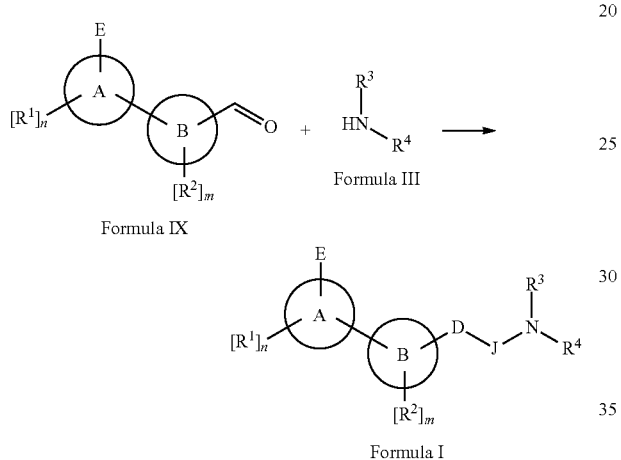

Formula IX

Formula III

Formula I

Compounds of Formula I, where D is CH$_2$ and J is a bond, can be prepared from compounds of Formula IX by reaction with compounds of Formula III in the presence of a reducing agent such as NaCN(BH)$_3$, NaBH(OAc)$_3$ or PS—BH$_3$CN, in an appropriate organic solvent such as MeOH or dichloromethane, with or without acetic acid, at a temperature ranging from room temperature to 50° C. Sometimes it was found advantageous to react the compound of Formula IX with the compound of Formula III in a suitable solvent such as benzene or toluene, at reflux temperature, using Dean-Stark conditions prior to the addition of the reducing agent.

General Method 6: Functional group interconversion(s) to unmask E from Y in Formula X. Compounds of Formula I can be prepared by hydrolysis of a nitrile to carboxamide (Y=CN, E=CONH$_2$) or aminolysis of an ester to carboxamide (Y=CO$_2$R, E=CONH$_2$).

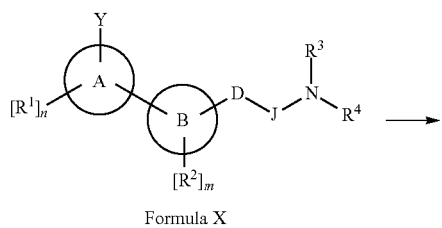

Formula X

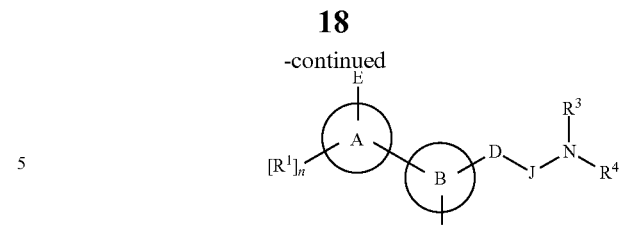

Formula I

General Method 7: Removal of protecting group from Compounds of Formula X wherein Y is a suitably protected heteroaryl or heterocyclyl. Compounds of Formula I can be readily prepared from compounds of Formula X by removal of a protecting group (ie. POM, SEM, or Boc) using known literature procedures. Compounds of Formula X can be prepared using a method described herein or through synthetic methods known to one skilled in the art of organic chemistry.

EXPERIMENTAL

Reverse phase chromatography was performed on an Agilent 1100 series instrument using a Phenomenex Luna 5 micron C18 column (150×21.1 mm). The gradient was 50% to 90% acetonitrile containing 0.1% trifluoroacetic acid/water containing 0.1% trifluoroacetic acid. Normal phase chromatography was performed on the ISCO Sg 100c combiflash system.

Intermediate A-1-1

3'-hydroxy-4-biphenylcarboxamide

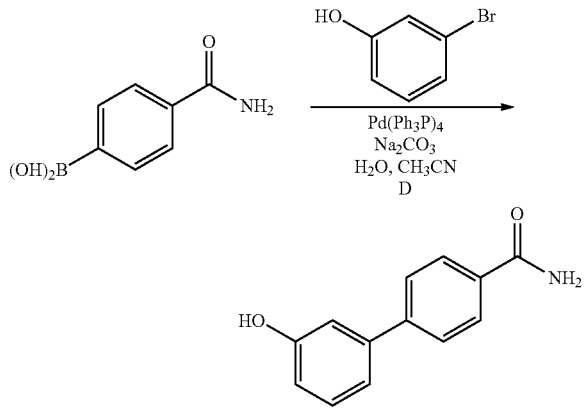

Δ = heat

A mixture of 4-benzamide boronic acid (1.0 g, 0.006 mol), 3-bromophenol (1.0 g, 0.006 mol) and 30 mL of 0.4M Na$_2$CO$_3$ in 30 mL of acetonitrile was degassed for 10 min. with nitrogen. Tetrakis(triphenylphosphine)palladium (0.04 g, 0.03 mmol) was added and the mixture was placed in a preheated oil bath at 90° C. After 2.5 hr the hot reaction mixture was filtered through celite and concentrated to one-half volume in vacuo. The residue was extracted with mixtures of ethyl acetate and dichloromethane. The combined organic extracts were dried (Na$_2$SO$_4$), filtered and concentrated in vacuo to give 3'-hydroxy-4-biphenylcarboxamide as a tan solid. (M+H) 214, t$_R$ 1.8 min. (LC/MS method A). This product was used without further purification.

TABLE A

Synthesis of Intermediates of Formula II

| Example # | Structure and Name | Characterization Data | Comments |
|---|---|---|---|
| D-1-1 | 4'-hydroxy-3-biphenylcarboxamide | LC/MS (Method A)<br>$t_R$ 1.77 min<br>(M + H) 214 | Prepared in a manner similar to A-1-1 using 3-benzamide boronic acid and 4-bromophenol[1] |
| H-1-1 | 3'-hydroxy-biphenylcarboxamide | (M + H) 214, $t_R$ 1.86 min<br>(LC/MS Method A) | Prepared in a manner similar to A-1-1 using 3-benzamide boronic acid and 3-bromophenol |
| J-1-1 | 4'-hydroxy-4-biphenylcarboxamide | (M + H) 214, $t_R$ 1.82 min<br>(LC/MS Method A) | Prepared in a manner similar to A-1-1 using 4-benzamide boronic acid and 4-bromophenol |
| L-1-2 | 3'-hydroxy-2-methyl-4-biphenylcarboxamide | (M + H) 228, $t_R$ 1.94 min<br>(LC/MS Method A) | Prepared in a manner similar to A-1-1 using Intermediate IV-4 and 3-hydroxyphenyl boronic acid |
| N-1-2 | 2-fluoro-3'-hydroxy-4-biphenylcarboxamide | (M + H) 232, $t_R$ 1.88 min<br>(LC/MS Method A) | Prepared in a manner similar to A-1-1 using Intermediate IV-5 and 3-hydroxyphenyl boronic acid |

TABLE A-continued

Synthesis of Intermediates of Formula II

| Example # | Structure and Name | Characterization Data | Comments |
|---|---|---|---|
| O-1-1 | 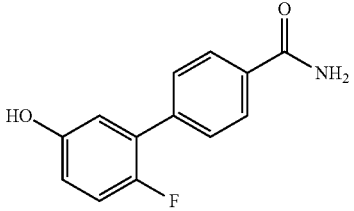<br>2′-fluoro-5′-hydroxy-4-biphenylcarboxamide | (M + H) 232, $t_R$ 1.88 min (LC/MS Method A) | Prepared in a manner similar to A-1-1 using 4-benzamideboronic acid and 3-bromo-4-fluorophenol |
| HH-1-1 | 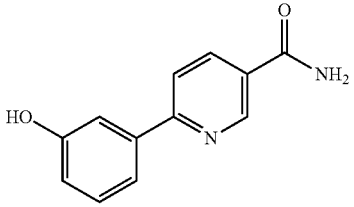<br>6-(3-hydroxyphenyl)-3-pyridinecarboxamide | (M + H) 215, $t_R$ 1.49 min (LC/MS method A) | Prepared in a manner similar to A-1-1 using 6-chloro-3-pyridinecarboxamide and 3-hydroxyphenyl boronic acid |
| JJ-1-1 | 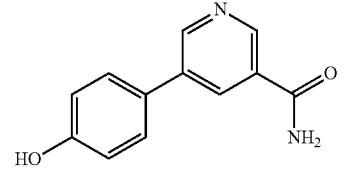<br>5-(4-hydroxyphenyl)-3-pyridinecarboxamide | $^1$H NMR (400 MHz, DMSO-$d_6$) δ ppm 6.85 (d, 2 H) 7.60 (m, 3 H) 8.20 (s, 1 H) 8.39 (s, 1 H) 8.90 (d, 2H) 9.72 (s, 1 H) | Prepared in a manner similar to A-1-1 using 5-bromo-3-pyridinecarboxamide and 4-hydroxyphenyl boronic acid[1)] |
| KK-1-1 | 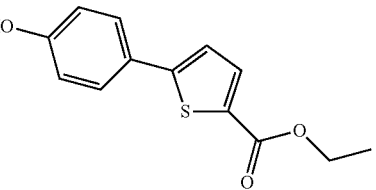<br>ethyl 5-(4-hydroxyphenyl)-2-thiophenecarboxylate | $^1$H NMR (400 MHz, CDCl$_3$) δ ppm 1.38 (t, 3 H), 4.35 (q, 2 H) 6.85 (d, 2 H) 7.17 (s, 1 H) 7.56 (d, 2 H) 7.74 (s, 1 H) | Prepared in a manner similar A-1-1 using ethyl 5-chloro-2-thiophenecarboxylate and 4-hydroxy phenylboronic acid[1)] |
| KK-2-3 | 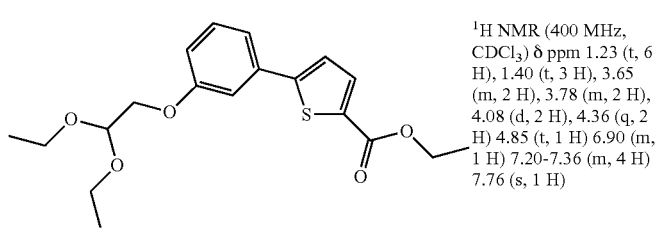<br>ethyl 5-(3-{[2,2-bis(ethyloxy)ethyl]oxy}phenyl)-2-thiophene carboxylate | $^1$H NMR (400 MHz, CDCl$_3$) δ ppm 1.23 (t, 6 H), 1.40 (t, 3 H), 3.65 (m, 2 H), 3.78 (m, 2 H), 4.08 (d, 2 H), 4.36 (q, 2 H) 4.85 (t, 1 H) 6.90 (m, 1 H) 7.20-7.36 (m, 4 H) 7.76 (s, 1 H) | Note 2 |

TABLE A-continued

Synthesis of Intermediates of Formula II

| Example # | Structure and Name | Characterization Data | Comments |
|---|---|---|---|
| LL-1-3 | 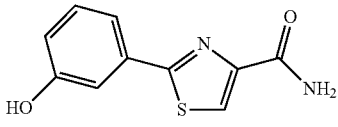<br>2-(3-hydroxyphenyl)-1,3-thiazole-4-carboxamide | $^1$H NMR (400 MHz, DMSO-$d_6$) δ ppm 6.88 (m, 1 H), 7.30 (m, 1 H), 7.40 (m, 2 H), 7.61 (s, 1 H), 7.80 (s, 1 H), 8.22 (s, 1 H), 9.78 (s, 1 H) | Prepared in a manner similar A-1-1 using Intermediate IV-18 and 3-hydroxyphenylboronic acid[1)] |

Note 1:
DME was used as the solvent in lieu of Acetonitrile.

Note 2:
Prepared in a manner similar to A-1-1 using a mixture of ethyl 5-chloro-2-thiophenecarboxylate and (3-{[2,2-Bis(ethyloxy)ethyl]oxy}phenyl)boronic acid[2)] (prepared according to the procedure in Dack, Kevin Neil; Fray, Michael Jonathan; Whitlock, Gavin Alistair; Lewis, Mark Llewellyn; Thomson, Nicholas Murray: WO 2000/074681).

Compounds of Formula II

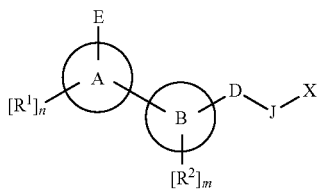

Formula II

Example II-1

3'-[(2-chloroethyl)oxy]-4-biphenylcarboxamide and 3'-[(2-bromoethyl)oxy]-4-biphenylcarboxamide

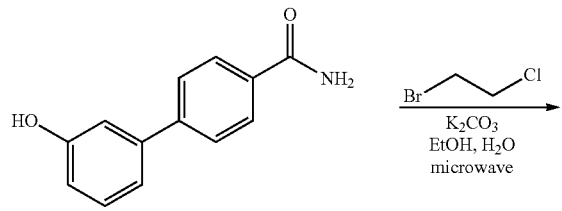

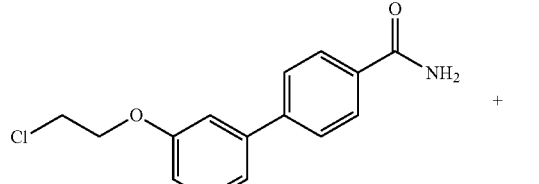

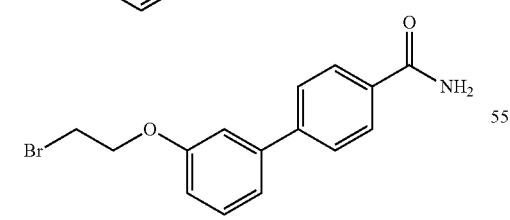

Into three separate microwave vials was distributed equally a mixture of 3'-hydroxy-4-biphenylcarboxamide (Intermediate A-1-1) (1.0 g, 0.005 mol), 1-bromo-2-chloroethane (2.8 g, 0.02 mol) and potassium carbonate (2.8 g, 0.02 mol) in ethanol (2.2 mL) and water (1.8 mL) was placed in a microwave at 150° C. until the reaction was complete as determined by LC/MS. The contents of the vials were combined and diluted with ethyl acetate and water. The aqueous phase was extracted with ethyl acetate. The combined organic phase was dried (Na$_2$SO$_4$), filtered and concentrated in vacuo to give 3'-[(2-chloroethyl)oxy]-4-biphenylcarboxamide and 3'-[(2-bromoethyl)oxy]-4-biphenylcarboxamide as an off-white solid. LC/MS indicates that this product is a mixture of the chloroethoxy (M+H) 276, 2.34 min. (LC/MS method A) and the bromoethoxy (M+H) 320, $t_R$ 2.42 min. in a ratio of ~81/19% respectively. This product was used without further purification.

Example II-2

3'-[(2-chloroethyl)oxy]-4-biphenylcarboxamide

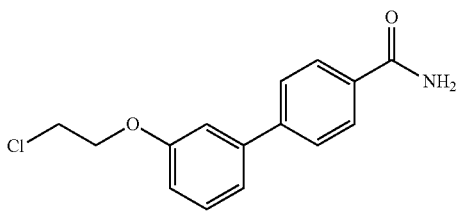 [SMILES: NC(=O)c1ccc(-c2cccc(OCCCl)c2)cc1]

The title compound was prepared in a manner similar to that described for Example A-1-1 using a mixture of 4-benzamide boronic acid and 3-bromophenyl 2-chloroethylether. (M+H) 276, $t_R$ 2.32 min. (LC/MS method A).

Example II-3

4'-[(2-chloroethyl)oxy]-3-biphenylcarboxamide and 4'-[(2-bromoethyl)oxy]-3-biphenylcarboxamide

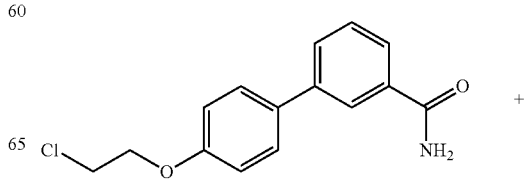

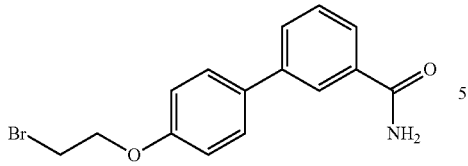

The mixture of title compounds was prepared similar to Example II-1 using 4'-hydroxy-3-biphenyl carboxamide (Intermediate D-1-1). The chloroethoxy (M+H) 276, $t_R$ 2.35 min. (LC/MS method A) and the bromoethoxy (M+H) 320, $t_R$ 2.44 min. were obtained in a ratio of ~84/16% respectively.

Example II-4

4'-[(2-chloroethyl)oxy]-3-biphenylcarboxamide

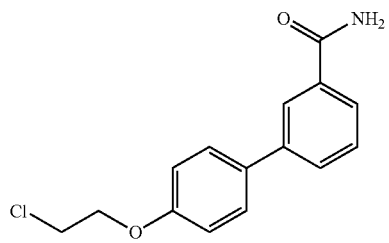 [SMILES: NC(=O)c1cccc(-c2ccc(OCCCl)cc2)c1]

The title compound was prepared in a manner similar to Example A-1-1 using a mixture of 3-benzamide boronic acid and 4-bromophenyl 2-chloroethylether with PdCl$_2$(dppf).CH$_2$Cl$_2$ in lieu of Pd(PPh$_3$)$_4$ in DME. Purification of the desired product was accomplished by either recrystallization from EtOH or silica gel chromatography using Hexanes/Ethyl Acetate. (LC/MS Method A) $t_R$ 2.33 min, m/z 276 (M+H).

Example II-5

3'-[(2-chloroethyl)oxy]-3-biphenylcarboxamide and 3'-[2-bromoethyl)oxy]-3-biphenylcarboxamide

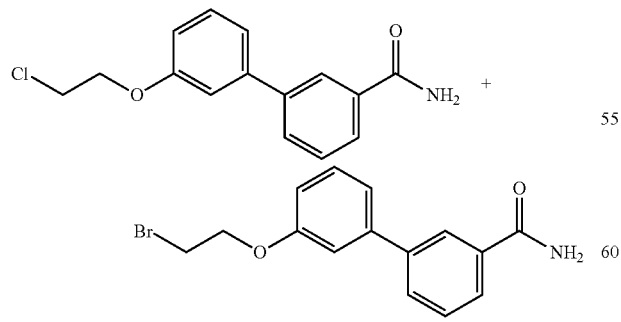

The mixture of title compounds was prepared similar to Example II-1 using 3'-hydroxy-3-biphenylcarboxamide (Intermediate H-1-1). The chloroethoxy (M+H) 276, $t_R$ 2.38 min. (LC/MS method A) and the bromoethoxy (M+H) 320, $t_R$ 2.45 min. (LC/MS method A) were obtained in a ratio of ~65/35% respectively.

Example II-6

4'-[(2-chloroethyl)oxy]-4-biphenylcarboxamide and 4'-[(2-bromo ethyl)oxy]-4-biphenylcarboxamide

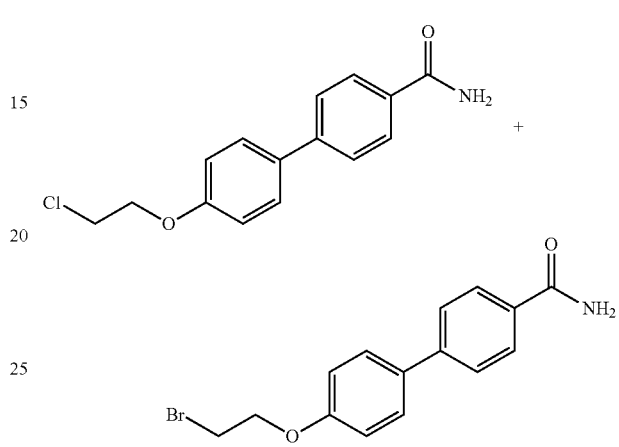

The mixture of title compounds was prepared similar to Example II-1 using 4'-hydroxy-4-biphenylcarboxamide (Intermediate J-1-1). LC/MS of the brown solid indicates that this product is a mixture of the chloroethoxy (M+H) 276, $t_R$ 2.47 min. (LC/MS method A) and the bromoethoxy (M+H) 320, $t_R$ 2.54 min. (LC/MS method A) in a ratio of ~74/26% respectively.

Example II-7

3'-[(2-chloroethyl)oxy]-2-methyl-4-biphenylcarboxamide and 3'-[(2-bromo ethyl)oxy]-2-methyl-4-biphenylcarboxamide

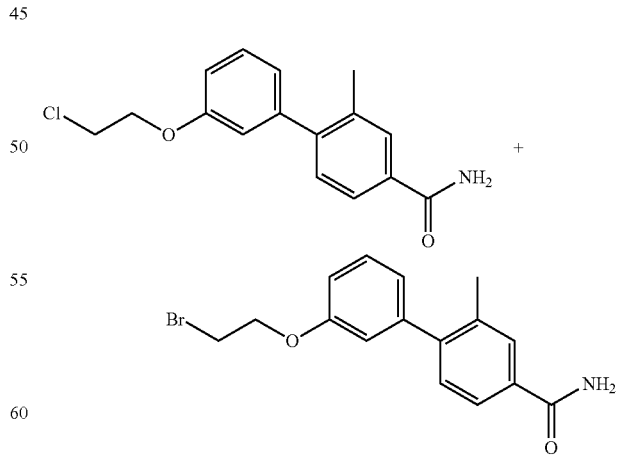

The mixture of title compounds was prepared similar to Example II-1 using 3'-hydroxy-2-methyl-4-biphenyl carboxamide (Intermediate L-1-2). LC/MS indicates that this product is a mixture of the chloroethoxy (M+H) 290.2, $t_R$ 2.42 min. (LC/MS method A) and the bromoethoxy (M+H) 334, $t_R$ 2.50 min. (LC/MS method A) in a ratio of ~73/27% respectively.

Example II-8

3'-[(2-chloroethyl)oxy]-2-methyl-4-biphenylcarboxamide

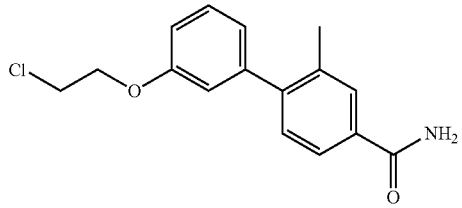 [SMILES: Cc1cc(C(N)=O)ccc1-c1cccc(OCCCl)c1]

A mixture of 3'-hydroxy-2-methyl-4-biphenylcarboxamide (1.65 g, 0.007 mol. Intermediate L-1-2), 2-chloroethyl-p-toluenesulfate (1.88 g, 0.008 mol) and potassium carbonate (1.11 g, 0.008 mol) in acetonitrile (25 mL) was heated at reflux for 40 hr. The reaction mixture was concentrated in vacuo to remove acetonitrile. The residue was partitioned between ethyl acetate and water. The ethyl acetate phase was washed with brine, dried (Na$_2$SO$_4$), filtered and concentrated in vacuo. The residue was purified by silica gel chromatography to give 3'-[(2-chloroethyl)oxy]-2-methyl-4-biphenylcarboxamide as a white solid. (M+H) 290, $t_R$ 2.49 min. (LC/MS method B).

Example II-9

3'-[(2-chloroethyl)oxy]-2-fluoro-4-biphenylcarboxamide and 3'-[(2-bromo ethyl)oxy]-2-fluoro-4-biphenylcarboxamide

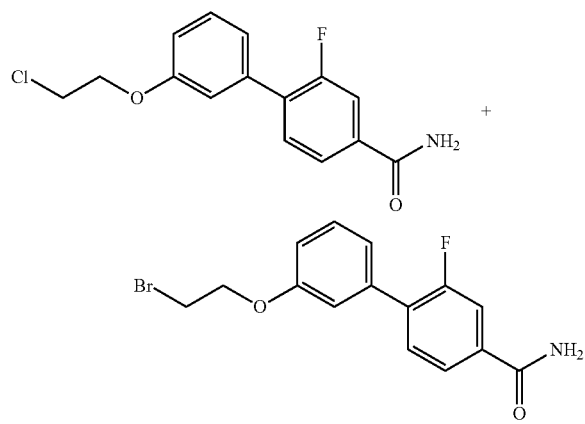

The mixture of title compounds was prepared similar to Example II-1 using 2-fluoro-3'-hydroxy-4-biphenyl carboxamide (Intermediate N-1-2). LC/MS indicates that this product is a mixture of the chloroethoxy (M+H) 294, $t_R$ 2.41 min. (LC/MS method A) and the bromoethoxy (M+H) 338, 2.49 min. (LC/MS method A) in a ratio of ~65/35% respectively.

Example II-10

5'-[(2-chloroethyl)oxy]-2'-fluoro-4-biphenylcarboxamide and 5'-[(2-bromo ethyl)oxy]-2'-fluoro-4-biphenylcarboxamide

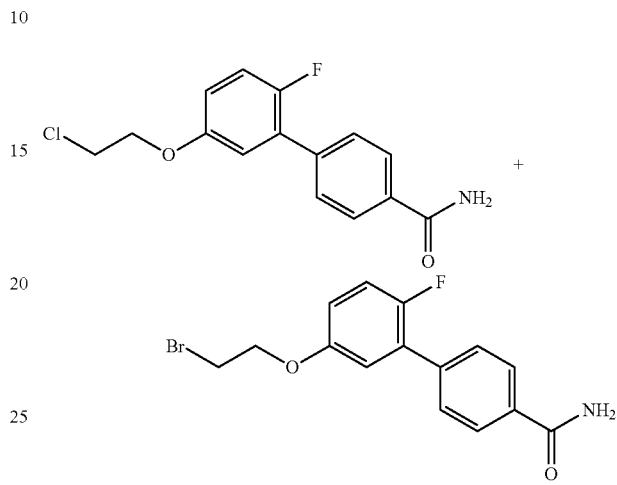

The mixture of title compounds was prepared similar to Example II-1 using 2'-fluoro-5'-hydroxy-4-biphenyl carboxamide (Intermediate O-1-1). LC/MS indicates that this product is a mixture of the chloroethoxy (M+H) 294, $t_R$ 2.38 min. (LC/MS method A) and the bromoethoxy (M+H) 338, $t_R$ 2.45 min. (LC/MS method A) in a ratio of ~74/26% respectively.

Example II-11

3'-[(3-chloropropyl)oxy]-4-biphenylcarboxamide and 3'-[(3-bromo propyl)oxy]-4-biphenylcarboxamide

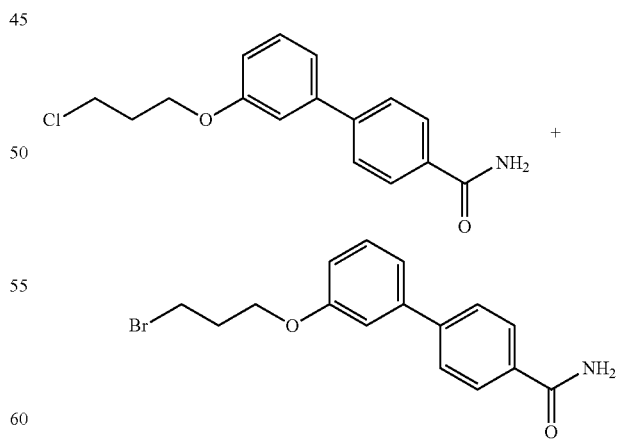

The mixture of title compounds was prepared similar to Example II-1 using 3'-hydroxy-4-biphenylcarboxamide (Intermediate A-1-1) and 1-bromo-3-chloropropane. LC/MS indicates that this product is a mixture of the chloropropoxy (M+H) 290, $t_R$ 2.57 min. (LC/MS method A) and the bromopropoxy (M+H) 334, $t_R$ 2.62 min. (LC/MS method A) in a ratio of ~75/25% respectively.

Example II-12

6-{3-[(2-chloroethyl)oxy]phenyl}-3-pyridinecarboxamide

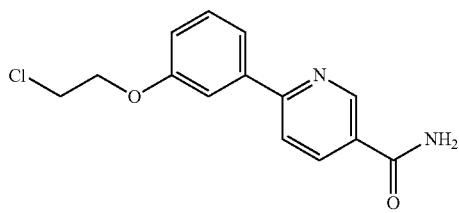 [SMILES: NC(=O)c1ccc(-c2cccc(OCCCl)c2)nc1]

The title compound was prepared in a manner similar to Example II-8 using 6-(3-hydroxyphenyl)-3-pyridinecarboxamide (Intermediate HH-1-1). $^1$H NMR (400 MHz, DMSO-d$_6$) δ ppm 3.95 (t, 2H) 4.38 (t, 2H) 7.05 (d, 1H) 7.40 (t, 1H) 7.60 (br, 1H) 7.75 (m, 2H) 8.10 (d, 1H) 8.20 (br, 1H) 8.28 (d, 1H) 9.05 (s, 1H).

Example II-13

5-{4-[(2-chloroethyl)oxy]phenyl}-3-pyridinecarboxamide

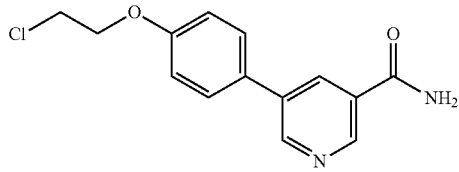 [SMILES: NC(=O)c1cncc(-c2ccc(OCCCl)cc2)c1]

The title compound was prepared in a similar fashion to Example II-8 using 5-(4-hydroxyphenyl)-3-pyridinecarboxamide (Intermediate JJ-1-1). $^1$H NMR (400 MHz, DMSO-d$_6$) δ ppm 3.95 (t, 2H) 4.35 (t, 2H) 7.10 (d, 2H) 7.60 (s, 1H) 7.75 (d, 2H) 8.12 (s, 1H) 8.40 (s, 1H) 8.92 (s, 1H) 8.98 (s, 1H).

Example II-14

5-{4-[(2-chloroethyl)oxy]phenyl}-2-thiophenecarboxamide

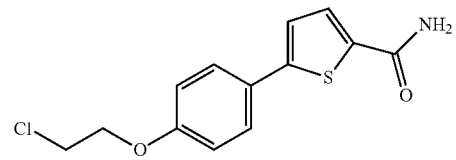 [SMILES: NC(=O)c1ccc(-c2ccc(OCCCl)cc2)s1]

To a suspension of ammonium chloride (2.12 g, 39.6 mmol) in 10 ml of toluene at 5° C. was added dropwise 19.8 ml of 2M trimethylaluminum in toluene solution. The mixture was stirred for 2 h at the room temperature and ethyl 5-(4-hydroxyphenyl)-2-thiophene carboxylate (Intermediate KK-1-1) (1.98 g, 7.03 mmol) was added. The resulting mixture was heated at 55-60° C. for 15 h, cooled to 5° C. and quenched with ethanol (10 ml). All solvents were removed in vacuo and the residue was treated with 80 ml of 0.5M HCl solution. A yellow solid was collected by filtration, washed with water and air-dried (1.64 g). The product was added to a mixture of 2-chloroethyl p-toluenesulfonate (4.07 ml, 22.5 mmol) and potassium carbonate (3.11 g, 22.5 mmol) in 100 ml of acetonitrile. After heating at reflux for 40 h, the reaction mixture was filtered to remove the solids, concentrated to dryness in vacuo and purified by silica gel column chromatography using Hexanes and EtOAc to give the title compound as a light yellow solid.

$^1$H NMR (400 MHz, CDCl$_3$) δ ppm 3.90 (t, 2 H), 4.28 (t, 2 H) 7.00 (d, 2 H) 7.39 (m, 2 H) 7.60 (m, 3 H) 7.90 (s, 1 H); (M+H) 282, $t_R$ 2.28 min (LC/MS method A).

Example II-15

5-{3-[(2-chloroethyl)oxy]phenyl}-2-thiophenecarboxamide

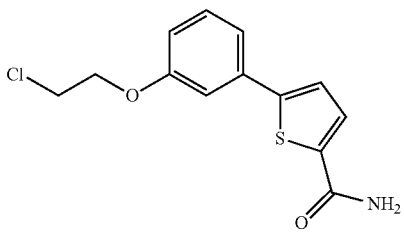 [SMILES: NC(=O)c1ccc(-c2cccc(OCCCl)c2)s1]

Step 1: Ethyl 5-{3-[(2-oxoethyl)oxy]phenyl}-2-thiophenecarboxylate

Ethyl 5-(3-{[2,2-bis(ethyloxy)ethyl]oxy}phenyl)-2-thiophenecarboxylate (Intermediate KK-2-3) (1.41 g, 3.87 mmol) was dissolved in 20 ml of chloroform and cooled to 0° C. 5 ml of 50% aqueous trifluoroacetic acid solution was added. The mixture was stirred for 15 h at room temperature and 6 h at 65° C., cooled, diluted with chloroform and neutralized with saturated sodium bicarbonate solution. The organic layer was separated, washed with brine, dried over magnesium sulfate and concentrated in vacuo. The residue was purified by silica gel column chromatography (10 to 50% ethyl acetate in hexanes) to afford the title compound as a white crystalline solid.

$^1$H NMR (400 MHz, CDCl$_3$) δ ppm 1.40 (t, 3 H), 4.38 (q, 2 H) 4.63 (s, 2 H) 6.85 (m, 1 H) 7.24-7.38 (m, 4 H) 7.77 (s, 1 H), 9.90 (s, 1 H).

Step 2: 5-(3-Hydroxyphenyl)-2-thiophenecarboxamide

The mixture of ethyl 5-{3-[(2-oxoethyl)oxy]phenyl}-2-thiophenecarboxylate (1.3 g, 4.48 mmol), 2N aqueous lithium hydroxide solution (5 ml, 10 mmol) and tetrahydrofuran (10 ml) was heated to reflux for 12 h. The reaction mixture was cooled, concentrated in vacuo to remove tetrahydrofuran, acidified to pH1-2 with 2N HCl, and extracted with ethyl acetate three times. The combined extracts were washed with brine, dried over magnesium sulfate and concentrated in vacuo. The solid residue (0.75 g) was dissolved in dry tetrahydrofuran (15 ml) and cooled to 0° C. (Chloromethylene)

dimethylammonium chloride (Aldrich, 0.52 g, 4 mmol) was added in one portion. The mixture was stirred at 0° C. for 4 h. The pre-cooled (0° C.) mixture of 28% ammonium hydroxide aqueous solution (2.5 ml) and water (2.5 ml) was added, and the reaction mixture was stirred at the room temperature. Tetrahydrofuran was removed in vacuo and the residue was extracted with ethyl acetate three times. The combined extracts were washed with brine, dried over magnesium sulfate and concentrated in vacuo. The residue was purified by silica gel column chromatography (80% ethyl acetate in hexanes) to give the title compound as a brown solid.

$^1$H NMR (400 MHz, DMSO-$d_6$) δ ppm 6.75 (d, 1 H) 7.01 (s, 1 H) 7.08 (d, 1H) 7.20 (t, 1 H) 7.40 (m, 2 H) 7.65 (d, 1 H) 7.97 (br., 1 H) 9.62 (s, 1 H); (M+H) 220, $t_R$ 1.78 min (LC/MS method A).

Step 3: 5-{3-[(2-Chloroethyl)oxy]phenyl}-2-thiophenecarboxamide 5-(3-Hydroxyphenyl)-2-thiophenecarboxamide (0.31 g, 1.41 mmol), 2-chloroethyl p-toluenesulfonate (1.327 g, 5.65 mmol) and potassium carbonate (0.782 g, 5.65 mmol) in 20 ml of acetonitrile were heated to reflux for 15 h. The reaction mixture was concentrated in vacuo and purified by silica gel column chromatography (50 to 80% ethyl acetate in hexanes) to give the title compound as a white solid.

$^1$H NMR (400 MHz, Acetone-$d_6$) δ ppm 3.95 (t, 2 H) 4.40 (t, 2 H) 6.68 (br., 1 H) 7.00 (d, 1 H) 7.28-7.40 (m, 3 H) 7.50 (d, 1 H) 7.72 (d, 1 H).

Example II-16

2-{3-[(2-chloroethyl)oxy]phenyl}-1,3-thiazole-4-carboxamide

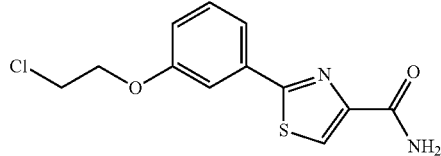 [SMILES: NC(=O)c1csc(-c2cccc(OCCCl)c2)n1]

The title compound was prepared in a similar fashion to Example II-8 using 2-(3-Hydroxyphenyl)-1,3-thiazole-4-carboxamide (Intermediate LL-1-3). (M+H) 283, $t_R$ 2.34 min (LC/MS method A).

Example II-17

2-{4-[(2-chloroethyl)oxy]phenyl}-1,3-thiazole-4-carboxamide

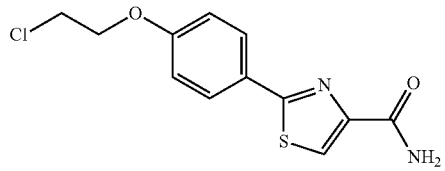 [SMILES: NC(=O)c1csc(-c2ccc(OCCCl)cc2)n1]

Step 1:
2-(4-Hydroxyphenyl)-1,3-thiazole-4-carboxylic Acid

4-Hydroxybenzenecarbothioamide (1.53 g, 10 mmol) and potassium hydroxide (1.50 g, 26.8 mmol) were dissolved in a mixture of 60 ml of water and 15 ml of methanol. A solution of bromopyruvic acid (1.67 g, 10 mmol) in 10 ml of methanol was added dropwise at room temperature. The resulting mixture was heated to reflux for 1.5 h, cooled to room temperature, poured into 100 ml of water and adjusted with 0.2N HCl solution to pH2. The mixture was placed in a refrigerator for 15 h. The title compound was obtained by filtration as a brown solid.

$^1$H NMR (400 MHz, DMSO-$d_6$) δ ppm 6.82 (d, 2 H), 7.78 (d, 2 H), 8.37 (s, 1 H), 10.05 (s, 1 H), 13.00 (s, 1 H).

Step 2:
2-(4-Hydroxyphenyl)-1,3-thiazole-4-carboxamide 2-(4-Hydroxyphenyl)-1,3-thiazole-4-carboxylic acid (0.835 g, 3.77 mmol) was dissolved in 20 ml of dry tetrahydrofuran and cooled to 0° C. (Chloromethylene)dimethylammonium chloride (0.58 g, 4.53 mmol) was added in one portion. The mixture was stirred at 0° C. for 5 h. 28% Ammonium hydroxide aqueous solution (5 ml) was added, and the reaction mixture was stirred for 15 h at the room temperature. The organic solvent was removed in vacuo and the residue was partitioned between ethyl acetate and saturated sodium carbonate solution. The organic layer was separated and the aqueous phase was extracted twice with ethyl acetate. The combined extracts were washed with brine, dried over magnesium sulfate and concentrated in vacuo. The residue was purified by silica gel column chromatography (0 to 10% methanol in dichloromethane) to give the title compound as beige solid.

$^1$H NMR (400 MHz, DMSO-$d_6$) δ ppm 6.83 (d, 2 H) 7.60 (s, 1 H) 7.80 (m, 3 H) 8.12 (s, 1 H) 10.05 (s, 1 H); (M+H) 221, $t_R$ 1.69 min (LC/MS method A).

Step 3: 2-{4-[(2-Chloroethyl)oxy]phenyl}-1,3-thiazole-4-carboxamide

Proceeding in a similar manner to Example II-8 using 2-(4-hydroxyphenyl)-1,3-thiazole-4-carboxamide gave the title compound as a yellow solid.

$^1$H NMR (400 MHz, CDCl$_3$) δ ppm 3.82 (t, 2 H) 4.30 (t, 2 H) 5.68 (s, 1 H) 7.00 (d, 2 H) 7.28 (s, 1 H) 7.90 (d, 2 H) 8.09 (s, 1 H)

Compounds of Formula III

Formula III

Example III-1

4,4-dimethylcyclohexylamine hydrochloride

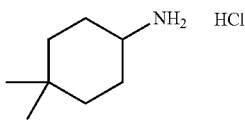

Prepared similarly to the procedure of Johnston, T. P.; McCaleb, G. S.; Opliger, P. S.; Laster, W. R.; Montgomery J. A. *J. Med. Chem.* 1971, 14 (7), 600.

Step 1: 4,4-Dimethylcyclohexanone

A mixture of 4,4-dimethyl-2-cyclohexene-1-one (5.5 g) and 10% Pd/C (0.25 g, wet, Degussa type E101) in EtOAc (50 mL) was hydrogenated under 15 psi for 3 h at room temperature. The mixture was filtered through Celite and the filtrate was concentrated in vacuo affording the title compound as a colorless solid. $^1$H NMR (400 MHz, CDCl$_3$) δ ppm 1.07 (s, 6H), 1.65 (t, J=7 Hz, 4H), 2.35 (t, J=7 Hz, 4H).

Step 2: 4,4-dimethylcyclohexanone oxime

To a solution of 4,4-dimethylcyclohexanone (3.0 g, 0.024 mole) and hydroxylamine hydrochloride (2.2 g, 0.031 mole) in ethanol (15 mL) and water (20 mL) at room temperature was added a solution of sodium carbonate (3.3 g, 0.031 mol) in water (10 mL), dropwise. The mixture was heated under reflux for 3 hr, cooled to room temperature and ethanol was removed in vacuo. The aqueous residue was extracted several times with ethyl acetate, combined extracts were dried over MgSO$_4$ and concentrated in vacuo affording the title compound as a white solid, used without further purification. $^1$H NMR (400 MHz, DMSO-d$_6$) δ ppm 0.93 (s, 6H), 1.28 (t, J=6.6 Hz, 2H), 1.35 (t, J=6.6 Hz, 2H), 2.11 (t, J=6.6 Hz, 2H), 2.36 (t, J=6.6 Hz, 2H), 10.12 (s, 1H).

Step 3: 4,4-dimethylcyclohexylamine hydrochloride

A mixture of 4,4-dimethylcyclohexanone oxime (3.0 g, 0.021 mole) and Raney 2800 Nickel (0.8 g, slurry in water) in ethanol (100 mL) was hydrogenated under 50 psig H$_2$ using a Parr hydrogenation apparatus. After hydrogen absorption ceased the mixture was filtered through Celite. To the filtrate was added a solution of HCl in Et$_2$O (50 mL of a 1M solution), the mixture was concentrated in vacuo. The residue was triturated with diethyl ether, solid was collected by filtration, washed with diethyl ether and air dried to give the title compound as a white solid. $^1$H NMR (400 MHz, DMSO-d6) δ ppm 0.86 (s, 3H), 0.87 (s, 3H), 1.19 (m, 2H), 1.36 (m, 2H), 1.48 (m, 2H), 1.70 (m, 2H), 2.87 (m, 1H), 7.93 (br. s, 3H).

Example III-2

[(4,4-dimethylcyclohexyl)methyl]amine hydrochloride

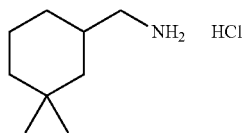

Step 1: (4,4-dimethylcyclohexylidene)methyl methyl ether

To a mixture of methoxymethyl triphenylphosphonium chloride (35.5 g, 0.104 mol) in THF (400 mL) at 0° C. was added n-BuLi (33.1 mL of a 2.8M solution in hexanes; 0.095 mol). The mixture was stirred at 0° C. for 30 min., cooled to −78° C. and a solution of 4,4-dimethyl cyclohexanone (10.0 g, 0.079 mol) in THF (100 mL) was added, dropwise. After 1 hr at −78° C. the mixture was slowly warmed to 0° C., diluted with satd ammonium chloride (400 mL) and ethyl acetate (100 mL) and stirred at room temperature for 48 hr. Layers were separated and the aqueous phase was extracted with ethyl acetate. Combined organics were washed with brine, dried over Na$_2$SO$_4$, filtered and concentrated in vacuo. The residue was triturated with hexanes, solids were removed by filtration and the filtrated was concentrated in vacuo. The residue was dissolved in dichloromethane (40 mL), PS-TsNHNH$_2$ (8 g; ca. 3.7 mmol/g) and acetic acid (2 drops) were added and the mixture was stirred at room temperature for 24 hr. Resin was removed by filtration and washed (CH$_2$Cl$_2$, MeOH, CH$_2$Cl$_2$). Combined filtrate/washings were concentrated in vacuo, affording (4,4-dimethyl cyclohexylidene)methyl methyl ether as an oil.
$^1$H NMR (400 MHz, CDCl$_3$) δ ppm 0.91 (s, 6 H); 1.27 (m, 5 H); 1.95 (m, 2 H); 2.18 (m, 2 H); 3.52 (s, 3 H).

Step 2: 4,4-dimethylcyclohexanecarbaldehyde

A solution of (4,4-dimethyl cyclohexylidene)methyl methyl ether (6.7 g, 0.043 mol) in THF (200 mL) containing 6M HCl (aq) (60 mL) was stirred at room temperature for 24 hr. The reaction mixture was diluted with a mixture of ethyl ether, hexanes, brine and water. The mixture was separated and the aqueous phase was extracted with ethyl ether. The combined organic phase was washed with brine, dried over Na$_2$SO$_4$, and concentrated in vacuo, affording 4,4-dimethyl-cyclohexanecarbaldehyde as a yellow oil, used without further purification.

Step 3: [(4,4-dimethylcyclohexyl)methyl](phenylmethyl)amine

A solution of 4,4-dimethylcyclohexanecarbaldehyde (6.6 g, 0.047 mol), benzylamine (5.0 g, 0.047 mol) and acetic acid (1 mL) in methanol (60 mL) was stirred for 30 min at room temperature. Sodium triacetoxyborohydride (10.0 g, 0.047 mol) was added in one portion and the mixture was stirred at room temperature for 16 hr. The reaction mixture was concentrated in vacuo and partitioned between dichloromethane and water. The organic phase was washed with brine, silica gel was added and the mixture was concentrated in vacuo.

The residue was purified by flash chromatography (CH$_2$Cl$_2$/MeOH), affording [(4,4-dimethyl cyclohexyl)methyl](phenylmethyl)amine as a white solid. (M+H) 232, 1.76 min. (LC/MS method B).

Step 4: [(4,4-dimethylcyclohexyl)methyl]amine hydrochloride

A mixture of [(4,4-dimethylcyclohexyl)methyl](phenylmethyl)amine (4.37 g, 0.019 mol) and 10% Pd/C (50% w/w with water) (0.75 g) in ethanol (100 mL) was hydrogenated under 50 psi H$_2$ using a Parr hydrogenation apparatus for 24 h and filtered through Celite. To the filtrate was added HCl in Et$_2$O (30 mL of a 1M solution) and the mixture was concentrated in vacuo. The residue was triturated with Et$_2$O, filtered, washed (Et$_2$O) and dried to give [(4,4-dimethylcyclohexyl)methyl]amine hydrochloride as a white solid. $^1$H NMR (400 MHz, DMSO-d$_6$) δ ppm 0.83 (s, 3 H); 0.86 (s, 3 H); 1.11 (m, 4 H); 1.33 (m, 2 H); 1.46 (m, 1 H); 1.53 (m, 2H); 2.64 (br s, 2H); 7.91 (br s, 3H).

Example III-3 rac 3,3-dimethylcyclohexylamine hydrochloride

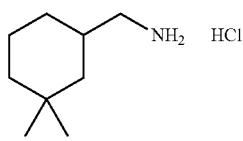

The title compound was prepared from 3,3-dimethylcyclohexanone in a manner similar to Example III-1 steps 2-3, with the exception that the intermediate oxime was not characterized.
$^1$H NMR (400 MHz, DMSO-d$_6$) δ ppm 0.85 (s, 3 H); 0.90 (s, 3 H); 0.97-1.16 (m, 3 H); 1.29 (br d, 1 H); 1.34-1.46 (m, 1H); 1.53-1.63 (m, 2H); 1.90 (br d, 1H); 3.05 (m, 1H); 7.99 (br s, 3H).

Example III-4

[(1S)-3,3-dimethylcyclohexyl]amine hydrochloride and [(1R)-3,3-dimethylcyclohexyl]amine hydrochloride

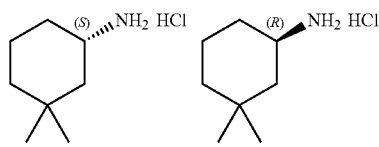

Step 1: rac-phenylmethyl (3,3-dimethylcyclohexyl)carbamate

To a solution of (3,3-dimethylcyclohexyl)amine hydrochloride (10.0 g, 0.060 mol) and N,N-diisopropylethylamine (15.8 g, 0.12 mol) in acetonitrile (125 mL) at ice bath temperature was added a solution of benzyl chloroformate (11.4 g, 0.067 mol) in acetonitrile (25 mL), dropwise. The mixture was stirred overnight, gradually warming to ambient temperature, and concentrated in vacuo. The residue was partitioned between ethyl acetate/5% citric acid solution and the layers were separated. The organic layer was washed with brine, dried over Na$_2$SO$_4$, adsorbed onto silica gel and purified by flash chromatography (CH$_2$Cl$_2$/hexanes) affording the title compound as a colorless oil. $^1$H NMR (400 MHz, DMSO-d$_6$) δ ppm: 0.85 (s, 6H), 0.92-1.02 (m, 3 H), 1.25 (d, 1 H), 1.36-1.52 (m, 3 H), 1.76 (br. d, 1 H), 3.36-3.44 (m, 1 H), 4.96 (s, 2H), 7.10 (d, 1 H), 7.27-7.36 (m, 5H).

Step 2: phenylmethyl [(1S)-3,3-dimethylcyclohexyl]carbamate and phenylmethyl [(1R)-3,3-dimethylcyclohexyl]carbamate rac-Phenylmethyl (3,3-dimethylcyclohexyl)carbamate (11.2 g) was separated into enantiomers on a 30 mm Chiralpak AS column by supercritical fluid chromatography (CO$_2$/EtOH, 75:4 g/min respectively at 140 bar, 40° C.). Earlier-eluting enantiomer: $^1$H NMR (400 MHz, DMSO-d$_6$) δ ppm: 0.85 (s, 6H), 0.93-1.01 (m, 3 H), 1.25 (d, 1 H), 1.33-1.52 (m, 3 H), 1.75 (br d, 1 H), 3.35-3.44 (m, 1 H), 4.96 (s, 2H), 7.08 (d, 1 H), 7.25-7.35 (m, 5H). Later-eluting enantiomer: $^1$H NMR (400 MHz, DMSO-d$_6$) δ ppm: 0.85 (s, 6H), 0.92-1.01 (m, 3 H), 1.25 (d, 1 H), 1.33-1.52 (m, 3 H), 1.75 (br dl 1 H), 3.36-3.44 (m, 1 H), 4.96 (s, 2H), 7.08 (d, 1 H), 7.26-7.35 (m, 5H). Comparison of experimentally measured vibrational circular dichroism (VCD) spectra with the calculated (ab initio) VCD spectrum for [(1R)-3,3-dimethylcyclohexyl]carbamate indicated the later-eluting enantiomer had the (R)-configuration.

Step 3: [(1S)-3,3-dimethylcyclohexyl]amine hydrochloride and [(1R)-3,3-dimethylcyclohexyl]amine hydrochloride The preparation of [(1S)-3,3-dimethylcyclohexyl]amine hydrochloride is given as representative. Phenylmethyl [(1S)-3,3-dimethylcyclohexyl]carbamate (1.0 g, 4.0 mmol) and 10% Pd/C (0.15 g) in 10 mL of MeOH was stirred under an atmosphere of H$_2$ for 24 hours and filtered through Celite. To the filtrate was added HCl in Et$_2$O (2.5 mL of a 1M solution), the mixture was aged overnight at room temperature and concentrated in vacuo. The residue was triturated with Et$_2$O, solid was collected by filtration washed (Et$_2$O) and dried in vacuo affording the title compound as a white solid. $^1$H NMR (400 MHz, DMSO-d$_6$) δ ppm: 0.89 (s, 3H), 0.93 (s, 3H), 1.00-1.17 (m, 3H), 1.33 (br. d, 1 H), 1.38-1.49 (br. q, 1 H), 1.58-1.63 (m, 2H), 1.92 (br d, 1 H), 3.06-3.14 (m, 1H), 7.86 (s, 3H). [(1R)-3,3-dimethylcyclohexyl]amine hydrochloride was obtained from [(1R) 3,3-dimethylcyclohexyl]carbamate according to the procedure described above for [(1S)-3,3-dimethylcyclohexyl]amine hydrochloride. $^1$H NMR (400 MHz, DMSO-d$_6$) δ ppm: 0.85 (s, 3H), 0.90 (s, 3H), 0.96-1.14 (m, 3H), 1.29 (br. d, 1 H), 1.35-1.45 (br q., 1 H), 1.53-1.61 (m, 2H), 1.89 (br d, 1 H), 3.02-3.09 (m, 1 H), 7.88 (s, 3H).

Example III-5

3,3,5,5-tetramethycyclohexylamine hydrochloride

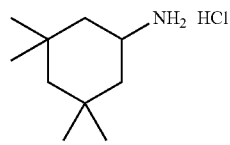

The title compound was prepared from 3,3,5,5-tetramethylcyclohexanone in a manner similar to Example III-1 steps 2-3, with the exception that the intermediate oxime was not characterized.

$^1$H NMR (400 MHz, DMSO-$d_6$) δ ppm 0.89 (s, 6 H); 0.96 (s, 6 H); 0.92-1.12 (m, 3 H); 1.22 (br d, 1 H); 1.67 (br s, 2H); 3.24 (m, 1H); 8.01 (br s, 3H).

Example III-6 isohexylamine hydrobromide

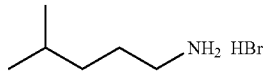

Step 1: 2-(4-methylpentyl)-1H-isoindole-1,3(2H)-dione

To a solution of 1-bromo-4-methylpentane (5.0 g, 0.030 mol) in DMF (20 mL) was added potassium phthalimide (5.9 g, 0.032 mol) in one portion at room temperature. After stirring at room temperature of 1 hr, the mixture was heated at 55° C. for 16 hr. Chloroform (30 mL) was added to the reaction mixture and the resulting mixture was poured into water (100 mL). The aqueous phase was extracted with chloroform and the combined organic phase was washed with 0.25 M NaOH (aq) and water. The organic phase was dried (Na$_2$SO$_4$), filtered and concentrated in vacuo to give 2-(4-methylpentyl)-1H-isoindole-1,3(2H)-dione as a pale yellow oil. (M+H) 232, 2.80 min. (LC/MS method A).

Step 2: isohexylamine hydrobromide

A solution of 2-(4-methylpentyl)-1H-isoindole-1,3(2H)-dione (6.5 g, 0.028 mol) in 48% aqueous hydrogen bromide (10 mL) and acetic acid (25 mL) was heated under reflux for 28 hr. The hot reaction mixture was diluted water (40 mL), chilled in an ice bath and aged at room temperature for 18 hr. Precipitated solids were separated by filtration, and the filtrate was concentrated the in vacuo Residue from the filtrate was triturated with water, insoluble solids were separated by filtration and the filtrate was concentrated in vacuo. Residue from the filtrate was triturated with ether, solids were collected by filtration, washed with ether and dried to give the title compound as a beige solid. $^1$H NMR (400 MHz, DMSO-$d_6$) δ ppm 0.84 (d, 3 H); 0.96 (s, 3 H); 1.16 (m, 2 H); 1.50 (m, 3 H); 2.73 (m, 2H); 7.68 (br s, 3H).

Example III-7

2-cyclohexylethylamine hydrochloride

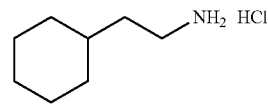

A mixture of 2-(1-cyclohexenyl)ethylamine (5.60 g) and 10% Pd/C (0.6 g, wet, Degussa type E101) in 60 mL of methanol was hydrogenated under 55 psi H$_2$ using a Parr hydrogenation apparatus for 5 h at room temperature. The mixture was filtered through Celite and the filtrate was concentrated in vacuo. The residue was dissolved in CH$_2$Cl$_2$ (5 mL) and HCl in Et$_2$O (3 mL of a 1M solution) was added. Solid was collected by filtration, affording the title compound as a white solid. $^1$H NMR (400 MHz, DMSO-$d_6$) δ ppm 0.85 (m, 2H), 1.02-1.36 (m, 5H), 1.41 (m, 2H), 1.55-1.76 (m, 4H), 2.75 (m, 2H), 7.90 (br, 3H).

Example III-8

(2-cyclohexyl-2,2-difluoroethyl)amine hydrochloride

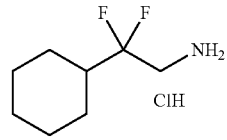 [SMILES: NCC(F)(F)C1CCCCC1 ; Cl]

Step 1: ethyl cyclohexyl(oxo)acetate

To a suspension of magnesium turnings (2.20 g, 90.32 mmol) in THF (100 mL) was added cyclohexyl bromide (9.27 mL, 75.27 mmol). The mixture was sonicated (note 1) for 30 min, the supernatant liquid was decanted into an addition funnel and added to a solution of diethyloxalate (22.0 g, 146.14 mmol) in THF (240 mL) at −10° C. over one hour. After 30 minutes, 10% HCl (75 mL) was added the mixture was and stirred 15 minutes. Layers were separated and the aqueous layer was extracted with Et$_2$O (100 mL). Combined organics were washed (brine), dried over Na$_2$SO$_4$, and concentrated in vacuo. The residue was purified by flash chromatography (EtOAc/hexanes), affording the title compound as a clear oil. $^1$H NMR (400 MHz, CDCl$_3$) δ ppm 1.15-1.40 (m, 5H) 1.56-1.94 (m, 8H) 2.97-3.05 (m, 1H) 4.30 (q, J=7.32 Hz, 2H).

Note 1: A conventional ultrasonic cleaning bath was used.

Step 2: ethyl cyclohexyl(difluoro)acetate

To a solution of ethyl cyclohexyl(oxo)acetate (2.94 g, 15.95 mmol) in 5 mL CH$_2$Cl$_2$ at −5° C. was added bis(2-methoxyethyl)aminosulfur trifluoride (deoxo-fluor; 5.0 mL, 27 mmol) in 5 mL CH$_2$Cl$_2$. EtOH (0.185 mL, 0.78 mmol) was added, the mixture was stirred 16 hours at ambient temperature and poured onto ice. The layers were separated and the aqueous layer was extracted with CH$_2$Cl$_2$ (10 mL). Combined organics were washed (satd NaHCO$_3$, brine), dried over Na$_2$SO$_4$ and concentrated in vacuo. The residue was purified by flash chromatography (EtOAc/hexanes), affording the title compound as a clear oil. $^1$H NMR (400 MHz, CDCl$_3$) δ ppm 1.13-1.37 (m, 5H) 1.48-1.85 (m, 8H) 1.98-2.08 (m, 1H) 4.30 (q, J=7.08 Hz, 2H).

Step 3: 2-cyclohexyl-2,2-difluoroacetamide

A solution of ethyl cyclohexyl(difluoro)acetate (2.63 g, 12.75 mmol) in EtOH (6 mL) was sparged with anhyd ammonia for 15 minutes at ambient temperature. The mixture was sealed in a pressure tube and allowed to stand overnight. Volatiles were removed in vacuo and the solid residue was recrystallized from dichloromethane-hexanes affording the title compound as a waxy solid. $^1$H NMR (400 MHz, CDCl$_3$) δ ppm 1.13-1.37 (m, 5H) 1.48-1.85 (m, 8H) 1.98-2.08 (m, 1H) 4.30 (q, J=7.08 Hz, 2H)

Step 4: (2-cyclohexyl-2,2-difluoroethyl)amine hydrochloride

To a solution of the 2-cyclohexyl-2,2-difluoroacetamide in 20 mL of THF at ambient temperature, under nitrogen, was added borane-tetrahydrofuran complex (56 mL, 56 mmol). The mixture was heated under reflux for 18 hours, cooled to ambient temperature, and MeOH was added slowly, with stirring. The mixture was heated under reflux for 30 minutes, cooled and concentrated in vacuo. Aq. HCl (5 mL, 6M) was added, the mixture was heated briefly (ca. 1 min) under reflux and cooled. The mixture pH was adjusted to ca. 10 with satd NaHCO$_3$ and the whole was extracted with CH$_2$Cl$_2$ (×2). Combined extracts were dried over Na$_2$SO$_4$ and concentrated in vacuo. The residue was taken up in EtOH and briefly sparged with a stream of anhyd HCl (ca. 1 min). Precipitated solid was collected by filtration and air-dried affording the title compound as a white solid. $^1$H NMR (400 MHz, DMSO-d$_6$) δ ppm 1.04-1.25 (m, 5H) 1.56-1.65 (m, 1H) 1.67-1.81 (m, 4H) 1.87-1.98 (m, 1H) 3.35 (t, J=16.4 Hz, 2H) 8.37 (br. s, 2H).

Example III-9

5,6-difluoro-2,3-dihydro-1H-inden-2-amine (and Corresponding Hydrochloride Salt)

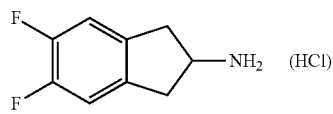

Step 1: 5,6-difluoro-2,3-dihydro-1H-inden-1-one

To a solution of 3,4-difluorophenyl propionic acid (30.45 g; 163.6 mmol) and 2 drops of DMF in CH$_2$Cl$_2$ (200 mL) was added oxalyl chloride (41.4 g, 327 mmol) over 20 min. The resulting solution was stirred for 24 hr and concentrated in vacuo (chased 1×PhMe, ca. 100 mL). The residue was dissolved in CS$_2$ (300 mL), cooled to 0° C. and AlCl$_3$ (76.4 g, 573 mmol) was added over 10 min. The mixture was stirred 30 min at 0° C., then heated under reflux for 4 hr. Upon cooling to room temperature the solution was carefully poured onto crushed ice, the carbon disulfide layer was separated and the aqueous layer extracted with EtOAc. Combined organics were dried over MgSO$_4$ and the concentrated in vacuo. The residue was purified by flash chromatography (EtOAc/hexanes), affording the title compound as a white solid. $^1$H NMR (400 MHz, CDCl$_3$) δ 7.50 (t, 1H, J=8.0 Hz), 7.24 (t, 1H, J=6.6 Hz), 3.09 (t, 2H, J=5.5 Hz), 2.72-2.69 (m, 2H).

Step 2: 5,6-difluoro-2,3-dihydro-1H-inden-2-amine

To a solution of 5,6-difluoro-2,3-dihydro-1H-inden-1-one (4.60 g, 27.4 mmol) in MeOH (90 mL) at 40° C. was added isoamyl nitrite (4.17 g, 35.6 mmol) followed by concentrated HCl (2.7 mL). Upon heating for 45 min the solution was cooled to room temperature and water was added. Precipitated solid was collected by filtration and rinsed thoroughly with water affording 3.97 g of a light orange solid. The solid was dissolved in HOAc (100 mL), conc HCl (8 mL) was added, followed by 10% Pd/C (1.07 g). The mixture was hydrogenated under 50 psi H$_2$ for 24 hr using a Parr hydrogenation apparatus, and filtered through a bed of Celite (CHCl$_3$ wash). The filtrate was concentrated in vacuo and the residue was dissolved in water. The aqueous solution was basified with solid K$_2$CO$_3$, extracted with CHCl$_3$ (3×), combined extracts were dried over MgSO$_4$ and concentrated in vacuo. The residue was purified by flash chromatography (MeOH/CH$_2$Cl$_2$) affording the title compound as a brown oil. $^1$H NMR (400 MHz, CDCl$_3$) δ 6.95 (t, 2H, J=8.9 Hz), 3.83 (m, 1H), 3.10 (dd, 2H, J=15.8 & 6.8 Hz), 2.60 (dd, 2H, J=15.8 & 5.0 Hz); (M+H) 170, 0.68 min (LC/MS method A).

The above oil was dissovled in Et$_2$O (ca. 5 mL) and HCl in dioxane (4 mL of a 4M solution) was added. Precipitated solid was triturated with Et$_2$O and collected by filtration, affording the corresponding hydrochloride salt.

Example III-10 rac 5-fluoro-2,3-dihydro-1H-inden-2-amine (and Corresponding Hydrochloride Salt)

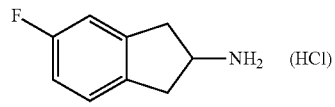

To a solution of 5-fluoro-1-indanone (10.0 g; 66.7 mmol) in MeOH at 40° C. was added n-butyl nitrite (13.2 mL; 113 mmol), dropwise over 3 minutes, followed by conc HCl (10 mL), dropwise at such a rate that the internal temp was maintained below 55° C. The mixture was stirred 30 min and concentrated in vacuo. The residue was diluted with EtOAc and sat'd NaHCO$_3$, filtered, and the layers were separated. The aqueous layer was extracted with EtOAc, combined organics were washed (H$_2$O, brine), dried over Na$_2$SO$_4$, and concentrated in vacuo. The residue was purified by flash chromatography (EtOAc/hexanes), affording an 7.59 g of an orange solid. The solid was dissolved in HOAc/H$_2$SO$_4$ (250/12.5 mL respectively), 10% Pd—C was added (4.5 g; wet, DeGussa type E101) and the mixture was hydrogenated under 50 psi H$_2$ for 18 h using a Parr hydrogenation apparatus. The mixture was filtered through Celite (H$_2$O wash), partially concentrated to an aqueous mixture, and the mixture pH was adjusted to ca. 11 by addition of 1N NaOH. The whole was extracted with CHCl$_3$ (×5), combined organics were washed (brine), dried over Na$_2$SO$_4$, and concentrated in vacuo, affording the title compound as an amber oil. $^1$H NMR (400 MHz, DMSO-d$_6$) δ 1.69 (br. s, 2H), 2.53 (m, 2H, overlapping solvent), 2.99 (m, 2H), 3.69 (quint, J=6.2 Hz, 1H), 6.89 (partially resolved ddd, J=9.8, ~7.7, 2.5 Hz, 1H), 6.99 (partially resolved dd, J=9.3, ~2.3 Hz, 1H), 7.16 (partially resolved dd, J=8.3, 5.6 Hz, 1H).

The corresponding hydrochloride salt was obtained as a colorless solid from an analogous preparation of the amine freebase (smaller scale), by addition of ca. 2.5 equivalents HCl in dioxane (4M solution) to the dried chloroform extracts prior to concentration. $^1$H NMR (400 MHz, DMSO-$d_6$) δ ppm 2.84-3.07 (m, 2 H), 3.25 (td, J=17.12, 7.67 Hz, 2 H), 3.91-4.09 (m, 1 H), 6.94-7.06 (m, 1 H), 7.08-7.15 (m, J=9.44, 9.15, 1.05, 1.05 Hz, 1 H), 7.28 (dd, J=8.20, 5.35 Hz, 1 H), 8.40 (br. s., 3 H).

Example III-11

(2S)- and (2R)-5-fluoro-2,3-dihydro-1H-inden-2-amine hydrochloride

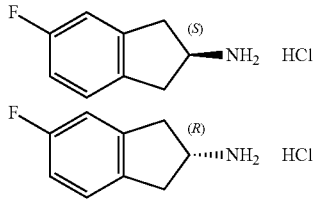

Step 1:
rac-(5-fluoro-2,3-dihydro-1H-inden-2-yl)benzyl carbamate

To a mixture of 5-fluoro-2,3-dihydro-1H-inden-2-amine (5.79 g; 38.3 mmol; Example III-9 above) and satd $Na_2CO_3$ (200 mL) at room temperature was added benzyl chloroformate (6.9 mL; 46 mmol). The mixture was stirred 1 h at room temperature and extracted with EtOAc (×3). Combined organics were washed ($H_2O$, brine), dried over $Na_2SO_4$ and concentrated in vacuo. The residue was purified by flash chromatography (EtOAc/hexanes), affording the title compound as an off-white solid. $^1$H NMR (400 MHz, DMSO-$d_6$) δ 2.77 (m, 2H), 3.12 (m, 2H), 4.29 (app. sext., J=7.1 Hz, 1H), 5.02 (s, 2H), 6.94 (m, 1H), 7.03 (partially resolved dd, J=9.2, ~2.4 Hz, 1H), 7.19 (partially resolved dd, J=8.2, 5.5 Hz, 1 H), 7.28-7.40 (m, 5H), 7.64 (d, J=6.8 Hz, 1H).

Step 2: Resolution of rac-(5-Fluoro-2,3-dihydro-1H-inden-2-yl)benzyl carbamate into [(2S)-5-fluoro-2,3-dihydro-1H-inden-2-yl]benzyl carbamate and [(2R)-5-fluoro-2,3-dihydro-1H-inden-2-yl]benzyl carbamate rac-(5-Fluoro-2,3-dihydro-1H-inden-2-yl)benzyl carbamate was separated into individual enantiomers on an AD-H prep column (30 mm ID×25 mm, 5 μm particle size) by supercritical fluid chromatography (MeOH/$CO_2$ 17:83, 90 g/min total flow at 140 bar, 33° C.).

Chromatographic bands eluting from the column were detected at 215 nm.

Assignment of absolute configurations for the enantiomers obtained above were made by comparison of experimentally measured vibrational circular dichroism (VCD) spectra with the calculated (ab initio) VCD spectrum for [(2S)-5-fluoro-2,3-dihydro-1H-inden-2-yl]benzyl carbamate. The earlier-eluting enantiomer from the chiral separation described above was found to have VCD bands of the same relative sign as the (S)-configuration model used for ab initio calculations, and thus assigned the (S)-configuration. In contrast, the latter-eluting enantiomer was found to was found to have VCD bands of the opposite relative sign as the (S)-configuration model used for ab initio calculations, and thus assigned the (R)-configuration.

Step 3: (S)- and (R)-5-fluoro-2,3-dihydro-1H-inden-2-amine hydrochloride

The preparation of (S)-5-fluoro-2,3-dihydro-1H-inden-2-amine hydrochloride is given as representative. To a solution of [(2S)-5-fluoro-2,3-dihydro-1H-inden-2-yl]benzyl carbamate (2.26 g; 7.93 mmol) in EtOAc/EtOH (40 mL ea) was added 10% Pd/C (0.85 g, wet, DeGussa type E101). The mixture was stirred under an atmosphere of $H_2$ for 5 h and filtered through a 0.45 μm PTFE membrane filter. HCl in dioxane (5 mL of a 4M solution) was added to the filtrate and the whole was concentrated to dryness, affording the title compound as a tan solid. $^1$H NMR (400 MHz, DMSO-$d_6$) δ 2.97 (m, 2H), 3.24 (m, 2H), 4.00 (m, 1), 7.01 (m, 1H), 7.13 (partially resolved dd, J=9.2, ~2.4 Hz, 1H), 7.28 (dd, J=8.4, 5.4 Hz, 1H), 8.40 (br. s, 2H). (M+H) 152, $t_R$ 0.73 min (LC/MS method C). (R)-5-Fluoro-2,3-dihydro-1H-inden-2-amine hydrochloride was prepared in an analogous fashion; $^1$H NMR spectrum and LC/MS retention time were identical to those of the (S)-isomer.

Example III-12 rac 2-amino-2,3-dihydro-1H-indene-5-carbonitrile hydrochloride

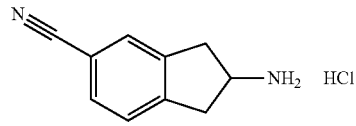 [SMILES: N#Cc1ccc2c(c1)CC(N)C2 ; Cl]

Step 1: 1,1-Dimethylethyl (5-bromo-2,3-dihydro-1H-inden-2-yl)carbamate

To a slurry of (5-bromo-2,3-dihydro-1H-inden-2-yl)amine hydrobromide (5.61 g; 19.1 mmol; prepared according to Prashad, M; Hu, B.; Har, D.; Repic, O.; Blacklock, T.; Acemoglub, M. *Adv. Synth. Catal.* 2001, 343 (5), 461) in $CH_2Cl_2$ (40 mL) was added $Et_3N$ (5.8 mL; 42 mmol) in one portion. The mixture was stirred 15 min, $(Boc)_2O$ (4.58 g; 21 mmol) was added in one portion and stirring was continued. After 2 h the whole was adsorbed onto a minimal amount of silica gel and purified by flash chromatography (EtOAc/hexanes), affording 5.94 g of the title compound as a colorless solid. $^1$H NMR (400 MHz, DMSO-$d_6$) δ 1.39 (s, 9H), 2.73 (m, 2H), 3.08 (m, 2H), 4.20 (app. sext, J=7.0 Hz, 1H), 7.14 (d, J=8.2 Hz, 1H), 7.19 (br. d, J=6.8 Hz, 1H), 7.30 (partially resolved dd, J=8.0, ~1.9 Hz, 1H), 7.38 (m, 1H) ppm.

Step 2: 1,1-dimethylethyl (5-cyano-2,3-dihydro-1H-inden-2-yl)carbamate

A flask charged with 1,1-dimethylethyl (5-bromo-2,3-dihydro-1H-inden-2-yl)carbamate (3.0 g, 9.26 mmol; step 1 above), dppf (645 mg, 1.16 mmol), Pd₂dba₃ (532 mg, 0.58 mmol), ZnCN₂ (1.50 g, 12.8 mmol) and water in 50 mL DMF was evacuated/backfilled with nitrogen (×4), and stirred at 110° C. for 21 hours. Upon cooling, the mixture was diluted with satd NH₄Cl and extracted with ethyl acetate. The organic extract was washed with (water 3×, brine), dried over MgSO₄ and concentrated in vacuo. The residual oil was purified by flash chromatography (ethyl acetate/hexanes) affording title compound as an off-white solid. $^1$H NMR (400 MHz, CDCl₃) δ 7.47 (s, 1H), 7.45 (d, 1 H, J=7.9 Hz), 7.28 (d, 1 H, J=7.7 Hz), 4.69 (br.s, 1 H), 4.47 (br. s, 1 H), 3.33-3.25 (m, 2H), 2.86-2.80 (m, 2H), 2.79 (s, 9H).

Step 3:
2-amino-2,3-dihydro-1H-indene-5-carbonitrile hydrochloride

To a solution of 1,1-dimethylethyl (5-cyano-2,3-dihydro-1H-inden-2-yl)carbamate (1.85 g, 7.18 mmol) in dioxane (30 mL) at room temperature was added HCl in dioxane (18 mL of a 4.0 M solution; 72 mmol). The mixture was stirred for ca. 18 hr and diluted with ether. Solids were collected by filtration and rinsed thoroughly with ether, affording the title compound as a tan solid. $^1$H NMR (400 MHz, methanol-d₄) δ ppm 7.65 (s, 1H), 7.59 (d, 1H, J=7.9 Hz), 7.46 (d, 1H, J=7.9 Hz), 4.14 (m, 1H), 3.51-3.43 (m, 2H), 3.10-3.04 (m, 1 H).

Example III-13 rac 5-(methyloxy)-2,3-dihydro-1H-inden-2-amine hydrochloride

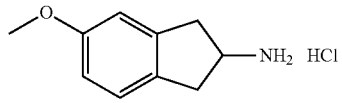

Step 1: (2Z)-5-(methyloxy)-1H-indene-1,2(3H)-dione 2-oxime

To a solution of 5-(methyloxy)-2,3-dihydro-1H-inden-1-one (1.0 g, 6.2 mmol) in methanol (15 mL) at 40° C. was added n-butyl nitrite (0.8 mL, 6.25 mmol) followed by conc HCl (0.6 mL). The reaction was stirred 30 min, precipitated solid was collected by filtration, air-dried and used without further purification. $^1$H NMR (400 MHz, DMSO-d₆) δ ppm 3.60 (br.s, 2H) 3.86 (s, 3H) 6.99 (dd, J=8.54 Hz, 2.2 Hz, 1H) 7.12 (d, J=1.71 Hz, 1H) 7.66 (d, J=8.55 Hz, 1 H) 12.45 (s, 1H).

Step 2:
5-(methyloxy)-2,3-dihydro-1H-inden-2-amine hydrochloride

To a solution of (2Z)-5-(methyloxy)-1H-indene-1,2(3H)-dione 2-oxime (0.96 g, 5.02 mmol) in HOAc/conc H₂SO₄ (25/2 mL respectively) was added 10% Pd/C (0.200 g, wet) and the mixture was hydrogenated under 50 psi H2 for 7 h at room temperature using a Parr hydrogenation apparatus and filtered over Celite (2×10 mL MeOH wash). The filtrate was partially concentrated and basified ca. pH 12, and the whole was extracted with CH₂Cl₂ (2×100 mL). Combined organics were dried over Na₂SO₄, and concentrated to ca. 100 mL. The remaining solution was sparged with anhyd HCl (ca. 1 min), aged 15 min and concentrated to dryness affording the title compound. $^1$H NMR (400 MHz, DMSO-d₆) δ ppm 2.84-2.98 (m, 2H), 3.09-3.24 (m, 2H), 3.75 (s, 3H), 3.92 (br. s, 1 H), 6.73 (dd, J=8.3, 2.44 Hz, 1 H), 6.83 (d, J=2.2 Hz, 1 H), 7.13 (d, J=8.1 Hz, 1 H), 8.40 (br.s, 2H).

Example III-14 rac 4-(methyloxy)-2,3-dihydro-1H-inden-2-amine hydrochloride

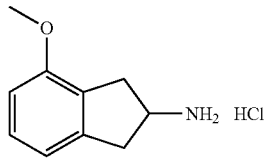

The title compound was prepared from 4-(methyloxy)-2,3-dihydro-1H-inden-1-one according to the method described in example III-13 Steps 1-2 above. $^1$H NMR (400 MHz, DMSO-d₆) δ ppm 2.84-2.98 (m, 2H), 3.10-3.27 (m, 2H), 3.75 (s, 3H), 3.95 (br.s, 1 H), 6.79 (d, J=8.1 Hz, 1 H), 6.84 (d, J=7.3 Hz, 1 H), 7.16 (t, J=7.8 Hz, 1 H), 8.31 (br.s, 2H).

Example III-15

5,6-bis(methyloxy)-2,3-dihydro-1H-inden-2-amine hydrochloride

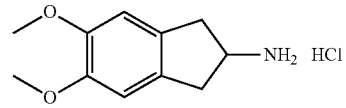

The title compound was prepared from 5,6-bis(methyloxy)-2,3-dihydro-1H-inden-1-one according to the method described in example III-13 Steps 1-2 above. $^1$H NMR (400 MHz, DMSO-d₆) δ ppm 2.84-2.98 (m, 2H), 3.10-3.27 (m, 2H), 3.75 (s, 3H), 3.95 (br.s, 1H), 6.79 (d, J=8.1 Hz, 1H), 6.84 (d, J=7.3 Hz, 1H), 7.16 (t, J=7.8, Hz, 1 H), 8.31 (br.s, 2H).

Example III-16

2-methyl-2,3-dihydro-1H-inden-2-amine hydrochloride

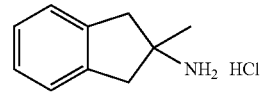

Step 1: methyl 2-methyl-1-oxo-2,3-dihydro-1H-indene-2-carboxylate

To a solution of diisopropylamine (2.06 mL, 14.6 mmol) in THF (14 mL) at 0° C. was a solution of n-butyl lithium (5.55 mL of a 2.5 M in solution in hexanes; 14.6 mmol), dropwise over 15 min. Meanwhile, a solution of 2-methyl-1-indanone (2.03 g, 13.9 mmol) in THF (10 mL) was prepared and cooled to −78° C. under N₂. After 30 minutes the above solution of LDA was cooled to −78° C. and added to the above solution of indanone, dropwise over 15 min via double-ended needle. The mixture was stirred 30 min and methyl cyanoformate (1.32 mL, 16.7 mmol) was added. The mixture was stirred 40 minutes, gradually warming ca. to −20° C., quenched with satd NH₄Cl and extracted with Et₂O (2×25 mL). Combined organics were washed (brine), dried over Na₂SO₄ and concentrated in vacuo, affording the title compound which was used without further purification. $^1$H NMR (400 MHz, CDCl₃) δ ppm 1.52 (s, 3H), 3.00 (d, J=17.3 Hz, 1H), 3.67-3.73 (m, 4H), 7.41 (t, J=7.57 Hz, 1H), 7.47 (m, 1H), 7.63 (m, 1 H), 7.79 (d, J=7.57 Hz, 1 H).

Step 2: methyl 2-methyl-2,3-dihydro-1H-indene-2-carboxylate

A mixture of the methyl 2-methyl-1-oxo-2,3-dihydro-1H-indene-2-carboxylate (2.04 g, 9.99 mmol) and 10% Pd/C (0.200 g; wet) in HOAc/conc H$_2$SO$_4$ (22/2 mL respectively) was hydrogenated under 50 psi H2 for 4 h using a Parr hydrogenation apparatus. The mixture was filtered through Celite (2×MeOH wash) and the filtrate was partially concentrated in vacuo. The residue was neutralized with satd Na$_2$CO$_3$ and the whole was extracted with EtOAc (2×25 mL). Combined organics were washed with brine, dried over Na$_2$SO$_4$ and concentrated in vacuo affording the title compound. $^1$H NMR (400 MHz, CDCl$_3$) δ ppm 1.35 (s, 3H), 2.81 (d, J=15.6 Hz, 2 H), 3.47 (d, J=15.6 Hz, 2 H), 3.71 (s, 3H), 7.12-7.23 (m, 4H).

Step 3: 2-Methyl-2,3-dihydro-1H-indene-2-carboxylic acid

To a solution of methyl 2-methyl-2,3-dihydro-1H-indene-2-carboxylate (1.80 g, 9.46 mmol) in THF/water/MeOH (4/1/1 mL respectively) was added lithium hydroxide monohydrate (1.19 g, 28.4 mmol). The reaction mixture stirred at ambient temperature 4 h, acidified to pH 3 with 1 N HCl and extracted with Et$_2$O (2×25 mL). Combined organics were washed (water, brine), dried over Na$_2$SO$_4$ and concentrated in vacuo affording the title compound as a white solid. $^1$H NMR (400 MHz, CDCl$_3$) δ ppm 1.39 (s, 3H), 2.83 (d, J=15.9 Hz, 2 H), 3.50 (d, J=15.9 Hz, 2 H), 7.12-7.23 (m, 4H).

Step 4: phenylmethyl (2-methyl-2,3-dihydro-1H-inden-2-yl)carbamate

To a solution of 2-methyl-2,3-dihydro-1H-indene-2-carboxylic acid (0.200 g, 1.14 mmol) and triethylamine (0.17 mL, 1.2 mmol) in benzene (2 mL) at 0° C. was added diphenyl phosphorylazide (0.257 g, 1.19 mmol). The mixture was stirred 15 min, benzyl alcohol (0.123 mL, 1.19 mmol) was added and the reaction was heated under reflux for 16 hours. Upon cooling, the mixture was diluted with 10% HCl and extracted with ethyl acetate (2×25 mL). Combined organics were washed with brine, dried over Na$_2$SO$_4$ and concentrated in vacuo. The residue was purified by flash chromatography (EtOAc/hexanes) affording the title compound. $^1$H NMR (400 MHz, CDCl$_3$) δ ppm 1.55 (s, 3H), 2.98 (d, J=15.9 Hz, 2 H), 3.28 (d, J=15.9 Hz, 2 H), 7.12-7.18 (m, 4H), 7.29-7.37 (m, 5H).

Step 5: (2-methyl-2,3-dihydro-1H-inden-2-yl)amine hydrochloride

A mixture phenylmethyl (2-methyl-2,3-dihydro-1H-inden-2-yl)carbamate (0.271 g; 0.963 mmol), and 10% Pd/C (0.050 g, wet) in EtOH (2 mL) of was hydrogenated under 40 psi H$_2$ for 4 h at using a Parr hydrogenation apparatus and filtered over Celite. The filtrate was concentrated to an oil, dissolved in ethyl acetate, cooled to −70° C. and sparged with anhyd HCl until saturated. The mixture was stirred for 1 hour and concentrated to dryness affording the title compound as a white solid. $^1$H NMR (400 MHz, methanol-d$_4$) δ ppm 1.56 (s, 3H), 3.17 (br.s, 4H), 7.19-7.29 (m, 4H).

Compounds of Formula IV

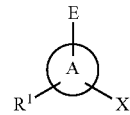

Formula IV

Example IV-1

3-bromo-4-methylbenzamide

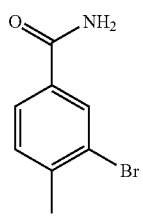

To a slurry of 3-bromo-4-methylbenzoic acid (2.53 g, 85% purity; 10 mmol) in CH$_2$Cl$_2$ (20 mL) at 0° C., under N$_2$, was added oxalyl chloride (0.91 mL; 10.5 mmol), followed by dropwise addition of DMF (0.04 mL; 0.5 mmol). The mixture was stirred 5 min at 0° C., 15 min at rt, and then heated at reflux under N$_2$ for 1 h. The mixture was cooled, and poured into NH$_4$OH (30 mL; ca. 30% NH$_3$). Precipitated solids were collected by filtration and purified by flash chromatography (EtOAc/hexanes), affording the title compound as a colorless solid. LC/MS (method A) t$_R$ 2.05 min; m/z 214, 216 (M+H, Br isotopes).

The following were prepared by a procedure similar to Example IV-1, from the appropriate carboxylic acids.

TABLE B

Synthesis of Compounds of Formula IV from benzoic acids

| Ex | Structure/Name | Characterization Data | Comments |
|---|---|---|---|
| IV-2 | 3-bromo-2-methylbenzamide | LC/MS (method A) t$_R$ 1.87 min; m/z 223, 225 (M + H, Br isotopes) | Note 1 |
| IV-3 | 5-bromo-2-methylbenzamide | LC/MS (method B) t$_R$ 1.80 min; m/z 214, 216 (M + H, Br isotopes) | Note 1, 3 |
| IV-4 | 4-bromo-3-methylbenzamide | LC/MS (method A) t$_R$ 2.06 min; m/z 214 ([M + H]$^+$) | Note 1, 2 |

TABLE B-continued

Synthesis of Compounds of Formula IV from benzoic acids

| Ex | Structure/Name | Characterization Data | Comments |
|---|---|---|---|
| IV-5 | 4-bromo-3-fluorobenzamide | LC/MS (method A) $t_R$ 1.88 min; m/z 218 ([M + H]$^+$) | Note 1, 2 |
| IV-6 | 3-bromobenzamide | LC/MS (method B) $t_R$ 1.79 min; m/z 200, 202 (M + H, Br isotopes) | Note 1, 4 |
| IV-7 | 4-bromo-2-fluorobenzamide | LC/MS (method A) $t_R$ 1.72 min; m/z 218 (M + H). | Notes 1, 2 |

Note 1
Chromatographic purification step omitted.
Note 2
Preparation of acid chloride using 4 equivalents of oxalyl chloride at room temperature for 3 hours.
Note 3
5-Bromo-2-methylbenzoic acid may be obtained commercially from various sources (e.g., Ryan Scientific, Inc., Mt. Pleasant, SC, USA).
Note 4
Acid activation with oxalyl chloride/DMF was omitted; commercially available 3-bromobenzoyl chloride was used (Sigma-Aldrich, St. Louis, MO, USA).

Example IV-8

3-Bromo-5-chlorobenzamide

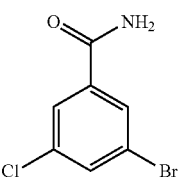 [SMILES: NC(=O)c1cc(Cl)cc(Br)c1]

To a solution of 3-bromo-5-chlorobenzoic acid (2.88 g; 12.2 mmol; Note 1) and pyridine (1.04 mL; 12.8 mmol) in MeCN (100 mL) at room temperature was added (Boc)$_2$O (3.47 g; 15.9 mmol) in one portion. The mixture was aged 30 min, (NH$_4$)$_2$CO$_3$ was added in one portion.

After stirring approximately 16 h at room temperature, volatiles were removed in vacuo. The residue was partitioned between EtOAc/water and the layers were separated. The aqueous layer was extracted with EtOAc (×2), combined organics were washed (10% HCl, brine), dried over Na$_2$SO$_4$ and concentrated in vacuo. The residue was purified by flash chromatography (EtOAc/hexanes), affording the title compound as a colorless solid. LC/MS (method A) $t_R$ 1.65 min; m/z 234, 236 (M+H, Br isotopes).

Note 1: 3-bromo-5-chlorobenzoic acid was obtained commercially from Biofine International Inc., Blaine, Wash., USA.

The following were prepared by a procedure similar to Example IV-8 from the appropriate carboxylic acids.

TABLE C

Compounds of Formula IV from benzoic acids and (NH$_4$)$_2$CO$_3$

| Ex | Structure/Name | Characterization Data | Comments |
|---|---|---|---|
| IV-9 | 3-bromo-5-methylbenzamide | LC/MS (method A) $t_R$ 2.12 min; m/z 214, 216 (M + H, Br isotopes) | Note 1 Carboxylic acid from SALOR (Aldrich) |
| IV-10 | 3-bromo-5-(trifluoromethyl)benzamide | LC/MS (method B) $t_R$ 2.38 min; m/z 268, 270 (M + H, Br isotopes) [M − H]$^-$ | Note 2 Carboxylic acid from Matrix Scientific, Columbia, SC, USA |

TABLE C-continued

Compounds of Formula IV from benzoic acids and $(NH_4)_2CO_3$

| Ex | Structure/Name | Characterization Data | Comments |
|---|---|---|---|
| IV-11 | ![structure] 6-bromo-2-pyridinecarboxamide | LC/MS (method B) $t_R$ 1.43 min; m/z 201, 203 (M + H, Br isotopes) | Note 2 |
| IV-12 | ![structure] 4-chloro-2-pyridinecarboxamide | LC/MS (method B) $t_R$ 1.36 min; m/z 157 | Note 2 |
| IV-13 | ![structure] 3-bromo-2-chlorobenzamide | LC/MS (method A) $t_R$ 1.65 min; m/z 234, 236 (M + H, Br isotopes) | Note 3 |

Note 1
Pyridine was added to solution of carboxylic acid and $(Boc)_2O$.
Note 2
Chromatographic purification step omitted.
Note 3
3-Bromo-2-chlorobenzoic acid may be obtained from the commercially available 3-bromo-2-chlorotoluene according to the procedure of Liedholm, B. *Acta Chem. Scand. B Org. Chem. Biochem.* 1984, B38(8), 713.

Example IV-14

3-bromo-2-methoxybenzamide

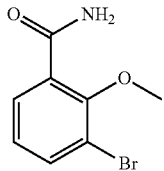

Step 1: 3-bromo-2-hydroxybenzonitrile

To a solution of o-cyanophenol (0.595 g; 5.00 mmol) and diisopropylamine (0.060 mL; 0.40 mmol) in PhMe (50 mL) at 70° C. was added NBS (0.980 g; 5.50 mmol) in one portion. The mixture was stirred 2 h, an additional portion of NBS (0.089 g; 0.5 mmol) was added and heating continued until disappearance of starting material was observed (TLC). The mixture was cooled, diluted with EtOAc washed (water, brine), dried over $Na_2SO_4$ and concentrated in vacuo. Attempted resolution of the two reaction products by flash chromatography (EtOAc/hexanes), was unsuccessful; thus the mixture of products was dissolved in DMF (10 mL), $K_2CO_3$ (2.07 g; 15.0 mmol) and MeI (0.47 mL; 7.5 mmol) were added and the mixture was stirred overnight at room temperature. The mixture was poured into water and extracted with $Et_2O$ (×3). Combined organics were washed (water, brine), dried over $Na_2SO_4$ and concentrated in vacuo. The residue was purified by flash chromatography (EtOAc/hexanes), affording the title compound as a colorless solid. $^1H$ NMR (400 MHz, DMSO-d6) δ ppm 3.97 (s, 3 H), 7.26 (app. t, J=7.9 Hz, 1 H), 7.86 (dd, J=7.8, 1.5 Hz, 1 H), 8.01 (dd, J=8.1, 1.5 Hz, 1 H). The product obtained above was combined with that of a similar reaction wherein N-methylbenzylamine (0.08 equiv) was substituted for the above diisopropylamine catalyst.

Step 2: 3-bromo-2-methoxybenzamide

To a slurry of 3-bromo-2-methoxybenzamide (0.933 g; 4.40 mmol) and $K_2CO_3$ (0.304 g; 2.2 mmol) in DMSO (10 mL) at 0° C. was added $H_2O_2$ (0.5 mL of a 30 wt % solution; ~4.8 mmol), dropwise over 2 min. The cooling bath was removed, the mixture was stirred at room temperature 3 days, poured into water and precipitated solid was collected by filtration. The filtrate was extracted 3×EtOAc, combined organics were washed (water, brine), dried over $Na_2SO_4$ and concentrated in vacuo. The residue was combined with the above precipitated solid and the whole was purified by flash chromatography (EtOAc/hexanes), affording the title compound as a colorless solid. LC/MS (method A) $t_R$ 1.88 min; m/z 230, 232 (M+H, Br isotopes).

The following were prepared from the appropriate benzonitriles by a procedure similar to Example IV-14, Step 2.

TABLE D

Compounds of Formula IV via the corresponding benzonitrile

| Ex | Structure/Name | Characterization Data | Comments |
|---|---|---|---|
| IV-15 | 2-(3-bromophenyl)acetamide | LC/MS (method A) $t_R$ 1.78 min; m/z 214, 216 (M + H, Br isotopes) | Chromatographic purification step omitted |
| IV-16 | 3-bromo-2-fluorobenzamide | LC/MS (method B) $t_R$ 1.73 min; m/z 218, 220 (M + H, Br isotopes) | Nitrile from Oakwood Products, Inc. West Columbia, SC, USA. |
| IV-17 | 3-bromo-5-fluorobenzamide | $^1$H NMR (400 MHz, DMSO-d6) δ ppm 7.68 (br. s, 1H), 7.69 (ddd, J = 9.6, 1.2 Hz, 2 H, overlapping 7.68), 7.75 (ddd, J = 8.2, 2.5, 1.6 Hz, 1 H), 7.92 (partially resolved dd, J = 1.4 Hz, 1 H), 8.16 (br. s., 1 H) | Nitrile from Matrix Scientific, Columbia, SC, USA. |

Example IV-18

2-Bromo-1,3-thiazole-4-carboxamide

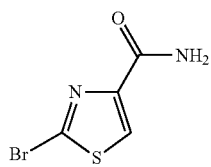

Step 1: 2-Bromo-1,3-thiazole-4-carboxylic Acid

A mixture of methyl 2-bromo-1,3-thiazole-4-carboxylate (4.2 g, 18.9 mmol), THF (120 mL) and 1N lithium hydroxide (50 mL) was heated at 70° C. for 1 h. The organic solvent was removed in vacuo. The residual aqueous solution was cooled to 0-5° C. and acidified to pH1 with 1N HCl solution. The tile compound was obtained by filtration, as a white solid.

$^1$H NMR (400 MHz, DMSO-d$_6$) δ ppm 8.43 (s, 1 H) 13.30 (s, 1 H).

Step 2: 2-Bromo-1,3-thiazole-4-carboxamide

To a suspension of 2-bromo-1,3-thiazole-4-carboxylic acid (3.82 g, 18.4 mmol) and a catalytic amount of DMF in CH$_2$Cl$_2$ (100 mL) at 0° C. was slowly added thionyl chloride (14 mL of a 2M solution in CH$_2$Cl$_2$). The resulting mixture was stirred for 12 h at the room temperature and then heated to reflux for 1 h. The mixture was concentrated to dryness in vacuo. The white solid obtained was taken up in ethyl acetate, added to a pre-cooled (0° C.) 9-10% aqueous ammonium hydroxide solution (90 ml) and stirred for 1 h at 0° C. The organic layer was separated and the aqueous phase was extracted twice with ethyl acetate. The combined ethyl acetate solution was washed with brine, dried over magnesium sulfate and concentrated in vacuo, affording the title compound was obtained as an off-white solid. $^1$H NMR (400 MHz, DMSO-d$_6$) δ ppm 7.60 (s, 1 H), 7.82 (s, 1 H), 8.22 (s, 1 H).

Example IV-1

4-iodo-3-(methyloxy)benzamide

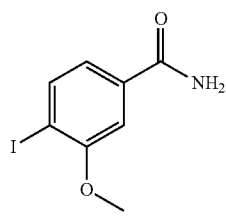

Step 1: methyl 4-iodo-3-(methyloxy)benzoate

To a solution of 3-hydroxy-4-iodobenzoic acid (3.0 g, 0.011 mol) in acetone (50 mL) was added in one portion potassium carbonate (3.9 g, 0.028 mol). Dimethyl sulfate (3.5 g, 0.028 mol) was added dropwise and the mixture was heated at reflux overnight. The mixture was concentrated in vacuo and the residue was partitioned between ethyl acetate and aqueous saturated sodium bicarbonate solution. The organic phase was washed with brine, dried over sodium sulfated and concentrated in vacuo to give methyl 4-iodo-3-(methyloxy) benzoate as a yellow oil. $^1$H NMR (DMSO-d$_6$) δ ppm 3.83 (s, 3H, Me), 3.87 (s, 3H, Me), 7.30 (dd, J=8.0, 1.8 Hz, 1H, Ar), 7.40 (d, J=1.7 Hz, 1H, Ar), 7.92 (d, J=8.0 Hz, 1H, Ar).

Step 2: 4-iodo-3-(methyloxy)benzoic acid

A mixture of methyl 4-iodo-3-(methyloxy)benzoate (3.25 g, 0.011 mol), sodium hydroxide (0.48 g, 0.012 mol) and water (30 mL) in methanol (30 mL) was heated in an oil bath at 65° C. for 3 hr. The mixture was concentrated in vacuo to remove the methanol and the aqueous residue was chilled in an ice bath. Concentrated aqueous hydrogen chloride was added until the pH was acidic and the mixture was stirred at ice bath temperature. The resulting solid was filtered, washed with water and dried to give 4-iodo-3-(methyloxy)benzoic acid as a white solid, used without further purification. LC/MS (method A) $t_R$ 2.35 min; m/z 279 (M+H).

Step 3: 4-iodo-3-(methyloxy)benzamide

Oxalyl chloride (5.1 g, 0.04 mol) was added dropwise to a mixture of 4-iodo-3-(methyloxy)benzoic acid (2.9 g, 0.01 mol) and DMF (3 drops) in dichloromethane (60 mL) at room temperature. After 3 hr, the mixture was concentrated in vacuo. The residue was dissolved in dichloromethane (30 mL) and this solution was added dropwise to concentrated ammonium hydroxide (40 mL) at ice bath temperature. The mixture was stirred at room temperature overnight. The mixture was partially concentrated in vacuo and the aqueous residue was extracted with ethyl acetate. The organic extract was washed (satd $Na_2CO_3$, brine), dried with sodium sulfate and concentrated in vacuo to give 4-iodo-3-(methyloxy)benzamide as a white solid, used without further purification. LC/MS (method A) $t_R$ 1.95 min; m/z 278 (M+H).

Example IV-20

4-(aminocarbonyl)-2-chlorophenyl trifluoromethane sulfonate

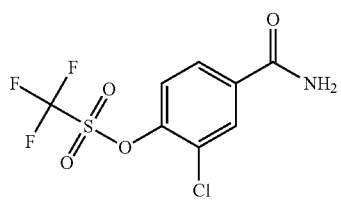 [SMILES: NC(=O)c1ccc(OS(=O)(=O)C(F)(F)F)c(Cl)c1]

Step 1: 4-(aminocarbonyl)-2-chlorophenyl 1,1-dimethylethyl carbonate

To a solution of 3-chloro-4-hydroxybenzoic acid (4.0 g, 0.022 mol) and pyridine (0.8 mL) in acetonitrile (50 mL) was added di-tert-butyl dicarbonate (9.6 g, 0.044 mol) in one portion followed by ammonium bicarbonate (3.5 g, 0.044 mol) in one portion and the mixture was stirred at ambient temperature for 18 hr. The reaction mixture was concentrated in vacuo and the residue was partitioned between ethyl acetate and water. The ethyl acetate phase was washed with 5% aqueous sodium bicarbonate, 0.1N HCl and brine. The organic phase was dried over sodium sulfate, filtered and concentrated in vacuo to give 4-(aminocarbonyl)-2-chlorophenyl 1,1-dimethylethyl carbonate as a viscous yellow oil, used without further purification. LC/MS (method A) $t_R$ 2.25 min; m/z (M+H) 272.

Step 2: 3-chloro-4-hydroxybenzamide

A mixture of 4-(aminocarbonyl)-2-chlorophenyl 1,1-dimethylethyl carbonate (6.86 g, 0.025 mol) and 4N HCl in dioxane (50 mL) in dioxane (30 mL) was heated at reflux for 4 hr. The reaction mixture was cooled, and precipitated solid was collected by filtration affording 3-chloro-4-hydroxybenzamide as a white solid, used without further purification. LC/MS (method E) $t_R$ 0.88 min; m/z 172 (M+H).

Step 3: 4-(aminocarbonyl)-2-chlorophenyl trifluoromethane sulfonate

To a mixture of 3-chloro-4-hydroxybenzamide (3.3 g, 0.019 mol) and pyridine (3.0 g, 0.038 mol) in dichloromethane (30 mL) at ice bath temperature was added dropwise trifluoromethanesulfonic anhydride (5.9 g, 0.021 mol). The mixture was allowed to come to ambient temperature overnight. The reaction mixture was washed (water, brine), dried by passing through a plug of sodium sulfate and concentrated in vacuo affording 4-(aminocarbonyl)-2-chlorophenyl trifluoromethane sulfonate as a pale yellow solid, used without further purification. LC/MS (method B) $t_R$ 2.48 min; m/z 304 (M+H).

Compounds of Formula IV (Heterocycles)

Example IV-21

2-(3-Bromophenyl)-1H-imidazole

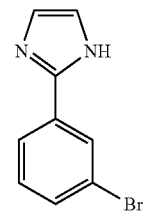

Step 1: Methyl 3-bromobenzenecarboximidoate hydrochloride

A solution of m-bromobenzonitrile (1.82 g; 10 mmol) in MeOH (20 mL) at 0° C. was sparged with HCl gas for 30 min, the reaction flask was stoppered and aged in a refrigerator (ca. 5° C.) for 3 h. The mixture was sparged with $N_2$ to remove excess HCl, concentrated in vacuo (2×PhMe chase) and dried under high vacuum ca. 45 min, affording the title compound as a colorless solid which was used directly for Step 2 below. LC/MS (method A) $t_R$ 0.81 min, m/z 214, 216 (M+H, Br isotopes).

Step 2: N-[2,2-bis(ethyloxy)ethyl]-3-bromobenzene carboximidamide

To a solution of methyl 3-bromobenzenecarboximidoate hydrochloride (Step 1 above) in MeOH (10 mL) at 0° C. was added [2,2-bis(ethyloxy)ethyl]amine (1.74 mL; 12 mmol) in one portion and the mixture was gradually warmed to room temperature (overnight). The mixture was concentrated in vacuo, partitioned between $CH_2Cl_2$/1M NaOH and the layers were separated. The aqueous layer was extracted with $CH_2Cl_2$ (×2), combined organics were washed ($H_2O$, brine), dried over $Na_2SO_4$, filtered and concentrated in vacuo affording the title compound as a light brown oil which was used directly for Step 3 below. LC/MS (method A) $t_R$ 1.25 min, m/z 315, 317 (M+H, Br isotopes, 4%), 223, 225 (M+H−2EtOH, Br isotopes, 100%).

Step 3: 2-(3-Bromophenyl)-1H-imidazole

A solution of N-[2,2-bis(ethyloxy)ethyl]-3-bromobenzenecarboximidamide (2.85 g; 9.04 mmol; Step 2 above) in $HCO_2H$ (15 mL) was heated at 80° C. for 1 h and concentrated in vacuo (2×PhMe chase). The residue was purified by flash chromatography (MeOH/$NH_4OH$/$CH_2Cl_2$), affording the title compound as a light pink solid. LC/MS (method A) $t_R$ 1.19 min, m/z 223, 225 (M+H, Br isotopes).

Example IV-22

2-(4-bromophenyl)-1H-imidazole

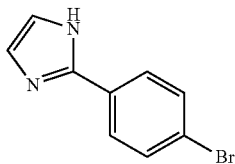 [SMILES: Brc1ccc(-c2ncc[nH]2)cc1]

The title compound was prepared from p-bromobenzonitrile as described for the preparation Example IV-21, with the exception that purification of the title compound consisted of a combination of recrystallization (i-PrOH) and flash chromatography (EtOAc/hexanes). LC/MS (method A) $t_R$ 1.25 min, m/z 223, 225 (M+H, Br isotopes).

Example IV-23

3-(3-Bromophenyl)-1-({[2-(trimethylsilyl)ethyl]oxy}methyl)-1H-1,2,4-triazole and 5-(3-bromophenyl)-1-({[2-(trimethylsilyl)ethyl]oxy}methyl)-1H-1,2,4-triazole

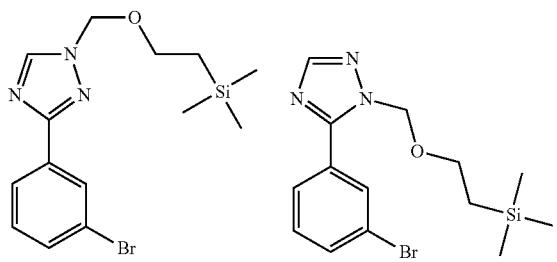

Step 1: 3-(3-Bromophenyl)-1H-1,2,4-triazole

To a slurry of methyl 3-bromobenzenecarboximidoate hydrochloride (example IV-21 Step 1; 0.541 g; 2.18 mmol) in pyridine (3 mL) at 0° C. was added a solution of formic hydrazide (0.157 g; 2.62 mmol). The flask was stoppered and gradually warmed to room temperature (overnight) and poured into water (~20 mL). Precipitated solid was collected by filtration and the filtrate was extracted with EtOAc (×3). Combined extracts were washed (water, brine), dried over Na$_2$SO$_4$, concentrated in vacuo. The residue obtained was combined with the above precipitate, and the whole was purified by flash chromatography (EtOAc/hexanes), affording the title compound as a colorless solid. LC/MS (method A) $t_R$ 2.49 min, m/z 224, 226 (M+H, Br isotopes).

Step 2: 3-(3-Bromophenyl)-1-({[2-(trimethylsilyl)ethyl]oxy}methyl)-1H-1,2,4-triazole and 5 (3-bromophenyl)-1-({[2-(trimethylsilyl)ethyl]oxy}methyl)-1H-1,2,4-triazole To a slurry of hexanes-washed NaH (0.085 g of a 60 wt % suspension in mineral oil; ~2.1 mmol) in DMF (3 mL) at 0° C. was added a solution of 3-(3-bromophenyl)-1H-1,2,4-triazole (0.238 g; 1.06 mmol; Step 1 above) in DMF (1 mL), dropwise over 2 min. The mixture was stirred 30 min and SEM-Cl (0.22 mL; 1.27 mmol) was added, dropwise. The mixture was gradually warmed to room temperature (overnight), poured into water and extracted with EtOAc (×3). Combined organics were washed (water, brine), dried over Na$_2$SO$_4$ and concentrated in vacuo. The residue was purified by flash chromatography (EtOAc/hexanes), affording two regioisomeric N-protected triazoles. The earlier-eluting regioisomer was a colorless gum; the later-eluting regioisomer was a colorless, waxy solid (ratio ~2:5 earlier:later). Earlier-eluting isomer $^1$H NMR (400 MHz, CDCl$_3$) δ ppm 0.02 (s, 9 H), 0.95-1.05 (m, 2 H), 3.77-3.86 (m, 2 H), 5.51 (s, 2 H), 7.39 (t, J=7.94 Hz, 1 H), 7.65 (ddd, J=8.07, 2.01, 0.98 Hz, 1 H), 7.89 (ddd, J=7.71, 1.65, 0.98 Hz, 1 H), 7.97 (s, 1 H), 8.12 (app. t, J=1.87 Hz, 1 H). Later-eluting isomer $^1$H NMR (400 MHz, CDCl$_3$) d ppm 0.01 (s, 9 H), 0.93-1.00 (m, 2 H), 3.66-3.73 (m, 2 H), 5.53 (s, 2 H), 7.33 (t, J=7.94 Hz, 1 H), 7.54 (ddd, J=7.94, 2.05, 1.07 Hz, 1 H), 8.06 (ddd, J=7.76, 1.52, 1.07 Hz, 1 H), 8.27 (s, 1 H), 8.31 (app. t, J=1.78 Hz, 1 H).

Example IV-24

[3-(3-Bromophenyl)-1H-1,2,4-triazol-1-yl]methyl 2,2-dimethylpropanoate

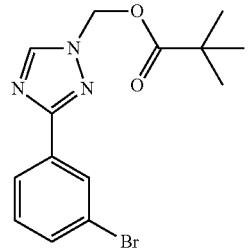 [SMILES: CC(C)(C)C(=O)OCn1cnc(-c2cccc(Br)c2)n1]

Step 1: 3-(3-Bromophenyl)-1H-1,2,4-triazole (Alternate Preparation)

A slurry of 3-bromobenzamide (77.4 g; 387 mmol) in DMF-DMA (150 mL) was prepared at room temperature and heated to 80° C. for 5 h. The mixture was cooled, poured into ice water (~2 L) and stirred at room temperature 2 h. Precipitated solid was collected by filtration and washed with water (3×500 mL) and hexanes (2×200 mL), and the cake was air-dried on the filter. The above solid was added to a solution of hydrazine monohydrate (18.0 mL; 370 mmol) in acetic acid (500 mL) at room temperature (internal temp RT→~40° C. during addition). The mixture was stirred 5 min and heated to 90° C. for 90 min. The mixture was cooled, and partially concentrated in vacuo to approximately 100 mL. The mixture was poured into ice water (~3 L) and stirred 1 h. Precipitated solid was collected by filtration, washed with water and the cake was air-dried on the filter overnight. The solid was recrystallized from benzene, affording the title compound as a colorless solid. LC/MS (method E) $t_R$ 0.61 min, m/z 224, 226 (M+H Br isotopes).

Step 2: [3-(3-Bromophenyl)-1H-1,2,4-triazol-1-yl]methyl 2,2-dimethylpropanoate A slurry of 3-(3-bromophenyl)-1H-1,2,4-triazole (58.5 g; 261 mmol; Step 1 above), anhydrous K$_2$CO$_3$ (43.2 g; 313 mmol), and chloromethylpivalate (45 mL; 313 mmol) in dry MeCN (250 mL) was heated to 80° C. (Note 1) for 1 hour. The mixture was cooled, solid was collected by filtration and the filtrate was concentrated in vacuo Residue from the filtaret was combined with the filtered solid and the whole was stirred with water approximately 20 minutes. Solid was collected by filtration, washed with water (×3) and recrystallized from MeOH/water, affording the title compound as a colorless solid. LC/MS (method E) $t_R$ 0.88 min, m/z 338, 340 (M+H, Br isotopes).

The following were prepared from the appropriate benzamides by a procedure similar to Example IV-25.

TABLE E

Compounds of Formula IV from the corresponding benzamide

| Ex | Structure/Name | Characterization Data | Comments |
|---|---|---|---|
| IV-26 | [3-(3-bromo-2-fluorophenyl)-1H-1,2,4-triazol-1-yl]methyl 2,2-dimethylpropanoate | LC/MS (method B) $t_R$ 2.75 min, m/z 356 (79Br), 358 (Br isotopes) | Note 1, 2, 3 DMF used as solvent for Step 2. Used IV-16 benzamide |
| IV-27 | [3-(3-bromo-2-methylphenyl)-1H-1,2,4-triazol-1-yl]methyl 2,2-dimethylpropanoate | LC/MS (method A) $t_R$ 2.85 min, m/z 352 (79Br), 354 (Br isotopes) | Note 1, 2, 3 Used IV-2 benzamide |
| IV-28 | [3-(3-bromo-2-chlorophenyl)-1H-1,2,4-triazol-1-yl]methyl 2,2-dimethylpropanoate | LC/MS (method A) $t_R$ 2.72 min, m/z 372 (79Br), 374 (Br isotopes) | Note 1, 2, 3 Used IV-13 benzamide |
| IV-29 | [3-(3-bromophenyl)-1H-pyrazol-1-yl]methyl 2,2-dimethylpropanoate | LC/MS (method A) $t_R$ 2.89 min, m/z 235 (79Br), 237 (Br isotopes) | Note 4 |

TABLE E-continued

Compounds of Formula IV from the corresponding benzamide

| Ex | Structure/Name | Characterization Data | Comments |
|---|---|---|---|
| IV-30 | [3-(4-bromophenyl)-1H-1,2,4-triazol-1-yl]methyl 2,2-dimethylpropanoate | 1H NMR (400 MHz, CDCl$_3$) δ ppm 1.09-1.28 (s, 9 H), 6.06 (s, 2 H), 7.57 (d, J = 8.55 Hz, 2 H), 7.98 (d, J = 8.55 Hz, 2 H), 8.35 (s, 1 H) | Note 1, 2 |
| IV-31 | [3-(4-bromo-3-methylphenyl)-1H-1,2,4-triazol-1-yl]methyl 2,2-dimethylpropanoate | 1H NMR (400 MHz, CDCl$_3$) δ ppm 1.18 (s, 9 H), 2.45 (s, 3 H), 6.06 (s, 2 H), 7.59 (d, J = 8.30 Hz, 1 H), 7.78 (dd, J = 8.06, 1.71 Hz, 1 H), 7.99 (s, 1 H), 8.34 (s, 1 H) | Note 1, 2 Used IV-4 benzamide |
| IV-32 | [3-(4-bromo-3-fluorophenyl)-1H-1,2,4-triazol-1-yl]methyl 2,2-dimethylpropanoate | (M + H) 356, (Br isotopes) 358, t$_R$ 0.91 min LC/MS (method B, gradient time = 1.5 min) | Note 1, 2, 3 Used IV-5 benzamide |

Note 1
In some cases, benzamide adducts with DMF-DMA (step 1) were more conveniently isolated by solvent extraction after pouring the reaction mixture into water rather than recrystalliztion.
Note 2
N—H triazole product of step 1 was used directly for Step 2 without recrystallization.
Note 3
N-alkylated triazole product of Step 2 was purified by flash chromatography (EtOAc/hexanes)
Note 4
Step 2 only (N-alkylation); Cs$_2$CO$_3$ was substituted for K$_2$CO$_3$. 5-(3-bromophenyl)-1H-pyrazole may be obtained from commercial sources (e.g., Sigma-Aldrich, St. Louis, MO, USA).

Example IV-33

[4-(3-bromophenyl)-1H-1,2,3-triazol-1-yl]methyl 2,2-dimethylpropanoate

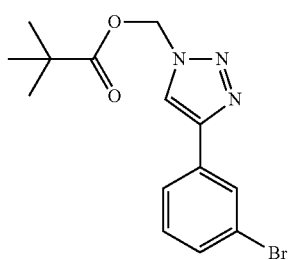 [SMILES: CC(C)(C)C(=O)OCn1cc(-c2cccc(Br)c2)nn1]

To a mixture of 1-bromo-3-ethynylbenzene (0.430 g; 2.38 mmol; Note 1), and azidomethyl 2,2-dimethylpropanoate (0.391 g; 2.49 mmol; Note 2) in t-BuOH/water (3.5/3.0 mL respectively) at room temperature was added a solution of CuSO$_4$.5H$_2$O in water (0.030 g/0.5 mL), followed by sodium ascorbate (0.141 g; 0.71 mmol) in one portion. The mixture was stirred 25 h at room temperature, diluted with water and extracted with EtOAc (×3). Combined organics were washed (5% NH$_4$OH, water, brine), dried over Na$_2$SO$_4$ and concentrated in vacuo affording the title compound as a tan solid which was used without further purification. LC/MS (method B) 2.77 min, m/z 338, 340 (M+H, Br isotopes).

Note 1 1-Bromo-3-ethynylbenzene may be obtained according to the procedure of Wettergren, J; Minidis, A. *Tetrahedron. Lett.* 2003, 44(41), 7611.

Note 2 Azidomethyl 2,2-dimethylpropanoate may be obtained according to the procedure of Loren, J; Krasiński, A.; Fokin, V.; Sharpless, K. B. *Synlett* 2005, 18, 2847.

Example IV-34

3-(3-bromophenyl)-5-isoxazolamine

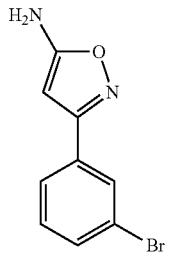

To a solution of 3-(3-bromophenyl)-3-oxopropanenitrile (1.12 g; 5.00 mmol; Note 1) in EtOH (20 mL) was added a solution of hydroxylamine hydrochloride (1.74 g; 25 mmol) and NaOAc (2.46 g; 30 mmol) in water (20 mL). The mixture was heated under reflux for 1 h, cooled and concentrated in vacuo. The residue was slurried in 1N NaOH and extracted with Et$_2$O (×1). The organic layer was washed (water, brine), dried over Na$_2$SO$_4$ and concentrated in vacuo affording the title compound as a pale yellow solid which was used without further purification. LC/MS (method B) 2.21 min, m/z 239, 241 (Br isotopes).

Example IV-35

1-(3-bromophenyl)-1,3-dihydro-2H-imidazol-2-one

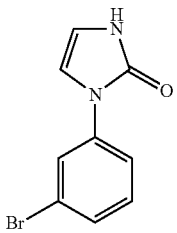 [SMILES: O=c1[nH]ccn1-c1cccc(Br)c1]

A solution of 1-bromo-3-isocyanatobenzene (1.0 mL, 8.01 mmol) and [2,2-bis(methyloxy)ethyl]amine (0.86 mL, 8.01 mmol) in CH$_2$Cl$_2$ (15 mL) was stirred at room temperature for 16 hr. The solution was concentrated in vacuo and the residue taken up in a mixture of CH$_3$CN (10 mL) and H$_2$O (3 mL). TFA (3 mL) was added and the solution stirred at room temperature for 4 hr. The solution was concentrated in vacuo, the residue taken up in EtOAc then washed with satd NaHCO$_3$, H$_2$O, and brine. The organics were then dried over Na$_2$SO$_4$, concentrated in vacuo and the residue recrystallized from EtOAc to give 1-(3-bromophenyl)-1,3-dihydro-2H-imidazol-2-one as a white solid. $^1$H NMR (400 MHz, DMSO-d$_6$) δ ppm 6.60 (d, J=3.0 Hz, 1H), 7.03 (d, J=3.0 Hz, 1H), 7.34-7.36 (m, 2H); 7.70-7.72 (m, 1H), 8.06 (s, 1H), 10.39 (br s, 1H).

Intermediate IV-36

4-(3-bromophenyl)-2-(triphenylmethyl)-2,4-dihydro-3H-1,2,4-triazol-3-one

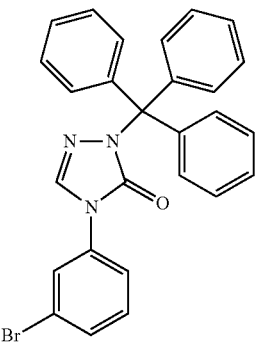 [SMILES: O=c1n(-c2cccc(Br)c2)cnn1C(c1ccccc1)(c1ccccc1)c1ccccc1]

Step 1: 4-(3-bromophenyl)-2,4-dihydro-3H-1,2,4-triazol-3-one

A mixture of 3-bromoaniline (1.0 mL, 9.18 mmol), methyl hydrazinocarboxylate (788 mg, 8.75 mmol), triethyl orthoformate (0.96 mL, 8.75 mmol), and TsOH (25 mg) in MeOH (20 mL) was stirred at 65° C. for 3 hr. After cooling to room temperature, NaOMe (1.47 g, 26.2 mmol) was added and the mixture stirred at room temperature for 16 hr. After concentration in vacuo the residue was taken up in EtOAc and H$_2$O then acidified with 1N HCl. The aqueous phase was extracted with EtOAc and the combined organics washed with H$_2$O then extracted twice with 1N NaOH. Combined NaOH extracts were acidified with conc. HCl and aged 5 min. Resulting solids were collected by filtration, washed with H$_2$O and dried to give 4-(3-bromophenyl)-2,4-dihydro-3H-1,2,4-triazol-3-one as a white solid. $^1$H NMR (400 MHz, DMSO-d$_6$) δ ppm 7.42-7.46 (m, 1H), 7.53 (d, J=7.8 Hz, 1H), 7.72 (d, J=7.8 Hz, 1H), 7.98 (s, 1H), 8.43 (s, 1H), 12.03 (s, 1H).

Step 2: 4-(3-bromophenyl)-2-(triphenylmethyl)-2,4-dihydro-3H-1,2,4-triazol-3-one A mixture of 4-(3-bromophenyl)-2,4-dihydro-3H-1,2,4-triazol-3-one (250 mg, 1.04 mmol) and NaH (50 mg of a 60% dispersion in mineral oil, 1.25 mmol) in DMF (3 mL) was stirred at room temperature for 30 min. To the solution was added 1,1',1''-(chloromethanetriyl)tribenzene (305 mg, 1.09 mmol) and the mixture stirred at room temperature for 4 hr. The reaction mixture was diluted with EtOAc, washed with H$_2$O and brine, dried over Na$_2$SO$_4$ then concentrated in vacu. The residue was purified by silica gel chromatography (EtOAc/Hexanes) to give 4-(3-bromophenyl)-2-(triphenylmethyl)-2,4-dihydro-3H-1,2,4-triazol-3-one as a pale yellow foam. 1H NMR (400 MHz, DMSO-d6) δ 7.22-7.31 (m, 15 H), 7.40-7.42 (m, 1H), 7.51 (d, J=7.8 Hz, 1H), 7.63 (d, J=7.8 Hz, 1H), 7.90 (s, 1H), 8.60 (s, 1H).

Intermediate IV-37

1-(3-bromophenyl)-3-(triphenylmethyl)-2,4-imidazolidinedione

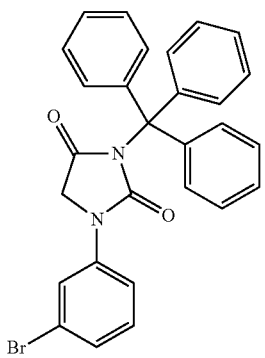 [SMILES: O=C1CN(c2cccc(Br)c2)C(=O)N1C(c1ccccc1)(c1ccccc1)c1ccccc1]

Step 1: 1-(3-bromophenyl)-2,4-imidazolidinedione

A solution of 3-bromoaniline (1.0 mL, 9.18 mmol) and chloroacetyl isocyanate (0.780 mL, 9.18 mmol) in dioxane (100 mL) was stirred at room temperature for 2 hr. Dioxane (50 mL) and DBU (3.40 mL, 23.0 mmol) were added and the solution stirred at room temperature for 16 hr. The solution was concentrated in vacuo and the residue taken up in EtOAc and $H_2O$. The mixture was then acidified with 1N HCl, then the aqueous phase extracted with EtOAc. The combined organics were then washed with $H_2O$ and brine and dried over $Na_2SO_4$. The solution was concentrated in vacuo and the residue recrystallized from EtOAc/hexanes to give 1-(3-bromophenyl)-2,4-imidazolidinedione as a tan solid. 1H NMR (400 MHz, DMSO-$d_6$) δ ppm 4.42 (s, 2H), 7.24-7.30 (m, 2H), 7.50-7.52 (m, 1H), 7.87 (s, 1H), 11.27 (s, 1H).

Step 2: 1-(3-bromophenyl)-3-(triphenylmethyl)-2,4-imidazolidinedione

The trityl protection to render the title compound was performed in a manner similar to that described in the preparation of IV-36 Step 2. $^1$H NMR (CDCl$_3$) δ ppm 4.20 (s, 2H), 7.17-7.22 (m, 4H), 7.25-7.28 (m, 8H), 7.46-7.48 (m 6H), 7.79 (s, 1H).

Intermediate IV-38

1-(3-bromophenyl)-2-imidazolidinone

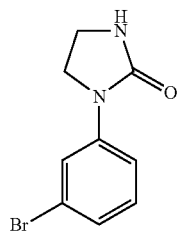 [SMILES: O=C1NCCN1c1cccc(Br)c1]

1-Chloro-2-isocyanatoethane (1.18 mL, 13.8 mmol) was added dropwise to a solution of 3-bromoaniline (1.5 mL, 13.8 mmol) in DMF (30 mL) at 0° C. then stirred at room temperature for 16 hr, then 70° C. for 2 hr. The solution was cooled to room temperature and 1-chloro-2-isocyanatoethane (0.40 mL, 4.69 mmol) was added. After stirring at room temperature for 2 hr, the solution was diluted with DMF (120 mL), cooled to 0° C. and NaH (660 mg, 60% dispersion in mineral oil, 16.5 mmol) added in portions. The mixture was stirred at room temperature for 64 hr, then diluted with EtOAc. After washing with $H_2O$ three times then brine the solution was dried over $Na_2SO_4$, concentrated in vacuo and the residue purified by silica gel chromatography (EtOAc/hexanes) to give 1-(3-bromophenyl)-2-imidazolidinone as a white solid. 1H NMR (400 MHz, CDCl$_3$) δ ppm 3.56-3.62 (m, 2H), 3.88-3.92 (m, 2H), 5.20 (br s, 1H), 7.15-7.20 (m, 2H), 7.49-7.51 (m, 1H), 7.71 (s, 1H).

Intermediate IV-39

2-(3-bromophenyl)-1,2,5-thiadiazolidine 1,1-dioxide

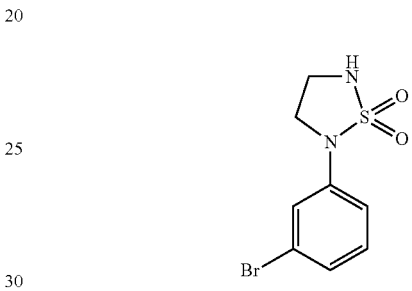

A solution of SO$_2$Cl$_2$ (12.6 mL, 0.155 mol) and 2-chloroethylamine hydrochloride (3.0 g, 25.9 mmol) in CH$_3$CN (100 mL) was stirred at 75° C. for 16 hr. The solution was concentrated and the residue dried in vacuo. The residue was then extracted with two 15 mL portions of Et$_2$O and the combined washes then added dropwise to a solution of 3-bromoaniline (1.70 mL, 15.5 mmol) and TEA (7.20 mL, 51.7 mmol) in Et$_2$O (15 mL) at −78° C. After stirring at room temperature for 16 hr, the mixture was diluted with EtOAc then washed with $H_2O$ and brine, dried over $Na_2SO_4$ and concentrated. To the residue was added DMSO (100 mL) and K$_2$CO$_3$ (3.60 g, 26.0 mmol). After stirring at room temperature for 2 hr the mixture was poured into $H_2O$ (500 mL), extracted twice with EtOAc and the combined organics washed with $H_2O$ and brine then concentrated. The residue was recrystallized from EtOAc/hexanes to give 2-(3-bromophenyl)-1,2,5-thiadiazolidine 1,1-dioxide as a light brown solid. $^1$H NMR (400 MHz, DMSO-$d_6$) δ ppm 3.48-3.49 (m, 2H), 3.82-3.85 (m, 2H), 7.15 (d, J=8.0 Hz, 1H), 7.23 (d, J=8.0 Hz, 1H), 7.29-7.33 (m, 2H), 7.85 (br s, 1H).

Intermediate IV-40

2-(3-bromophenyl)isothiazolidine 1,1-dioxide

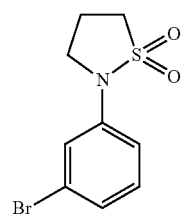 [SMILES: O=S1(=O)CCCN1c1cccc(Br)c1]

To a solution of 3-bromoaniline (1.0 mL, 9.18 mmol) and TEA (2.60 mL, 18.5 mmol) in CH₂Cl₂ (20 mL) was added 3-chloro-1-propanesulfonyl chloride (1.40 mL, 11.5 mmol) at 0° C. After stirring at room temperature for 16 hr, 3-chloro-1-propanesulfonyl chloride (1.40 mL, 11.5 mmol) and TEA (2.6 mL, 18.5 mmol) was added and the solution stirred at room temperature for 2 hr.

The solution was then washed with HCl (1.0 N, aq) and brine, dried over Na₂SO₄ then concentrated in vacuo. The residue was then taken up in DMF (40 mL) and DBU (4.10 mL, 27.6 mmol) was added. The mixture was stirred at room temperature for 64 hr, diluted with EtOAc, then washed with 1N HCl and brine then concentrated. The residue was purified by silica gel chromatography (EtOAc/hexanes) to give 2-(3-bromophenyl)isothiazolidine 1,1-dioxide as an off-white solid. ¹H NMR (400 MHz, CDCl₃) δ ppm 2.50-2.54 (m, 2H), 3.37 (t, J=7.5 Hz, 2H), 3.74 (t, J=7.5 Hz, 2H), 7.22-7.24 (m, 3H), 7.33 (s, 1H).

Compounds of Formula V

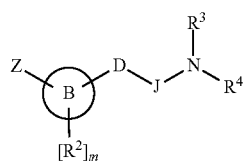

Formula V

Example V-1

[(5-bromo-2-thienyl)methyl][2-(3-fluorophenyl)ethyl]amine

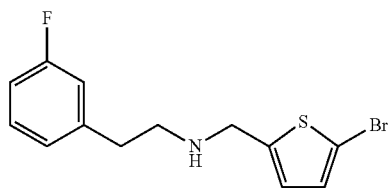 [SMILES: Fc1cccc(CCNCc2ccc(Br)s2)c1]

To a 100 mL round bottom flask was added 5-bromo-2-thiophenecarbaldehyde (0.24 mL, 2 mmol), [2-(3-fluorophenyl)ethyl]amine (0.29 mL, 2.2 mmol), HOAc (0.12 mL, 1 mmol), sodium triacetoxyborohydride (1.2 g, 6 mmol) and 1,2-dichloroethane (10 mL). The reaction was stirred overnight at room temperature, quenched with H₂O, and extracted with CH₂Cl₂ three times. The mixture was washed with brine, dried with MgSO₄ and concentrated under reduced pressure. The crude material was purified by silica gel column chromatography (ethyl acetate/hexane) affording the title compound. LC/MS (method A) t_R 1.54 min; m/z 315 (M+H).

The following examples were prepared from the appropriate heteroaromatic aldehydes and amines using a procedure similar to Example V-3.

TABLE F

Compounds of Formula V from the corresponding heteroaromatic aldehyde

| Ex | Structure/Name | Characterization Data | Comments |
|---|---|---|---|
| V-2 | [(5-bromo-2-thienyl)methyl][2-(2-thienyl)ethyl]amine | LC/MS (method A) t_R 1.37 min; m/z 302, 304 (M + H, Br isotopes) | |
| V-3 | [(5-bromo-2-thienyl)methyl](3-methylbutyl)amine | LC/MS (method A) t_R 1.35 min; m/z 262, 264 (M + H, Br isotopes) | |
| V-4 | [(4-bromo-2-thienyl)methyl](3-methylbutyl)amine | LC/MS (method A) t_R 1.26 min; m/z 262, 264 (M + H, Br isotopes) | |

TABLE F-continued

Compounds of Formula V from the corresponding heteroaromatic aldehyde

| Ex | Structure/Name | Characterization Data | Comments |
|---|---|---|---|
| V-5 | [(4-bromo-2-thienyl)methyl][2-(2-thienyl)ethyl]amine | LC/MS (method A) $t_R$ 1.30 min, m/z 302, 304 (M + H, Br isotopes) | |
| V-6 | [(4-bromo-2-thienyl)methyl][2-(3-fluorophenyl)ethyl]amine | LC/MS (method A) $t_R$ 1.47 min; m/z 314, 316 (M + H, Br isotopes) | |
| V-7 | [(4-bromo-2-thienyl)methyl](4,4-dimethylcyclohexyl)amine | LC/MS (method A) $t_R$ 1.59 min; m/z 303, 305 (M + H, Br isotopes) | amine = Ex. III-1 |

Example V-8

1,1-dimethylethyl {2-[(4-bromophenyl)oxy]ethyl}(4,4-dimethylcyclohexyl) carbamate

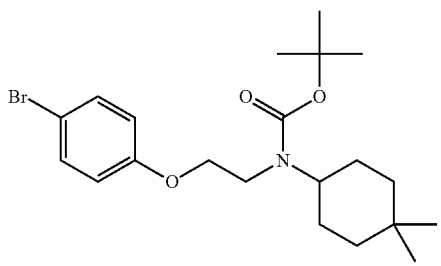 [SMILES: CC1(C)CCC(N(CCOc2ccc(Br)cc2)C(=O)OC(C)(C)C)CC1]

Step 1: [(4-Bromophenyl)oxy]acetonitrile

A mixture of p-bromophenol (2.61 g; 15.1 mmol), bromoacetonitrile (1.11 mL; 15.9 mmol), and $Cs_2CO_3$ (7.40 g; 22.7 mmol) in anhyd MeCN (25 mL) was heated at 80° C., under $N_2$ overnight. The mixture was cooled, filtered through a pad of Celite and concentrated in vacuo. The residue was dissolved in a minimal amount of EtOAc/hexanes and filtered through a short pad of silica gel (EtOAc/hexanes eluent), affording the title compound as a colorless, waxy solid which was used without further purification. $^1$H NMR (400 MHz, $CDCl_3$) δ 4.75 (s, 2H), 6.88 (m, 2H), 7.46 (m, 2H).

Step 2: {2-[(4-Bromophenyl)oxy]ethyl}amine

To a solution of [(4-bromophenyl)oxy]acetonitrile (3.07 g; 14.5 mmol; step 1 above) in anhyd THF (10 mL) at 0° C. was added $BH_3$.DMS (18.1 mL of a 2M solution in THF; 36.2 mmol), dropwise over 5 min. The mixture was heated under reflux for 1.5 h, cooled, and 2M HCl (ca. 50 mL) was slowly added. The acidic mixture was extracted with $Et_2O$ (×2) and the extracts set aside. NaOH pellets were added to the aqueous residue until ca. pH 14, and the whole was extracted with $Et_2O$ (×3). Combined extracts of the basic mixture were washed (brine), dried over $Na_2SO_4$, and concentrated in vacuo, affording the first batch of title compound as a pale yellow liquid. The reserved $Et_2O$ extracts (from acidic mixture) were concentrated in vacuo, the residue was heated at near reflux in 15 wt % NaOH (aq) for 15 min, cooled, and extracted with $CH_2Cl_2$ (×3). Combined organics were washed (brine) and concentrated in vacuo. The residue was slurried in 4M HCl and insoluble material was removed by filtration. The filtrate was extracted with $Et_2O$ (×2), pH was adjusted to ca. pH 14 by addition of NaOH pellets and extracted with $Et_2O$ (×5). Combined extracts from the basic mixture were washed (brine), dried over $Na_2SO_4$, filtered and concentrated in vacuo, affording a second batch of the title compound, which was combined with the first batch. LC/MS (method D) 1.15 min, m/z 216 (M+H, $^{79}$Br), 218 (M+H, $^{81}$Br).

Step 3: 1,1-Dimethylethyl {2-[(4-bromophenyl)oxy]ethyl}(4,4-dimethylcyclohexyl)carbamate To a solution of {2-[(4-bromophenyl)oxy]ethyl}amine (1.89 g; 8.74 mmol; step 2 above), 4,4-dimethylcyclohexanone (1.10 g; 8.74 mmol; Example III-1 Step 1) and HOAc (0.50 mL) in MeOH (50 mL) at rt was added NaBH$_3$CN (0.549 g; 8.74 mmol) in one portion and the mixture was stirred at room temperature. Upon consumption of {2-[(4-bromophenyl)oxy]ethyl}amine (Note 1), volatiles were removed in vacuo and the residue was partitioned between 1M NaOH/CH$_2$Cl$_2$. Layers were separated and the aqueous layer was extracted with CH$_2$Cl$_2$ (×2). Combined organics were washed (H$_2$O, brine), dried over Na$_2$SO$_4$, filtered and concentrated in vacuo. The residue was dissolved in CH$_2$Cl$_2$ (40 mL) along with Et$_3$N (1.22 mL; 8.74 mmol), and a solution of (Boc)$_2$O (1.91 g; 8.74 mmol) in CH$_2$Cl$_2$ (10 mL) was added. After 13 h the mixture was diluted with CH$_2$Cl$_2$, washed (H$_2$O, brine), dried over Na$_2$SO$_4$, filtered and concentrated in vacuo. The residue was purified by flash chromatography (EtOAc/hexanes), affording the title compound as a colorless, waxy solid. LC/MS (method A) 3.42 min, m/z 426, 428 (M+H, Br isotopes, 11-12%), 326, 328 ([M-Boc]+H, Br isotopes, 96-100%).

Note 1 Reaction progress was monitored by LC/MS; HOAc (~1 equiv), and small portions of NaBH$_3$CN (0.1-0.25 equiv) and 4,4-dimethylcyclohexanone (0.05 equiv) were added as necessary to effect consumption of the amine.

The following examples were prepared from the appropriate amines and 4,4-dimethylcyclohexanone (III-1 Step 1) according to the procedure described in Example V-8 Step 3, with any significant deviations noted below table.

TABLE G

Compounds of Formula V via reductive alkylation of the corresponding amine and ketone

| Ex | Structure/Name | Characterization Data | Comments |
|---|---|---|---|
| V-9 | 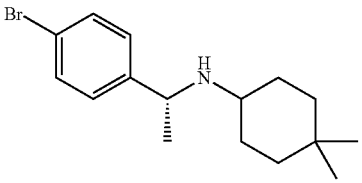 [SMILES: C[C@@H](NC1CCC(C)(C)CC1)c1ccc(Br)cc1]<br>[(1R)-1-(4-bromophenyl)ethyl](4,4-dimethylcyclohexyl)amine | LC/MS (method B) t$_R$ 1.93 min; m/z 310, 312 (M + H, Br isotopes) | Note 1 |
| V-10 | 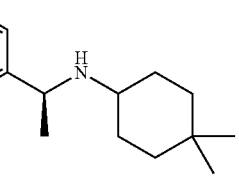<br>[(1S)-1-(4-bromophenyl)ethyl](4,4-dimethylcyclohexyl)amine | LC/MS (method B) t$_R$ 1.91 min; m/z 310, 312 (M + H, Br isotopes) | Note 1 |
| V-11 | 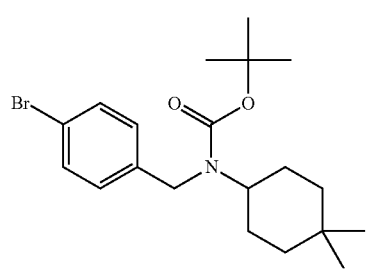 [SMILES: CC1(C)CCC(N(Cc2ccc(Br)cc2)C(=O)OC(C)(C)C)CC1]<br>1,1-dimethylethyl [(4-bromophenyl)methyl](4,4-dimethylcyclohexyl) carbamate | LC/MS (method A) t$_R$ 3.36 min, m/z 396, 398 (M + H, Br isotopes, 18-20%), 340, 342 ([M - C$_4$H$_8$] + H, Br isotopes, 94-100%) | 4-Bromobenzylamine hydrochloride used HOAc omitted from reductive amination. |
| V-12 | 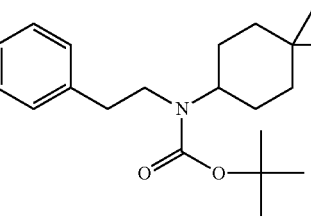<br>1,1-Dimethylethyl [2-(4-bromo phenyl)ethyl](4,4-dimethyl cyclohexyl) carbamate | LC/MS (method A) t$_R$ 3.44 min, m/z 410, 412 (M + H, Br isotopes, 6%), 354 (79Br, 93%), 356 ([M − C4H8] + H, Br isotopes, 93-100%). | |

TABLE G-continued

Compounds of Formula V via reductive alkylation of the corresponding amine and ketone

| Ex | Structure/Name | Characterization Data | Comments |
|---|---|---|---|
| V-13 | <br>1,1-dimethylethyl [(4-bromophenyl)methyl]2,3-dihydro-1H-inden-2-ylcarbamate | Note 2 | Note 2 |

Note 1:
N—Boc carbamate formation was not observed within 6 h under example conditions. The reaction was worked up per example V-8 Step 3, and the title compound was purified by flash chromatography (EtOAc/hexanes).
Note 2:
2-Aminoindane hydrochloride and 4-bromobenzaldehyde were used. The amine hydrochloride was admixed with an eqimolar amount of Et$_3$N in 1:1 THF/MeOH before addition to the aldehyde. 1H NMR (400 MHz, DMSO-d6) δ ppm 1.32 (s, 9 H), 2.87-3.03 (m, 4 H), 4.41 (br. s., 2 H), 4.71 (br. s., 1 H), 6.99-7.26 (m, 4 H), 7.44-7.61 (m, 2 H).

Example V-14

1,1-dimethylethyl [2-(3-bromophenyl)ethyl]carbamate

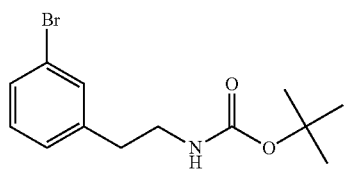 [SMILES: CC(C)(C)OC(=O)NCCc1cccc(Br)c1]

To a solution of 2-bromophenethyl amine (2.0 g, 0.01 mol) in acetonitrile at room temperature was added di-tert-butyl dicarbonate (2.1 g, 0.01 mol) in one portion. After stirring at room temperature for 72 hr the reaction mixture was concentrated in vacuo and the residue was dissolved in ethyl acetate. The solution was washed with brine, dried (Na$_2$SO$_4$), filtered and concentrated in vacuo to give 1,1-dimethylethyl [2-(3-bromophenyl)ethyl]carbamate as a yellow oil. LC/MS (method A) t$_R$ 2.73 min; m/z 300 (M+H).

Example V-15

1,1-Dimethylethyl {2-[(4-bromo-3-methylphenyl)oxy]ethyl}carbamate

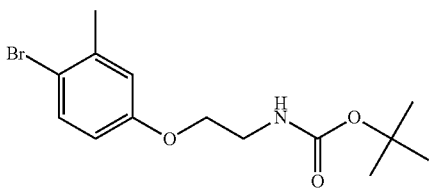 [SMILES: Cc1cc(OCCNC(=O)OC(C)(C)C)ccc1Br]

To a solution of 4-bromo-3-methylphenol (0.187 g; 1.00 mmol), N-Boc aminoethanol (0.39 mL; 2.5 mmol) and PPh$_3$ (0.655 g; 2.5 mmol) in anhyd PhH (5 mL) at 0° C. was added DIAD (0.49 mL; 2.5 mmol), dropwise over 15 min. The mixture was stirred 16 h at room temperature, diluted with Et$_2$O, washed (2×satd Na$_2$CO$_3$, 2×H$_2$O, brine), dried over Na$_2$SO$_4$, filtered and concentrated in vacuo. The residue was purified by flash chromatography (EtOAc/hexanes), affording the title compound as a colorless gum, which solidified on standing. LC/MS (method A) t$_R$ 2.95 min, m/z 330, 332 (M+H, Br isotopes, 2%), 352, 354 (M+Na, Br isotopes, 40-43%), 230, 232 ([M-Boc]+H, Br isotopes, 100%).

Example V-16

1,1-Dimethylethyl 6-{[(trifluoromethyl)sulfonyl]oxy}-3,4-dihydro-2(1H)-isoquinolinecarboxylate

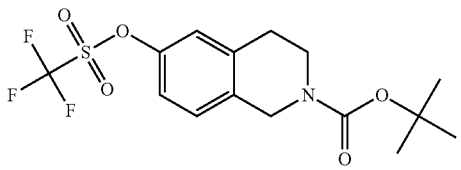 [SMILES: CC(C)(C)OC(=O)N1CCc2cc(OS(=O)(=O)C(F)(F)F)ccc2C1]

Step 1: 1,2,3,4-Tetrahydro-6-isoquinolinol hydrobromide

The title compound was synthesized in two steps from m-methoxyphenethylamine, according to the procedure of Sall, D. J.; Grunewald, G. L. *J. Med. Chem.* 1987, 30, 2208 with the exception that methyl chloroformate was replaced with ethyl chloroformate in the Bischler-Naperalski cyclization of 3-methoxyphenethylamine to intermediate 6-(methyloxy)-3,4-dihydro-1(2H)-isoquinolinone. $^1$H NMR (400 MHz, DMSO-d$_6$) δ 2.90 (t, J=6.2 Hz, 2H), 3.32 (m, 2H), 4.13 (t, J=4.6 Hz, 2H), 6.59 (d, J=2.2 Hz, 1H), 6.65 (dd, J=8.4, 2.3 Hz, 1H), 7.00 (d, J=8.3 Hz, 1H), 9.00 (br. s, 2H).

Step 2: 1,1-Dimethylethyl 6-hydroxy-3,4-dihydro-2(1H)-isoquinolinecarboxylate To a slurry of 1,2,3,4-tetrahydro-6-isoquinolinol hydrobromide (1.29 g; 5.63 mmol; step 1 above) and Et$_3$N (3.13 mL; 22.5 mmol) in CH$_2$Cl$_2$ (30 mL) and THF (5 mL) at rt was added a solution of (Boc)$_2$O (2.46 g; 11.3 mmol) in THF (20 mL). The mixture was stirred 72 h at rt and concentrated in vacuo. The residue was dissolved in CH$_2$Cl$_2$ and washed with H$_2$O. The aqueous wash was back-extracted with CH$_2$Cl$_2$ (×2), Combined organics were washed (H$_2$O, brine), dried over Na$_2$SO$_4$, filtered and concentrated in vacuo. The residue was dissolved in CH$_2$Cl$_2$ (30 mL), piperidine (30 mL) was added, the mixture was stirred overnight at rt and concentrated in vacuo. The residue was dissolved in EtOAc, washed (3×H$_2$O, brine), dried over Na$_2$SO$_4$, filtered and concentrated in vacuo. The residue was re-dissolved in EtOAc, washed (2×1M KHSO$_4$, H$_2$O, brine), dried over Na$_2$SO$_4$, filtered and concentrated in vacuo. The residue was purified by flash chromatography (EtOAc/hexanes), affording the title compound as a colorless gum. $^1$H NMR (400 MHz, CDCl$_3$) δ 1.49 (s, 9H), 2.76 (t, J=5.9 Hz, 2H), 3.61 (br. t, J=5.8 Hz, 2H), 4.49 (s, 2H), 5.58 (br. s, 1H), 6.63 (unresolved d, 1H), 6.68 (br. d, J=8.4 Hz, 1H), 6.95 (d, J=8.2 Hz, 1H).

Step 3: 1,1-dimethylethyl 6-{[(trifluoromethyl)sulfonyl]oxy}-3,4-dihydro-2(1H)-isoquinolinecarboxylate To a solution of 1,1-dimethylethyl 6-hydroxy-3,4-dihydro-2(1H)-isoquinolinecarboxylate (0.146 g; 0.586 mmol) and Et$_3$N (0.17 mL; 1.2 mmol) in CH$_2$Cl$_2$ (5 mL) at 0° C. was added Tf$_2$O (0.11 mL; 0.67 mmol(, dropwise over 2 min. The mixture was stirred overnight, gradually warming to room temperature, diluted with CH$_2$Cl$_2$, washed (water, brine), dried over Na$_2$SO$_4$ and concentrated in vacuo. The residue was purified by flash chromatography (EtOAc/hexanes), affording the title compound as a colorless gum which slowly solidified. $^1$H NMR (400 MHz, CDCl$_3$) δ 1.49 (s, 9H), 2.87 (t, J=5.7 Hz, 2H), 3.66 (br. t, J=5.5 Hz, 2H), 4.59 (s, 2H), 7.04-7.12 (m, 2H), 7.18 (d, J=8.4 Hz, 1H).

Example V-17 (u23368-24-1)

1,1-Dimethylethyl 7-{[(trifluoromethyl)sulfonyl]oxy}-3,4-dihydro-2(1H)-isoquinolinecarboxylate

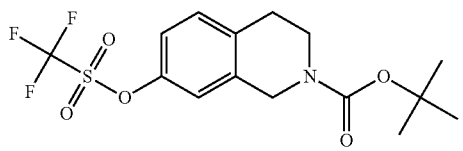 [SMILES: CC(C)(C)OC(=O)N1CCc2ccc(OS(=O)(=O)C(F)(F)F)cc2C1]

The title compound was obtained from 4-methoxyphenethylamine according to the procedure described for Example V-16, with the exceptions that during N-protection with (Boc)$_2$O (step 2): example V-17 used 1:1 EtOH/1M NaOH as solvent; Et$_3$N was omitted; after stirring 1 h at room temperature, the reaction was concentrated in vacuo, the residue was acidified with 2M KHSO$_4$, extracted with EtOAc, dried and concentrated in vacuo affording the intermediate 1,1-dimethylethyl 7-hydroxy-3,4-dihydro-2(1H)-isoquinolinecarboxylate directly as a tan solid. 7-Hydroxy-intermediate (u22816-72-3): $^1$H NMR (400 MHz, CDCl$_3$) δ 1.42 (s, 9H), 2.63 (unresolved t, 2H), 3.49 (unresolved t, 2H), 4.38 (br. s, 2H), 6.51 (br. s, 1H), 6.57 (br. d, J=7.9 Hz, 1H), 6.93 (d, J=7.9 Hz, 1H), 9.21 (br. s, 1H). 7-Triflate (title compound): $^1$H NMR (400 MHz, CDCl$_3$) δ 1.50 (s, 9H), 2.85 (t, J=5.5 Hz, 2H), 3.66 (t, J=5.4 Hz, 2H), 4.59 (s, 2H), 7.03 (unresolved d, 1H), 7.07 (partially resolved dd, J$_{ortho}$=8.5 Hz, 1H), 7.21 (d, J=8.4 Hz, 1H).

Example V-18

1,1-Dimethylethyl (4,4-dimethylcyclohexyl)(2-{[4-(4,4,5,5-tetramethyl-1,3,2-dioxaborolan-2-yl)phenyl]oxy}ethyl)carbamate

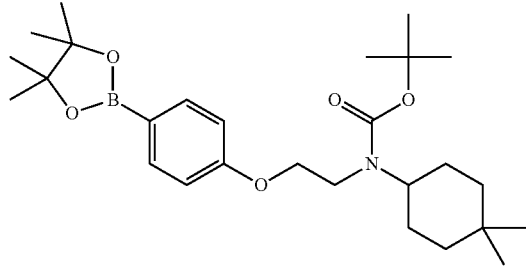

A mixture of {2-[(4-bromophenyl)oxy]ethyl}(4,4-dimethylcyclohexyl) carbamate (0.529 g; 1.24 mmol; Example V-8 above), bis(pinacolato)diboron (0.439 g; 1.86 mmol), KOAc (0.365 g; 3.72 mmol), and PdCl$_2$(dppf).CH$_2$Cl$_2$ (0.030 g; 0.037 mmol) in anhyd DMSO (5 mL) was sparged with N$_2$ for 5 min, then heated to 80° C. under N$_2$. After 16.5 h the mixture was cooled, poured into H$_2$O and extracted with EtOAc (×3). Combined organics were washed (H$_2$O, brine), dried over Na$_2$SO$_4$, adsorbed onto a small amount of silica gel and purified by flash chromatography (EtOAc/hexanes), affording the title compound as a colorless gum. LC/MS method A) t$_R$ 3.50 min, m/z 474 (M+H, 26%), 374 ([M−Boc]+H, 100%).

Example V-19

1,1-dimethylethyl (4,4-dimethylcyclohexyl){[4-(4,4,5,5-tetramethyl-1,3,2-dioxaborolan-2-yl)phenyl]methyl}carbamate

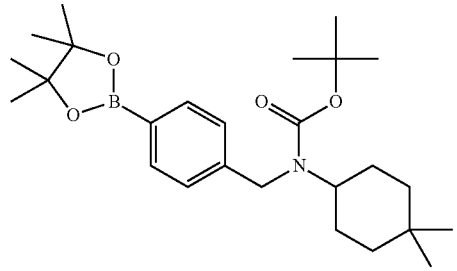

The title compound was synthesized from 1,1-dimethylethyl [(4-bromophenyl)methyl] (4,4-dimethylcyclohexyl) carbamate (Example V-11) according to the procedure described in Example V-18. LC/MS (method A) $t_R$ 3.48 min, m/z 444 (M+H, 19%), 466 (M+Na, 100%).

Example V-20

1,1-dimethylethyl 6-(4,4,5,5-tetramethyl-1,3,2-dioxaborolan-2-yl)-3,4-dihydro-2(1H)-isoquinolinecarboxylate

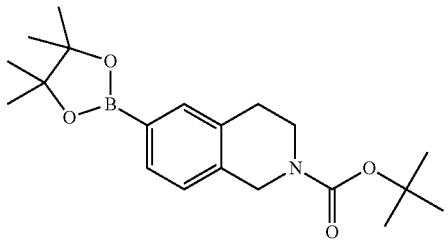 [SMILES: CC(C)(C)OC(=O)N1CCc2cc(B3OC(C)(C)C(C)(C)O3)ccc2C1]

The title compound was prepared from 1,1-dimethylethyl 6-{[(trifluoromethyl)sulfonyl]oxy}-3,4-dihydro-2(1H)-isoquinolinecarboxylate (Example V-16) according to the procedure described in Example V-18. $^1$H NMR (400 MHz, DMSO-d$_6$) δ ppm 1.28 (s, 12 H), 1.42 (s, 9 H), 2.78 (t, J=6.1 Hz, 2 H), 3.54 (t, J=6.0 Hz, 2 H), 4.50 (br. s., 2 H), 7.16 (d, J=7.8 Hz, 1 H), 7.45 (d, J=1.4 Hz, 2 H).

Example V-21

5-bromo-N-(4,4-dimethylcyclohexyl)-2,3-dihydro-1H-inden-1-amine

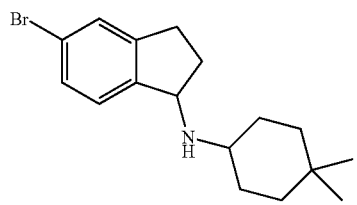 [SMILES: CC1(C)CCC(NC2CCc3cc(Br)ccc32)CC1]

To a slurry of 5-bromo-1-indanone (0.449 g; 2.13 mmol) and 4,4-dimethylcyclohexanamine (2.24 mmol; Note 1) under N$_2$ was added Ti(OiPr)$_4$ (0.94 mL; 3.2 mmol) via syringe. The mixture was stirred 16 h at room temperature, a solution of NaBH$_3$CN (0.134 g; 2.13 mmol) in EtOH (5 mL) was added and stirring continued an additional 4 h. Water was added and the whole was filtered through a pad of Celite (washed 2×EtOH, 2×THF). Combine filtrate and washings were concentrated in vacuo, the residue was taken up in CH$_2$Cl$_2$ and stirred under 1N NaOH for 1 h. Layers were separated, the aqueous layer was extracted with CH$_2$Cl$_2$ (×2), combined organics were washed (water, brine), dried over Na$_2$SO$_4$ and concentrated in vacuo. The residue was dissolved in MeOH/THF/HOAc (15/3/0.3 mL respectively), NaBH$_3$CN (0.134 g; 2.13 mmol) was added and the mixture was stirred at room temperature overnight. After 17 h the mixture was concentrated in vacuo, partitioned between CH$_2$Cl$_2$/1N NaOH and the layers were separated. The aqueous layer was extracted with CH$_2$Cl$_2$ (×2), combined organics were washed (water, brine), dried over Na$_2$SO$_4$ and concentrated in vacuo. The residue was purified by flash chromatography (EtOAc/hexanes; Note 2), affording the title compound as a pale yellow syrup. LC/MS (method A) $t_R$ 1.79 min; m/z 322, 324 (M+H, Br isotopes).

Note 1: 4,4-dimethylcyclohexanamine was obtained from an equimolar amount of the hydrochloride salt (Example III-1 Step 1) by partitioning between satd Na$_2$CO$_3$/Et$_2$O, drying the organic layer over Na$_2$SO$_4$, and concentrating in vacuo before use.

Note 2: Amine-functionalized silica gel (Teledyne Isco catalog#68-2203-102) was used for purification.

Example V-22

{4-[(2,3-dihydro-1H-inden-2-ylamino)methyl]-3,5-difluorophenyl}boronic acid

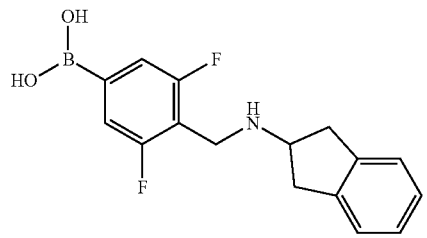 [SMILES: OB(O)c1cc(F)c(CNC2Cc3ccccc3C2)c(F)c1]

A mixture of 2,3-dihydro-1H-inden-2-amine (0.780 mL, 5.99 mmol), (3,5-difluoro-4-formylphenyl)boronic acid (1.0 g, 5.99 mmol) and acetic acid (0.710 mL, 12.0 mmol) in THF (12 mL) was stirred at room temperature for 1 hr. To the solution was added NaBH(OAc)$_3$ (3.81 g, 18.0 mmol) and the mixture stirred at room temperature for 16 hr. The mixture was diluted with EtOAc then washed with satd Na$_2$CO$_3$. The combined layers were filtered and the filter cake washed with H$_2$O and EtOAc to give {4-[(2,3-dihydro-1H-inden-2-ylamino)methyl]-3,5-difluorophenyl}boronic acid as a beige glass. LC/MS (method A) $t_R$ 0.48 min; m/z 304 (M+H).

Compounds of Formula VI

Formula VI

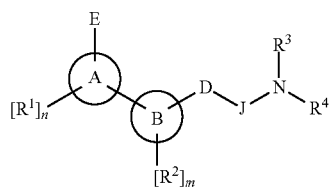

($R^3$ = protecting group, such as Boc)

Example VI-1

1,1-dimethylethyl (2-{[4'-(acetylamino)-4-biphenylyl]oxy}ethyl)(4,4-dimethylcyclohexyl)carbamate

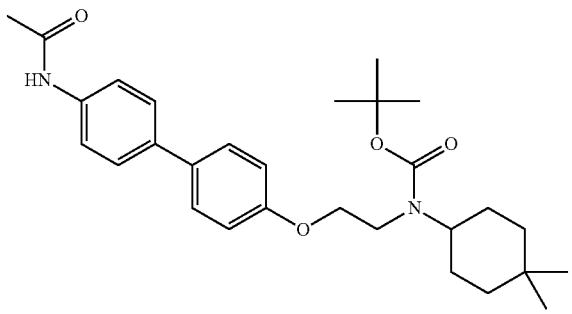 [SMILES: CC(=O)Nc1ccc(-c2ccc(OCCN(C(=O)OC(C)(C)C)C3CCC(C)(C)CC3)cc2)cc1]

A mixture of 1,1-dimethylethyl {2-[(4-bromophenyl)oxy]ethyl}(4,4-dimethylcyclohexyl) carbamate (0.085 g; 0.20 mmol; Example V-8), [4-(acetylamino)phenyl]boronic acid (0.040 g; 0.22 mmol), PdCl$_2$(dppf).CH$_2$Cl$_2$ (0.005 g; 0.006 mmol), Na$_2$CO$_3$ (2 mL of a 2M solution) and DME (2 mL) was sparged with N$_2$ for 10 minutes at room temperature and heated at 80° for 1 h (until consumption of the aryl bromide, as judged by LC/MS). Upon cooling, the mixture was partitioned between EtOAc/H$_2$O, layers were separated and the aqueous layer was extracted with EtOAc (×2). Combined organics were washed (brine), dried over Na$_2$SO$_4$, filtered and concentrated in vacuo. The residue was purified by flash chromatography (EtOAc/hexanes), affording the title compound as a pale yellow solid. LC/MS (method A) t$_R$ 3.29 min, m/z 481 (M+H, 53%), 381 ([M-Boc]+H, 100%).

The following examples were prepared from the appropriate aryl halide/triflate and aryl boronic acid/ester according to the procedure described for Example VI-1, with any significant deviation noted below table.

TABLE H

| | Compounds of Formula VI from Suzuki coupling of Compounds of Formula IV or V. | | |
|---|---|---|---|
| Ex | Structure/Name | Characterization Data | Comments |
| VI-2 | 1,1-dimethylethyl (2-{[3'-(acetylamino)-4-biphenylyl]oxy} ethyl)(4,4-dimethylcyclohexyl) carbamate | LC/MS (method A) t$_R$ 3.31 min, m/z 481 (M + H, 28%), 381 ([M − Boc] + H, 100%) | Aryl bromide V-8 and 3-(acetylamino phenylboronic acid used |
| VI-3 | 1,1-dimethylethyl (4,4-dimethylcyclohexyl)[2-({3'-[(methylsulfonyl)amino]-4-biphenylyl}oxy)ethyl]carbamate | LC/MS (method A) t$_R$ 3.26 min, m/z 515 (M − H). | Aryl bromide V-8 and 3-[(methylsulfonyl)amino]-phenylboronic acid used |

TABLE H-continued

Compounds of Formula VI from Suzuki coupling of Compounds of Formula IV or V.

| Ex | Structure/Name | Characterization Data | Comments |
|---|---|---|---|
| VI-4 | 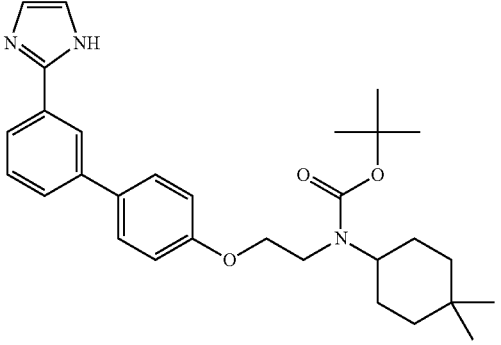 [SMILES: CC1(C)CCC(N(CCOc2ccc(-c3cccc(-c4ncc[nH]4)c3)cc2)C(=O)OC(C)(C)C)CC1]<br>1,1-dimethylethyl (4,4-dimethylcyclohexyl)(2-{[3'-(1H-imidazol-2-yl)-4-biphenylyl]oxy}ethyl)carbamate | LC/MS (method A) $t_R$ 2.60 min, m/z 488 (M − H). | Aryl bromide IV-21 and aryl boronate V-18 used. |
| VI-5 | 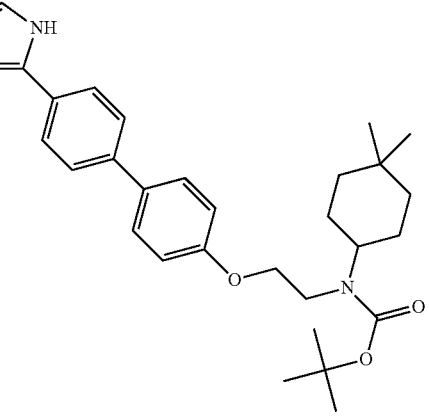<br>1,1-dimethylethyl (4,4-dimethylcyclohexyl)(2-{[4'-(1H-imidazol-2-yl)-4-biphenylyl]oxy}ethyl)carbamate | LC/MS (method A) 2.55 min; m/z 490 (M + H). | Aryl bromide IV-22 and aryl boronate V-18 used. Pd(PPh3)4 used as catalyst |
| VI-6 | 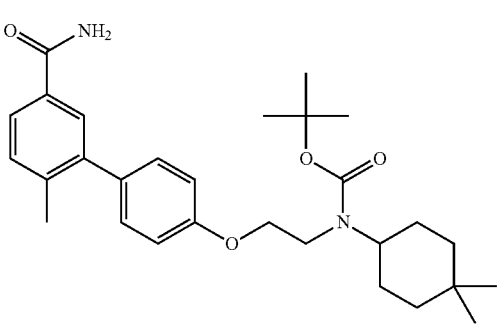 [SMILES: Cc1ccc(C(N)=O)cc1-c1ccc(OCCN(C(=O)OC(C)(C)C)C2CCC(C)(C)CC2)cc1]<br>1,1-dimethylethyl (2-{[5'-(aminocarbonyl)-2'-methyl-4-biphenylyl]oxy}ethyl)(4,4-dimethylcyclohexyl)carbamate | LC/MS (method A) $t_R$ 3.23 min; m/z 481 (M + H, 24%), 503 (M + Na, 100%).. | Aryl bromide IV-1 and aryl boronate V-18 used. |

TABLE H-continued

Compounds of Formula VI from Suzuki coupling of Compounds of Formula IV or V.

| Ex | Structure/Name | Characterization Data | Comments |
|---|---|---|---|
| VI-7 | 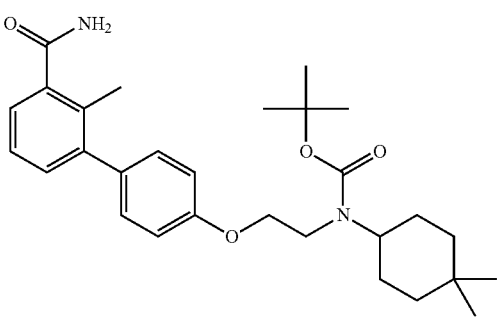 [SMILES: Cc1c(C(N)=O)cccc1-c1ccc(OCCN(C(=O)OC(C)(C)C)C2CCC(C)(C)CC2)cc1]<br>1,1-dimethylethyl (2-{[3'-(aminocarbonyl)-2'-methyl-4-biphenylyl]oxy}ethyl)(4,4-dimethylcyclohexyl)carbamate | LC/MS (method A) $t_R$ 3.27 min; m/z 481 (M + H, 5%), 503 (M + Na, 100%).. | Aryl bromide IV-2 and aryl boronate V-18 used. |
| VI-8 | 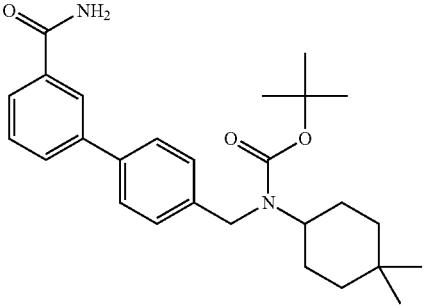 [SMILES: CC1(C)CCC(N(Cc2ccc(-c3cccc(C(N)=O)c3)cc2)C(=O)OC(C)(C)C)CC1]<br>1,1-dimethylethyl {[3'-(aminocarbonyl)-4-biphenylyl]methyl}(4,4-dimethylcyclohexyl)carbamate | Note 1 | Used aryl bromide V-11 and 3-(aminocarbonyl) phenylboronic acid. |
| VI-9 | 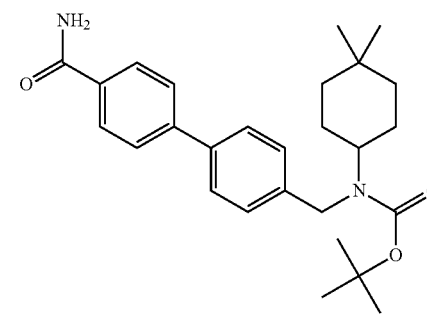<br>1,1-dimethylethyl {[4'-(aminocarbonyl)-4-biphenylyl]methyl}(4,4-dimethylcyclohexyl)carbamate | LC/MS (method A) $t_R$ 3.09 min; m/z 437 (M + H, 81%), 381 ([M − $C_4H_8$] + H, 100%) | Used aryl bromide V-11 and 4-(aminocarbonyl) phenylboronic acid. |

TABLE H-continued

Compounds of Formula VI from Suzuki coupling of Compounds of Formula IV or V.

| Ex | Structure/Name | Characterization Data | Comments |
| --- | --- | --- | --- |
| VI-10 | 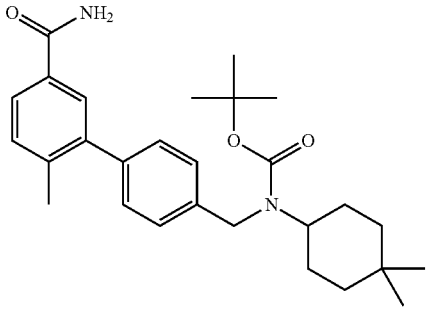 [SMILES: Cc1ccc(C(N)=O)cc1-c1ccc(CN(C(=O)OC(C)(C)C)C2CCC(C)(C)CC2)cc1]<br>1,1-dimethylethyl {[5'-(aminocarbonyl)-2'-methyl-4-biphenylyl]methyl}(4,4-dimethylcyclohexyl)carbamate | LC/MS (method A) $t_R$ 3.21 min; m/z 451 (M + H, 12%), 395 ([M − $C_4H_8$] + H, 100%) | Used aryl bromide IV-1 and aryl boronate V-19. |
| VI-11 | 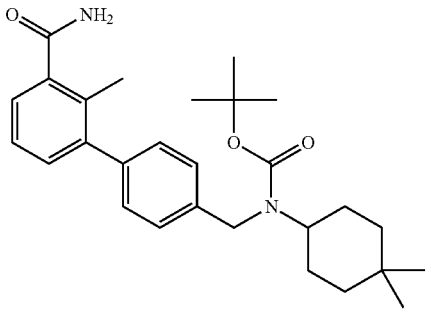 [SMILES: Cc1c(C(N)=O)cccc1-c1ccc(CN(C(=O)OC(C)(C)C)C2CCC(C)(C)CC2)cc1]<br>1,1-dimethylethyl {[3'-(aminocarbonyl)-2'-methyl-4-biphenylyl]methyl}(4,4-dimethylcyclohexyl)carbamate | LC/MS (method A) $t_R$ 3.21 min; m/z 451 (M + H, 25%), 473 (M + Na, 100%), 395 ([M − $C_4H_8$] + H, 66%) | Used aryl bromide IV-2 and aryl boronate V-19. |
| VI-12 | 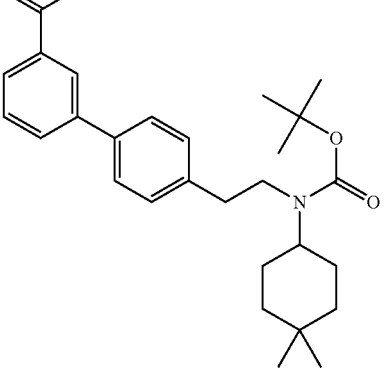<br>1,1-dimethylethyl {2-[3'-(aminocarbonyl)-4-biphenylyl]ethyl}(4,4-dimethylcyclohexyl)carbamate | LC/MS (method A) $t_R$ 3.19 min, m/z 451 (M + H, 24%), 901 (2M + H, 100%), 351 ([M − Boc] + H, 30%) | Used aryl bromide V-12 and 3-aminocarbonyl phenylboronic acid |

TABLE H-continued

Compounds of Formula VI from Suzuki coupling of Compounds of Formula IV or V.

| Ex | Structure/Name | Characterization Data | Comments |
|---|---|---|---|
| VI-13 | 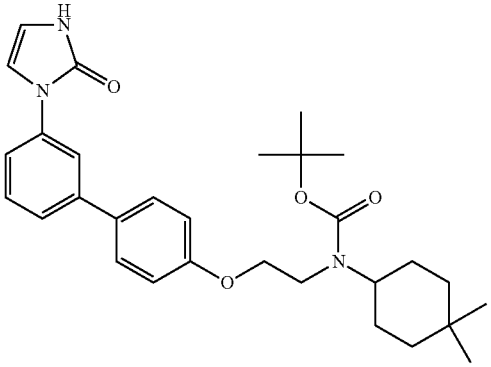 [SMILES: CC1(C)CCC(N(CCOc2ccc(-c3cccc(-n4cc[nH]c4=O)c3)cc2)C(=O)OC(C)(C)C)CC1]
1,1-dimethylethyl (4,4-dimethyl cyclohexyl)(2-{[3'-(2-oxo-2,3-dihydro-1H-imidazol-1-yl)-4-biphenylyl]oxy}ethyl)carbamate | LC/MS (method E) $t_R$ 1.13 min, m/z 450 ([M − $C_4H_8$] + H, 100%), 406 ([M − Boc] + H, 55%) | Used aryl bromide IV-35 and aryl boronate V-18. |
| VI-14 | 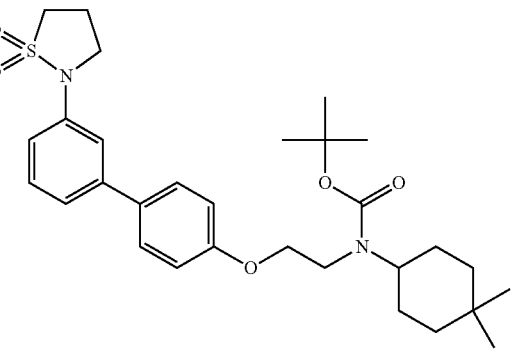
1,1-dimethylethyl (4,4-dimethylcyclohexyl)(2-{[3'-(1,1-dioxido-2-isothiazolidinyl)-4-biphenylyl]oxy}ethyl)carbamate | LC/MS (method E) $t_R$ 1.12 min, m/z 544 (M + H, 10%), 488 ([M − $C_4H_8$] + H, 100%) | Used aryl bromide IV-40 and aryl boronate V-18. |

Note 1:
$^1$H NMR (400 MHz, CDCl$_3$) δ 0.86 (s, 3H), 0.88 (s, 3H), 1.13-1.74 (m, 17 H), 3.42-4.10 (m, 1H), 4.35-4.54 (m, 2H), 5.74 (br. s, 1H), 6.19 (br. s, 1H), 7.30-7.36 (m, 2H), 7.51 (app. t, J = 7.7 Hz, 1H), 7.56 (m, 2H), 7.75 (m, 2H), 8.06 (br. s, 1H).

Example VI-15

1,1-Dimethylethyl (4,4-dimethylcyclohexyl)(2-{[3'-(1,2,4-oxadiazol-3-yl)-4-biphenylyl]oxy}ethyl)carbamate

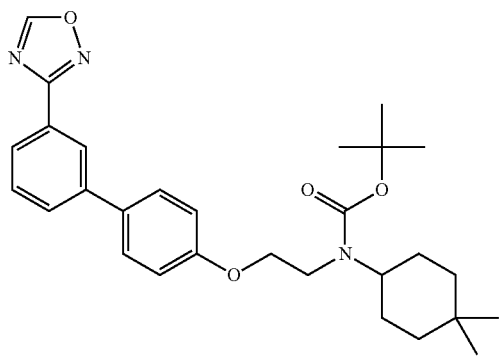 [SMILES: CC1(C)CCC(N(CCOc2ccc(-c3cccc(-c4ncon4)c3)cc2)C(=O)OC(C)(C)C)CC1]

Step 1: 1,1-dimethylethyl {2-[(3'-cyano-4-biphenylyl)oxy]ethyl}(4,4-dimethylcyclohexyl)carbamate A mixture of m-cyanophenyl boronic acid (0.086 g; 0.59 mmol), 1,1-dimethylethyl {2-[(4-bromophenyl)oxy]ethyl}(4,4-dimethylcyclohexyl)carbamate (0.250 g; 0.59 mmol; Example V-8), PdCl$_2$(dppf).CH$_2$Cl$_2$, 2M Na$_2$CO$_3$ (4 mL) and DME (4 mL) was sparged 5 min with N$_2$ and then heated to 80° C. for 5 h. Upon cooling, the mixture was diluted with EtOAc, washed with water and the washing was back-extracted with EtOAc (×2). Combined organics were washed (water, brine), dried over Na$_2$SO$_4$, adsorbed onto a minimal amount of silica gel and purified by flash chromatography (EtOAc/hexanes), affording the title compound as a colorless gum. $^1$H NMR (400 MHz, CDCl$_3$) δ 0.92 (s, 3H), 0.94 (s, 3H, partially overlapping 0.92), 1.21-1.87 (m, 17H), 3.45-3.63 (m, 2H), 3.88 (br. s, 1H), 4.10 (br. s, 2H), 7.00 (m, 2H), 7.49 (m, 2H), 7.52 (d, J=7.8 Hz, 1H; partially overlapping 7.49), 7.58 (d, J=7.6 Hz, 1H), 7.77 (partially resolved ddd, J$_{ortho}$=7.8 Hz, 1H), 7.82 (unresolved dd, 1H).

Step 2: 1,1-Dimethylethyl (4,4-dimethylcyclohexyl) (2-{[3'-(1,2,4-oxadiazol-3-yl)-4-biphenylyl]oxy}ethyl)carbamate To a solution of 1,1-dimethylethyl {2-[(3'-cyano-4-biphenyl)oxy]ethyl}(4,4-dimethylcyclohexyl)carbamate (0.125 g; 0.279 mmol; step 1 above) in EtOH (2.5 mL) at room temperature was added a solution of hydroxylamine (0.25 mL of a 50 wt % aq solution). The mixture was stirred 70 h at room temperature and volatiles were removed in vacuo (1×PhMe chase). The residue was dissolved in trimethyl orthoformate (2 mL), TsOH.H$_2$O (0.0025 g; 0.013 mmol) was added and the mixture was heated at 100° C. in a sealed vial for 1 h. Upon cooling, the mixture was adsorbed onto a small amount of silica gel and purified by flash chromatography (EtOAc/hexanes), affording the title compound as a colorless gum. LC/MS (method A) t$_R$ 3.34 min, m/z 492 (M+H, 5%), 514 (M+Na, 100%), 392 ([M-Boc]+H, 53%).

Example VI-16

1,1-dimethylethyl (4,4-dimethylcyclohexyl)[(3'-{[(2-phenylethyl)amino]carbonyl}-4-biphenylyl)methyl]carbamate

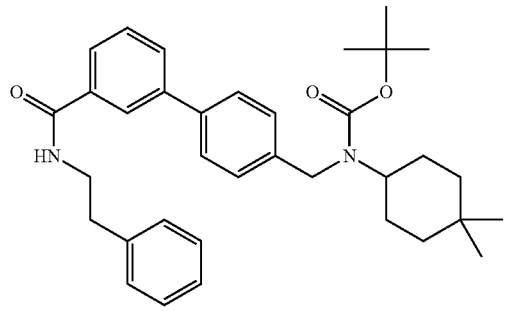 [SMILES: CC1(C)CCC(N(Cc2ccc(-c3cccc(C(=O)NCCc4ccccc4)c3)cc2)C(=O)OC(C)(C)C)CC1]

Step 1: methyl 4'-[((4,4-dimethylcyclohexyl){[(1,1-dimethylethyl)oxy]carbonyl}amino)methyl]-3-biphenylcarboxylate A flask equipped with a septum-sealed reflux condenser was charged with 1,1-dimethylethyl [(4-bromophenyl)methyl] (4,4-dimethylcyclohexyl)carbamate (0.988 g; 2.49 mmol; Example V-11), {3-[(methyloxy)carbonyl]phenyl}boronic acid (0.493 g; 2.74 mmol), Pd(OAc)$_2$ (0.0028 g; 0.012 mmol) and 2-(2',6'-dimethoxybiphenyl)di-cyclohexylphosphine (S-Phos; 0.010 g; 0.025 mmol;) was evacuated and back-filled with N$_2$ several times. PhMe/EtOH (4:1 v/v, 7.5 mL), and 2M Na$_2$CO$_3$ were added via syringe through the condensers septum and the mixture was heated under reflux for 2 h (until consumption of the aryl bromide was observed). Upon cooling, the mixture was poured into EtOAc/water, the whole was filtered through a 0.45 μm PTFE membrane filter and the layers were separated. The aqueous layer was extracted with EtOAc, combined organics were washed (brine), dried over Na$_2$SO$_4$ and concentrated in vacuo. The residue was purified by flash chromatography (EtOAc/hexanes), affording the title compound as a colorless gum/syrup. $^1$H NMR (400 MHz, DMSO-d$_6$) δ ppm 0.85 (s, 6 H), 1.07-1.79 (m, 18 H), 3.89 (s, 3 H), 4.42 (br. s., 2 H), 7.36 (d, J=8.03 Hz, 2 H), 7.62 (t, J=7.85 Hz, 1 H), 7.67 (d, J=8.03 Hz, 2 H), 7.95 (t, J=6.96 Hz, 2 H), 8.18 (s, 1 H).

Step 2: 4'-[((4,4-dimethylcyclohexyl){[(1,1-dimethylethyl)oxy]carbonyl}amino)-methyl]-3-biphenylcarboxylic acid A mixture of methyl 4'-[((4,4-dimethylcyclohexyl){[(1,1-dimethylethyl)oxy]carbonyl}-amino)methyl]-3-biphenylcarboxylate (0.850 g; 1.88 mmol), LiOH.H$_2$O (0.395 g; 9.40 mmol), water (2 mL) and THF (20 mL) was heated under reflux for 24 h, cooled and concentrated in vacuo. The residue was partitioned between EtOAc/1N KHSO$_4$, layers were separated and the organic layer was extracted with EtOAc (×2). combined organics were washed (water, brine), dried over Na$_2$SO$_4$ and concentrated in vacuo affording the title compound as a colorless foam. LC/MS (method E) t$_R$ 0.77 min; m/z 464 (M−H).

Step 3: 1,1-dimethylethyl (4,4-dimethylcyclohexyl)[(3'-{[(2-phenylethyl)amino]-carbonyl}-4-biphenylyl)methyl]carbamate To a solution of 4'-[((4,4-dimethylcyclohexyl){[(1,1-dimethylethyl)oxy]carbonyl}amino)-methyl]-3-biphenylcarboxylic acid (0.100 g; 0.23 mmol) in DMF (2 mL) was added DIEA (0.035 mL; 0.25 mmol), and HATU (0.095 g; 0.25 mmol). The solution was aged 5 min at room temperature and phenethylamine (0.031 mL; 0.25 mmol) was added. After 45 min the mixture was partitioned between EtOAc and half-satd Na$_2$CO$_3$, layers were separated and the aqueous layer was extracted with EtOAc (×2). Combined organics were washed (water, brine), dried over Na$_2$SO$_4$ and concentrated in vacuo. The residue was purified by flash chromatography (EtOAc/hexanes), affording the title compound as a colorless gum. LC/MS (method E) t$_R$ 1.19 min; m/z 541 (M+H).

The following were prepared from 4'-[((4,4-dimethylcyclohexyl){[(1,1-dimethylethyl)oxy]-carbonyl}amino)methyl]-3-biphenylcarboxylic acid (Example VI-16 Step 2) and the appropriate amines according to the procedure described for Example VI-16 Step 3.

TABLE I

Compounds of Formula VI from amide coupling to Example VI-16 Step 2

| Ex | Structure/Name | Characterization Data | Comments |
|---|---|---|---|
| VI-17 | 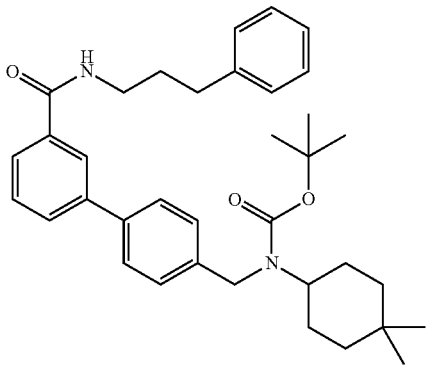 [SMILES: CC1(C)CCC(N(Cc2ccc(-c3cccc(C(=O)NCCCc4ccccc4)c3)cc2)C(=O)OC(C)(C)C)CC1]<br>1,1-dimethylethyl (4,4-dimethyl-cyclohexyl)[(3'-{[(3-phenylpropyl)-amino]carbonyl}-4-biphenylyl)-methyl]carbamate | LC/MS (method E) $t_R$ 1.22 min; m/z 555 (M + H). | |
| VI-18 | 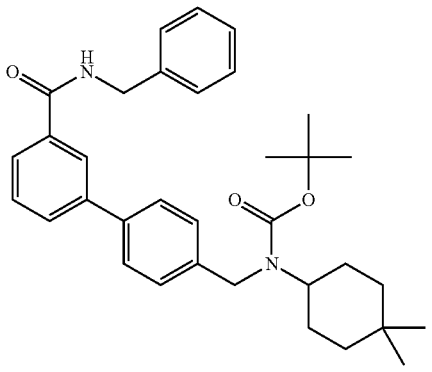 [SMILES: CC1(C)CCC(N(Cc2ccc(-c3cccc(C(=O)NCc4ccccc4)c3)cc2)C(=O)OC(C)(C)C)CC1]<br>1,1-dimethylethyl (4,4-dimethyl-cyclohexyl)[(3'-{[(phenylmethyl)-amino]carbonyl}-4-biphenylyl)-methyl]carbamate | LC/MS (method E) $t_R$ 1.17 min; m/z 527 (M + H). | |
| VI-19 | 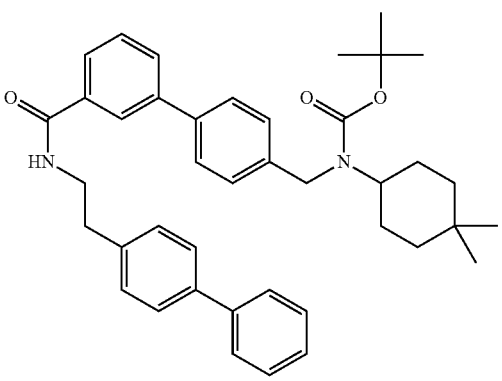 [SMILES: CC1(C)CCC(N(Cc2ccc(-c3cccc(C(=O)NCCc4ccc(-c5ccccc5)cc4)c3)cc2)C(=O)OC(C)(C)C)CC1]<br>1,1-dimethylethyl {[3'-({[2-(4-biphenylyl)ethyl]amino}carbonyl)-4-biphenylyl]methyl}(4,4-dimethylcyclohexyl)carbamate | LC/MS (method E) $t_R$ 1.27 min; m/z 617 (M + H) | |

Example VI-20

1,1-dimethylethyl 2,3-dihydro-1H-inden-2-yl{[3'41H-imidazol-4-yl)-4-biphenylyl]methyl}carbamate

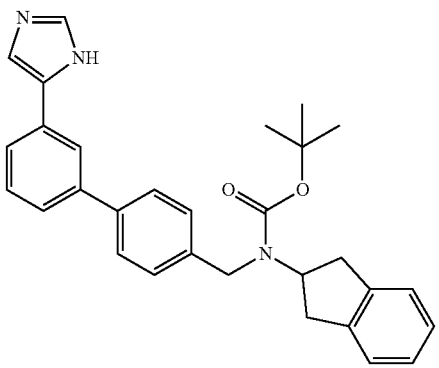 [SMILES: CC(C)(C)OC(=O)N(Cc1ccc(-c2cccc(-c3cnc[nH]3)c2)cc1)C1Cc2ccccc2C1]

Step 1: 1,1-dimethylethyl 2,3-dihydro-1H-inden-2-yl[(3'-formyl-4-biphenylyl)-methyl]carbamate The title compound was prepared from 1,1-dimethylethyl [(4-bromophenyl)methyl]2,3-dihydro-1H-inden-2-ylcarbamate (Example V-13) and 3-formylphenylboronic acid according to the procedure described in Example VI-16 Step 1. 1H NMR (400 MHz, DMSO-$d_6$) δ ppm 1.35 (s, 9 H), 3.00 (d, J=8.56 Hz, 4 H), 4.51 (br. s., 2 H), 7.06-7.19 (m, 4 H), 7.34 (d, J=8.03 Hz, 2 H), 7.69 (t, J=7.67 Hz, 1 H), 7.72-7.77 (m, 2 H), 7.86-7.91 (m, 1 H), 8.01-8.06 (m, 1 H), 8.19-8.24 (m, 1 H), 10.10 (s, 1 H).

Step 2: 1,1-dimethylethyl 2,3-dihydro-1H-inden-2-yl[(3'-{4-[(4-methylphenyl)-sulfonyl]-4,5-dihydro-1,3-oxazol-5-yl}-4-biphenylyl)methyl]carbamate To a solution of 1,1-dimethylethyl 2,3-dihydro-1H-inden-2-yl[(3'-formyl-4-biphenylyl)-methyl]carbamate (0.188 g; 0.44 mmol) and TosMIC (0.086 g; 0.44 mmol) in EtOH at room temperature was added NaCN (0.002 g; 0.04 mmol). The mixture was stirred 30 min, diluted with water and extracted with EtOAc (×3). combined organics were washed (water, brine), dried over $Na_2SO_4$ and concentrated in vacuo affording the title compound as a colorless gum, used without further purification. 1H NMR (400 MHz, DMSO-$d_6$) δ ppm 1.35 (s, 9 H), 2.41 (s, 3 H), 2.99 (d, J=8.38 Hz, 4 H), 4.50 (br. s., 2 H), 5.65 (dd, J=5.98, 1.69 Hz, 1 H), 5.96 (d, J=5.89 Hz, 1 H), 7.07-7.18 (m, 5 H), 7.25 (partially resolved dd, J=7.85 Hz, 1 H), 7.28-7.34 (m, 2 H), 7.40 (unresolved dd, 1 H), 7.46-7.52 (m, 3 H), 7.57-7.64 (m, 2 H), 7.68 (dd, J=8.03, 1.25 Hz, 1 H), 7.74 (d, J=1.25 Hz, 1 H), 7.83-7.90 (m, 2 H).

Step 3: 1,1-dimethylethyl 2,3-dihydro-1H-inden-2-yl{[3'-(1H-imidazol-4-yl)-4-biphenylyl]methyl}carbamate A mixture of 1,1-dimethylethyl 2,3-dihydro-1H-inden-2-yl[(3'-{4-[(4-methylphenyl)-sulfonyl]-4,5-dihydro-1,3-oxazol-5-yl}-4-biphenyl)methyl]carbamate (0.260 g; 0.418 mmol) and $NH_3$ in MeOH (5 mL of a 7M solution) was sealed in a pressure tube and heated at 90° C. After 51 h, volatiles were removed in vacuo, a fresh charge of $NH_3$ in MeOH was added to the residue and heating was continued an additional 15 h. Upon cooling, the whole was adsorbed onto a minimal amount of Celite and purified by flash chromatography (EtOAc/hexanes), affording the title compound as a colorless film. 1H NMR (400 MHz, $CDCl_3$) δ ppm 1.42 (s, 9 H), 2.94-3.18 (m, J=15.87, 15.79, 15.79, 8.20 Hz, 4 H), 4.48 (br. s., 2 H), 4.65-5.22 (br. m, 1H), 7.13 (s, 6H), 7.24 (m, 2 H), 7.36 (s, 1 H), 7.39-7.51 (m, 3 H), 7.54-7.60 (m, 2 H), 7.64-7.71 (m, 3 H), 7.96 (br. s., 1 H).

Compounds of Formula VII

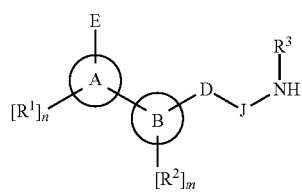

Formula VII

Intermediates of Formula VII

Intermediate I-VII-1

1,1-Dimethylethyl (2-{[3'-(aminocarbonyl)-2-methyl-4-biphenylyl]oxy}ethyl)carbamate

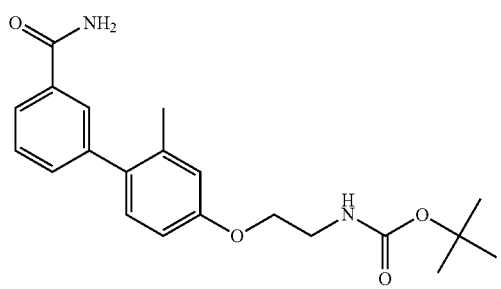 [SMILES: Cc1cc(OCCNC(=O)OC(C)(C)C)ccc1-c1cccc(C(N)=O)c1]

A mixture of 1,1-dimethylethyl {2-[(4-bromo-3-methylphenyl)oxy]ethyl}carbamate (0.102 g, 0.31 mmol; Example V-15), 3-(aminocarbonyl)phenylboronic acid (0.056 g; 0.34 mmol), $PdCl_2(dppf)\cdot CH_2Cl_2$ (0.0075 g; 0.01 mmol), DME (2 mL) and 2M $Na_2CO_3$ (2 mL) was degassed by sparging with $N_2$, (5-10 min) then stirred at 80° C. for 5.5 h. Upon cooling, the mixture was diluted with EtOAc washed (water, brine), dried over $Na_2SO_4$ and concentrated in vacuo. The residue was purified by flash chromatography (EtOAc/hexanes), affording the title compound as a colorless foam. LC/MS (method A) 2.59 min, m/z 371 (M+1, 2%), 392 (M+Na, 53%), 271 ([M−Boc]+H, 100%).

The following intermediates were prepared from the appropriate aryl halide/triflate and aryl boronic acid/boronate according to the procedure described for I-VII-1, with any significant deviations noted below table.

TABLE J

Intermediates to Compounds of Formula VII

| Ex | Structure/Name | Characterization Data | Comments |
|---|---|---|---|
| I-VII-2 | 1,1-dimethylethyl {2-[4'-(amino-carbonyl)-3-biphenylyl]ethyl} carbamate | Note 5 | Used aryl bromide V-14 and 4-(aminocarbonyl)phenylboronic acid. Note 1, 2 |
| I-VII-3 | 1,1-dimethylethyl 4-[4'-(amino-carbonyl)-3-biphenylyl]-1-piperidinecarboxylate | Note 6 | Used 4(aminocarbonyl)-phenyl boronic acid and the corresponding aryl halide. Note 1, 2 |
| I-VII-4 | 1,1-dimethylethyl {5-[3-(aminocarbonyl)phenyl]-2,3-dihydro-1H-inden-2-yl}carbamate | Note 7 | Used product of Ex III-12 Step 1 as aryl bromide and 3-(aminocarbonyl)-phenyl boronic acid. Note 3 |
| I-VII-5 | 1,1-dimethylethyl 6-[3-(aminocarbonyl)-2-methylphenyl]-3,4-dihydro-2(1H)-isoquinolinecarboxylate | LC/MS (method A) 2.61 min; m/z 367 (M + H) | Used aryl bromide IV-2 and aryl boronate V-20. Note 3 |

TABLE J-continued

Intermediates to Compounds of Formula VII

| Ex | Structure/Name | Characterization Data | Comments |
|---|---|---|---|
| I-VII-6 | 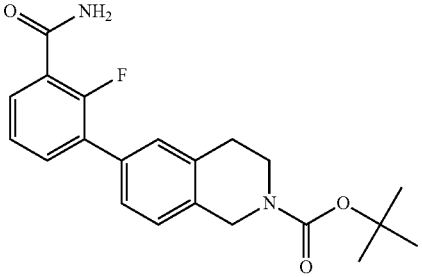 [SMILES: CC(C)(C)OC(=O)N1CCc2cc(-c3cccc(C(N)=O)c3F)ccc2C1]<br>1,1-dimethylethyl 6-[3-(aminocarbonyl)-2-fluorophenyl]-3,4-dihydro-2(1H)-isoquinolinecarboxylate | LC/MS (method A) 2.6 min; m/z 371 (M + H, 5%), 315 ([M − C4H8] + H, 100%), 271 ([M − Boc] + H, 70%) | Used aryl bromide IV-16 and aryl boronate V-20. Note 3 |
| I-VII-7 | 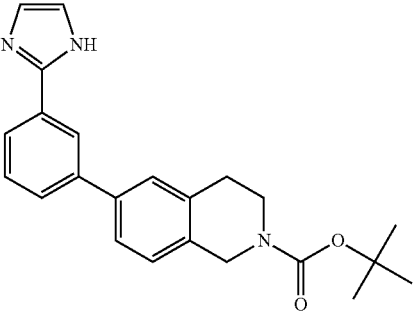 [SMILES: CC(C)(C)OC(=O)N1CCc2cc(-c3cccc(-c4ncc[nH]4)c3)ccc2C1]<br>1,1-dimethylethyl 6-[3-(1H-imidazol-2-yl)phenyl]-3,4-dihydro-2(1H)-isoquinolinecarboxylate | LC/MS (method A) 2.02 min; m/z 376 (M + H) | Used aryl bromide IV-21 and aryl boronate 20. Note 3 |
| I-VII-8 | 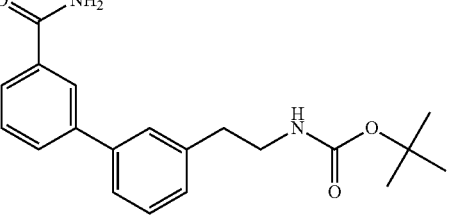<br>1,1-dimethylethyl {2-[3'-(aminocarbonyl)-3-biphenylyl]ethyl}carbamate | LC/MS (method E) 0.73 min; m/z 341 (M + H) | Used aryl bromide V-14 and 3-(aminocarbonyl)-phenyl boronic acid Note 2, 3, 4. |

Note 1
1:1 Acetonitrile/0.4M Na$_2$CO$_3$ was used instead of DME/2M Na$_2$CO$_3$. Pd(PPh$_3$)$_4$ was used instead of PdCl$_2$(dppf)•CH$_2$Cl$_2$.

Note 2
Chromatographic purification omitted.

Note 3
4:1 PhMe/EtOH used instead of DME.

Note 4
2-(2',6'-dimethoxybiphenyl)di-cyclohexylphosphine (S-Phos)/Pd(OAc)$_2$ was used instead of PdCl$_2$(dppf)•CH$_2$Cl$_2$.

Note 5
(I-VII-2) $^1$H NMR (400 MHz, DMSO-d$_6$) delta ppm 1.33 (s, 9 H); 2.75 (t, J = 7.3 Hz, 2 H); 3.19 (m, 2 H); 6.91 (t, J = 5.5 Hz, 1 H); 7.20 (d, J = 7.51, 1 H); 7.38 (m, 2H); 7.53 (m, 2H); 7.72 (d, J = 8.2, 2H); 7.92 (d, J = 8.4, 2H); 8.01 (br. s, 1H).

Note 6
(I-VII-3) $^1$H NMR (400 MHz, DMSO-d$_6$) δ ppm 1.39 (s, 9H), 1.50-1.61 (qd, 2H), 1.78 (br. d, 2H), 2.71-2.77 (br. m, 3H), 4.01-4.09 (br. d, 2H), 7.25 (d, 1H), 7.36-7.40 (m, 2H), 7.52-7.56 (m, 2H), 7.73 (d, 2H), 7.93 (d, 2H), 8.00 (s, 1H).

Note 7
(I-VII-4) $^1$H NMR (400 MHz, DMSO-d$_6$) δ ppm 1.40 (s, 9 H), 2.82 (td, J = 15.1, 7.0 Hz, 2 H), 3.16 (td, J = 14.3, 7.7 Hz, 2 H), 4.26 (app. sext, J = 7.0 Hz, 1 H), 7.21 (d, J = 6.6 Hz, 1 H), 7.29 (d, J = 7.7 Hz, 1 H), 7.43 (br. s., 1 H), 7.46-7.54 (m, 2 H), 7.55 (s, 2 H), 7.77 (d, J = 8.0 Hz, 1 H), 7.82 (d, J = 7.7 Hz, 1 H), 8.07-8.15 (m, 2 H).

Intermediate I-VII-9

1,1-dimethylethyl 6-[3-(aminocarbonyl)phenyl]-3,4-dihydro-2(1H)-isoquinolinecarboxylate

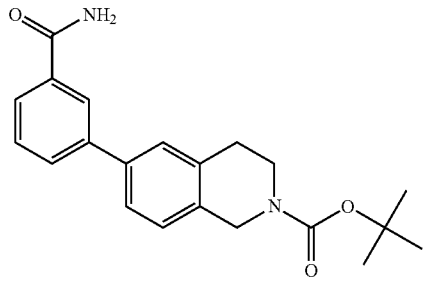 [SMILES: CC(C)(C)OC(=O)N1CCc2cc(-c3cccc(C(N)=O)c3)ccc2C1]

A solution of 3-(aminocarbonyl)phenyl boronic acid (0.663 g; 4.0 mmol), 1,1-dimethylethyl 6-{[(trifluoromethyl)sulfonyl]oxy}-3,4-dihydro-2(1H)-isoquinoline carboxylate (1.28 g; 3.35 mmol; Ex V-16) in DMF (10 mL) was sparged with $N_2$ for 10 min, $K_3PO_4$ (1.7 g; 8.0 mmol) and $Pd(PPh_3)_4$ (0.193 g; 0.17 mmol) were added and the mixture was stirred at 100° C. for 2 h. Upon cooling, the mixture was poured into water and extracted with EtOAc (×3). Combined organics were washed ($H_2O$, brine), and dried over $Na_2SO_4$. Residual solids were collected from the aqueous layer by filtration, air-dried, dissolved in hot EtOH and combined with the dried EtOAc extracts. The whole was adsorbed onto a minimal amount of silica gel and purified by flash chromatography (EtOAc/hexanes), affording the title compound as a as a colorless solid. LC/MS (method B) 2.69 min; m/z 297 ([M−$C_4H_8$]+H, 70%), 253 ([M−Boc]+H, 74%).

Intermediate I-VII-10

1,1-dimethylethyl 7-[4-(amino-carbonyl)phenyl]-3,4-dihydro-2(1H)-isoquinolinecarboxylate

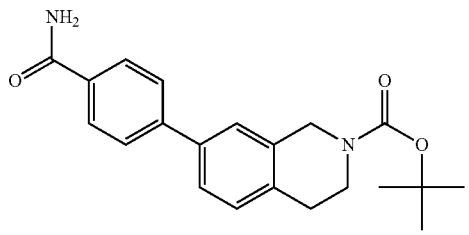 [SMILES: CC(C)(C)OC(=O)N1CCc2ccc(-c3ccc(C(N)=O)cc3)cc2C1]

The title compound was prepared from 1,1-dimethylethyl 7-{[(trifluoromethyl)sulfonyl]oxy}-3,4-dihydro-2(1H)-isoquinoline carboxylate (Ex V-17) and 4-(aminocarbonyl)-phenyl boronic acid according to the procedure described for I-VII-9. Tan solid; LC/MS (method A) 2.62 min; m/z 353 (M+H, 75%), 297 ([M−$C_4H_8$]+H, 100%).

Note Intermediates I-VII-9 and I-VII-10 may also be prepared using conventional biphasic conditions similar to I-VII-1, however, in our hands, the anhydrous conditions described above proved higher yielding for tetrahydroisoquinoline (THiQ) triflates.

Compounds of Formula VII

Example VII-1

4'-[(2-Aminoethyl)oxy]-2'-methyl-3-biphenylcarboxamide trifluoroacetate

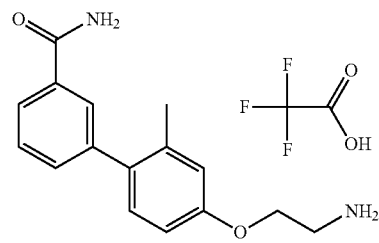 [SMILES: Cc1cc(OCCN)ccc1-c1cccc(C(N)=O)c1 ; O=C(O)C(F)(F)F]

To a solution of 1,1-dimethylethyl (2-{[3'-(aminocarbonyl)-2-methyl-4-biphenylyl]oxy}ethyl)carbamate (0.090 g; 0.24 mmol; I-VII-2) and $Et_3SiH$ (0.1 mL; 0.6 mmol) in $CH_2Cl_2$ (5 mL) at room temperature was added TFA (1 mL) in one portion. The mixture was aged 2 h and concentrated in vacuo, affording the title compound as a pale yellow gum which was used without further purification. LC/MS (method A) 1.18 min, m/z 271 (M+H).

Example VII-2

3'(2-aminoethyl)-4-biphenylcarboxamide

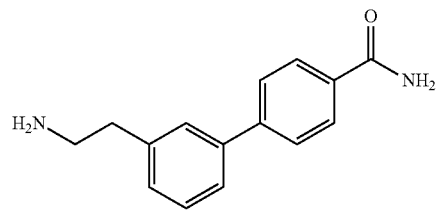 [SMILES: NCCc1cccc(-c2ccc(C(N)=O)cc2)c1]

To a solution of 1,1-dimethylethyl {2-[4'-(aminocarbonyl)-3-biphenylyl]ethyl}-carbamate (1.81 g, 0.005 mol) in $CH_2Cl_2$ (50 mL) at room temperature was added trifluoroacetic acid (15 mL) in one portion. After 1 hr the mixture was cooled in an ice bath and 1M $K_2CO_3$ (200 mL) and chloroform were added. The aqueous phase was extracted several times with mixtures of ethyl acetate, dichloromethane and chloroform. Residual solids were collected by filtration, affording the title compound as a white solid; LC/MS (method A) 1.04 min; m/z 241 (M+H). Combined organic extracts were dried over $Na_2SO_4$ and concentrated in vacuo affording an additional batch of the title compound (combined with the solid collected above). This product was used without further purification.

Example VII-3

3'-(4-piperidinyl)-4-biphenylcarboxamide hydrochloride

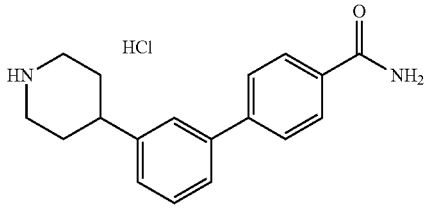 [SMILES: NC(=O)c1ccc(-c2cccc(C3CCNCC3)c2)cc1 ; Cl]

A mixture of 1,1-dimethylethyl 4-[4'-(aminocarbonyl)-3-biphenylyl]-1-piperidine carboxylate (0.95 g, 0.0025 mol; I-VII-3) and 4N HCl in dioxane (5 mL) in dichloromethane (5 mL) was stirred at ambient temperature for 3 hr. The resulting solid was collected by filtration, washed with dichloromethane, diethyl ether and air-dried to give the title compound as a white solid, used without further purification. LC/MS (method A) 1.17 min; m/z 281 (M+H).

Example VII-4

3-(1,2,3,4-tetrahydro-6-isoquinolinyl)benzamide

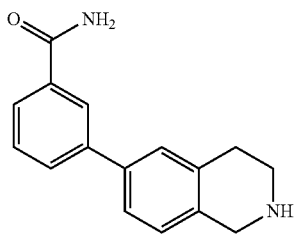 [SMILES: NC(=O)c1cccc(-c2ccc3c(c2)CCNC3)c1]

To a solution of 1,1-dimethylethyl 6-[3-(aminocarbonyl)phenyl]-3,4-dihydro-2(1H)-isoquinolinecarboxylate (0.725 g; 2.20 mmol; I-VII-9) and $Et_3SiH$ (0.88 mL; 5.5 mmol) in $CH_2Cl_2$ (25 mL) at room temperature was added TFA (10 mL) in one portion. The mixture was aged 3 h and concentrated in vacuo (2×PhMe chase). The residue was partitioned between satd $Na_2CO_3/CHCl_3$ (Note 1), layers were separated and the aqueous layer was extracted with $CHCl_3$ (×4). Combined organics were washed (water, brine), dried over $Na_2SO_4$ and concentrated in vacuo, affording the title compound as a colorless solid. $^1H$ NMR (400 MHz, DMSO-$d_6$) δ ppm 2.76 (t, J=5.7 Hz, 2 H), 2.96 (t, J=5.8 Hz, 2 H), 3.87 (s, 2 H), 7.11 (d, J=7.9 Hz, 1 H), 7.40-7.48 (m, 3 H), 7.51 (t, J=7.8 Hz, 1 H), 7.78 (ddd, J=7.7, 1.8, 1.1 Hz, 1 H), 7.82 (ddd, J=7.8, 1.4, 1.3 Hz, 1 H), 8.10 (s, 1 H), 8.12 (t, J=1.6 Hz, 1 H).

Note 1 A small amount of MeOH was added during extraction with $CHCl_3$ to facilitate dissolution of the solid residue.

Example VII-5

3-(2-amino-2,3-dihydro-1H-inden-5-yl)benzamide

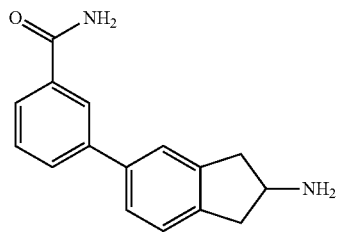 [SMILES: NC(=O)c1cccc(-c2ccc3c(c2)CC(N)C3)c1]

The title compound was prepared from 1,1-dimethylethyl {5-[3-(amino-carbonyl)phenyl]-2,3-dihydro-1H-inden-2-yl}carbamate (I-VII-4) according to the procedure described in Example VII-4. $^1H$ NMR (400 MHz, DMSO-$d_6$) δ ppm 1.71 (br. s., 2 H), 2.55-2.69 (m, 2 H), 3.00-3.14 (m, 2 H), 3.68-3.77 (m, 1 H), 7.28 (d, J=7.7 Hz, 1 H), 7.42 (s, 1 H), 7.46 (dd, J=7.7, 1.8 Hz, 1 H), 7.51 (t, J=7.8 Hz, 1 H), 7.54 (s, 1 H), 7.77 (app. ddd, J=7.8, 1.8, 1.1 Hz, 1 H), 7.82 (app. ddd, J=7.8, 1.7, 1.2 Hz, 1 H), 8.10 (br. s., 1 H), 8.12 (t, J=1.7 Hz, 1 H).

Example VII-6

3'-(2-aminoethyl)-3-biphenylcarboxamide

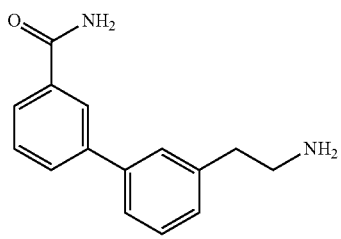 [SMILES: NCCc1cccc(-c2cccc(C(N)=O)c2)c1]

The title compound was prepared from 1,1-dimethylethyl {2-[3'-(aminocarbonyl)-3-biphenylyl]ethyl}carbamate (I-VII-8) according to the procedure described in Example VII-4. $^1H$ NMR (400 MHz, DMSO-$d_6$) δ ppm 1.43 (br. s., 2 H), 2.68-2.75 (m, 2 H), 2.79-2.85 (m, 2 H), 7.23 (d, J=7.7 Hz, 1 H), 7.39 (app. t, J=7.8 Hz, 1 H), 7.44 (br. s., 1 H), 7.50-7.56 (m, 3 H), 7.81 (app. ddd, J=7.8, 1.8, 1.2 Hz, 1 H), 7.85 (app. ddd, J=7.7, 1.6, 1.1 Hz, 1 H), 8.11 (br. s., 1 H), 8.14 (app. t, J=1.6 Hz, 1 H).

Example VII-7

4'-(2-aminoethyl)-3-biphenylcarboxamide

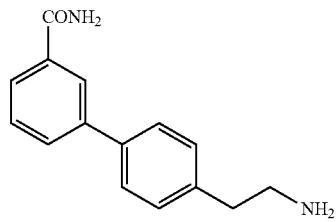 [SMILES: NCCc1ccc(-c2cccc(C(N)=O)c2)cc1]

The title compound was prepared from 3-(aminocarbonyl)-phenyl boronic acid and 4-bromophenethylamine according to the procedure described for intermediate I-VII-1 with the exceptions that 4:1 PhMe/EtOH was sued as organic solvent (instead of DME) and the chromatographic purification step was omitted. LC/MS (method E) 0.53 min; m/z 241 (M+H).

Compounds of Formula IX

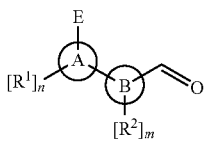

Formula IX

Formula IX Intermediates

The following compounds were employed as precursors of Formula IX compounds, and at the time of this writing were not readily available from commercial suppliers.

Intermediate I-IX-1

4-bromo-3-methylbenzaldehyde

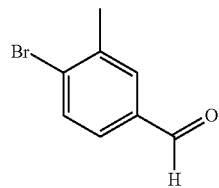

To a solution of 4-bromo-3-methylbenzonitrile (0.975 g; 5.00 mmol) in anhyd $CH_2Cl_2$ (7.5 mL) at −40° C. was added DIBAL-H (7.5 mL of a 1M solution in hexanes; 7.5 mmol), dropwise over 5 min. The mixture was stirred 30 min at −40° C., removed from the cooling bath and stirred 1 h at rt. The mixture was cooled in an ice bath, and excess hydride was quenched by dropwise addition of MeOH. After stirring 20 min, Rochelle's salt (satd aq. solution) was added, the mixture was stirred at rt overnight, and the layers were separated. The aqueous layer was extracted with $CH_2Cl_2$ (×2), combined organics were washed ($H_2O$, brine), dried over $Na_2SO_4$, filtered and concentrated in vacuo. The residue was purified by flash chromatography (EtOAc/hexanes), affording the title compound as a colorless solid (Note 1). $^1$H NMR (400 MHz, $CDCl_3$) δ 2.49 (s, 1H), 7.56 (dd, J=8.2 Hz, 1.8 Hz, 1H), 7.72 (d, J=8.2 Hz, 1H), 7.74 (d, J=1.7 Hz, 1H, partially overlapping 7.72), 9.96 (s, 1H).

Note 1 The title compound was oxidized rapidly on standing in air to a mixture of benzaldehyde and benzoic acid.

Intermediate I-IX-2

4-bromo-2-methylbenzaldehyde

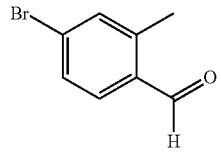

The title compound was prepared from 4-bromo-2-methylbenzonitrile according to the procedure described for Example I-IX-1 with exceptions as follows: the reaction temperature was −78° C. (instead of −40° C.); the reaction was quenched with MeOH at −78° C. (instead of ice bath temp), followed by addition of 6M HCl at −78° C. (instead of satd Rochelle's salt); after quenching the reaction mixture was stirred 30 min at room temperature (instead of overnight). Colorless oil; $^1$H NMR (400 MHz, $CDCl_3$) δ 2.65 (s, 3H), 7.45 (br. s, 1H), 7.51 (dd, J=8.3, 1.7 Hz, 1H), 7.66 (d, J=8.2 Hz, 1H), 10.22 (s, 1H).

Intermediate I-IX-3

4-formyl-2-(methoxy)phenyl trifluoromethanesulfonate

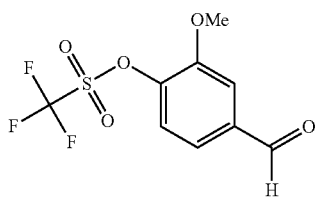 [SMILES: COc1cc(C=O)ccc1OS(=O)(=O)C(F)(F)F]

To a solution of 4-hydroxy-3-(methoxy)benzaldehyde (0.760 g; 5.00 mmol) and $Et_3N$ (1.39 mL; 10.0 mmol) in anhyd $CH_2Cl_2$ (10 mL) at 0° C. was added $Tf_2O$ (0.92 mL; 5.5 mmol), dropwise over 2 min. The mixture was allowed to warm slowly to room temperature (overnight), diluted with $CH_2Cl_2$, washed (water, brine), dried over $Na_2SO_4$ and concentrated in vacuo. The residue was purified by flash chromatography (EtOAc/hexanes), affording the title compound as a colorless oil. $^1$H NMR (400 MHz, $CDCl_3$) δ 4.01 (s, 3H), 7.42 (d, J=8.2 Hz, 1H), 7.52 (dd, J=8.2, 1.8 Hz, 1H), 7.57 (d, J=1.7 Hz, 1H), 9.99 (s, 1H).

Intermediate I-IX-4 (I-17)

2-chloro-4-formylphenyl trifluoromethanesulfonate

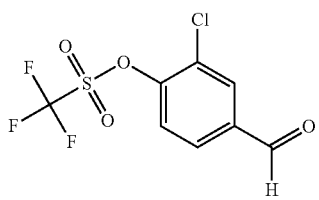 [SMILES: O=Cc1ccc(OS(=O)(=O)C(F)(F)F)c(Cl)c1]

The title compound was synthesized from 3-chloro-4-hydroxybenzaldehyde, as described for the synthesis of Example I-IX-3 above. ¹H NMR (400 MHz, CDCl₃) δ 7.56 (d, J=8.5 Hz, 1H), 7.89 (dd, J=8.5 Hz, 1.9 Hz, 1H), 8.07 (d, J=1.9 Hz, 1H), 10.01 (s, 1H).

Intermediate I-IX-5 (I-18)

2-fluoro-4-formylphenyl trifluoromethanesulfonate

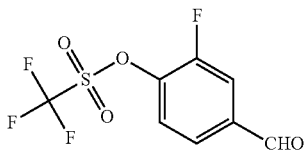 [SMILES: O=Cc1ccc(OS(=O)(=O)C(F)(F)F)c(F)c1]

The title compound was synthesized from 3-fluoro-4-hydroxybenzaldehyde, as described for the synthesis of Example I-IX-3 above. ¹H NMR (400 MHz, CDCl₃) δ 7.56 (m, 1H), 7.80 (m, 2H), 10.01 (d, J=1.5 Hz, 1H).

Intermediate I-IX-6 (I-19)

4-iodo-3-(trifluoromethyl)benzonitrile

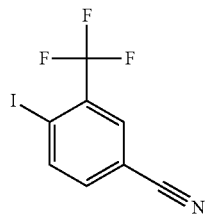 [SMILES: N#Cc1ccc(I)c(C(F)(F)F)c1]

To a slurry of 4-amino-3-(trifluoromethyl)benzonitrile (5.48 g; 29.5 mmol) in HBF₄ (50 mL; 48%) at −10° C. was added NaNO₂ (2.24 g; 32.4 mmol), portionwise over 10 min. The mixture was stirred 30 min, precipitated solids were collected by filtration (Note 1) and (without delay) added portionwise to a solution of KI (7.84 g; 47.2 mmol) in acetone/water (50 mL of a 40% v/v solution). The mixture was decolorized by addition of 10 wt % Na₂S₂O₃, precipitate was collected by filtration, washed with water and slurried in PhMe. The slurry was concentrated to dryness, affording the title compound as a pale orange solid, used without further purification.

¹H NMR (400 MHz, DMSO-d₆) δ 7.83 (dd, J=8.1, 1.6 Hz, 1H), 8.27 (d, J=1.5 Hz, 1H), 8.37 (d, J=8.1 Hz, 1H).

Note 1 Solid was not allowed to dry completely on the filter.

Intermediate I-IX-7

2-[4-iodo-2-(trifluoromethyl)phenyl]-1,3-dioxolane

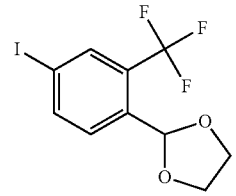 [SMILES: FC(F)(F)c1cc(I)ccc1C1OCCO1]

To a solution of 4-iodo-2-(trifluoromethyl)benzonitrile (1.89 g; 6.38 mmol, Note 1) in CH₂Cl₂ (15 mL) at −40° C. was added DIBAL-H (9.6 mL of a 1.0M solution in CH₂Cl₂; 9.6 mmol), dropwise over 5 min. The mixture was stirred 30 min, quenched by dropwise addition of MeOH and removed from the cooling bath. To the still-cold mixture was slowly added HCl (10 mL of a 6M solution), and after stirring 30 min at room temperature the layers were separated. The aqueous layer was extracted with CH₂Cl₂ (×2), combined organics were washed (water, brine), dried over Na₂SO₄ and concentrated in vacuo. The residue was dissolved in PhH (15 mL), along with TsOH.H₂O (0.12 g; 0.64 mmol) and ethylene glycol (3.5 mL; 63 mmol), and the solution was heated under reflux for 2 h using a Dean-Stark trap to remove water. Upon cooling, the mixture was diluted with <solvent>, washed (water, brine), dried over Na₂SO₄, and concentrated in vacuo. The residue was purified by flash chromatography (EtOAc/hexanes), affording the title compound as a pale yellow oil. ¹H NMR (400 MHz, CDCl₃) δ ppm 4.00-4.11 (m, 2 H), 4.11-4.24 (m, 2 H), 6.06 (s, 1 H), 7.54 (d, J=8.4 Hz, 1 H), 7.93 (d, J=8.4 Hz, 1 H), 7.99 (s, 1 H).

Note 1: 4-iodo-2-(trifluoromethyl)benzonitrile is commercially available from various commercial suppliers; e.g., Apollo Scientific Ltd, Bredbury, Stockport, Cheshire, UK.

Intermediate I-IX-8

4-(1,3-dioxolan-2-yl)-3-(trifluoromethyl)phenylboronic acid

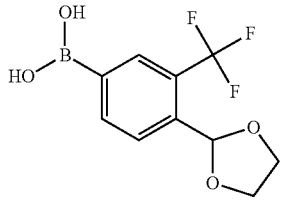

The title compound was prepared from 2-[4-iodo-2-(trifluoromethyl)phenyl]-1,3-dioxolane (Example I-IX-7) according to the procedure described for Example V-18, with the following exceptions: the aryl iodide and i-PrMgCl were aged 45 min before introduction of the electrophile (instead of 30 min); trimethyl borate was used as the electrophile (instead of 2-isopropoxy-4,4,5,5-tetramethyl-1,3,2-dioxaborolane); the dried organic extracts were concentrated to dryness and triturated with Et₂O/hexanes (instead of flash chromatography). White solid. LC/MS (method A) 2.22 min, m/z 417 ({2[M-gylcol]-H₂O}—H, 23%), 217 ([M-glycol]-H, 57%), 189 (100%, −ve ion).

Formula IX Compounds

Example IX-1

4'-formyl-3-biphenylcarboxamide

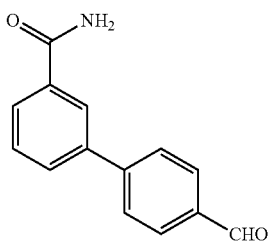 [SMILES: NC(=O)c1cccc(-c2ccc(C=O)cc2)c1]

A mixture of 4-bromobenzaldehyde (2.78 g; 15.0 mmol), [3-(aminocarbonyl)-phenyl]boronic acid (2.72 g; 16.5 mmol), $PdCl_2(dppf)·CH_2Cl_2$ (0.306 g; 0.38 mmol), DME (25 mL) and $Na_2CO_3$ (25 mL of a 2M solution) was sparged 20 min with $N_2$ and heated under reflux for 90 min (consumption of aryl bromide observed by LC/MS). Upon cooling, the mixture was partitioned between $EtOAc/H_2O$, layers were separated, and the aqueous layer was extracted with EtOAc (×2). Combined organics were washed ($H_2O$, brine), dried over $Na_2SO_4$ and concentrated in vacuo. The residue was purified by flash chromatography (EtOAc/hexanes), affording the title compound as a tan solid. LC/MS (method A) 1.91 min, m/z 226 (M+H).

The following examples were prepared from the appropriate aryl halide/triflate and aryl boronic acid/boronate according to the procedure described for example IX-1, with any significant deviations noted below table.

TABLE K

Compounds of Formula IX from aryl halides of Formula IV or Intermediates of Formula IX through Suzuki cross-coupling

| Ex | Structure | Characterization Data | Comments |
|---|---|---|---|
| IX-2 | 4'-formyl-2-methyl-1,1'-biphenyl-3-carboxamide | LC/MS (method A) 1.88 min, m/z 240 (M + H) | Used IV-2 and 4-formylphenyl boronic acid. |
| IX-3 | 4'-formyl-6-methyl-3-biphenylcarboxamide | LC/MS (method A) 2.13 min; m/z 240 (M + H) | Used IV-1 and 4-formylphenyl boronic acid. |
| IX-4 | 4'-formyl-2'-methyl-3-biphenylcarboxamide | LC/MS (method A) 2.05 min; m/z 240 (M + H) | Used 3-(aminocarbonyl)-phenyl boronic acid and I-IX-1. |

TABLE K-continued

Compounds of Formula IX from aryl halides of Formula IV or Intermediates of Formula IX through Suzuki cross-coupling

| Ex | Structure | Characterization Data | Comments |
|---|---|---|---|
| IX-5 | 3'-formyl-3-biphenylcarboxamide | LC/MS (method A) 1.90 min; m/z 226 (M + H) | Used 3-(aminocarbonyl)phenyl boronic acid and 3-bromobenz-aldehyde. |
| IX-6 | 3'-formyl-4-biphenylcarboxamide | LC/MS (method A) 1.87 min; m/z 226 (M + H) | Used 4-(aminocarbonyl)-phenyl boronic acid and 3-bromobenz-aldehyde. |
| IX-7 | 3'-(1H-imidazol-2-yl)-4-biphenylcarbaldehyde | LC/MS (method B) 1.36 min; /z 249 (M + H) | Used IV-21 and 4-formylphenyl boronic acid. Note 1, 2 |
| IX-8 | 4'-formyl-2'-(methoxy)-3-biphenylcarboxamide | LC/MS (method A) 1.94 min; /z 256 (M + H) | Used 3-(aminocarbonyl)-phenyl boronic acid and I-IX-3. Note 1, 2 |

TABLE K-continued

Compounds of Formula IX from aryl halides of Formula IV or Intermediates of Formula IX through Suzuki cross-coupling

| Ex | Structure | Characterization Data | Comments |
| --- | --- | --- | --- |
| IX-9 | 2'-chloro-4'-formyl-3-biphenylcarboxamide | LC/MS (method A) 2.09 min; m/z 256 (M + H) | Used 3-(aminocarbonyl)-phenyl boronic acid and I-IX-4. Note 1,2 |
| IX-10 | 2'-fluoro-4'-formyl-3-biphenylcarboxamide | LC/MS (method A) 1.98 min; m/z 244 (M + H) | Used 3-(aminocarbonyl)-phenyl boronic acid and I-IX-5. Note 1, 2 |
| IX-11 | 4'-formyl-5-methyl-3-biphenylcarboxamide | LC/MS (method A) 2.09 min; m/z 240 (M + H) | Used IV-9 and 4-formylphenyl boronic acid. |
| IX-12 | 2-fluoro-4'-formyl-3-biphenylcarboxamide | LC/MS (method B) 1.92 min; m/z 244 (M + H) | Used IV-16 and 4-formylphenyl boronic acid. Note 1, 2 |

TABLE K-continued

Compounds of Formula IX from aryl halides of Formula IV or Intermediates of Formula IX through Suzuki cross-coupling

| Ex | Structure | Characterization Data | Comments |
|---|---|---|---|
| IX-13 | 2-chloro-4'-formyl-3-biphenylcarboxamide | LC/MS (method B) 1.85 min; m/z 260 (M + H) | Used IV-13 and 4-formylphenyl boronic acid. Note 2 |
| IX-14 | 4'-formyl-2-(methyloxy)-3-biphenylcarboxamide | LC/MS (method B) 2.01 min; m/z 256 (M + H) | Used IV-14 and 4-formylphenyl boronic acid. Note 2 |
| IX-15 | 3'-fluoro-4'-formyl-3-biphenylcarboxamide | LC/MS (method A) 1.86 min, m/z 288 (M + H, acetal) 2.02 min; m/z 244 (M + H aldehyde) | Used IV-6 and 3-fluoro-4-formyl-phenyl boronic acid (Aldrich). Note 2, 7, 10 |
| IX-16 | 4'-formyl-3'-methyl-3-biphenylcarboxamide | LC/MS (method A) 2.09 min; m/z 240 (M + H) | Used 3-(aminocarbonyl)-phenyl boronic acid and I-IX-2 Note 2 |

TABLE K-continued

Compounds of Formula IX from aryl halides of Formula IV or Intermediates of Formula IX through Suzuki cross-coupling

| Ex | Structure | Characterization Data | Comments |
|---|---|---|---|
| IX-17 | 4'-formyl-4-methyl-3-biphenylcarboxamide | LC/MS (method A) 1.96 min; m/z 240 (M + H) | Used IV-3 and 4-formylphenyl boronic acid. Note 2 |
| IX-18 | 4'-(1H-imidazol-2-yl)-3-biphenylcarbaldehyde | Note 8 | Used IV-22 and 3-formylphenyl boronic acid. Note 2 |
| IX-19 | 3-(5-formyl-2-pyridinyl)-benzamide | LC/MS (method B) 1.63 min; m/z 227 (M + H) | Used 3-(aminocarbonyl)-phenyl boronic acid and 3-formyl-6-bromopyridine. Note 2 |
| IX-20 | 2-(4'-formyl-1,1'-biphenyl-3-yl)acetamide | LC/MS (method B) 2.04 min, m/z 240 (M + H) | Used IV-15 and 4-formylphenyl boronic acid. Note 2 |

TABLE K-continued

Compounds of Formula IX from aryl halides of Formula IV or Intermediates of Formula IX through Suzuki cross-coupling

| Ex | Structure | Characterization Data | Comments |
|---|---|---|---|
| IX-21 | 3'-(5-amino-3-isoxazolyl)-4-biphenylcarbaldehyde | LC/MS (method B) 2.27 min; m/z 265 (M + H) | Used IV-34 and 4-formylphenyl boronic acid. Note 2, 3 |
| IX-22 | 2,3'-difluoro-4'-formyl-3-biphenylcarboxamide | Note 9 | Used IV-16 and 3-fluoro-4-formyl-phenyl boronic acid (Aldrich). Note 2, 3 |
| IX-23 | 3'-formyl-2-methyl-4-biphenylcarboxamide | LC/MS (method A) 1.99 min; m/z 240 (M + H) | Used IV-4 and 3-formylphenyl boronic acid. Note 2, 4 |
| IX-24 | 3-chloro-3'-formyl-4-biphenyl carboxamide. | LC/MS (method A) 1.92 min; m/z 260 (M + H) | Used IV-7 and 3-formylphenyl boronic acid. Note 2, 4 |

TABLE K-continued

Compounds of Formula IX from aryl halides of Formula IV or Intermediates of Formula IX through Suzuki cross-coupling

| Ex | Structure | Characterization Data | Comments |
|---|---|---|---|
| IX-25 | 3'-formyl-2-(methyloxy)-4-biphenylcarboxamide. | LC/MS (method A) 1.94 min; m/z 256 (M + H) | Used IV-19 and 3-formylphenyl boronic acid. Note 2, 4 |
| IX-26 | 2-chloro-3'-formyl-4-biphenyl carboxamide. | LC/MS (method A) 2.07 min; m/z 260 (M + H) | Used IV-20 and 3-formylphenyl boronic acid. Note 2, 4, 5 |
| IX-27 | 4'-fluoro-3'-formyl-4-biphenylcarboxamide. | LC/MS (method A) 1.99 min; m/z 244 (M + H) | Used 2-fluoro-5-bromobenzaldehyde and 4-(amino-carbonyl)phenyl boronic acid. Note 2, 4 |
| IX-28 | 2'-fluoro-3'-formyl-4-biphenylcarboxamide. | LC/MS (method A) 2.05 min; m/z 244 (M + H) | Used and 2-fluoro-3-formylboronic acid. Note 2, 4 |
| IX-29 | 2'-fluoro-5'-formyl-4-biphenylcarboxamide. | LC/MS (method A) 1.95 min; m/z 244 (M + H) | Used 3-bromo-4-fluorobenzaldehyde and 4-(aminocarbonyl phenyl)boronic acid. Note 2, 4 |

TABLE K-continued

Compounds of Formula IX from aryl halides of Formula IV or Intermediates of Formula IX through Suzuki cross-coupling

| Ex | Structure | Characterization Data | Comments |
|---|---|---|---|
| IX-30 | 3'-chloro-5'-formyl-4-biphenylcarboxamide. | LC/MS (method A) 2.25 min; m/z 260 (M + H) | Used 3-bromo-5-chlorobenzaldehyde and 4-(aminocarbonyl phenyl)boronic acid. Note 2, 4 |
| IX-31 | 2'-fluoro-3'-formyl-2-methyl-4-biphenylcarboxamide. | LC/MS (method A) 2.04 min; m/z 258 (M + H) | Used IV-4 and 2-fluoro-3-formylphenyl boronic acid. Note 2, 4 |
| IX-32 | 5'-formyl-2'-(methyloxy)-4-biphenylcarboxamide. | LC/MS (method B) 1.91 min; m/z 256 (M + H) | Used 4-bromo-benzamide and 5-formyl-2-methoxy-phenyl boronic acid. Note 2, 4 |
| IX-33 | 3'-(1,1-dioxidoiso-thiazolidin-2-yl)-1,1'-biphenyl-4-carbaldehyde | LC/MS (Method E) 0.79 min; m/z 302 (M + H) | Note 2 |

TABLE K-continued

Compounds of Formula IX from aryl halides of Formula IV or Intermediates of Formula IX through Suzuki cross-coupling

| Ex | Structure | Characterization Data | Comments |
|---|---|---|---|
| IX-34 | 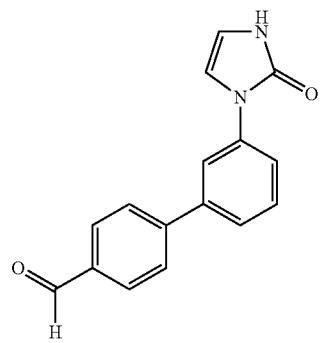 [SMILES: O=Cc1ccc(-c2cccc(-n3cc[nH]c3=O)c2)cc1]<br>3'-(2-oxo-2,3-dihydro-1H-imidazol-1-yl)-1,1'-biphenyl-4-carbaldehyde | LC/MS (Method E) 0.78 min; m/z 265 (M + H) | Used IV-35 and 4-formylphenyl boronic acid. |
| IX-35 | 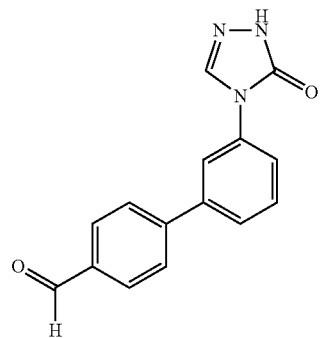 [SMILES: O=Cc1ccc(-c2cccc(-n3cn[nH]c3=O)c2)cc1]<br>3'-(5-oxo-1,5-dihydro-4H-1,2,4-triazol-4-yl)-1,1'-biphenyl-4-carbaldehyde | LC/MS (Method E) 0.73 min; m/z 266 (M + H) | Used IV-36 and 4-formylphenyl boronic acid. Note 2, 6 |
| IX-36 | 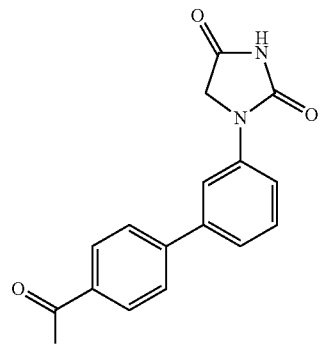<br>3'-(2,4-dioxoimidazolidin-1-yl)-1,1'-biphenyl-4-carbaldehyde | LC/MS (Method E) 0.76 min; m/z 281 (M + H) | Used IV-37 and 4-formylphenyl boronic acid. Note 2, 6 |

TABLE K-continued

Compounds of Formula IX from aryl halides of Formula IV or Intermediates of Formula IX through Suzuki cross-coupling

| Ex | Structure | Characterization Data | Comments |
|---|---|---|---|
| IX-37 | 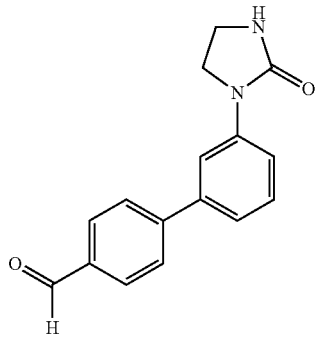 [SMILES: O=Cc1ccc(-c2cccc(N3CCNC3=O)c2)cc1] 3'-(2-oxoimidazolidin-1-yl)-1,1'-biphenyl-4-carbaldehyde | LC/MS (Method E) 0.81 min; m/z 267 (M + H) | Used IV-38 and 4-formylphenyl boronic acid. |
| IX-38 | 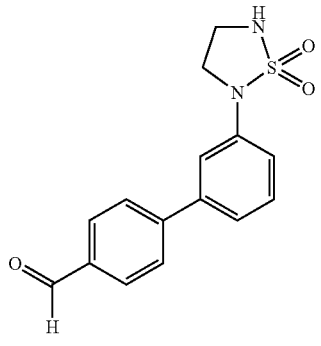 [SMILES: O=Cc1ccc(-c2cccc(N3CCNS3(=O)=O)c2)cc1] 3'-(1,1-dioxido-1,2,5-thiadiazolidin-2-yl)-1,1'-biphenyl-4-carbaldehyde | LC/MS (method E) 0.67 min; m/z 303 (M + H) | Used IV-39 and 4-formylphenyl boronic acid. |
| IX-39 | 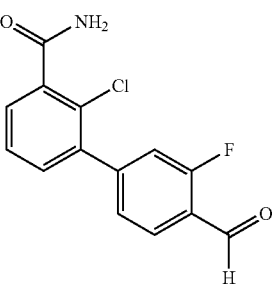 [SMILES: NC(=O)c1cccc(-c2ccc(C=O)c(F)c2)c1Cl] | LC/MS (method A) 1.90 min; m/z 278 (M + H). | Used IV-13 and 3-fluoro-4-formyl-phenyl boronic acid (Aldrich) |
| IX-40 | 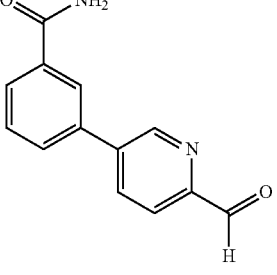 3-(6-formyl-3-pyridinyl)-benzamide | LC/MS (method B) 1.54 min; m/z 227 (M + H) | Used 5-bromo-2-formylpyridine and 3-(aminocarbonyl)phenyl boronic acid. |

Note 1
Used 4:1 v/v PhMe/EtOH as organic cosolvents (instead of DME).
Note 2
Used Pd(PPh$_3$)$_4$ as catalyst (instead of PdCl$_2$(dppf)•CH$_2$Cl$_2$).

TABLE K-continued

Compounds of Formula IX from aryl halides of Formula IV or Intermediates of Formula IX through Suzuki cross-coupling

| Ex | Structure | Characterization Data | Comments |
|----|-----------|----------------------|----------|

Note 3
Used Pd(OAc)$_2$/S-Phos as catalyst(instead of PdCl$_2$(dppf)•CH$_2$Cl$_2$).
Note 4
Used acetonitrile/0.4M Na$_2$CO$_3$ instead of DME/2M Na$_2$CO$_3$.
Note 5
Used K$_3$PO$_4$ as base and dioxane as solvent instead of (Na$_2$CO$_3$/DME).
Note 6
Heterocycle N-deprotection (TFA/CH$_2$Cl$_2$/RT) immediately following Suzuki reaction.
Note 7
In several cases, a (dimethyl)acetal and/or hemi-acetal of the title compound was observed by LC/MS, in addition to the expected title compound (presumably formed on the column from MeOH mobile phase, or sample solvent, and TFA mobile phase additive.
Note 8
(Ex IX-18) $^1$H NMR (400 MHz, DMSO-d$_6$) δ ppm 7.17 (br. s., 3 H), 7.71 (t, J = 7.67 Hz, 1 H), 7.84-7.88 (m, 2 H), 7.91 (ddd, J = 7.71, 1.29, 1.16 Hz, 1 H), 8.03-8.12 (m, 4 H), 8.07 (d, J = 8.56 Hz, 3 H), 8.28 (t, J = 1.61 Hz, 1 H), 10.11 (s, 1 H), 12.62 (br. s., 1 H)
Note 9
(Ex IX-22) $^1$H NMR (400 MHz, DMSO-d$_6$) δ ppm 7.40 (t, J = 7.69 Hz, 1 H), 7.62 (ddd, J = 13.37, 1.70, 1.30 Hz, 1 H), 7.65 (dt, J = 17.21, 1.70, 1.35 Hz, 1 H), 7.68-7.75 (m, J = 7.65, 7.58, 7.58, 1.74 Hz, 3 H), 7.84 (br. s., 1 H), 7.96 (t, J = 7.69 Hz, 1 H), 10.27 (s, 1 H)
Note 10
An alternate preparation of example IX-15 is given below.

Example IX-15

3'-fluoro-4'-formyl-3-biphenylcarboxamide (Alternate Preparation)

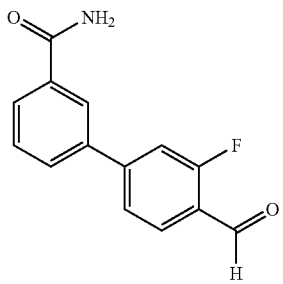 [SMILES: NC(=O)c1cccc(-c2ccc(C=O)c(F)c2)c1]

A 10 mL conical vial equipped with magnetic spin vane was charged with 3-bromobenzamide (0.200 g; 1.00 mmol; Ex IV-6), 3-fluoro-4-formyl-phenyl boronic acid (0.185 g; 1.1 mmol), tetra-n-butyl ammonium bromide (0.323 g; 1.0 mmol), Pd(OAc)$_2$ (0.0011 g; 0.005 mmol), K$_2$CO$_3$ (0.345 g; 2.5 mmol) and sealed with a septum. The vial was evacuated/backfilled with nitrogen (×3), water was added via syringe and the mixture was stirred at 80° C. for 2.5 h. Upon cooling, the mixture was poured into water, layered with Et$_2$O and sonicated ca. 2 min. Solid was collected by filtration and washed with Et$_2$O, affording the title compound as a cream-colored solid (used without further purification). LC/MS (method A) 2.02 min; m/z 244 (M+H).

The following examples were prepared from the appropriate aryl halide/triflate and aryl boronic acid/boronate according to the procedure described above for example IX-15, with any significant deviations noted below table.

TABLE L

Compounds of Formula IX from Suzuki reaction conditions used in Example IX-15

| Ex | Structure | Characterization Data | Comments |
|----|-----------|----------------------|----------|
| IX-41 | 3',5'-difluoro-4'-formyl-3-biphenylcarboxamide | LC/MS (method A) 1.86, 2.02 min; m/z 308 (M + H acetal, 1.86 min) 262 (M + H aldehyde, 2.02 min) | Used 3-(aminocarbonyl)-phenyl boronic acid and 4-bromo-2,6-difluorobenz-aldehyde. Note 1, 2 |

TABLE L-continued

Compounds of Formula IX from Suzuki reaction conditions used in Example IX-15

| Ex | Structure | Characterization Data | Comments |
|---|---|---|---|
| IX-42 | 3',5-difluoro-4'-formyl-3-biphenylcarboxamide | LC/MS (method A) 2.02, 2.16 min; m/z 308 (M + H acetal, 2.02 min) 260 (M − H aldehyde, 2.16 min) | Used IV-17 and 3-fluoro-4-formyl-phenyl boronic acid (Aldrich). Note 2 |
| IX-43 | 4'-formyl-N-methyl-3-biphenylcarboxamide | LC/MS (method B) 2.05 min; m/z 240 (M + H) | Used 3-(methyl-carbamoyl)phenyl boronic acid (Combi-Blocks) and 4-bromo-benzaldehyde. |
| IX-44 | 3'-chloro-4'-formyl-3-biphenylcarboxamide | LC/MS (method A) 2.08, 2.29 min; m/z 306 (M + H acetal, 2.08 min) 260 (M − H aldehyde, 2.29 min) | Used 3-(amino-carbonyl)phenyl boronic acid and 4-bromo-2-chloro-benzaldehyde. Note 2, 3 |

Note 1

4-bromo-2,6-difluorobenzaldehyde is commercially available from various suppliers; e.g., Apollo Scientific Ltd., Bredbury, Stockport, Cheshire, UK. Example IX-39 has also been prepared from 3-bromobenzamide (IV-6) and 3,5-difluoro-4-formylphenyl boronic acid (Aldrich), according to the procedure described for example IX-1, using Pd(OAc)$_2$/S-Phos as catalyst and PhMe/EtOH (4:1) as organic cosolvent.

Note 2

In several cases, a (dimethyl)acetal and/or hemi-acetal of the title compound was observed by LC/MS, in addition to the expected title compound (presumably formed on the column from MeOH mobile phase, or sample solvent, and TFA mobile phase additive.

Note 3

4-bromo-2-chlorobenzaldehyde is commercially available from various suppliers; e.g., Apollo Scientific Ltd., Bredbury, Stockport, Cheshire, UK.

Example IX-45

5-(4-formylphenyl)-3-pyridinecarboxamide

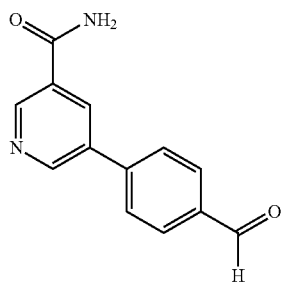 [SMILES: NC(=O)c1cncc(-c2ccc(C=O)cc2)c1]

A mixture of 5-bromonicotinamide (0.201 g; 1.00 mmol), 4-formylphenyl boronic acid (0.180 g; 1.2 mmol), Pd(OAc)$_2$ (0.0022 g; 0.010 mmol), S-Phos (0.0082 g; 0.020 mmol) and K$_2$CO$_3$ (0.345 g; 2.5 mmol) in n-butanol (3 mL) was sparged with nitrogen ca. 10 min, then heated at 80° C. for 1 h. Upon cooling, the mixture was poured into water, layered with Et$_2$O and sonicated at room temperature ca. 5 min. Solid was collected by filtration, and the cake was air-dried on the filter, affording the title compound as a colorless solid which was used without further purification. LC/MS (method A) 1.57 min; m/z 227 (M+H).

The following examples were prepared from the appropriate aryl halide/triflate and aryl boronic acid/boronate according to the procedure described for example IX-45, with any significant deviations noted below table.

TABLE M

Compounds of Formula IX from Suzuki cross-coupling conditions described in IX-45

| Ex | Structure/Name | Characterization Data | Comments |
|---|---|---|---|
| IX-46 | 2,2',3'-trifluoro-4'-formyl-3-biphenylcarboxamide | LC/MS (method B) (hemiacetal) 1.96 min; m/z 312 (M + H) (aldehyde) 2.08 min; m/z 280 (M + H) | Used IV-16 and 2,3-difluoro-4-formyl-phenyl boronic acid (Aldrich). Note 1, 2, 4 |
| IX-47 | 2',3'-difluoro-4'-formyl-3-biphenylcarboxamide | LC/MS (method A) (acetal) 2.00 min, m/z 308 (M + H) (aldehyde) 2.12 min; m/z 262 (M + H). | Used IV-6 and 2,3-difluoro-4-formyl-phenyl boronic acid (Aldrich). Note 1, 3, 4 |
| IX-48 | 5-fluoro-4'-formyl-3-biphenyl-carboxamide | LC/MS (method A) 2.15 min; m/z 242 (M − H) | Used IV-17 and 4-formylphenyl boronic acid. |

TABLE M-continued

Compounds of Formula IX from Suzuki cross-coupling conditions described in IX-45

| Ex | Structure/Name | Characterization Data | Comments |
|---|---|---|---|
| IX-49 | 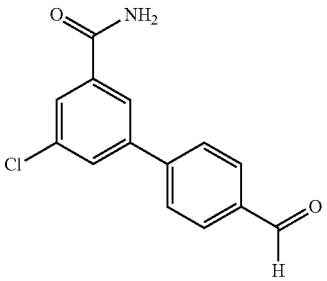<br>5-chloro-4'-formyl-3-biphenylcarboxamide | LC/MS (method B) 2.32 min; m/z 260 (M + H) | Used IV-8 and 4-formylphenyl boronic acid. Note 2 |
| IX-50 | 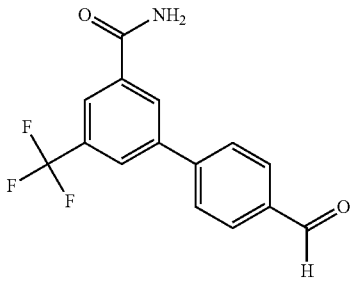<br>4'-formyl-5-(trifluoromethyl)-3-biphenylcarboxamide | LC/MS (method A) 2.38 min; m/z 292 (M − H) | Used IV-10 and 4-formylphenyl boronic acid. |
| IX-51 | 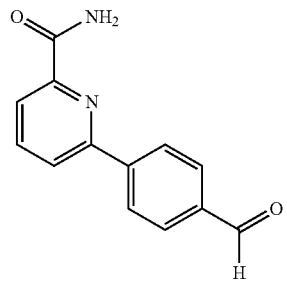<br>6-(4-formylphenyl)-2-pyridinecarboxamide | LC/MS (method A) 1.87 min; m/z 227 (M + H) | Used IV-11 and 4-formylphenyl boronic acid. |
| IX-52 | 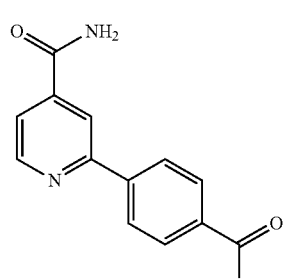<br>2-(4-formylphenyl)-4-pyridinecarboxamide | LC/MS (method A) 1.65 min; m/z 227 (M + H) | Used commercially available 2-chloro isonicotinamide from Maybridge Building Blocks and 4-formylphenyl boronic acid. |

TABLE M-continued

Compounds of Formula IX from Suzuki cross-coupling conditions described in IX-45

| Ex | Structure/Name | Characterization Data | Comments |
|---|---|---|---|
| IX-53 | 3'-fluoro-4'-formyl-2-methyl-3-biphenylcarboxamide | LC/MS (method A) 2.03 min; m/z 258 (M + H) | Used IV-2 and 3-fluoro-4-formylphenyl boronic acid (Aldrich). |

Note 1
K₃PO₄ was used as base (instead of K₂CO₃). PhMe was used as solvent (instead of n-butanol), reaction temperature was 90° C. (instead of 80° C.).
Note 2
Product was purified by flash chromatography (EtOAc/hexanes).
Note 3
An additional portion of the aryl boronic acid (0.5 equiv) was added after 5 h heating. Total reaction time was 21 h.
Note 4
In several cases, the title compounds were accompanied by the corresponding (dimethyl)acetals, presumably formed on the column from MeOH mobile phase (or sample solvent) and the trace acid mobile phase additive (TFA).

Example IX-54

4'-formyl-2'-(trifluoromethyl)-3-biphenylcarboxamide

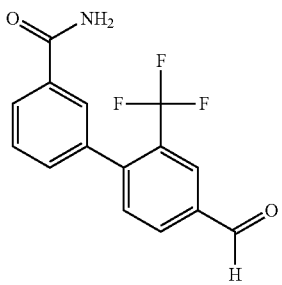 [SMILES: NC(=O)c1cccc(-c2ccc(C=O)cc2C(F)(F)F)c1]

Step 1: 4'-cyano-2'-(trifluoromethyl)-3-biphenylcarboxamide

The title compound was synthesized from 3-(aminocarbonyl)phenyl boronic acid and 4-iodo-3-(trifluoromethyl)benzonitrile (I-IX-6) according to the procedure described for Ex IX-10, using Pd(PPh₃)₄ catalyst and PhMe/EtOH (4:1) as organic cosolvents. LC/MS (method A) 2.18 min, m/z 291 (M+H).

Step 2: 4'-formyl-2'-(trifluoromethyl)-3-biphenylcarboxamide

To a solution of 4'-cyano-2'-(trifluoromethyl)-3-biphenylcarboxamide (0.239 g; 1.01 mmol; step 1 above) in CH₂Cl₂ (10 mL) at −78° C. was added DIBAL-H (2.5 mL of a 1.0M solution in CH₂Cl₂; 2.5 mmol), dropwise over 3 min. After 15 min the reaction was quenched by addition of 6M HCl (ca. 5 mL), removed from the cooling bath and stirred at room temperature for 20 min. The mixture was poured into water and extracted with CH₂Cl₂ (×3). Combined organics were filtered through a pad of Celite, washed (satd NaHCO₃, brine), dried over Na₂SO₄, filtered and concentrated in vacuo. The residue was purified by flash chromatography (EtOAc/hexanes), affording the title compound as a colorless gum. LC/MS (method B) 2.21 min, m/z 294 (M+H).

Example IX-55

4'-formyl-3'-(trifluoromethyl)-1,1-biphenyl-3-carboxamide

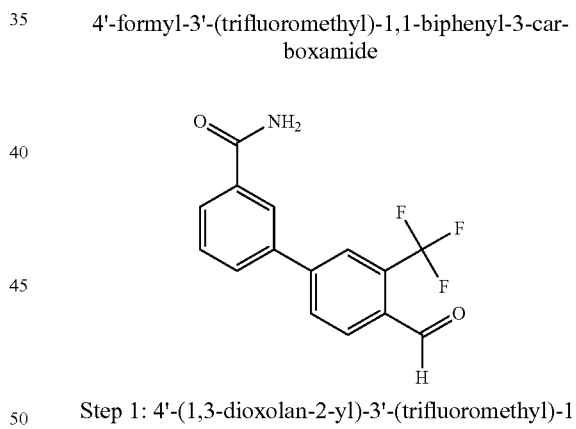

Step 1: 4'-(1,3-dioxolan-2-yl)-3'-(trifluoromethyl)-1,1-biphenyl-3-carboxamide

The title compound was prepared from 3-(aminocarbonyl)phenyl boronic acid and 2-[4-iodo-2-(trifluoromethyl)phenyl]-1,3-dioxolane (I-IX-7) according to the procedure described for IX-10, using PhMe/EtOH (4:1) as organic cosolvents. Colorless solid. LC/MS (method A) 2.38 min; m/z 338 (M+H).

Step 2: 4'-formyl-3'-(trifluoromethyl)-1,1-biphenyl-3-carboxamide

4'-(1,3-Dioxolan-2-yl)-3'-(trifluoromethyl)-1,1'-biphenyl-3-carboxamide (0.177 g; 0.525 mmol) was added to a solution of HOAc (4 mL) and water (1 mL) and the mixture was stirred at 65° C. in a sealed vial for 1 h. Upon cooling, the mixture was poured into satd NaHCO₃ and extracted with EtOAc (×3). Combined organics were washed (water, brine), dried over Na$_2$SO$_4$ and concentrated in vacuo affording the title compound, which was used without further purification.

$^1$H NMR (400 MHz, DMSO-d$_6$) δ ppm 7.55 (br. s., 1 H), 7.64 (t, J=7.76 Hz, 1 H), 7.98 (ddd, J=7.98, 1.38, 1.16 Hz, 1 H), 8.02 (ddd, J=7.76, 1.87, 1.07 Hz, 1 H), 8.18-8.26 (m, 3 H), 8.29 (dd, J=8.03, 1.78 Hz, 1 H), 8.31 (t, J=1.69 Hz, 1 H), 10.31 (q, J=1.96 Hz, 1 H)

Example IX-56

4'-formyl-2-methyl-3'-(trifluoromethyl)-3-biphenyl-carboxamide

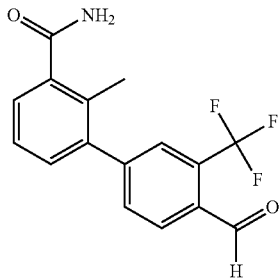 [SMILES: Cc1c(C(N)=O)cccc1-c1ccc(C=O)c(C(F)(F)F)c1]

Step 1: 4'-(1,3-dioxolan-2-yl)-3'-(trifluoromethyl)-3-biphenylcarboxamide

The title compound was prepared from 3-bromo-2-methylbenzamide (Ex IV-2) and 4-(1,3-dioxolan-2-yl)-3-(trifluoromethyl)phenylboronic acid (I-IX-8) according to the procedure described in Example IX-10, using PhMe/EtOH (4:1) as organic colsovent. LC/MS (method A) 2.36 min; m/z 351 (M+H).

Step 2: 4'-formyl-2-methyl-3'-(trifluoromethyl)-3-biphenylcarboxamide

The title compound was prepared from 4'-(1,3-dioxolan-2-yl)-3'-(trifluoromethyl)-3-biphenylcarboxamide (Step 1 above) according to the procedure described for example IX-55, Step 2. LC/MS (method A) 2.33 min; m/z 308 (M+H).

Example IX-57

3'-(1H-pyrazol-3-yl)-4-biphenylcarbaldehyde

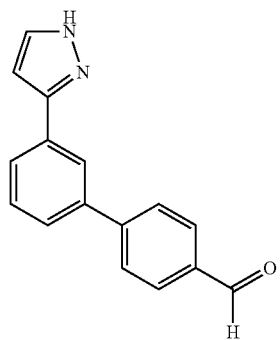 [SMILES: O=Cc1ccc(-c2cccc(-c3cc[nH]n3)c2)cc1]

Step 1: [3-(4'-formyl-3-biphenylyl)-1H-pyrazol-1-yl] methyl 2,2-dimethyl-propanoate The title compound was prepared from 3-(3-bromophenyl)-1H-pyrazol-1-yl]methyl 2,2-dimethylpropanoate (Ex IV-29) and 4-formylphenyl boronic acid according to the procedure described for IX-10, using PhMe/EtOH (4:1) as organic cosolvents. $^1$H NMR (400 MHz, DMSO-d$_6$) δ ppm 1.12 (s, 9 H), 6.11 (s, 2 H), 6.99 (d, J=2.50 Hz, 1 H), 7.57 (t, J=7.67 Hz, 1 H), 7.74 (ddd, J=7.85, 1.96, 1.07 Hz, 1 H), 7.91 (ddd, J=7.76, 1.61, 1.16 Hz, 1 H), 7.96-8.00 (m, 3 H), 8.01-8.05 (m, 2 H), 8.18 (t, J=1.61 Hz, 1 H), 10.07 (s, 1 H).

Step 2: 3'-(1H-pyrazol-3-yl)-4-biphenylcarbaldehyde

To a solution of [3-(4'-formyl-3-biphenylyl)-1H-pyrazol-1-yl]methyl 2,2-dimethyl-propanoate (0.162 g; 0.45 mmol) in 1:1 THF/MeOH (5 mL total vol) at room temperature was added NaOH (1.1 mL of a 1.0M solution; 1.1 mmol). After 30 min, HOAc (0.08 mL; 1.4 mmol) was added and the mixture was concentrated in vacuo. The residue was partitioned between EtOAc/water, layers were separated, the organic layer was washed (satd NaHCO$_3$, brine), dried over Na$_2$SO$_4$ and concentrated in vacuo. The residue was redissolved in EtOAc, washed (1M HCl, water, brine), dried over Na$_2$SO$_4$ and concentrated in vacuo, affording the title compound as a glassy semi-solid which was used without further purification. LC/MS (method A) 2.42 min; m/z 249 (M+H).

Compounds of Formula X

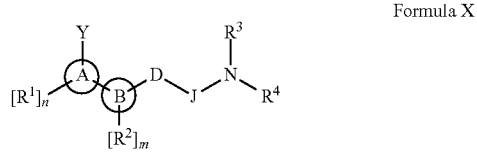

Formula X

Intermediates of Formula X

The following compounds were employed as precursors of Formula X compounds wherein Y is a suitably protected heteroaryl or heterocyclyl, cyano or ester, and at the time of this writing were not readily available from commercial suppliers.

Intermediate I-X-1

3'-[1-({[2-(trimethylsilyl)ethyl]oxy}methyl)-1H-1,2,4-triazol-3-yl]-4-biphenylcarbaldehyde and 3'-[1-({[2-(trimethylsilyl)ethyl]-oxy}methyl)-1H-1,2,4-triazol-5-yl]-4-biphenylcarbaldehyde

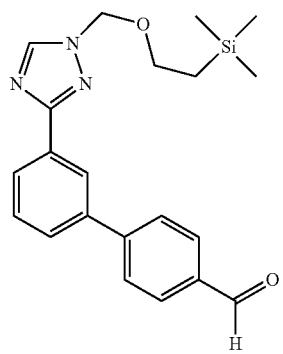

Intermediate I-X-2

[3-(4'-formyl-3-biphenylyl)-1H-1,2,4-triazol-1-yl]methyl 2,2-dimethylpropanoate

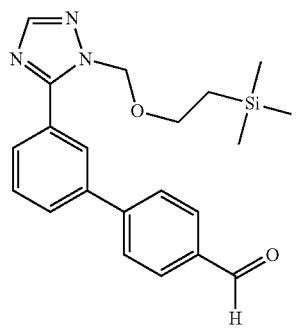

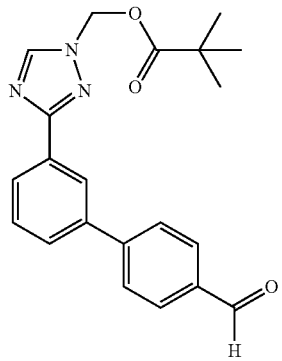 [SMILES: CC(C)(C)C(=O)OCn1cnc(-c2cccc(-c3ccc(C=O)cc3)c2)n1]

A mixture of 4-formylphenyl boronic acid (0.110 g; 0.737 mmol), 3-(3-bromophenyl)-1-({[2-(trimethylsilyl)ethyl]oxy}methyl)-1H-1,2,4-triazole and 5 (3-bromophenyl)-1-({[2-(trimethylsilyl)ethyl]oxy}methyl)-1H-1,2,4-triazole (0.236 g; 0.667 mmol, Ex V-23), Pd(PPh$_3$)$_4$ (0.039 g; 0.033 mmol), 2M Na$_2$CO$_3$ (0.80 mL; 1.6 mmol) and PhMe/EtOH (4:1, 8 mL) was sparged with N$_2$ for 10 min and heated under reflux for 16 h. Upon cooling, the mixture was diluted with EtOAc and washed with water. The aqueous wash was back-extracted with EtOAc (×2), combined organics were washed (water, brine), dried over Na$_2$SO$_4$ and concentrated in vacuo. The residue was purified by flash chromatography (EtOAc/hexanes), affording the title compounds as partially-resolved mixture. LC/MS (method B) isomer 1: 2.97 min, m/z 380 (M+H). LC/MS (method B) isomer 2: 3.02 min; m/z 380 (M+H). These regioisomers were combined, and carried on as a mixture.

A vial equipped with magnetic spin vane was charged with [[3-(3-Bromophenyl)-1H-1,2,4-triazol-1-yl]methyl 2,2-dimethylpropanoate (0.203 g; 0.60 mmol; Ex IV-24), 4-formylphenyl boronic acid (0.099 g; 0.66 mmol), and PdCl$_2$(dppf).CH$_2$Cl$_2$ (0.012 g; 0.015 mmol), was sealed with a septum and evacuated/backfilled with N$_2$ (×3). PhMe/EtOH (4:1, 3 mL) and 2M Na$_2$CO$_3$ (0.72 mL; 1.44 mmol) were added through the septum via syringe and the mixture was stirred at 80° C. for 2.5 h. Upon cooling, the mixture was partitioned between EtOAc/water and the layers were separated. The aqueous layer was extracted with EtOAc (×2), combined organics were washed (water, brine), dried over Na$_2$SO$_4$ and concentrated in vacuo. The residue was purified by flash chromatography (EtOAc/hexanes), affording the title compound as a colorless gum/film. LC/MS (method A) 2.60 min; m/z 364 (M+H).

The following intermediates were prepared from the appropriate aryl halide/triflate and aryl boronic acid/boronate ester according to the procedure described for intermediate I-X-2, with any significant deviation noted below table.

TABLE N

Compounds of Formula X from Suzuki cross-coupling similar to that described in I-X-2

| Ex | Structure/Name | Characterization Data | Comments |
|---|---|---|---|
| I-X-3 | [4-(4'-formyl-3-biphenylyl)-1H-1,2,3-triazol-1-yl]methyl 2,2-dimethylpropanoate | LC/MS (method B) 2.76 (min; m/z 364 (M + H) | Used IV-33 and 4-formylphenyl boronic acid. |

TABLE N-continued

Compounds of Formula X from Suzuki cross-coupling similar to that described in I-X-2

| Ex | Structure/Name | Characterization Data | Comments |
|---|---|---|---|
| I-X-4 | 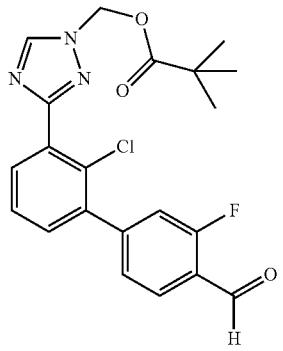<br>[3-(2-chloro-3'-fluoro-4'-formyl-3-biphenylyl)-1H-1,2,4-triazol-1-yl]methyl 2,2-dimethylpropanoate | LC/MS (method A)<br>acetal: 2.58 min; m/z 448 (M + H)<br>aldehyde: 2.74 min; m/z 416 (M + H) | Used IV-28 and 3-fluoro-4-formyl-phenyl boronic acid.<br>Note 1 |
| I-X-5 | 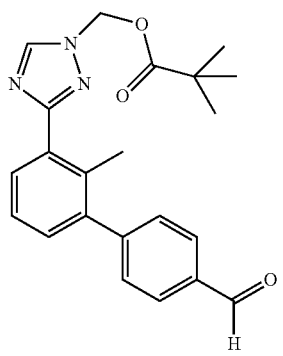<br>[3-(4'-formyl-2-methyl-3-biphenylyl)-1H-1,2,4-triazol-1-yl]methyl 2,2-dimethylpropanoate | LC/MS (method A) 2.7 min; m/z 378 (M + H) | Used IV-27 and 4-formylphenyl boronic acid. |
| I-X-6 | 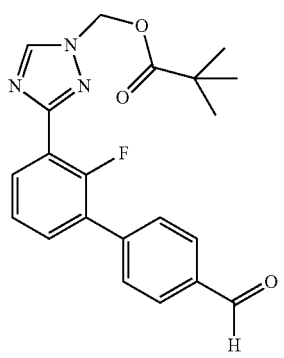<br>[3-(2-fluoro-4'-formyl-3-biphenylyl)-1H-1,2,4-triazol-1-yl]methyl 2,2-dimethylpropanoate | LC/MS (method A) 2.65 min; m/z 382 (M + H) | Used IV-26 and 4-formylphenyl boronic acid. |

TABLE N-continued

Compounds of Formula X from Suzuki cross-coupling similar to that described in I-X-2

| Ex | Structure/Name | Characterization Data | Comments |
|---|---|---|---|
| I-X-7 | [3-(2-chloro-4'-formyl-3-biphenylyl)-1H-1,2,4-triazol-1-yl]methyl 2,2-dimethylpropanoate | LC/MS (method A) 2.63 min; m/z 398 (M + H) | Used IV-28 and 4-formylphenyl boronic acid. |
| I-X-8 | [3-(3'-fluoro-4'-formyl-3-biphenylyl)-1H-1,2,4-triazol-1-yl]methyl 2,2-dimethylpropanoate | LC/MS (method A) hemiacetal: 2.67 min, m/z 414 (M + H); aldehyde: 2.85 min, m/z 382 (M + H). | Used IV-24 and 3-fluoro-4-formyl-phenyl boronic acid. Note 1 |
| I-X-9 | [3-(3',5'-difluoro-4'-formyl-3-biphenylyl)-1H-1,2,4-triazol-1-yl]methyl 2,2-dimethylpropanoate | Note 2 | Used IV-24 and 3,5-difluoro-4-formyl-phenyl boronic acid. Note 2 |
| I-X-10 | [3-(2'-fluoro-3'-formyl-4-biphenylyl)-1H-1,2,4-triazol-1-yl]methyl 2,2-dimethylpropanoate | Note 4 | Used IV-30 and 2-fluoro-3-formyl-phenyl boronic acid. Note 3 |

TABLE N-continued

Compounds of Formula X from Suzuki cross-coupling similar to that described in I-X-2

| Ex | Structure/Name | Characterization Data | Comments |
|---|---|---|---|
| I-X-11 | [3-(2,2'-difluoro-3'-formyl-4-biphenylyl)-1H-1,2,4-triazol-1-yl]methyl 2,2-dimethylpropanoate | Note 5 | Used IV-32 and 2-fluoro-3-formyl phenyl boronic acid. Note 3 Also prepared by microwave heating. |
| I-X-12 | [3-(2'-fluoro-5'-formyl-2-methyl-4-biphenylyl)-1H-1,2,4-triazol-1-yl]methyl 2,2-dimethylpropanoate | Note 6 | Used IV-31 and 2-fluoro-3-formylphenyl boronic acid. Note 3 |
| I-X-13 | [3-(2',4'-difluoro-3'-formyl-4-biphenylyl)-1H-1,2,4-triazol-1-yl]methyl 2,2-dimethylpropanoate | Note 7 | Used IV-30 and 2,4-difluoro-3-formyl phenyl boronic acid. Note 3 |
| I-X-14 | [3-(2',4'-difluoro-3'-formyl-3-biphenylyl)-1H-1,2,4-triazol-1-yl]methyl 2,2-dimethylpropanoate | Note 8 | Used IV-24 and 2,4-difluoro-3-formylphenyl boronic acid. Note 3 |
| I-X-15 | [3-(2'-fluoro-3'-formyl-3-biphenylyl)-1H-1,2,4-triazol-1-yl]methyl 2,2-dimethylpropanoate | LC/MS (method B) 0.87 min; m/z 382 (M + 1) | Used IV-24 and 3-formylphenyl boronic acid. Note 3 |

TABLE N-continued

Compounds of Formula X from Suzuki cross-coupling similar to that described in I-X-2

| Ex | Structure/Name | Characterization Data | Comments |
|---|---|---|---|
| I-X-16 | [3-(4'-fluoro-3'-formyl-3-biphenylyl)-1H-1,2,4-triazol-1-yl]methyl 2,2-dimethylpropanoate | LC/MS (method B) 0.88 min; m/z 382 (M + 1) | Used IV-24 and 4-fluoro-3-formyl-phenyl boronic acid. Note 3 |

Note 1
In several cases, a (dimethyl)acetal and/or hemi-acetal of the title compound was observed by LC/MS, in addition to the expected title compound; presumably formed on the column from MeOH mobile phase, or sample solvent, and TFA mobile phase additive.

Note 2
Pd(OAc)$_2$/S-Phos was used as catalyst. An alternate preparation of I-X-8 is given below.
$^1$H NMR (400 MHz, DMSO-d$_6$) δ ppm 1.13 (s, 9H), 6.21 (s, 2H), 7.65 (app. t, J = 7.94 Hz, 1H), 7.67-7.72 (m, 2H), 7.91 (app. ddd, J = 7.85, 1.96, 1.07 Hz, 1H), 8.13 (app. dd, J = 7.94, 1.34 Hz, 1H), 8.34 (app. t, J = 1.52 Hz, 1H), 8.83 (s, 1H), 10.25 (s, 1H).

Note 3
Used 2 equiv aryl boronic acid.

Note 4
1H NMR (400 MHz, CDCl3) δ ppm 1.20 (s, 9H), 6.10 (s, 2H), 7.35 (t, J = 7.69 Hz, 1H), 7.60-7.69 (m, 2H), 7.74 (td, J = 7.51, 1.83 Hz, 1H), 7.84-7.92 (m, 1H), 8.23 (d, J = 8.30 Hz, 2H), 8.39 (s, 1H), 10.46 (s, 1H).

Note 5
(I-X-11) 1H NMR (400 MHz, CDCl3) δ ppm 1.19 (s, 9H), 6.09 (s, 2H), 7.36 (t, J = 7.69 Hz, 1H), 7.48 (t, J = 7.69 Hz, 1H), 7.68 (t, J = 6.84 Hz, 1H), 7.88-8.07 (m, 3H), 8.39 (s, 1H), 10.44 (s, 1H).

Note 6
(I-X-12) 1H NMR (400 MHz, CDCl3) δ ppm 1.19 (s, 9H), 2.28 (s, 3H), 6.10 (s, 2H), 7.27-7.39 (m, 2H), 7.54 (td, J = 7.20, 1.46 Hz, 1H), 7.85-7.94 (m, 1H), 8.02 (d, J = 8.06 Hz, 1H), 8.09 (s, 1H), 8.38 (s, 1H), 10.43 (s, 1H).

Note 7
(I-X-13) 1H NMR (400 MHz, CDCl3) δ ppm 1.19 (s, 9H), 6.09 (s, 2H), 7.09 (t, J = 9.16 Hz, 1H), 7.59 (d, J = 6.84 Hz, 2H), 7.69 (td, J = 8.48, 6.23 Hz, 1H), 8.22 (d, J = 8.30 Hz, 2H), 8.38 (s, 1H), 10.43 (s, 1H).

Note 8
(I-X-14) 1H NMR (400 MHz, CDCl3) δ ppm 1.19 (s, 9H), 6.09 (s, 2H), 7.08 (t, J = 9.28 Hz, 1H), 7.53-7.59 (m, 2H), 7.73 (td, J = 8.48, 6.23 Hz, 1H), 8.14-8.21 (m, 1H), 8.25 (s, 1H), 8.39 (s, 1H), 10.43 (s, 1H).

Alternate preparation of Intermediate I-X-9

[3-(3',5'-difluoro-4'-formyl-3-biphenylyl)-1H-1,2,4-triazol-1-yl]methyl 2,2-dimethylpropanoate

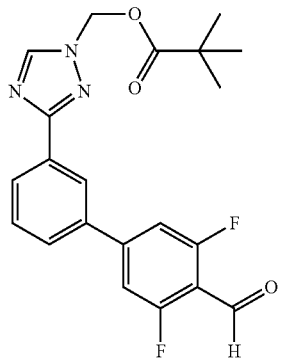 [SMILES: CC(C)(C)C(=O)OCn1cnc(-c2cccc(-c3cc(F)c(C=O)c(F)c3)c2)n1]

A flask was charged with PhMe/EtOH (4:1, 50 mL), water (25 mL) and NaHCO$_3$ (3.78 g; 45 mmol) and the mixture was sparged with N$_2$ for 15 min in an ultrasonic bath. [3-(3-bromophenyl)-1H-1,2,4-triazol-1-yl]methyl 2,2-dimethylpropanoate (5.07 g; 15.0 mmol; Ex IV-24), 3,5-difluoro-4-formyl-phenyl boronic acid (3.07 g; 16.5 mmol) and PdCl$_2$(dppf).CH$_2$Cl$_2$ (0.245 g; 0.30 mmol) were added in one portion and the mixture was heated under reflux for 10 h. Upon cooling, solids were collected by filtration, washed (Et$_2$O/hexane), dissolved in hot EtOAc and filtered without delay through a short pad of silica get (1:1 EtOAc/hexanes eluent). Filtrate collected from the reaction mixture was diluted with water/EtOAc, separated and the aqueous layer extracted with EtOAc (x3). Combined organics were washed (water, brine), dried over Na$_2$SO$_4$ and concentrated in vacuo. The residue obtained from the extracts was dissolved in hot EtOAc, filtered through silica (1:1 EtOAc/hexanes eluent), and the filtrate combined with that obtained from the crude reaction mixture solids. Combined filtrates were concentrated in vacuo, affording the title compound as a pale yellow solid.

In another preparation of the title compound, Pd(OAc)$_2$/S-Phos (0.005/0.010 equiv) were used as catalyst, NaHCO$_3$ (3 equiv) was used as base, and PhMe/water were used as solvents (without EtOH additive), reaction time 3 h/85° C. Product I-X-9 was isolated in a manner analogous to the above procedure.

Choice of base appears to be a key parameter in the cross-coupling of Ex. IV-24 under typical biphasic conditions. In our hands, NaHCO$_3$ was an effective and reliable base for preparation of I-X-9. On some occasions, the use of Na$_2$CO$_3$, as base resulted in stalled reactions; mixtures of IV-24 and I-X-9 were returned, accompanied by varying amounts of deprotected IV-24 (i.e., 3-bromo phenyl-1H-1,2,4-triazole).

Intermediate I-X-17

[3-(3'-formyl-4-biphenylyl)-1H-1,2,4-triazol-1-yl]methyl 2,2-dimethylpropanoate

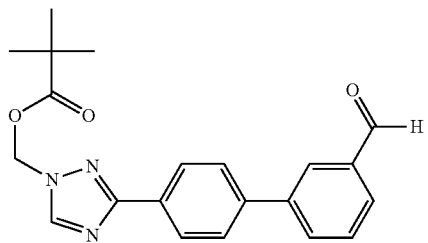 [SMILES: CC(C)(C)C(=O)OCn1cnc(-c2ccc(-c3cccc(C=O)c3)cc2)n1]

To a solution of [3-(4-bromophenyl)-1H-1,2,4-triazol-1-yl]methyl 2,2-dimethyl-propanoate (0.108 g, 0.32 mmol; IV-30), 3-formylphenyl boronic acid (0.099 g, 0.66 mmol), and PdCl$_2$(dppf).CH$_2$Cl$_2$ (0.024 g, 0.029 mmol) was added 2M Na$_2$CO$_3$ (aq) (0.38 mL, 0.76 mmol). The mixture was subjected to microwave heating (135° C./50 min), cooled, and partitioned between EtOAc and water. The aqueous layer was extracted with EtOAc, combined organic extracts were dried over Na$_2$SO$_4$ and concentrated in vacuo. The residue was purified by flash chromatography (EtOAc/hexanes), affording the title compound as a colorless solid. $^1$H NMR (400 MHz, CDCl3) δ ppm 1.20 (s, 9 H), 6.10 (s, 2 H), 7.63 (t, J=7.69 Hz, 1 H), 7.73 (d, J=8.06 Hz, 2 H), 7.90 (dd, J=14.65, 7.57 Hz, 2 H), 8.15 (m, 1 H), 8.23 (d, J=8.30 Hz, 2 H), 8.39 (s, 1 H), 10.10 (s, 1 H).

The following intermediates were prepared from the appropriate aryl halide/triflate and aryl boronic acid/boronate ester according to the procedure described for intermediate I-X-17, with any significant deviation noted below table.

TABLE O

Compounds of Formula X from Suzuki cross-coupling similar to that described in I-X-17

| Ex | Structure/Name | Characterization Data | Comments |
| --- | --- | --- | --- |
| I-X-18 | 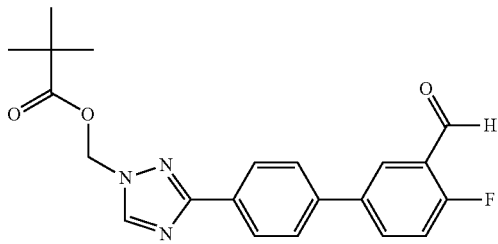<br>[3-(4'-fluoro-3'-formyl-4-biphenylyl)-1H-1,2,4-triazol-1-yl]methyl 2,2-dimethylpropanoate | Note 1 | Used IV-30 and (4-fluoro-3-formyl-phenyl)boronic acid, (140° C./40 min). |
| I-X-19 | 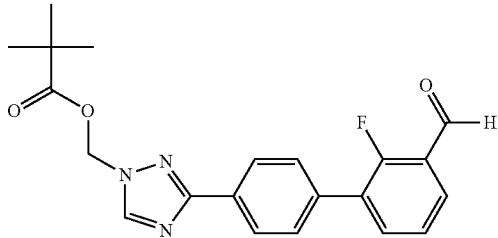<br>[3-(2'-fluoro-3'-formyl-4-biphenylyl)-1H-1,2,4-triazol-1-yl]methyl 2,2-dimethylpropanoate | Note 2 | Used IV-30 and 2-fluoro-3-formyl-phenyl boronic acid. Note 5. |
| I-X-20 | 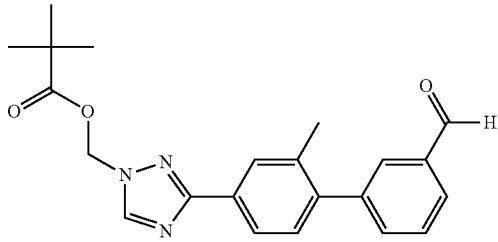<br>[3-(3'-formyl-2-methyl-4-biphenylyl)-1H-1,2,4-triazol-1-yl]methyl 2,2-dimethylpropanoate | Note 3 | Used IV-31 and 3-formylphenyl boronic acid. (140° C./1 h) |

TABLE O-continued

Compounds of Formula X from Suzuki cross-coupling similar to that described in I-X-17

| Ex | Structure/Name | Characterization Data | Comments |
|---|---|---|---|
| I-X-21 | ![structure] [3-(2-fluoro-3'-formyl-4-biphenylyl)-1H-1,2,4-triazol-1-yl]methyl 2,2-dimethylpropanoate | Note 4 | Used IV-32 and 3-formylphenyl boronic acid. (140° C./40 min). |

Note 1
(I-X-18) 1H NMR (400 MHz, CDCl3) δ ppm 1.20 (s, 9H), 6.09 (s, 2H), 7.25-7.31 (m, 1H), 7.66 (d, J = 8.06 Hz, 2H), 7.87 (m, 1H), 8.13 (dd, J = 6.47, 2.32 Hz, 1H), 8.21 (d, J = 8.30 Hz, 2H), 8.38 (s, 1H), 10.43 (s, 1H).
Note 2
(I-X-19) 1H NMR (400 MHz, CDCl3) δ ppm 1.20 (s, 9H), 6.10 (s, 2H), 7.35 (t, J = 7.69 Hz, 1H), 7.65 (d, J = 7.32 Hz, 2H), 7.74 (t, J = 6.84 Hz, 1H), 7.83-7.93 (m, 1H), 8.23 (d, J = 8.30 Hz, 2H), 8.39 (s, 1H), 10.46 (s, 1H).
Note 3
(I-X-20) 1H NMR (400 MHz, CDCl3) δ ppm 1.20 (s, 9H), 2.33 (s, 3H), 6.10 (s, 2H), 7.32 (d, J = 8.06 Hz, 1H), 7.56-7.66 (m, 2H), 7.82-7.92 (m, 2H), 8.01 (d, J = 8.06 Hz, 1H), 8.07 (s, 1H), 8.38 (s, 1H), 10.07 (s, 1H).
Note 4
(I-X-21) 1H NMR (400 MHz, CDCl3) δ ppm 1.20 (s, 9H), 6.09 (s, 2H), 7.56 (t, J = 7.93 Hz, 1H), 7.63 (t, J = 7.69 Hz, 1H), 7.85-7.98 (m, 3H), 8.01 (d, J = 8.06 Hz, 1H), 8.10 (s, 1H), 8.39 (s, 1H), 10.09 (s, 1H).
Note 5
100° C./10 min, then 120° C./20 min. Additional boronic acid and catalyst were added, and heating resumed; 120° C./20 min, then 135° C./30 min.

Intermediate I-X-22

1,1-dimethylethyl [(3'-amino-3,5-difluoro-4-biphenylyl)-methyl]2,3-dihydro-1H-inden-2-ylcarbamate

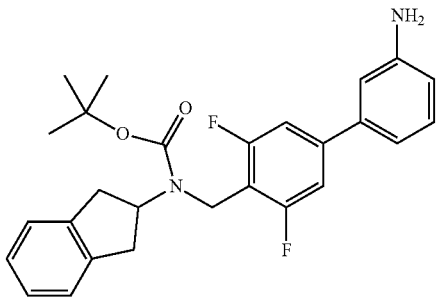 [SMILES: CC(C)(C)OC(=O)N(Cc1c(F)cc(-c2cccc(N)c2)cc1F)C1Cc2ccccc2C1]

Step 1: N-[(3,5-difluoro-3'-nitro-4-biphenylyl)methyl]-2,3-dihydro-1H-inden-2-amine A mixture of {4-[(2,3-dihydro-1H-inden-2-ylamino)methyl]-3,5-difluoro-phenyl}boronic acid (740 mg, 2.44 mmol; Ex V-22), 3-bromonitrobenzene (495 mg, 2.44 mmol), PdCl₂(dppf)₂ (100 mg, 0.12 mmol) and Na₂CO₃ (4.90 mL, 2.0 M (aq)) in DME (10 mL) was stirred at 80° C. for 45 min. The mixture was diluted with EtOAc then filtered through a pad of Celite and silica gel. The filtrate was washed with H₂O and brine, dried over Na₂SO₄ then concentrated to give N-[(3,5-difluoro-3'-nitro-4-biphenylyl)methyl]-2,3-dihydro-1H-inden-2-amine as a tan glass. LC/MS (method A) 0.62 min, (m/z) 381 (70%), 382 (100%).

Step 2: 1,1-dimethylethyl [(3'-amino-3,5-difluoro-4-biphenylyl)methyl]2,3-dihydro-1H-inden-2-ylcarbamate A solution of N-[(3,5-difluoro-3'-nitro-4-biphenylyl)methyl]-2,3-dihydro-1H-inden-2-amine (920 mg, 2.42 mmol; step 1), (Boc)₂O (630 mg, 2.90 mmol), and triethylamine (1.70 mL, 12.1 mmol) in THF (10 mL) was stirred at room temperature for 16 hr. The solution was diluted with EtOAc, washed with H₂O and brine, dried over Na₂SO₄ then concentrated. To the residue was added THF (10 mL) and Pd/C (100 mg) and the mixture stirred vigorously at room temperature under 1 atm H₂ for 45 min. The mixture was filtered through a pad of Celite and silica gel then concentrated to give 1,1-dimethylethyl [(3'-amino-3,5-difluoro-4-biphenylyl)methyl] 2,3-dihydro-1H-inden-2-ylcarbamate as a tan glass. LC/MS (method A) 1.02 min, (m/z) 451 (M+1).

Compounds of Formula X

Example X-1 ethyl 4-[5-({[2-(3-fluorophenyl)ethyl]amino}methyl)-2-furanyl]-benzoate

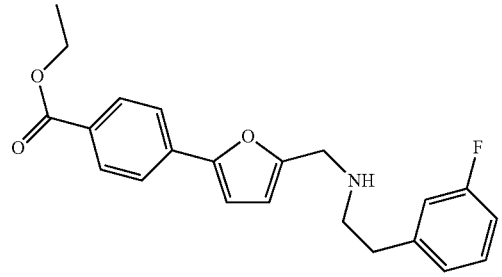 [SMILES: CCOC(=O)c1ccc(-c2ccc(CNCCc3cccc(F)c3)o2)cc1]

To a 100 mL round bottom flask was added ethyl 4-(5-formyl-2-furanyl)benzoate (100 mg, 0.41 mmol, commercially available), [2-(3-fluorophenyl)ethyl]amine (0.070 mL, 0.49 mmol), NaBH(OAc)₃ (261 mg, 1.23 mmol) and DCE (10 mL). The reaction was stirred at room temperature overnight, quenched with H₂O, and extracted with CH₂Cl₂ (×3). The organic layer was washed with brine, dried with MgSO₄ and concentrated under reduced pressure to give 150 mg of ethyl 4-[5-({[2-(3-fluorophenyl)-ethyl]amino}methyl)-2-furanyl] benzoate (used without further purification). LC/MS (method A) 1.97 min; m/z 368 (M+H).

The following examples were prepared from ethyl 4-(5-formyl-2-furanyl)benzoate and the appropriate compounds of Formula III according to the procedure described in Ex X-1, with any significant deviations noted below table.

TABLE P

Compounds of Formula X from reductive alkylation of Intermediates of Formula X

| Ex. | Structure/Name | Characterization Data | Comments |
|---|---|---|---|
| X-2 | ethyl 4-(5-{[(3-methylbutyl)-amino]methyl}-2-furyl)benzoate | LC/MS (method B) 1.95 min, m/z 316. | |

Example X-3

(3-{3'-[(2,3-dihydro-1H-inden-2-ylamino)methyl]-4-biphenylyl}-1H-1,2,4-triazol-1-yl)methyl 2,2-dimethylpropanoate

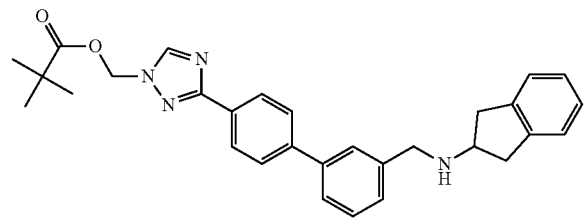 [SMILES: CC(C)(C)C(=O)OCn1cnc(-c2ccc(-c3cccc(CNC4Cc5ccccc5C4)c3)cc2)n1]

To a solution of [3-(3'-formyl-4-biphenylyl)-1H-1,2,4-triazol-1-yl]methyl 2,2-dimethylpropanoate (0.081 g, 0.22 mmol; I-X-17) and 2-aminoindane (0.045 mL, 0.35 mmol) in 1:1 THF/MeOH (2 mL) was added acetic acid (0.12 mL) and MP—BH$_3$CN (ca. 0.67 mmol, Note 1). The mixture was stirred at room temperature overnight, resin was remove by filtration (THF wash) and the filtrate was concentrated in vacuo. The residue was partitioned between EtOAc/5% Na$_2$CO$_3$, layers were separated and the aqueous layer was extracted with EtOAc. Combined organics were washed (water, brine), dried over Na$_2$SO$_4$, and concentrated in vacuo. The residue was purified by flash chromatography (MeOH/CH$_2$Cl$_2$), affording the title compound. $^1$H NMR (400 MHz, CDCl$_3$) δ ppm 1.20 (s, 9 H), 2.84 (dd, J=15.6, 6.4 Hz, 2 H), 3.20 (dd, J=15.6, 7.1 Hz, 2 H), 3.68-3.75 (m, 1 H), 3.93 (s, 2 H), 6.09 (s, 2 H), 7.08-7.23 (m, 4 H), 7.31-7.38 (m, 1 H), 7.41 (t, J=7.6 Hz, 1 H), 7.53 (d, J=7.6 Hz, 1 H), 7.63 (s, 1 H), 7.69 (d, J=8.3 Hz, 2 H), 8.19 (d, J=8.3 Hz, 2 H), 8.37 (s, 1 H).

Note 1 'MP—BH$_3$CN'=macroporous polymer-supported trialkylammonium cyanoborohydride (Argonaut Technologies).

The following examples were prepared from the appropriate intermediates of formula X and compounds of Formula III according to the procedure described in Ex X-3, with any significant deviations noted below table.

TABLE Q

Compounds of Formula X from reductive alkylation of Intermediates of Formula X having an N-protected heterocycle

| Ex | Structure/Name | Characterization Data | Comments |
|---|---|---|---|
| X-4 | (3-{3'-[(2,3-dihydro-1H-inden-2-ylamino)methyl]-4'-fluoro-4-biphenylyl}-1H-1,2,4-triazol-1-yl)methyl 2,2-dimethylpropanoate | 1H NMR (400 MHz, CDCl3) δ ppm 1.19 (s, 9H), 2.84 (dd, J = 15.38, 6.35 Hz, 2H), 3.20 (dd, J = 15.63, 7.08 Hz, 2H), 3.66-3.75 (m, 1H), 3.97 (s, 2H), 6.08 (s, 2H), 7.06-7.23 (m, 5H), 7.45-7.53 (m, 1H), 7.62-7.64 (d + m, 3H), 8.17 (d, J = 8.30 Hz, 2H), 8.37 (s, 1H) | Used I-X-18 |

TABLE Q-continued

Compounds of Formula X from reductive alkylation of Intermediates of Formula X having an N-protected heterocycle

| Ex | Structure/Name | Characterization Data | Comments |
|---|---|---|---|
| X-5 | (3-{3'-[(2,3-dihydro-1H-inden-2-ylamino)methyl]-2'-fluoro-4-biphenylyl}-1H-1,2,4-triazol-1-yl)methyl 2,2-dimethylpropanoate | 1H NMR (400 MHz, CDCl3) δ ppm 1.19 (s, 9H), 2.83 (dd, J = 15.50, 6.47 Hz, 2H), 3.20 (dd, J = 15.50, 6.96 Hz, 2H), 3.67-3.73 (m, 1H), 3.98 (s, 2H), 6.09 (s, 2H), 7.08-7.22 (m, 5H), 7.37 (t, J = 7.32 Hz, 2H), 7.63 (d, J = 7.08 Hz, 2H), 8.19 (d, J = 8.30 Hz, 2H), 8.37 (s, 1H) | Used I-X-19 |
| X-6 | (3-{3'-[(2,3-dihydro-1H-inden-2-ylamino)methyl]-2-methyl-4-biphenylyl}-1H-1,2,4-triazol-1-yl)methyl 2,2-dimethylpropanoate | 1H NMR (400 MHz, CDCl3) δ ppm 1.19 (s, 9H), 2.33 (s, 3H), 2.82 (dd, J = 15.50, 6.47 Hz, 2H), 3.18 (dd, J = 15.38, 7.08 Hz, 2H), 3.67-3.74 (m, 1H), 3.91 (s, 2H), 6.09 (s, 2H), 7.08-7.23 (m, 5H), 7.28-7.41 (m, 4H), 7.97 (d, J = 7.81 Hz, 1H), 8.03 (s, 1H), 8.37 (s, 1H) | Used I-X-20 |
| X-7 | [3-(3'-{[(4,4-dimethylcyclohexyl)amino]methyl}-2-methyl-4-biphenylyl)-1H-1,2,4-triazol-1-yl]methyl 2,2-dimethylpropanoate | (M + 1) 489.3 AP, 2.27 min (LC/MS Method B) | Used I-X-20 and III-1. Note 1 |
| X-8 | [3-(3'-{[(2-cyclohexylethyl)amino]methyl}-2-methyl-4-biphenylyl)-1H-1,2,4-triazol-1-yl]methyl 2,2-dimethylpropanoate | (M + 1) 489.3 AP, 2.34 min (LC/MS Method B) | Used I-X-20 and III-7. Note 1 |
| X-9 | (3-{3'-[(2,3-dihydro-1H-inden-2-ylamino)methyl]-2-fluoro-4-biphenylyl}-1H-1,2,4-triazol-1-yl)methyl 2,2-dimethylpropanoate | 1H NMR (400 MHz, CDCl3) δ ppm 1.20 (s, 9H), 2.83 (dd, J = 15.50, 6.47 Hz, 2H), 3.19 (dd, J = 15.63, 7.08 Hz, 2H), 3.68-3.75 (m, 1H), 3.93 (s, 2H), 6.09 (s, 2H), 7.09-7.22 (m, 4H), 7.34-7.45 (m, 2H), 7.45-7.60 (m, 3H), 7.88-7.93 (m, 1H), 7.96 (d, J = 8.06 Hz, 1H), 8.38 (s, 1H) | Used I-X-21. |

TABLE Q-continued

Compounds of Formula X from reductive alkylation of Intermediates of Formula X having an N-protected heterocycle

| Ex | Structure/Name | Characterization Data | Comments |
|---|---|---|---|
| X-10 | [3-(3'-{[(4,4-dimethylcyclohexyl)amino]methyl}-2-fluoro-4-biphenylyl)-1H-1,2,4-triazol-1-yl]methyl 2,2-dimethylpropanoate | (M + 1) 493.3 AP, 2.31 min (LC/MS Method B) | Used I-X-21 and III-1. Note 1 |
| X-11 | [3-(3'-{[(2-cyclohexylethyl)amino]methyl}-2-fluoro-4-biphenylyl)-1H-1,2,4-triazol-1-yl]methyl 2,2-dimethylpropanoate | (M + 1) 493.3 AP, 2.34 min (LC/MS Method B) | Used I-X-21 and III-7. Note 1 |
| X-12 | (3-{3'-[(2,3-dihydro-1H-inden-2-ylamino)methyl]-2,2'-difluoro-4-biphenylyl}-1H-1,2,4-triazol-1-yl)methyl 2,2-dimethylpropanoate | 1H NMR (400 MHz, CDCl3) δ ppm 1.20 (s, 9H), 2.83 (dd, J = 15.50, 6.23 Hz, 2H), 3.19 (dd, J = 15.63, 7.08 Hz, 2H), 3.66-3.72 (m, 1H), 3.98 (s, 2H), 6.09 (s, 2H), 7.08-7.23 (m, 5H), 7.32 (t, J = 6.84 Hz, 1H), 7.38-7.51 (m, 2H), 7.92 (dd, J = 10.99, 1.22 Hz, 1H), 7.97 (d, J = 8.06 Hz, 1H), 8.38 (s, 1H) Impurity present in NMR - material used in the next reaction without further purification. | Used I-X-11. Note 3 |
| X-13 | [3-(3'-{[(4,4-dimethylcyclohexyl)amino]methyl}-4-biphenylyl)-1H-1,2,4-triazol-1-yl]methyl 2,2-dimethylpropanoate | 1H NMR (400 MHz, CDCl3) δ ppm 0.89 (s, 3H), 0.90 (s, 3H), 1.12-1.26 (s + m, 11H), 1.27-1.45 (m, 4H), 1.71-1.80 (m, 2H), 2.41-2.52 (m, 1H), 3.88 (s, 2H), 6.09 (s, 2H), 7.32 (d, J = 7.32 Hz, 1H), 7.40 (t, J = 7.57 Hz, 1H), 7.52 (d, J = 7.57 Hz, 1H), 7.58 (s, 1H), 7.69 (d, J = 8.30 Hz, 2H), 8.18 (d, J = 8.06 Hz, 2H), 8.37 (s, 1H) | Used I-X-17 and III-1. Note 1 |

TABLE Q-continued

Compounds of Formula X from reductive alkylation of Intermediates of Formula X having an N-protected heterocycle

| Ex | Structure/Name | Characterization Data | Comments |
|---|---|---|---|
| X-14 | [3-(3'-{[(4,4-dimethylcyclohexyl)amino]methyl}-2'-fluoro-4-biphenylyl)-1H-1,2,4-triazol-1-yl]methyl 2,2-dimethylpropanoate | 1H NMR (400 MHz, CDCl3) δ ppm 0.89 (s, 3H), 0.90 (s, 3H), 1.08-1.26 (s + m, 11H), 1.26-1.45 (m, 4H), 1.67-1.81 (m, 2H), 2.38-2.50 (m, 1H), 3.92 (s, 2H), 6.09 (s, 2H), 7.17 (t, J = 7.57 Hz, 1H), 7.28-7.41 (m, 2H), 7.63 (d, J = 8.06 Hz, 2H), 8.19 (d, J = 8.30 Hz, 2H), 8.37 (s, 1H) | Used I-X-19 and III-1. Note 1 |
| X-15 | [3-(3'-{[(2-cyclohexylethyl)amino]methyl}-2'-fluoro-4-biphenylyl)-1H-1,2,4-triazol-1-yl]methyl 2,2-dimethylpropanoate | (M + 1) 493.2 AP, 0.75 min (LC/MS Method B, gradient time = 1.5 min) | Used I-X-19 and III-7. Note 1 |
| X-16 | [3-(3'-{[(4,4-dimethylcyclohexyl)amino]methyl}-2,2'-difluoro-4-biphenylyl)-1H-1,2,4-triazol-1-yl]methyl 2,2-dimethylpropanoate | Not characterized (Note 2) | Used I-X-11 and III-1. Note 1, 2 |
| X-17 | (3-{3'-[(2,3-dihydro-1H-inden-2-ylamino)methyl]-2'-fluoro-2-methyl-4-biphenylyl}-1H-1,2,4-triazol-1-yl)methyl 2,2-dimethylpropanoate | (M + 1) 513.3 AP, 0.71 min (LC/MS Method B, gradient time = 1.5 min) | Used I-X-12 and III-1. Note 3 |
| X-18 | [3-(3'-{[(4,4-dimethylcyclohexyl)amino]methyl}-2'-fluoro-2-methyl-4-biphenylyl}-1H-1,2,4-triazol-1-yl]methyl 2,2-dimethylpropanoate | Not characterized (Note 2) | Used I-X-12 and III-1. Note 2 |

TABLE Q-continued

Compounds of Formula X from reductive alkylation of Intermediates of Formula X having an N-protected heterocycle

| Ex | Structure/Name | Characterization Data | Comments |
|---|---|---|---|
| X-19 | (3-{3'-[(2,3-dihydro-1H-inden-2-ylamino)methyl]-2',4'-difluoro-4-biphenylyl}-1H-1,2,4-triazol-1-yl)methyl 2,2-dimethylpropanoate | (M + 1) 517.2 AP, 0.69 min (LC/MS Method B, gradient time = 1.5 min) | Used I-X-13. |
| X-20 | [3-(3'-{[(4,4-dimethylcyclohexyl)amino]methyl}-2',4'-difluoro-4-biphenylyl)-1H-1,2,4-triazol-1-yl]methyl 2,2-dimethylpropanoate | Not characterized (Note 2) | Used I-X-13 and III-1. Note 1, 2 |
| X-21 | (3-{3'-[(2,3-dihydro-1H-inden-2-ylamino)methyl]-2',4'-difluoro-3-biphenylyl}-1H-1,2,4-triazol-1-yl)methyl 2,2-dimethylpropanoate | 1H NMR (400 MHz, CDCl3) δ ppm 1.19 (s, 9H), 2.82 (dd, J = 15.63, 6.35 Hz, 2H), 3.18 (dd, J = 15.50, 6.96 Hz, 2H), 3.62-3.69 (m, 1H), 4.03 (s, 2H), 6.08 (s, 2H), 6.97 (t, J = 8.55 Hz, 1H), 7.09-7.16 (m, 2H), 7.16-7.23 (m, 2H), 7.35-7.43 (m, 1H), 7.49-7.59 (m, 2H), 8.13 (d, J = 7.08 Hz, 1H), 8.26 (s, 1H), 8.37 (s, 1H) | Used I-X-14. |
| X-22 | (3-(3'-((4,4-dimethylcyclohexylamino)methyl)-2',4'-difluorobiphenyl-3-yl)-1H-1,2,4-triazol-1-yl)methyl pivalate | 1H NMR (400 MHz, CDCl3) ppm 0.89 (s + s, 6H), 1.12-1.27 (s + m, 11H), 1.27-1.45 (m, 4H), 1.69-1.81 (m, 2H), 2.34-2.45 (m, 1H), 3.97 (s, 2H), 6.08 (s, 2H), 6.95 (t, J = 8.55 Hz, 1H), 7.33-7.42 (m, 1H), 7.48-7.60 (m, 2H), 8.12 (d, J = 7.32 Hz, 1H), 8.25 (s, 1H), 8.37 (s, 1H) | Used I-X-14 and III-1. Note 1, 4 |
| X-23 | [3-(3'-{[(2-cyclohexylethyl)amino]methyl}-2',4'-difluoro-3-biphenylyl)-1H-1,2,4-triazol-1-yl]methyl 2,2-dimethylpropanoate | Not characterized (Note 2) | Used I-X-14 and III-7. Note 1, 2, 4 |

TABLE Q-continued

Compounds of Formula X from reductive alkylation of Intermediates of Formula X having an N-protected heterocycle

| Ex | Structure/Name | Characterization Data | Comments |
|---|---|---|---|
| X-24 | 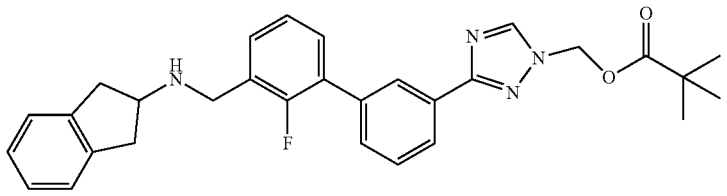<br>(3-{3'-[(2,3-dihydro-1H-inden-2-ylamino)methyl]-2'-fluoro-3-biphenylyl}-1H-1,2,4-triazol-1-yl)methyl 2,2-dimethylpropanoate | (M + 1) 499.2 AP, 0.80 min (LC/MS Method B, gradient time = 1.5 min)) | Used I-X-15. Note 4 |
| X-25 | 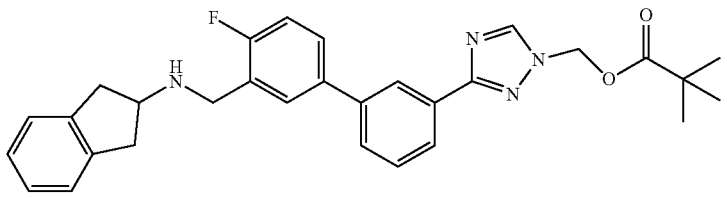<br>(3-{3'-[(2,3-dihydro-1H-inden-2-ylamino)methyl]-4'-fluoro-3-biphenylyl}-1H-1,2,4-triazol-1-yl)methyl 2,2-dimethylpropanoate | (M + 1) 499.2 AP, 0.82 min (LC/MS Method B, gradient time = 1.5 min) | Used I-X-16. Note 4 |
| X-26 | 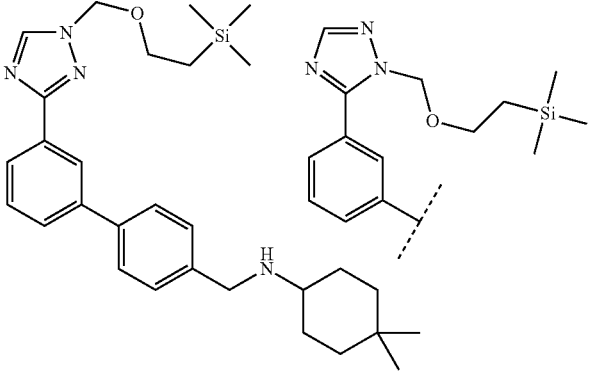<br>4,4-dimethyl-N-((3'-(1-((2-(trimethylsilyl)ethoxy)methyl)-1H-1,2,4-triazol-3-yl)biphenyl-4-yl)methyl)cyclohexanamine and 4,4-dimethyl-N-((3'-(1-((2-(trimethylsilyl)ethoxy)methyl)-1H-1,2,4-triazol-5-yl)biphenyl-4-yl)methyl)cyclohexanamine | Not characterized (Note 2) | Used I-X-1 and III-3 Note 1, 2 |
| X-27 | 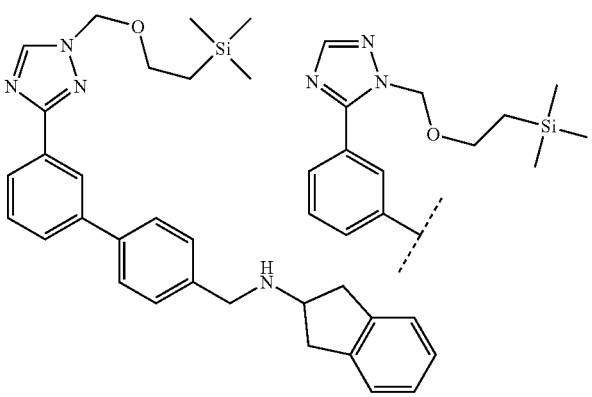<br>N-((3'-(1-((2-(trimethylsilyl)ethoxy)methyl)-1H-1,2,4-triazol-3-yl)biphenyl-4-yl)methyl)-2,3-dihydro-1H-inden-2-amine and N-((3'-(1-((2-(trimethylsilyl)ethoxy)methyl)-1H-1,2,4-triazol-5-yl)biphenyl-4-yl)methyl)-2,3-dihydro-1H-inden-2-amine | Not characterized (Note 2) | Used I-X-1 Note 1, 2 |

TABLE Q-continued

Compounds of Formula X from reductive alkylation of Intermediates of Formula X having an N-protected heterocycle

| Ex | Structure/Name | Characterization Data | Comments |
|---|---|---|---|
| X-28 | 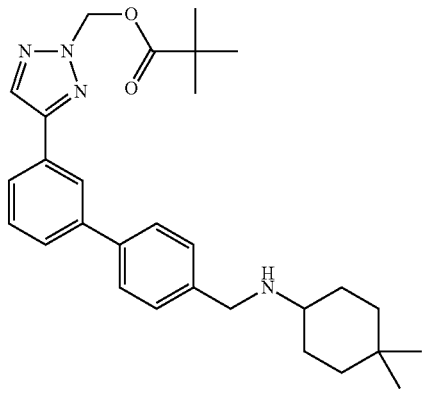<br>[4-(4'-{[(4,4-dimethylcyclohexyl)amino]methyl}-3-biphenylyl)-2H-1,2,3-triazol-2-yl]methyl 2,2-dimethylpropanoate | LC/MS (method A) 2.25 min; m/z 475 (M + H) | Used I-X-3 and III-1 Note 1 |
| X-29 | 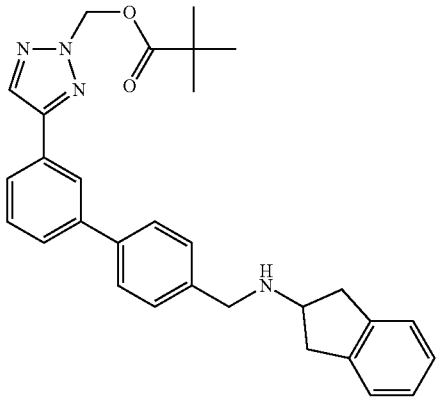<br>(4-{4'-[(2,3-dihydro-1H-inden-2-ylamino)methyl]-3-biphenylyl}-2H-1,2,3-triazol-2-yl)methyl 2,2-dimethylpropanoate | LC/MS (method A) 2.11 min; m/z 482 (M + H) | Used I-X-3 Note 1 |
| X-30 | 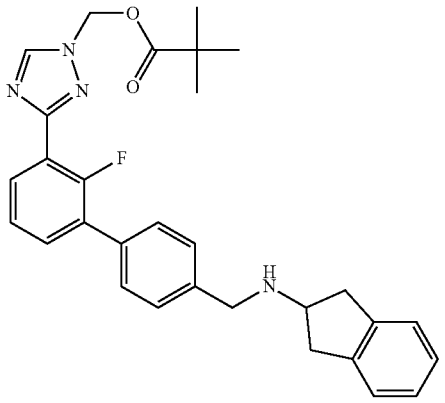<br>(3-{4'-[(2,3-dihydro-1H-inden-2-ylamino)methyl]-2-fluoro-3-biphenylyl}-1H-1,2,4-triazol-1-yl)methyl 2,2-dimethylpropanoate | Not characterized (Note 2) | Used I-X-6 Note 1, 2, 5 |

TABLE Q-continued

Compounds of Formula X from reductive alkylation of Intermediates of Formula X having an N-protected heterocycle

| Ex | Structure/Name | Characterization Data | Comments |
|---|---|---|---|
| X-31 | 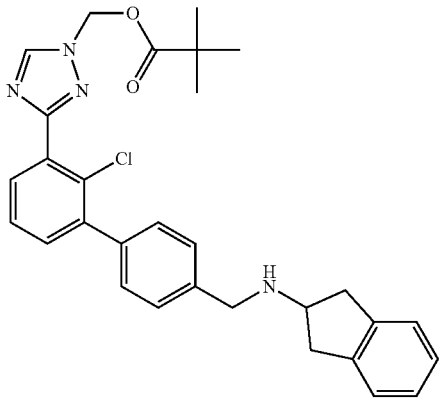<br>(3-{2-chloro-4'-[(2,3-dihydro-1H-inden-2-ylamino)methyl]-3-biphenylyl}-1H-1,2,4-triazol-1-yl)methyl 2,2-dimethylpropanoate | Not characterized (Note 2) | Used I-X-7<br>Note 1, 2, 5 |
| X-32 | 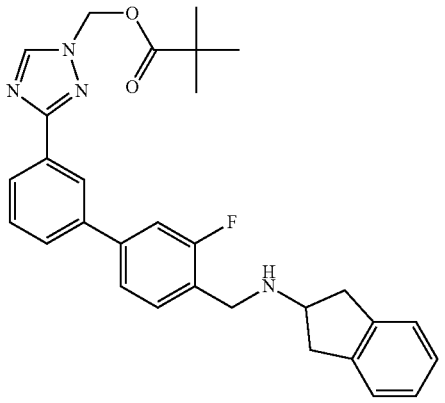<br>(3-{4'-[(2,3-dihydro-1H-inden-2-ylamino)methyl]-3'-fluoro-3-biphenylyl}-1H-1,2,4-triazol-1-yl)methyl 2,2-dimethylpropanoate | Note 5 | Used I-X-8<br>Note 1, 5 |
| X-33 | 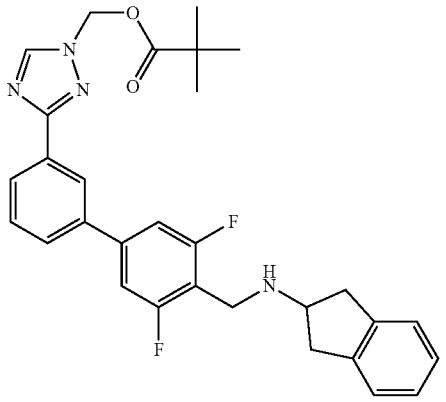 [SMILES: CC(C)(C)C(=O)OCn1cnc(-c2cccc(-c3cc(F)c(CNC4Cc5ccccc5C4)c(F)c3)c2)n1]<br>(3-{4'-[(2,3-dihydro-1H-inden-2-ylamino)methyl]-3',5'-difluoro-3-biphenylyl}-1H-1,2,4-triazol-1-yl)methyl 2,2-dimethylpropanoate | Note 6 | Used I-X-9<br>Note 1, 2, 5, 6 |

TABLE Q-continued

Compounds of Formula X from reductive alkylation of Intermediates of Formula X having an N-protected heterocycle

| Ex | Structure/Name | Characterization Data | Comments |
|---|---|---|---|
| X-34 | 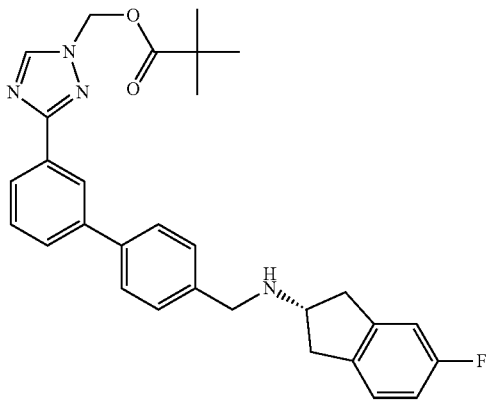<br>{3-[4'-({[(2S)-5-fluoro-2,3-dihydro-1H-inden-2-yl]amino}methyl)-3-biphenylyl]-1H-1,2,4-triazol-1-yl}methyl 2,2-dimethylpropanoate | LC/MS (method E) 0.79 min; m/z 499 (M + H) | Used I-X-2 and (S)-III-11 Note 1, 7 |
| X-35 | 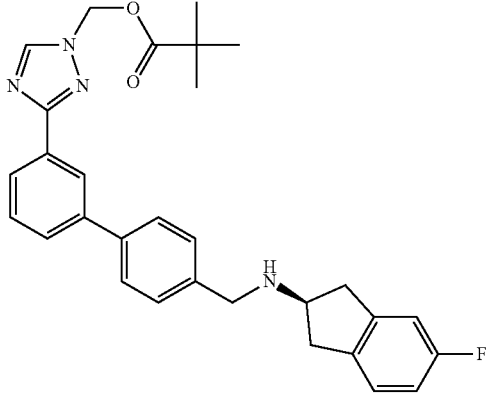<br>{3-[4'-({[(2R)-5-fluoro-2,3-dihydro-1H-inden-2-yl]amino}methyl)-3-biphenylyl]-1H-1,2,4-triazol-1-yl}methyl 2,2-dimethylpropanoate | LC/MS (method E) 0.79 min; m/z 499 (M + H) | Used I-X-2 and (R)-III-11 Note 1, 7 |
| X-36 | 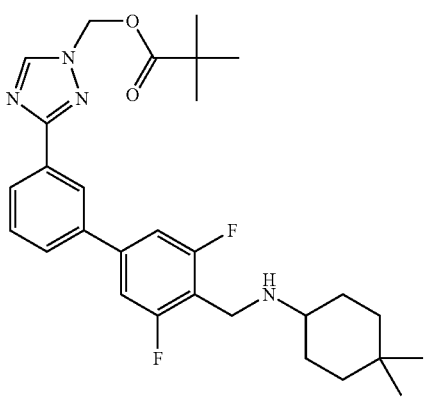<br>[3-(4'-{[(4,4-dimethylcyclohexyl)amino]methyl}-3',5'-difluoro-3-biphenylyl)-1H-1,2,4-triazol-1-yl]methyl 2,2-dimethylpropanoate | LC/MS (method E) 0.85 min; m/z 511 (M + H) | Used I-X-9 and III-1 Note 1, 8 |

TABLE Q-continued

Compounds of Formula X from reductive alkylation of Intermediates of Formula X having an N-protected heterocycle

| Ex | Structure/Name | Characterization Data | Comments |
|---|---|---|---|
| X-37 | 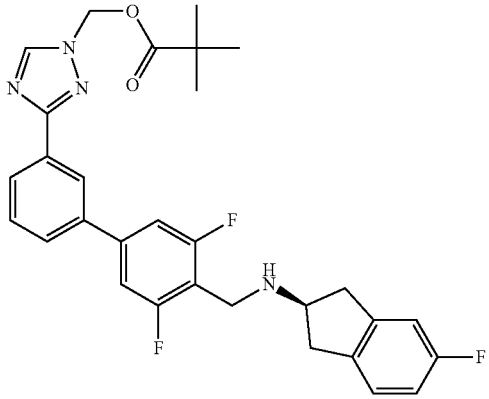<br>{3-[3′,5′-difluoro-4′-({[(2R)-5-fluoro-2,3-dihydro-1H-inden-2-yl]amino}methyl)-3-biphenylyl]-1H-1,2,4-triazol-1-yl}methyl 2,2-dimethylpropanoate | LC/MS (method E)<br>0.84 min; m/z 535<br>(M + H) | Used I-X-9 and<br>(R)-III-11<br>Note 1, 8 |
| X-38 | 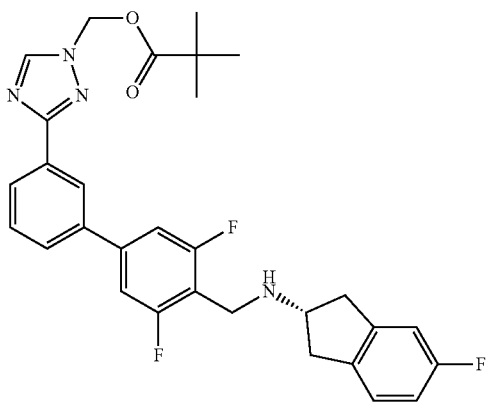<br>{3-[3′,5′-difluoro-4′-({[(2S)-5-fluoro-2,3-dihydro-1H-inden-2-yl]amino}methyl)-3-biphenylyl]-1H-1,2,4-triazol-1-yl}methyl 2,2-dimethylpropanoate | LC/MS (method E)<br>0.84 min; m/z 535<br>(M + H) | Used I-X-9 and<br>(S)-III-11<br>Note 1, 8 |
| X-39 | 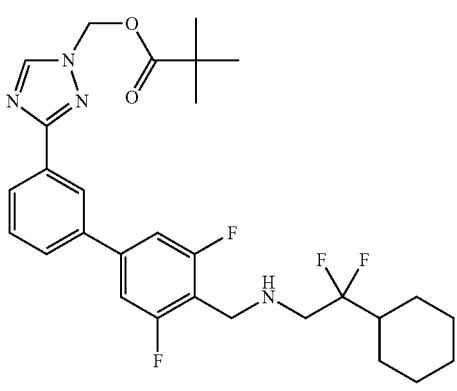<br>[3-(4′-{[(2-cyclohexyl-2,2-difluoroethyl)amino]methyl}-3′,5′-difluoro-3-biphenylyl)-1H-1,2,4-triazol-1-yl]methyl 2,2-dimethylpropanoate | LC/MS (method E)<br>1.05 min; m/z 547<br>(M + H) | Used I-X-9 and<br>III-8<br>Note 1, 8 |

TABLE Q-continued

Compounds of Formula X from reductive alkylation of Intermediates of Formula X having an N-protected heterocycle

| Ex | Structure/Name | Characterization Data | Comments |
|---|---|---|---|
| X-40 | 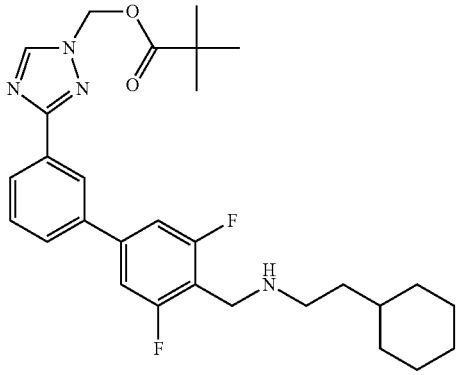<br>[3-(4'-{[(2-cyclohexylethyl)amino]methyl}-3',5'-difluoro-3-biphenylyl)-1H-1,2,4-triazol-1-yl]methyl 2,2-dimethylpropanoate | LC/MS (method E) 0.87 min; m/z 511 (M + H) | Used I-X-9 and III-7<br>Note 1, 8 |
| X-41 | 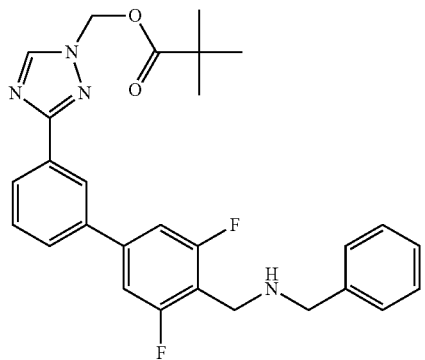<br>[3-(3',5'-difluoro-4'-{[(phenylmethyl)amino]methyl}-3-biphenylyl)-1H-1,2,4-triazol-1-yl]methyl 2,2-dimethylpropanoate | LC/MS (method E) 0.82 min; m/z 491 (M + H) | Used I-X-9<br>Note 8 |
| X-42 | 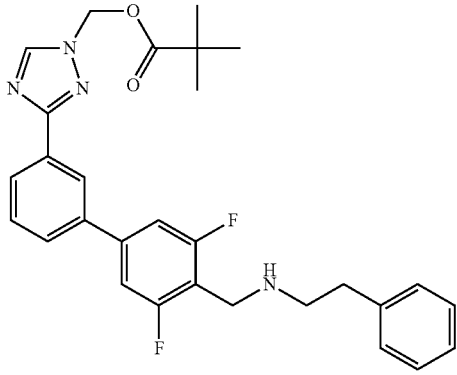<br>[3-(3',5'-difluoro-4'-{[(2-phenylethyl)amino]methyl}-3-biphenylyl)-1H-1,2,4-triazol-1-yl]methyl 2,2-dimethylpropanoate | LC/MS (method E) 83 min; m/z 505 (M + H) | Used I-X-9<br>Note 8 |

TABLE Q-continued

Compounds of Formula X from reductive alkylation of Intermediates of Formula X having an N-protected heterocycle

| Ex | Structure/Name | Characterization Data | Comments |
|---|---|---|---|
| X-43 | 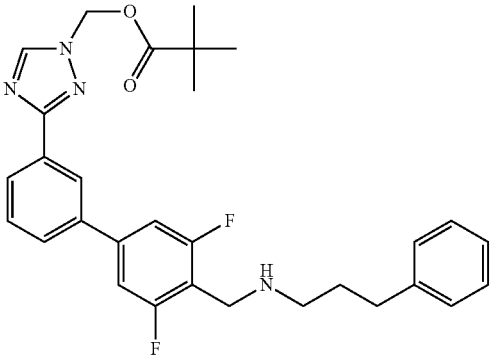<br>[3-(3′,5′-difluoro-4′-{[(3-phenylpropyl)amino]methyl}-3-biphenylyl)-1H-1,2,4-triazol-1-yl]methyl 2,2-dimethylpropanoate | LC/MS (method E)<br>0.84 min; m/z 519<br>(M + H) | Used I-X-9<br>Note 8 |
| X-44 | 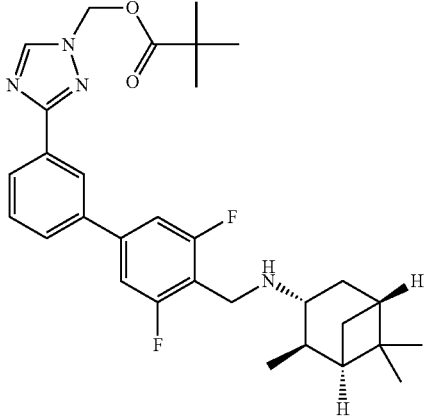<br>{3-[3′,5′-difluoro-4′-({[(1R,2R,3R,5R)-2,6,6-trimethylbicyclo[3.1.1]hept-3-yl]amino}methyl)-3-biphenylyl]-1H-1,2,4-triazol-1-yl}methyl 2,2-dimethylpropanoate | LC/MS (method E)<br>0.88 min; m/z 537<br>(M + H) | Used I-X-9<br>Note 8 |

Note 1

The amine hydrochloride salt used was admixed with an equimolar amount of Et$_3$N in THF/MeOH before use.

Note 2

In some cases, particularly on small-scale preparations, the compound of Formula X shown in the above table was carried onto the deprotection step without characterization (en route to Formula I).

Note 3

Title compound was purified by preparative HPLC (C-18 column, MeCN/water gradient with 0.1% TFA additive).

Note 4

Solution phase reductive amination conditions were used: 1.5 equiv ea amine/amine-HCl—Et$_3$N (Note 1) and NaBH(OAc)$_3$, ca. 5% v/v HOAc/CH$_2$Cl$_2$ solvent, room temperature. Formula X product purified by flash chromatography (CH$_2$CO$_2$/MeOH).

Note 5

Purified by flash chromatography using amine-functionalized silica gel (Teledyne-Isco # 68-2203-102, EtOAc/hexanes).

Note 6

Characterizing data for X-33 is given in the alternate preparation below.

Note 7

Title compounds also prepared using solution phase reductive amination conditions: 1.1 equiv ea amine-HCl—Et$_3$N (Note 1) and NaBH$_3$CN, ca. 5% v/v HOAc in MeOH as solvent, room temperature. Formula X product was purified by flash chromatography using amine-functionalized silica gel (Teledyne-Isco # 68-2203-102, EtOAc/hexanes).

Note 8

1:1 CH$_2$Cl$_2$/MeOH used as solvent instead of 1:1 THF/MeOH.

Alternate Preparation of X-33

(3-{4'-[(2,3-dihydro-1H-inden-2-ylamino)-methyl]-3',5'-difluoro-3-biphenylyl}-1H-1,2,4-triazol-1-yl) methyl 2,2-dimethylpropanoate

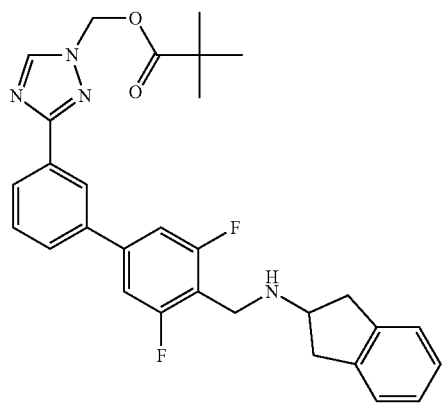

A mixture of [3-(3',5'-difluoro-4'-formyl-3-biphenylyl)-1H-1,2,4-triazol-1-yl]methyl 2,2-dimethylpropanoate (67.6 g; 0.17 mol; I-X-9), 2-aminoindane (22.9 g; 0.17 mol; freebase obtained commercially) and HOAc (0.48 mL; 0.0085 mol, Note 1) in PhH (350 mL) was heated under reflux using a Dean-Stark trap to remove water. After 1.5 h, volatiles were removed in vacuo, the residue was dissolved in $CH_2Cl_2$/HOAc (400:25 mL respectively), and $NaBH(OAc)_3$ (43 g; 0.203 mol) was added at room temperature. The mixture was stirred 12 h, and quenched by dropwise addition of water (250 mL). The mixture was stirred 30 min and separated into layers. The organic layer was washed (satd $NaHCO_3$, brine), filtered through a pad of $Na_2SO_4$ and concentrated in vacuo. The residue was triturated with MeOH (250 mL), the resulting slurry was diluted with water (250 mL) and stirred 30 min at room temperature. Solids were collected by filtration, and washed with water. The cake was air-dried overnight on the filter, affording the title compound as an off-white solid, used without further purification. $^1$H NMR (400 MHz, DMSO-$d_6$) δ ppm 1.1 (s, 9 H), 2.74 (dd, J=15.7, 6.1 Hz, 2 H), 3.09 (dd, J=15.8, 7.1 Hz, 2 H), 3.54 (quint, J=6.6 Hz, 1 H), 3.86 (s, 2 H), 6.21 (s, 2 H), 7.07-7.13 (m, 2 H), 7.15-7.21 (m, 2 H), 7.43-7.52 (m, 2 H), 7.60 (t, J=7.7 Hz, 1 H), 7.81 (ddd, J=7.9, 1.8, 1.1 Hz, 1 H), 8.06 (ddd, J=7.8, 1.3, 1.2 Hz, 1 H), 8.26 (t, J=1.7 Hz, 1 H), 8.82 (s, 1 H).

Note 1 $TsOH.H_2O$ (0.05 equiv) has also been used to catalyse imine formation between I-X-9 and compounds of Formula III as described above, with equivalent efficacy.

General Method 1 for Preparation of Compounds of Formula I

Example 1

3'-({2-[(4,4-dimethylcyclohexyl)amino]ethyl}oxy)-4-biphenylcarboxamide Hydrochloride

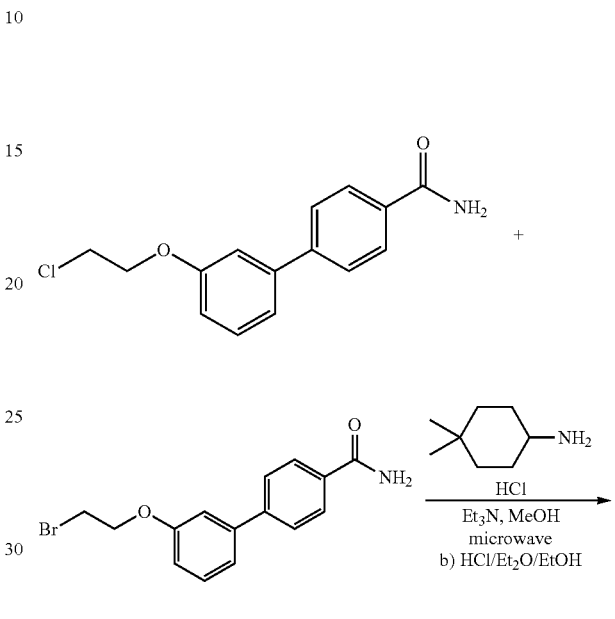

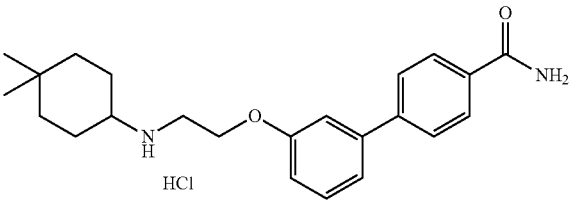

A mixture of 3'-[(2-chloroethyl)oxy]-4-biphenylcarboxamide and 3'-[(2-bromoethyl)oxy]-4-biphenylcarboxamide (Example II-1) (0.15 g), 4,4-dimethylcyclohexylamine hydrochloride (0.13 g, 0.8 mmol) (prepared according to J. Med. Chem. 1971, 14, p. 600-614) and triethylamine (0.14 g, 1.35 mmol) in methanol (2 mL) was placed in a microwave at 160° C. until the reaction was complete as monitored by LC/MS. The reaction mixture was poured into ethyl acetate and washed several times with 5% $Na_2CO_3$ (aq). Silica gel was added to the organic phase and the mixture was concentrated in vacuo. The residue was purified by silica gel chromatography. The fractions containing the desired product were combined and concentrated in vacuo. Dissolved the residue in ethanol, added 1.0N HCl in $Et_2O$ until acidic, added ethyl ether until turbid and let stand at room temperature. The resulting solid was filtered, washed with ethyl ether and dried to give 3'-({2-[(4,4-dimethylcyclohexyl)amino]ethyl}oxy)-4-biphenylcarboxamide hydrochloride as an off-white solid. (M+H) 367, 1.83 min. (LC/MS method A)

The following examples were prepared from the appropriate halide of Formula II and the corresponding amine of Formula III according to the procedure described for Example 1 of General Method 1, with any significant deviations being noted below the table.

TABLE 1

Compounds of Formula I Generated from Compounds of Formula II

| Ex. | Structure and Name | Characterization Data | Method/Comments |
|---|---|---|---|
| 2 | 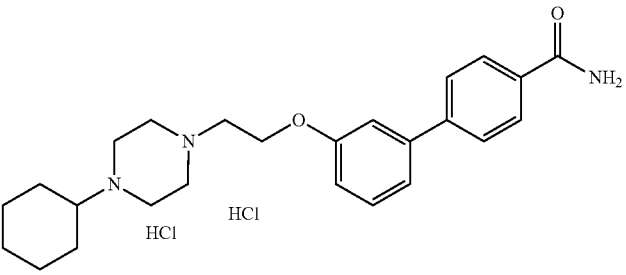<br>3'-{[2-(4-cyclohexyl-1-piperazinyl)ethyl]oxy}-4-biphenylcarboxamide dihydrochloride | (M + H) 408, $t_R$ 1.43 min. (LC/MS method A). | Used II-1 mixed halides |
| 3 | 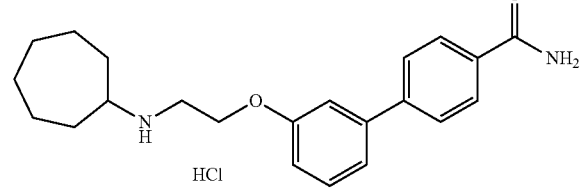<br>3'-{[2-(cycloheptylamino)ethyl]oxy}-4-biphenylcarboxamide dihydrochloride | (M + H) 353, $t_R$ 1.64 min. (LC/MS method A). | Used II-1 mixed halides |
| 4 | 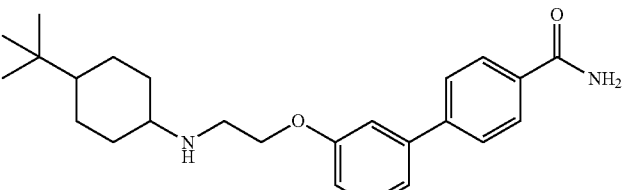<br>3'-[(2-{[4-(1,1-dimethylethyl)cyclohexyl]amino}ethyl)oxy]-4-biphenyl carboxamide hydrochloride | (M + H) 395, $t_R$ 2.02 min. (LC/MS method A). | Used II-1 mixed halides |
| 5 | 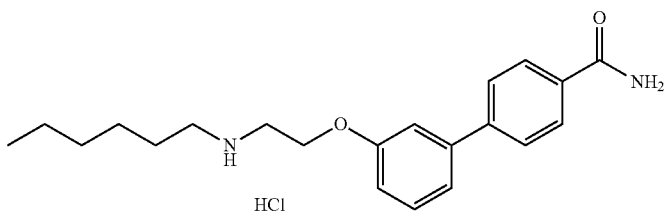<br>3'-{[2-(hexylamino)ethyl]oxy}-4-biphenylcarboxamide hydrochloride | (M + H) 341, $t_R$ 1.70 min. (LC/MS method A). | Used II-1 mixed halides |
| 6 | 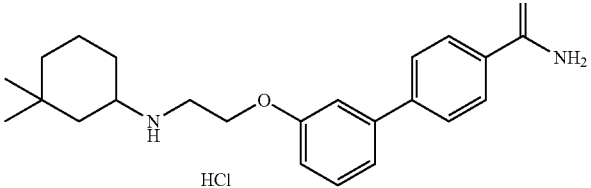<br>3'-({2-[(3,3-dimethylcyclohexyl)amino]ethyl}oxy)-4-biphenyl carboxamide | (M + H) 367, $t_R$ 1.75 min. (LC/MS method A). | Used II-1 mixed halides and III-3 amine |

TABLE 1-continued

Compounds of Formula I Generated from Compounds of Formula II

| Ex. | Structure and Name | Characterization Data | Method/Comments |
|---|---|---|---|
| 7 | 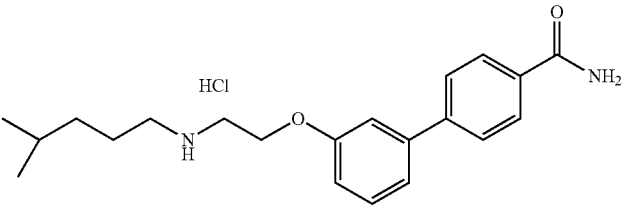<br>3'-({2-[(4-methylpentyl)amino]ethyl}oxy)-4-biphenylcarboxamide hydrochloride | (M + H) 341, $t_R$ 1.72 min. (LC/MS method A). | Used II-1 mixed halides and III-6 amine |
| 8 | 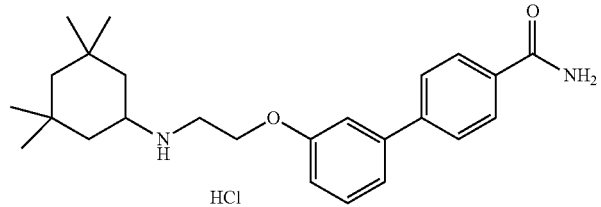<br>3'-({2-[(3,3,5,5-tetramethylcyclohexyl)amino]ethyl}oxy)-4-biphenyl carboxamide hydrochloride | (M + H) 395, $t_R$ 1.98 min. (LC/MS method A). | Used II-1 mixed halides and III-5 amine |
| 9 | 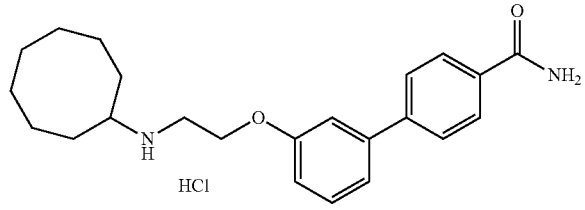<br>3'-{[2-(cyclooctylamino)ethyl]oxy}-4-biphenylcarboxamide hydrochloride | (M + H) 367, $t_R$ 1.75 min. (LC/MS method A). | Used II-1 mixed halides |
| 10 | 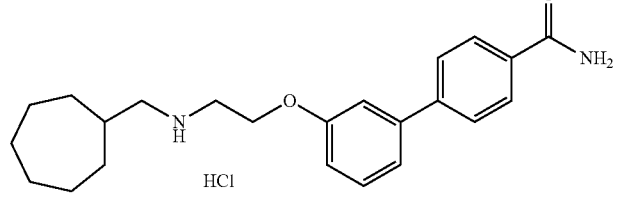<br>3'-({2-[(cycloheptylmethyl)amino]ethyl}oxy)-4-biphenylcarboxamide hydrochloride | (M + H) 367, $t_R$ 1.80 min. (LC/MS method B) | Used II-1 mixed halides |
| 11 | 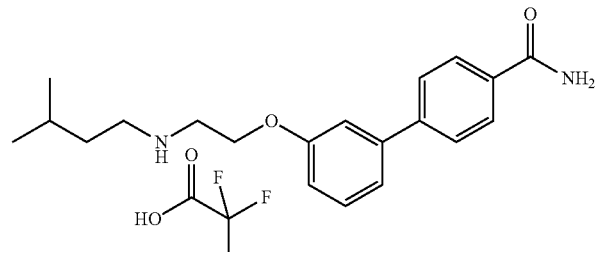<br>3'-({2-[(3-methylbutyl)amino]ethyl}oxy)-4-biphenylcarboxamide trifluoroacetate | (M + H) 327, $t_R$ 1.57 min. (LC/MS method A). | Used II-1 mixed halides[1)] |

TABLE 1-continued

Compounds of Formula I Generated from Compounds of Formula II

| Ex. | Structure and Name | Characterization Data | Method/Comments |
|---|---|---|---|
| 12 | 3'-({2-[(2-methylpropyl)amino]ethyl}oxy)-4-biphenylcarboxamide trifluoroacetate | (M + H) 313, $t_R$ 1.40 min. (LC/MS method A). | Used II-1 mixed halides[1] |
| 13 | 3'-[(2-{[(3-fluorophenyl)methyl]amino}ethyl)oxy]-4-biphenyl carboxamide trifluoroacetate | (M + H) 365, $t_R$ 1.60 min. (LC/MS method A). | Used II-1 mixed halides[1] |
| 14 | 3'-({2-[(cyclohexylmethyl)amino]ethyl}oxy)-4-biphenylcarboxamide trifluoroacetate | (M + H) 353, $t_R$ 1.69 min. (LC/MS method A). | Used II-1 mixed halides[1] |
| 15 | 3'-[(2-{[2-(3-fluorophenyl)ethyl]amino}ethyl)oxy]-4-biphenyl carboxamide trifluoroacetate | (M + H) 379, $t_R$ 1.62 min. (LC/MS method A). | Used II-1 mixed halides[1] |

TABLE 1-continued

Compounds of Formula I Generated from Compounds of Formula II

| Ex. | Structure and Name | Characterization Data | Method/Comments |
|---|---|---|---|
| 16 | 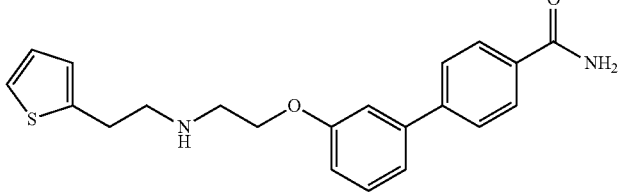<br>3'-[(2-{[2-(2-thienyl)ethyl]amino}ethyl)oxy]-4-biphenyl carboxamide | (M + H) 367, $t_R$ 1.55 min. (LC/MS method A). | Used II-1 mixed halides[1,2) |
| 17 | 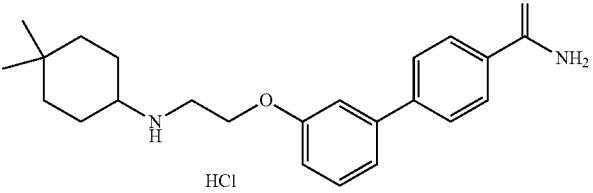<br>'-[(2-{[(4,4-dimethylcyclohexyl)methyl]amino}ethyl)oxy]-4-biphenylcarboxamide hydrochloride | (M + H) 381, $t_R$ 1.90 min. (LC/MS method A) | Used II-2 chloride and III-1 amine |
| 18 | 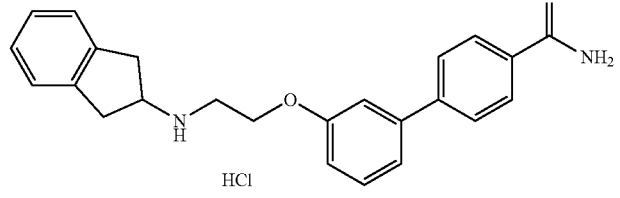<br>3'-{[2-(2,3-dihydro-1H-inden-2-ylamino)ethyl]oxy}-4-biphenyl carboxamide hydrochloride | (M + H) 373, $t_R$ 1.66 min. (LC/MS method B). | Used II-2 chloride |
| 19 | 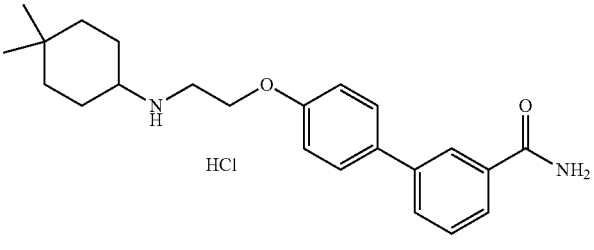<br>4'-({2-[(4,4-dimethylcyclohexyl)amino]ethyl}oxy)-3-biphenylcarboxamide hydrochloride | (M + H) 367, $t_R$ 1.77 min. (LC/MS method A) | Used II-3 mixed halides and III-1 amine |
| 20 | 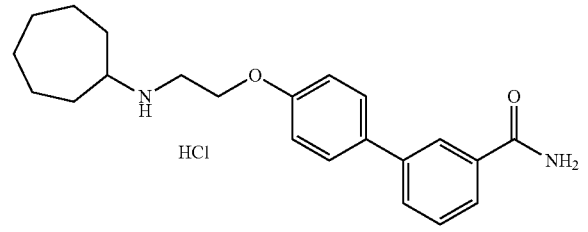<br>4'-{[2-(cycloheptylamino)ethyl]oxy}-3-biphenylcarboxamide hydrochloride | (M + H) 353, $t_R$ 1.65 min. (LC/MS method A). | Used II-3 mixed halides |

TABLE 1-continued

Compounds of Formula I Generated from Compounds of Formula II

| Ex. | Structure and Name | Characterization Data | Method/Comments |
|---|---|---|---|
| 21 | 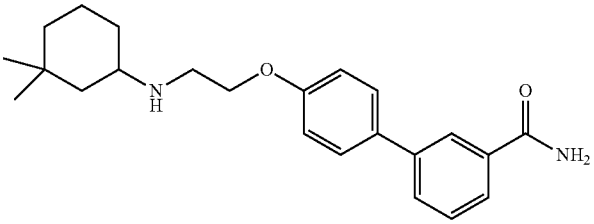<br>4'-({2-[(3,3-dimethylcyclohexyl)amino]ethyl}oxy)-3-biphenyl carboxamide | (M + H) 367, $t_R$ 1.75 min. (LC/MS method A). | Used II-3 mixed halides and III-3 amine[2)] Reaction time 6 hr (1.5 hr at 160° C. and 4.5 hr at 150° C.) |
| 22 | 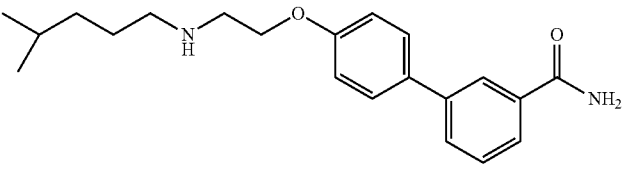<br>4'-({2-[(4-methylpentyl)amino]ethyl}oxy)-3-biphenylcarboxamide | (M + H) 341, $t_R$ 1.71 min. (LC/MS method A). | Used II-3 mixed halides[2)] |
| 23 | 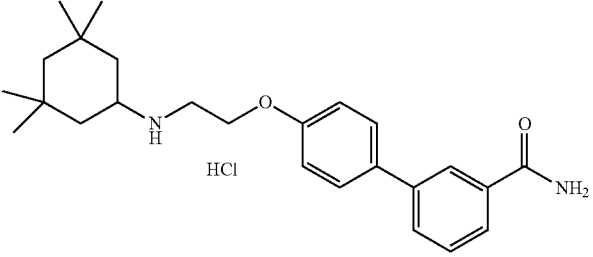<br>4'-({2-[(3,3,5,5-tetramethylcyclohexyl)amino]ethyl}oxy)-3-biphenyl carboxamide hydrochloride | (M + H) 395, $t_R$ 2.03 min. (LC/MS method A). | Used II-3 mixed halides and III-5 amine Used CH$_3$CN/ethyl ether to form HCl salt |
| 24 | 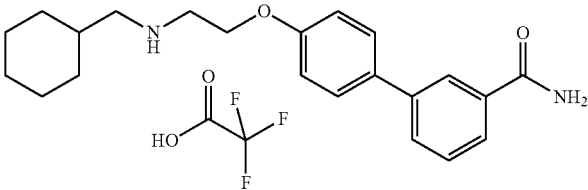<br>4'-({2-[(cyclohexylmethyl)amino]ethyl}oxy)-3-biphenyl carboxamide trifluoroacetate | (M + H) 353, $t_R$ 1.66 min (LC/MS method A) | Used II-3 mixed halides[1)] |
| 25 | 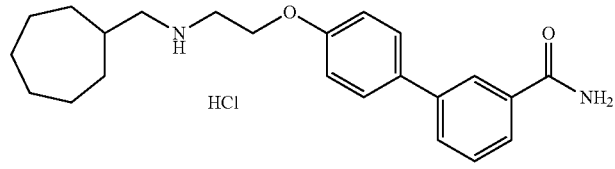<br>4'-({2-[(cycloheptylmethyl)amino]ethyl}oxy)-3-biphenylcarboxamide hydrochloride | (M + H) 367, $t_R$ 1.82 min. (LC/MS method B). | Used II-3 mixed halides |
| 26 | 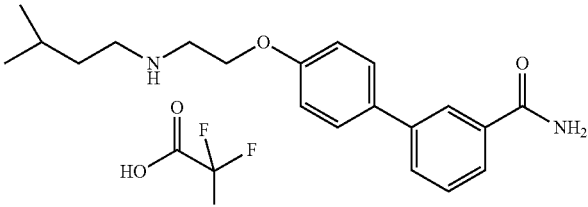<br>4'-({2-[(3-methylbutyl)amino]ethyl}oxy)-3-biphenylcarboxamide trifluoroacetate | (M + H) 327, $t_R$ 1.52 min. (LC/MS method A). | Used II-3 mixed halides[1)] |

TABLE 1-continued

Compounds of Formula I Generated from Compounds of Formula II

| Ex. | Structure and Name | Characterization Data | Method/Comments |
|---|---|---|---|
| 27 | 4'-[(2-{[2-(3-fluorophenyl)ethyl]amino}ethyl)oxy]-3-biphenyl carboxamide trifluoroacetate | (M + H) 379, $t_R$ 1.64 min. (LC/MS method A). | Used II-3 mixed halides[1)] |
| 28 | 4'-({2-[(2-phenylethyl)amino]ethyl}oxy)-3-biphenylcarboxamide trifluoroacetate | (LC/MS Method A) $t_R$ 1.59 min, m/z 361 (M + H, freebase) | Used II-4 chloride[1,3)]: 30 min NaI |
| 29 | 4'-({2-[methyl(2-phenylethyl)amino]ethyl}oxy)-3-biphenylcarboxamide trifluoroacetate | (LC/MS Method A) $t_R$ 1.63 min, m/z 375 (M + H, freebase) | Used II-4 chloride[1,3)]: 90 min, Bu$_4$NI used in lieu of NaI |
| 30 | 4'-({2-[(Phenylmethyl)amino]ethyl}oxy)-3-biphenylcarboxamide trifluoroacetate | (LC/MS Method A) $t_R$ 1.51 min, m/z 347 (M + H, freebase) | Used II-4 chloride[1,3,4)]: 45 min NaI |

TABLE 1-continued

Compounds of Formula I Generated from Compounds of Formula II

| Ex. | Structure and Name | Characterization Data | Method/Comments |
|---|---|---|---|
| 31 | 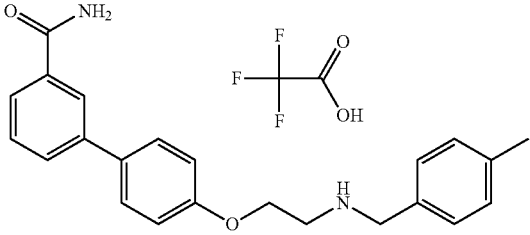<br>4'-[(2-{[(4-methylphenyl)methyl]amino}ethyl)oxy]-3-biphenylcarboxamide trifluoroacetate | (LC/MS Method A) $t_R$ 1.66 min, m/z 361 (M + H, freebase) | Used II-4 chloride[1,3,4]: 45 min NaI |
| 32 | 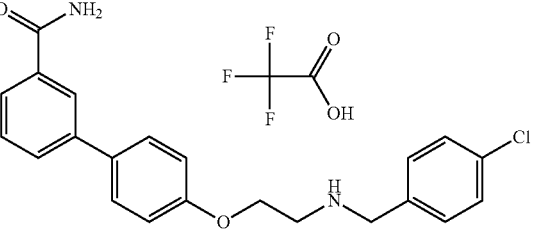<br>4'-[(2-{[(4-chlorophenyl)methyl]amino}ethyl)oxy]-3-biphenylcarboxamide trifluoroacetate | (LC/MS Method A) $t_R$ 1.70 min, m/z 381 (M + H, freebase) | Used II-4 chloride[1,3,4]: 45 min NaI |
| 33 | 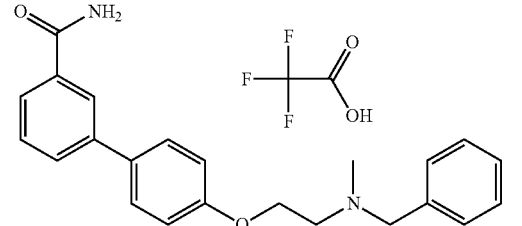<br>4'-({2-[methyl(phenylmethyl)amino]ethyl}oxy)-3-biphenylcarboxamide trifluoroacetate | (LC/MS Method A) $t_R$ 1.53 min, m/z 361 (M + H, freebase) | Used II-4 chloride[1,3,4]: 45 min NaI |
| 34 | 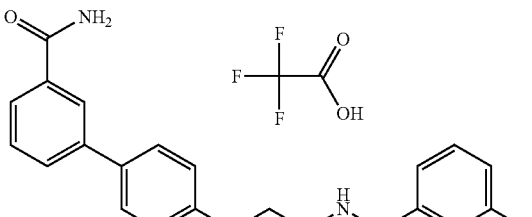<br>4'-[(2-{[(3-fluorophenyl)methyl]amino}ethyl)oxy]-3-biphenylcarboxamide trifluoroacetate | (LC/MS Method A) $t_R$ 1.56 min, m/z 365 (M + H, freebase) | Used II-4 chloride[3,4]: 30 min NaI |
| 35 | 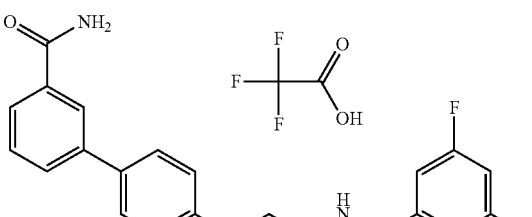<br>4'-[(2-{[(3,5-difluorophenyl)methyl]amino}ethyl)oxy]-3-biphenylcarboxamide trifluoroacetate | (LC/MS Method A) $t_R$ 1.59 min, m/z 383 (M + H, freebase) | Used II-4 chloride[1,3,4]: 30 min NaI |

TABLE 1-continued

Compounds of Formula I Generated from Compounds of Formula II

| Ex. | Structure and Name | Characterization Data | Method/Comments |
| --- | --- | --- | --- |
| 36 | 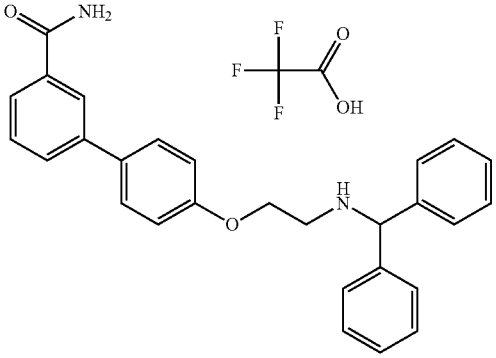<br>4'-({2-[(diphenylmethyl)amino]ethyl}oxy)-3-biphenyl carboxamide trifluoroacetate | (LC/MS Method A) $t_R$ 1.88 min, m/z 423 (M + H, freebase) | Used II-4 chloride[1,3,4]: 30 min NaI |
| 37 | 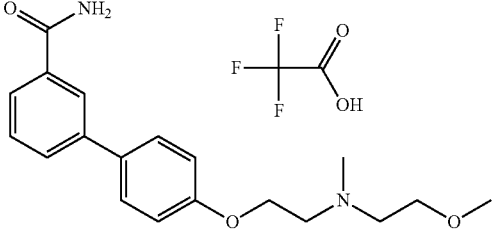<br>4'-[(2-{methyl[2-(methyloxy)ethyl]amino}ethyl)oxy]-3-biphenyl carboxamide trifluoroacetate | (LC/MS Method A) $t_R$ 1.20 min, m/z 329 (M + H, freebase) | Used II-4 chloride[1,3,4]: 30 min NaI |
| 38 | 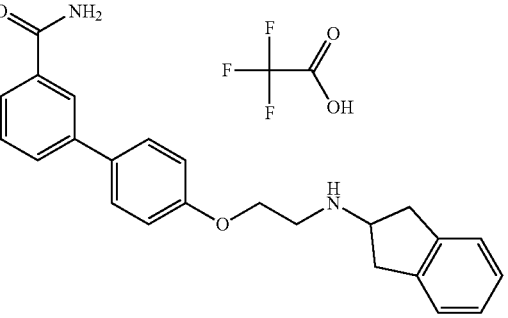<br>4'-{[2-(2,3-dihydro-1H-inden-2-ylamino)ethyl]oxy}-3-biphenylcarboxamide trifluoroacetate | (LC/MS Method A) $t_R$ 1.65 min, m/z 373 (M + H, freebase) | Used II-4 chloride[1,3,4]: 30 min NaI |
| 39 | 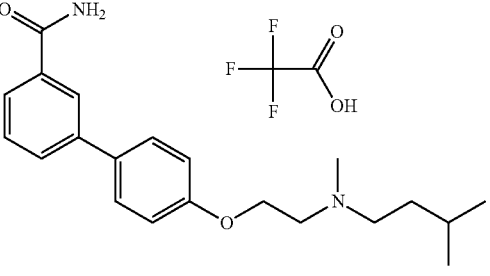<br>4'-({2-[methyl(3-methylbutyl)amino]ethyl}oxy)-3-biphenylcarboxamide trifluoroacetate | (LC/MS Method A) $t_R$ 1.55 min, m/z 341 (M + H, freebase) | Used II-4 chloride[1,3,4]: 30 min NaI |

TABLE 1-continued

Compounds of Formula I Generated from Compounds of Formula II

| Ex. | Structure and Name | Characterization Data | Method/Comments |
|---|---|---|---|
| 40 | 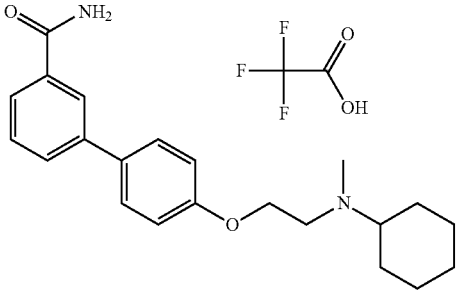<br>4'-({2-[cyclohexyl(methyl)amino]ethyl}oxy)-3-biphenylcarboxamide trifluoroacetate | (LC/MS Method A) $t_R$ 1.53 min, m/z 353 (M + H, freebase) | Used II-4 chloride[1,3,4]: 30 min NaI |
| 41 | 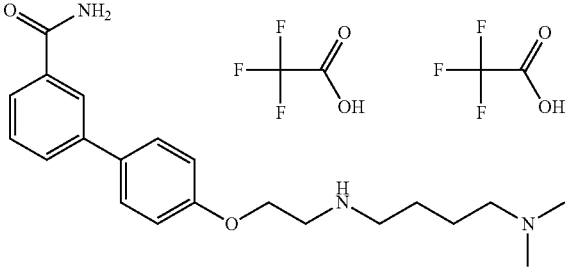<br>4'-[(2-{[4-(dimethylamino)butyl]amino}ethyl)oxy]-3-biphenylcarboxamide bis(trifluoroacetate) | (LC/MS Method A) $t_R$ 0.24 min, m/z 356 (M + H, freebase) | Used II-4 chloride[1,3,4]: 30 min NaI |
| 42 | 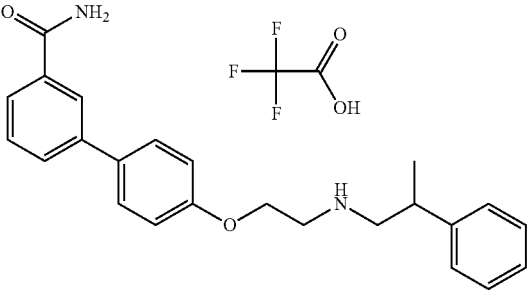<br>rac 4'-({2-[(2-phenylpropyl)amino]ethyl}oxy)-3-biphenyl carboxamide trifluoroacetate | (LC/MS Method A) $t_R$ 1.67 min, m/z 375 (M + H, freebase) | Used II-4 chloride[1,3,4]: 30 min NaI |
| 43 | 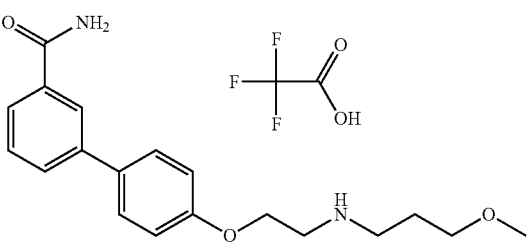<br>4'-[(2-{[3-(methyloxy)propyl]amino}ethyl)oxy]-3-biphenylcarboxamide trifluoroacetate | (LC/MS Method A) $t_R$ 1.37 min, m/z 343 (M + H, freebase) | Used II-4 chloride[1,3,4]: 30 min NaI |

TABLE 1-continued

Compounds of Formula I Generated from Compounds of Formula II

| Ex. | Structure and Name | Characterization Data | Method/Comments |
|---|---|---|---|
| 44 | 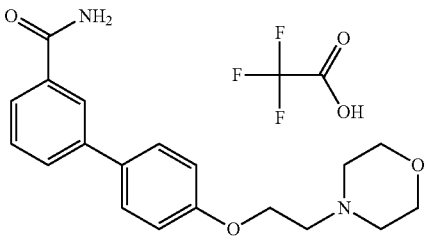<br>4'-{[2-(4-morpholinyl)ethyl]oxy}-3-biphenylcarboxamide trifluoroacetate | (LC/MS Method A) $t_R$ 1.04 min, m/z 327 (M + H, freebase) | Used II-4 chloride[1,3,4]:<br>30 min NaI |
| 45 | 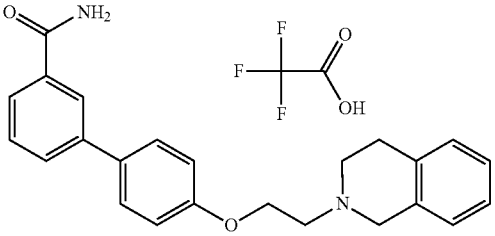<br>4'-{[2-(3,4-dihydro-2(1H)-isoquinolinyl)ethyl]oxy}-3-biphenylcarboxamide trifluoroacetate | (LC/MS Method A) $t_R$ 1.54 min, m/z 373 (M + H, freebase) | Used II-4 chloride[1,3,4]:<br>30 min NaI |
| 46 | 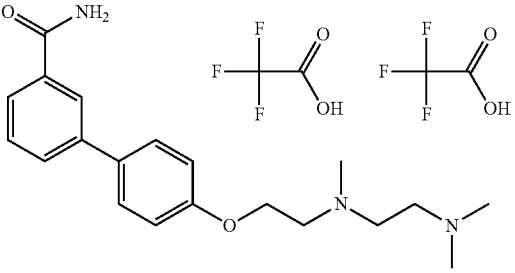<br>4'-({2-[[2-(dimethylamino)ethyl](methyl)amino]ethyl}oxy)-3-biphenylcarboxamide bis(trifluoroacetate) | (LC/MS Method A) $t_R$ 0.73 min, m/z 342 (M + H, freebase) | Used II-4 chloride[1,3,4]:<br>30 min NaI |
| 47 | 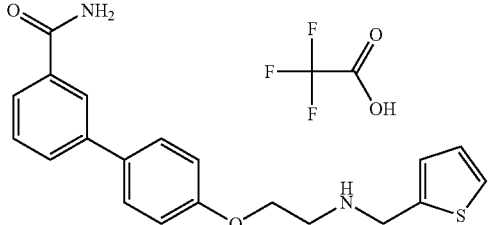<br>4'-({2-[(2-thienylmethyl)amino]ethyl}oxy)-3-biphenylcarboxamide trifluoroacetate | (LC/MS Method A) $t_R$ 1.45 min, m/z 353 (M + H, freebase) | Used II-4 chloride[1,3,4]:<br>30 min NaI |

TABLE 1-continued

Compounds of Formula I Generated from Compounds of Formula II

| Ex. | Structure and Name | Characterization Data | Method/Comments |
|---|---|---|---|
| 48 | 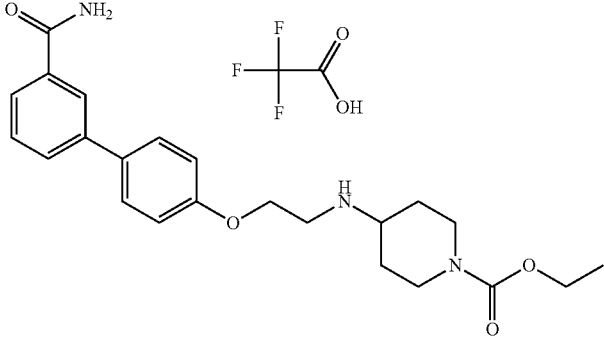  ethyl 4-[(2-{[3'-(aminocarbonyl)-4-biphenylyl]oxy}ethyl)amino]-1-piperidinecarboxylate trifluoroacetate | (LC/MS Method A) $t_R$ 1.47 min, m/z 412 (M + H, freebase) | Used II-4 chloride[1,3,4]: 30 min NaI |
| 49 | 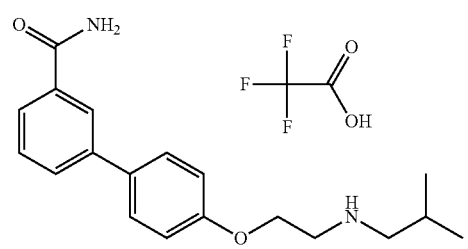  4'-({2-[(2-methylpropyl)amino]ethyl}oxy)-3-biphenylcarboxamide trifluoroacetate | (LC/MS Method A) $t_R$ 1.36 min, m/z 313 (M + H, freebase) | Used II-4 chloride[1,3,4]: 30 min NaI |
| 50 | 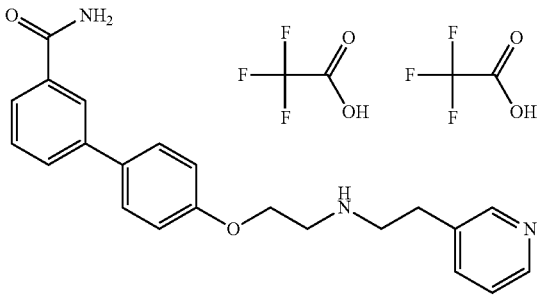  4'-[(2-{[2-(3-pyridinyl)ethyl]amino}ethyl)oxy]-3-biphenylcarboxamide bis(trifluoroacetate) | (LC/MS Method A) $t_R$ 0.83 min, m/z 362 (M + H, freebase) | Used II-4 chloride[1,3,4]: 30 min NaI |
| 51 | 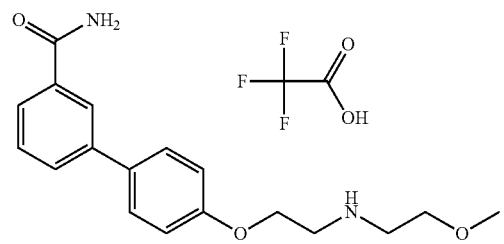  4'-[(2-{[2-(methyloxy)ethyl]amino}ethyl)oxy]-3-biphenylcarboxamide trifluoroacetate | (LC/MS Method A) $t_R$ 1.14 min, m/z 315 (M + H, freebase) | Used II-4 chloride[1,3,4]: 30 min NaI |

TABLE 1-continued

Compounds of Formula I Generated from Compounds of Formula II

| Ex. | Structure and Name | Characterization Data | Method/Comments |
|---|---|---|---|
| 52 | 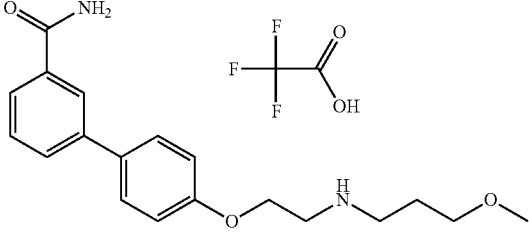<br>4'-[(2-{[3-(methyloxy)propyl]amino}ethyl)oxy]-3-biphenylcarboxamide trifluoroacetate | (LC/MS Method A) $t_R$ 1.24 min, m/z 329 (M + H, freebase) | Used II-4 chloride[1,3,4]: 30 min NaI |
| 53 | 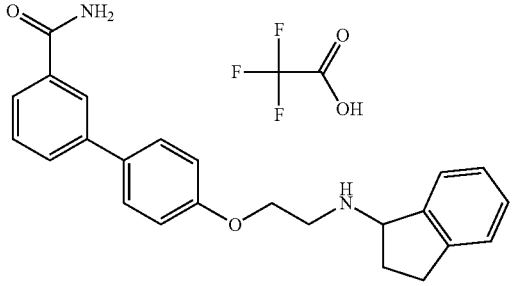<br>rac 4'-{[2-(2,3-dihydro-1H-inden-1-ylamino)ethyl]oxy}-3-biphenylcarboxamide trifluoroacetate | (LC/MS Method A) $t_R$ 1.66 min, m/z 373 (M + H, freebase) | Used II-4 chloride[1,3,4]: 30 min NaI |
| 54 | 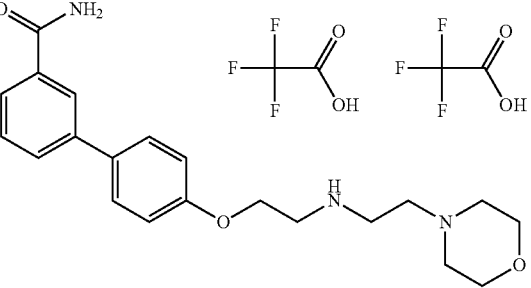<br>4'-[(2-{[2-(4-morpholinyl)ethyl]amino}ethyl)oxy]-3-biphenylcarboxamide bis(trifluoroacetate) | (LC/MS Method A) $t_R$ 0.85 min, m/z 370 (M + H, freebase) | Used II-4 chloride[1,3,4]: 30 min NaI |
| 55 | 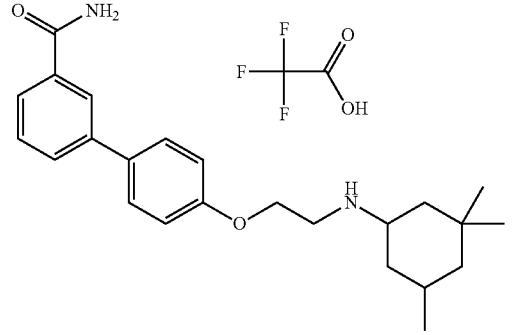<br>rac 4'-({2-[(3,3,5-trimethylcyclohexyl)amino]ethyl}oxy)-3-biphenylcarboxamide trifluoroacetate | (LC/MS Method B) $t_R$ 1.90 min, m/z 381 (M + H, freebase) | Used II-4 chloride[1,3,4]: 30 min NaI |

TABLE 1-continued

Compounds of Formula I Generated from Compounds of Formula II

| Ex. | Structure and Name | Characterization Data | Method/Comments |
|---|---|---|---|
| 56 | 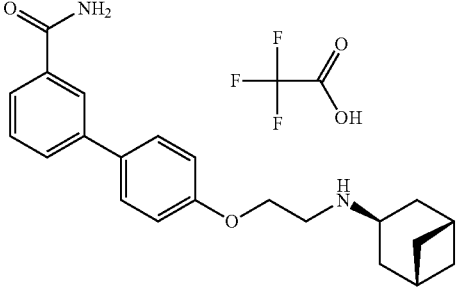<br>4'-({2-[(1R,3r,5S)-bicyclo[3.1.1]hept-3-ylamino]ethyl}oxy)-3-biphenylcarboxamide trifluoroacetate | (LC/MS Method B) $t_R$ 1.61 min, m/z 351 (M + H, freebase) | Used II-4 chloride[1,3,4]: 30 min NaI |
| 57 | 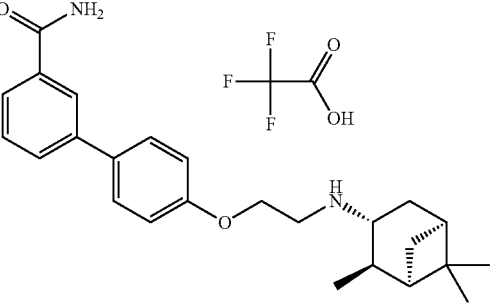<br>4'-[(2-{[(1R,2R,3R,5S)-2,6,6-trimethylbicyclo[3.1.1]hept-3-yl]amino}ethyl)oxy]-3-biphenylcarboxamide trifluoroacetate | (LC/MS Method B) $t_R$ 1.93 min, m/z 393 (M + H, freebase) | Used II-4 chloride[1,3,4]: 30 min NaI |
| 58 | 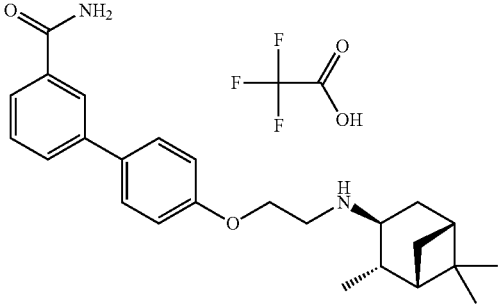<br>4'-[(2-{[(1S,2S,3S,5R)-2,6,6-trimethylbicyclo[3.1.1]hept-3-yl]amino}ethyl)oxy]-3-biphenylcarboxamide trifluoroacetate | (LC/MS Method B) $t_R$ 1.93 min, m/z 393 (M + H, freebase) | Used II-4 chloride[1,3,4]: 30 min NaI |
| 59 | 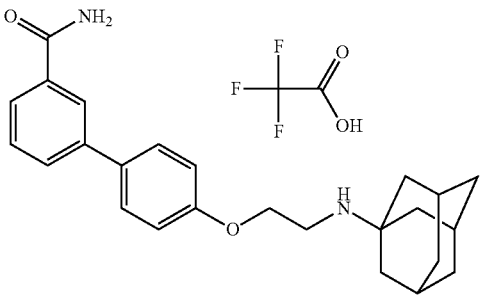<br>4'-{[2-(tricyclo[3.1.1.1[3,7]]dec-1-ylamino)ethyl]oxy}-3-biphenylcarboxamide trifluoroacetate | (LC/MS Method B) $t_R$ 1.77 min, m/z 391 (M + H, freebase) | Used II-4 chloride[1,3,4]: 30 min NaI |

TABLE 1-continued

Compounds of Formula I Generated from Compounds of Formula II

| Ex. | Structure and Name | Characterization Data | Method/Comments |
|---|---|---|---|
| 60 | 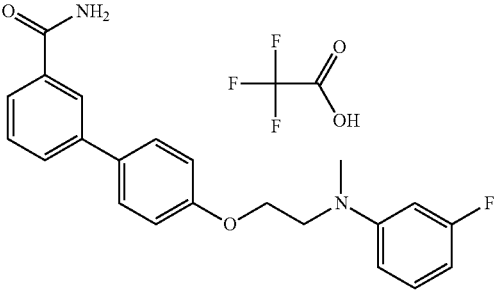<br>4'-({2-[3-fluorophenyl)(methyl)amino]ethyl}oxy)-3-biphenylcarboxamide trifluoroacetate | (LC/MS Method B) $t_R$ 2.82 min, m/z 365 (M + H, freebase) | Used II-4 chloride[1,3,4]: 30 min NaI |
| 61 | 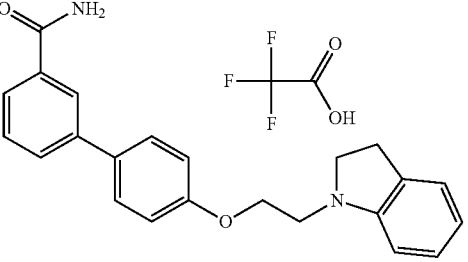<br>4'-{[2-(2,3-dihydro-1H-indol-1-yl)ethyl]oxy}-3-biphenylcarboxamide trifluoroacetate | (LC/MS Method B) $t_R$ 2.78 min, m/z 359 (M + H, freebase) | Used II-4 chloride[1,3,4]: 30 min NaI |
| 62 | 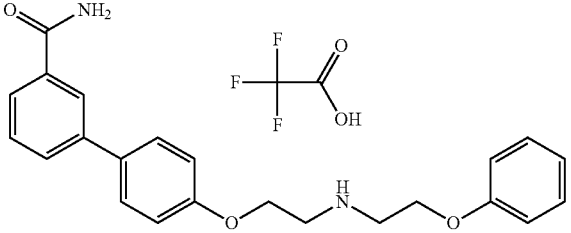<br>4'-[(2-{[2-(phenyloxy)ethyl]amino}ethyl)oxy]-3-biphenylcarboxamide trifluoroacetate | (LC/MS Method B) $t_R$ 1.66 min, m/z 377 (M + H, freebase) | Used II-4 chloride[1,3,4]: 30 min NaI |
| 63 | 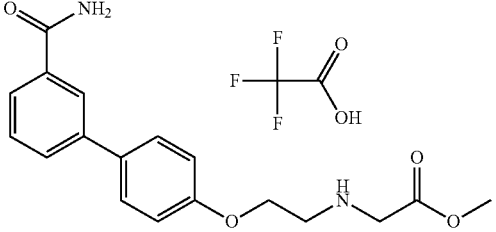<br>methyl N-(2-{[3'-(aminocarbonyl)-4-biphenylyl]oxy}ethyl)glycinate trifluoroacetate | (LC/MS Method B) $t_R$ 1.34 min, m/z 365 (M + H, freebase) | Used II-4 chloride[1,3,4]: 30 min NaI |
| 64 | 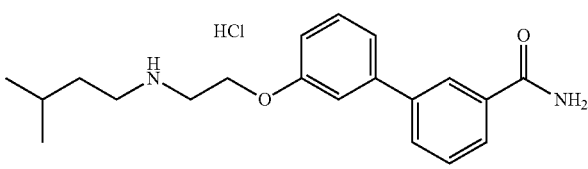<br>3'-({2-[(3-methylbutyl)amino]ethyl}oxy)-3-biphenylcarboxamide hydrochloride | (M + H) 327, $t_R$ 1.61 min. (LC/MS method A) | Used II-5 mixed halide |

TABLE 1-continued

Compounds of Formula I Generated from Compounds of Formula II

| Ex. | Structure and Name | Characterization Data | Method/Comments |
|---|---|---|---|
| 65 | 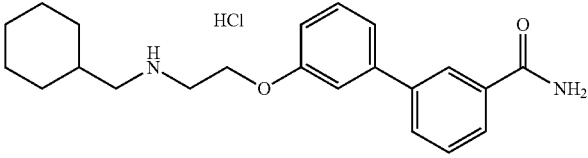  3'-({2-[(cyclohexylmethyl)amino]ethyl}oxy)-3-biphenylcarboxamide hydrochloride | (M + H) 353, $t_R$ 1.76 min. (LC/MS method A). | Used II-5 mixed halide |
| 66 | 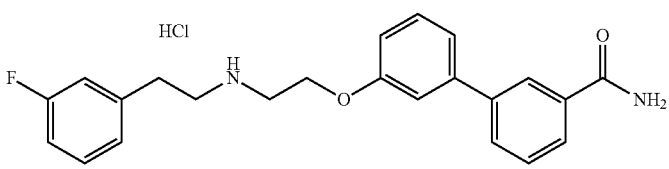  3'-[(2-{[2-(3-fluorophenyl)ethyl]amino}ethyl)oxy]-3-biphenyl carboxamide hydrochloride | (M + H) 379, $t_R$ 1.70 min. (LC/MS method A). | Used II-5 mixed halide |
| 67 | 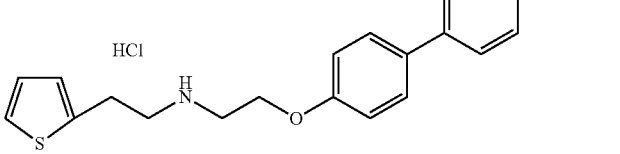  4'-[(2-{[2-(2-thienyl)ethyl]amino}ethyl)oxy]-4-biphenylcarboxamide Hydrochloride | (M + H) 367, $t_R$ 2.42 min. (LC/MS method A) | Used II-6 mixed halide Isolated from the reaction mixture using trituration with Et$_2$O and then proceeded as before to form the HCl salt |
| 68 | 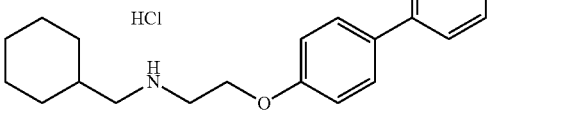  4'-({2-[(cyclohexylmethyl)amino]ethyl}oxy)-4-biphenylcarboxamide hydrochloride | (M + H) 353, $t_R$ 1.92 min. (LC/MS method A). | Used II-6 mixed halide Isolated from the reaction mixture using trituration with Et$_2$O and then proceeded as before to form the HCl salt |
| 69 | 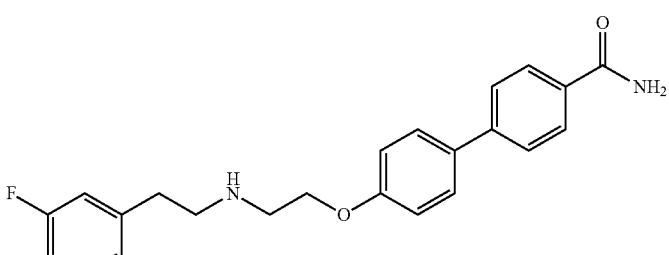  4'-[(2-{[2-(3-fluorophenyl)ethyl]amino}ethyl)oxy]-4-biphenyl carboxamide hydrochloride | (M + H) 379, $t_R$ 2.48 min. (LC/MS method A). | Used II-6 mixed halide Isolated from the reaction mixture using trituration with Et$_2$O and then proceeded as before to form the HCl salt |

TABLE 1-continued

Compounds of Formula I Generated from Compounds of Formula II

| Ex. | Structure and Name | Characterization Data | Method/Comments |
|---|---|---|---|
| 70 | 4'-({2-[(3-methylbutyl)amino]ethyl}oxy)-4-biphenylcarboxamide hydrochloride | (M + H) 327, $t_R$ 1.78 min. (LC/MS method A). | Used II-6 mixed halide Isolated from the reaction mixture using trituration with $Et_2O$ and then proceeded as before to form the HCl salt |
| 71 | 4'-[(2-{[(3-fluorophenyl)methyl]amino}ethyl)oxy-4-biphenyl carboxamide hydrochloride | (M + H) 365, $t_R$ 2.20 min. (LC/MS method A). | Used II-6 mixed halide Isolated from the reaction mixture using trituration with $Et_2O$ and then proceeded as before to form the HCl salt |
| 72 | 3'-{[2-(cycloheptylamino)ethyl]oxy}-2-methyl-4-biphenylcarboxamide hydrochloride | (M + H) 367, $t_R$ 1.73 min. (LC/MS method A) | Used II-7 mixed halide |
| 73 | 2-methyl-3'-({2-[(3-methylbutyl)amino]ethyl}oxy)-4-biphenyl carboxamide hydrochloride | (M + H) 341, $t_R$ 1.63 min. (LC/MS method A). | Used II-7 mixed halide |
| 74 | 3'-({2-[(cyclohexylmethyl)amino]ethyl}oxy)-2-methyl-4-biphenyl carboxamide hydrochloride | (M + H) 367, $t_R$ 1.84 min. (LC/MS method A). | Used II-7 mixed halide |

TABLE 1-continued

Compounds of Formula I Generated from Compounds of Formula II

| Ex. | Structure and Name | Characterization Data | Method/Comments |
|---|---|---|---|
| 75 | 3'-[(2-{[(4,4-dimethylcyclohexyl)methyl]amino}ethyl)oxy]-2-methyl-4-biphenylcarboxamide hydrochloride | (M + H) 395, $t_R$ 2.03 min. (LC/MS method B) | Used II-8 chloride |
| 76 | 3'-{[2-(2,3-dihydro-1H-inden-2-ylamino)ethyl]oxy}-2-methyl-4-biphenylcarboxamide trifluoroacetate | (M + H) 387, $t_R$ 1.78 min. (LC/MS method A) | Used II-8 chloride Prepared the HCl salt as before. Converted to free base and purified a second time using reverse phase chromatography. Triturated with dichloromethane as a final purification. |
| 77 | 3'-({2-[(cyclohexylmethyl)amino]ethyl}oxy)-2-fluoro-4-biphenylcarboxamide hydrochloride | (M + H) 371, $t_R$ 1.74 min. (LC/MS method A) | Used II-9 mixed halide |
| 78 | 2-fluoro-3'-({2-[(3-methylbutyl)amino]ethyl}oxy)-4-biphenyl carboxamide hydrochloride | (M + H) 345, $t_R$ 1.63 min. (LC/MS method A). | Used II-9 mixed halide |
| 79 | 2-fluoro-3'-[(2-{[2-(3-fluorophenyl)ethyl]amino}ethyl)oxy]-4-biphenyl carboxamide hydrochloride | (M + H) 397, $t_R$ 1.69 min. (LC/MS method A). | Used II-9 mixed halide |

TABLE 1-continued

Compounds of Formula I Generated from Compounds of Formula II

| Ex. | Structure and Name | Characterization Data | Method/Comments |
| --- | --- | --- | --- |
| 80 | 2'-fluoro-5'-({2-[(3-methylbutyl)amino]ethyl}oxy)-4-biphenylcarboxamide hydrochloride | (M + H) 345, $t_R$ 1.58 min. (LC/MS method A) | Used II-10 mixed halide |
| 81 | 5'-({2-[(cyclohexylmethyl)amino]ethyl}oxy)-2'-fluoro-4-biphenyl carboxamide hydrochloride | (M + H) 371, $t_R$ 1.72 min. (LC/MS method A). | Used II-10 mixed halide |
| 82 | 2'-fluoro-5'-[(2-{[2-(3-fluorophenyl)ethyl]amino}ethyl)oxy]-4-biphenyl carboxamide hydrochloride | (M + H) 397, $t_R$ 1.68 min. (LC/MS method A). | Used II-10 mixed halide |
| 83 | 3'-({3-[(3-methylbutyl)amino]propyl}oxy)-4-biphenylcarboxamide hydrochloride | (M + H) 341, $t_R$ 1.68 min. (LC/MS method A) | Used II-11 mixed halide |
| 84 | 6-(3-{[2-(Pentylamino)ethyl]oxy}phenyl)-3-pyridinecarboxamide Hydrochloride | (M + H) 328, $t_R$ 1.43 min (LC/MS method A) | Used II-12 chloride Isolated by filtration |

TABLE 1-continued

Compounds of Formula I Generated from Compounds of Formula II

| Ex. | Structure and Name | Characterization Data | Method/Comments |
|---|---|---|---|
| 85 | 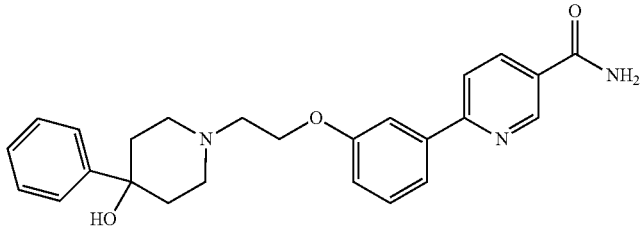<br>6-(3-{[2-(4-hydroxy-4-phenyl-1-piperidinyl)ethyl]oxy}phenyl)-3-pyridine carboxamide | (M + H) 418, $t_R$ 1.43 min (LC/MS method A) | Used II-12 chloride Isolated by filtration and then free-based using N,N-diisopropyl ethylamine. |
| 86 | 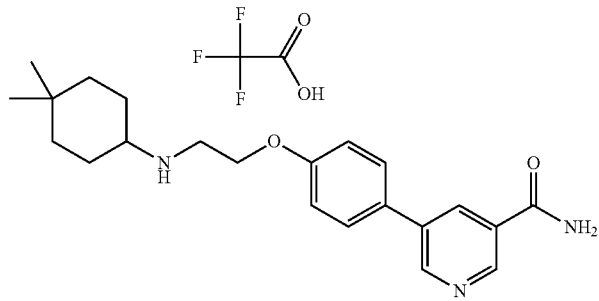<br>5-[4-({2-[(4,4-Dimethylcyclohexyl)amino]-ethyl}oxy)phenyl]-3-pyridinecarboxamide Trifluoroacetate | $^1$H NMR (400 MHz, DMSO-$d_6$) δ ppm 0.85 (s, 6H) 1.20 (m, 2H) 1.39-1.60 (m, 4H) 1.83 (m, 2H) 3.02 (m, 1H) 3.39 (br., 2H) 4.30 (m, 2H) 7.10 (d, 2H) 7.62 (s, 1H) 7.79 (d, 2H) 8.22 (s, 1H) 8.41 (s, 1H) 8.60 (br., 2H) 8.95 (s, 1H) 8.99 (s, 1H); (M + H) 368, 1.55 min (LC/MS method A) | Used II-13 chloride and III-1 amine[1] |
| 87 | 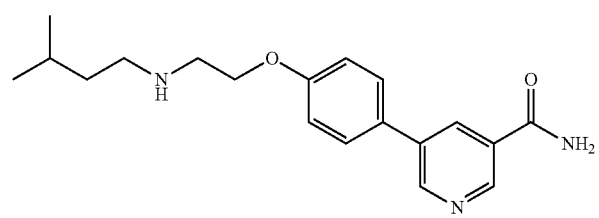<br>5-[4-({2-[(3-methylbutyl)amino]ethyl}oxy)phenyl]-3-pyridinecarboxamide hydrochloride | (M + H) 328, $t_R$ 1.28 min (LC/MS method A) | Used II-13 chloride Isolated by filtration from the reaction |
| 88 | 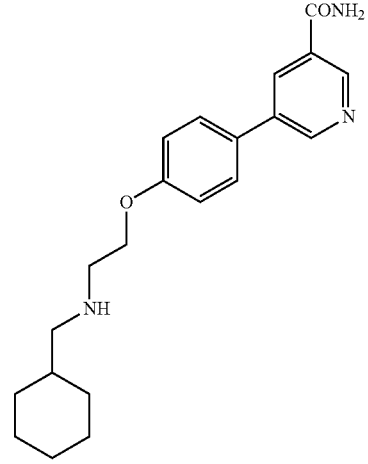<br>5-[4-({2-[(cyclohexylmethyl)amino]ethyl}oxy)phenyl]-3-pyridinecarboxamide | (M + H) 355, $t_R$ 1.41 min (LC/MS method A) | Used II-13 chloride |

TABLE 1-continued

Compounds of Formula I Generated from Compounds of Formula II

| Ex. | Structure and Name | Characterization Data | Method/Comments |
|---|---|---|---|
| 89 | 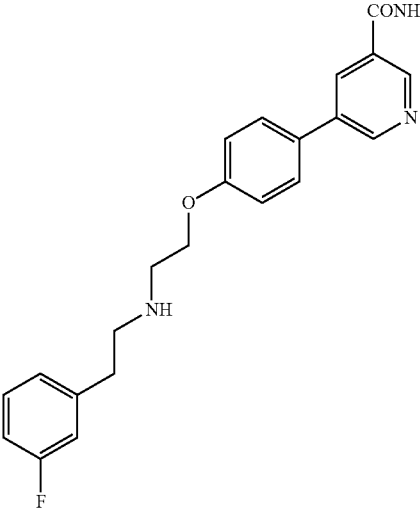<br>5-{4-[(2-{[2-(3-fluorophenyl)ethyl]amino}ethyl)oxy]phenyl}-3-pyridinecarboxamide | (M + H) 381, $t_R$ 1.37 min (LC/MS method A) | Used II-13 chloride |
| 90 | 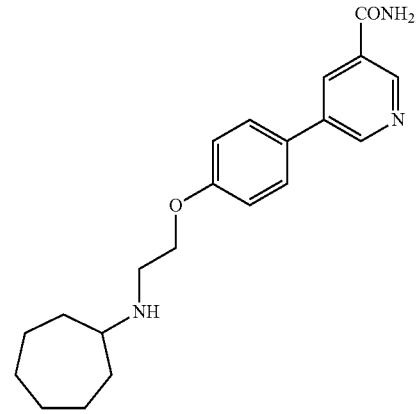<br>5-(4-{[2-(cycloheptylamino)ethyl]oxy}phenyl)-3-pyridinecarboxamide | (M + H) 355, $t_R$ 1.37 min (LC/MS method A) | Used II-13 chloride<br>Isolated by filtration from the reaction |
| 91 | 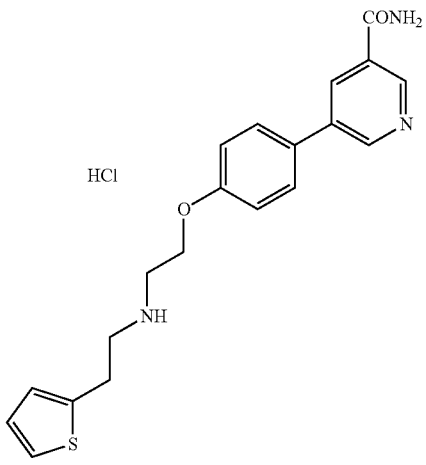<br>5-{4-[(2-{[2-(2-thienyl)ethyl]amino}ethyl)oxy]phenyl}-3-pyridinecarboxamide hydrochloride | (M + H) 368, $t_R$ 1.23 min (LC/MS method A) | Used II-13 chloride<br>Isolated by filtration from the reaction |

TABLE 1-continued

Compounds of Formula I Generated from Compounds of Formula II

| Ex. | Structure and Name | Characterization Data | Method/Comments |
|---|---|---|---|
| 92 | 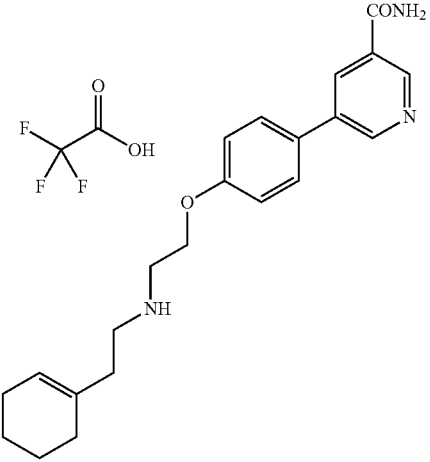<br>5-{4-[(2-{[2-(1-cyclohexen-1-yl)ethyl]amino}ethyl)oxy]phenyl}-3-pyridine carboxamide trifluoroacetate | (M + H) 366, $t_R$ 1.57 min (LC/MS method A) | Used II-13 chloride[1) |
| 93 | 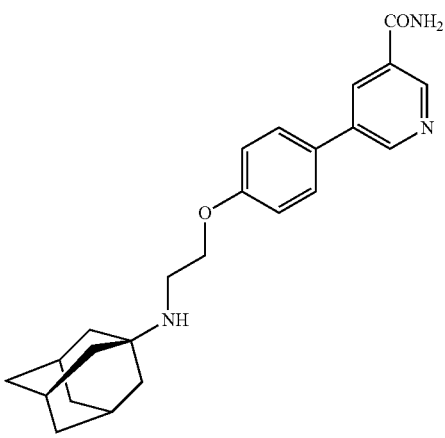<br>5-[4-({2-[(1S,3s)tricycle[3.3.1.1[3,7]]dec-1-ylamino]ethyl}oxy)phenyl]-3-pyridinecarboxamide | (M + H) 392, $t_R$ 1.50 min (LC/MS method A) | Used II-13 chloride |
| 94 | 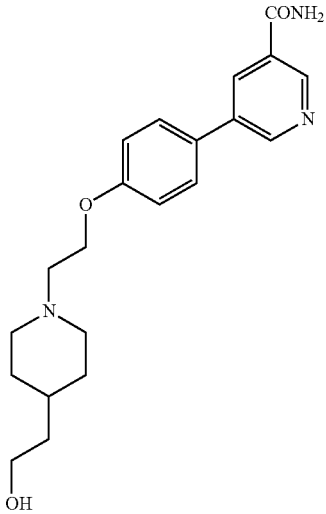<br>5-[4-({2-[4-(2-hydroxyethyl)-1-piperidinyl]ethyl}oxy)phenyl]-3-pyridinecarboxamide | (M + H) 370, $t_R$ 0.75 min (LC/MS method A) | Used II-13 chloride |

TABLE 1-continued

Compounds of Formula I Generated from Compounds of Formula II

| Ex. | Structure and Name | Characterization Data | Method/Comments |
|---|---|---|---|
| 95 | 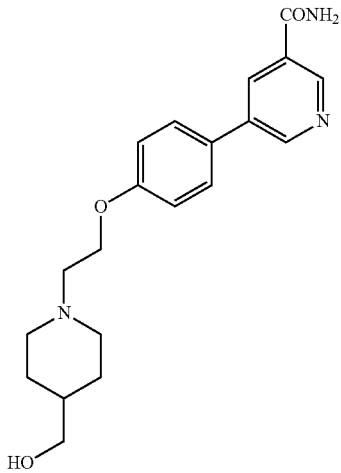<br>5-[4-({2-[4-(hydroxymethyl)-1-piperidinyl]ethyl}oxy)phenyl]-3-pyridine carboxamide | (M + H) 356, $t_R$ 0.64 min (LC/MS method A) | Used II-13 chloride |
| 96 | 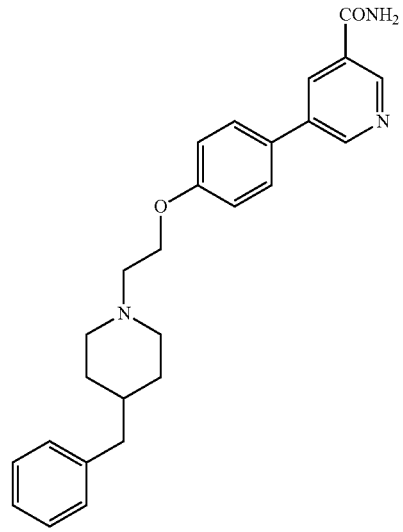<br>5-[4-({2-[4-(phenylmethyl)-1-piperidinyl]ethyl}oxy)phenyl]-3-pyridine carboxamide | (M + H) 416, $t_R$ 1.57 min (LC/MS method A) | Used II-13 chloride Isolated and submitted as the free-base after chromatography step |

TABLE 1-continued

Compounds of Formula I Generated from Compounds of Formula II

| Ex. | Structure and Name | Characterization Data | Method/Comments |
|---|---|---|---|
| 97 | 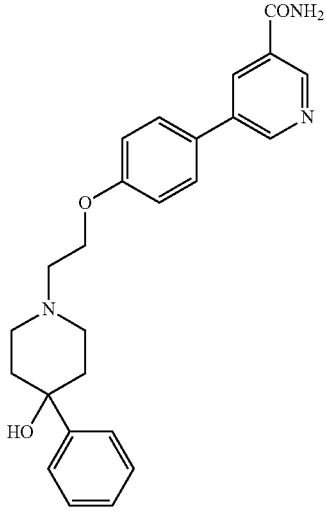<br>5-(4-{[2-(4-hydroxy-4-phenyl-1-piperidinyl)ethyl]oxy}phenyl)-3-pyridine carboxamide | (M + H) 418, $t_R$ 1.25 min (LC/MS method A) | Used II-13 chloride Isolated by filtration from the reaction |
| 98 | 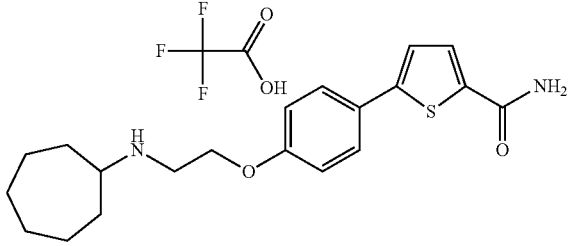<br>5-(4-{[2-(Cycloheptylamino)ethyl]oxy}-phenyl)-2-thiophenecarboxamide Trifluoroacetate | (M + H) 359, $t_R$ 1.61 min (LC/MS method A) | Used II-14 chloride[1) |
| 99 | 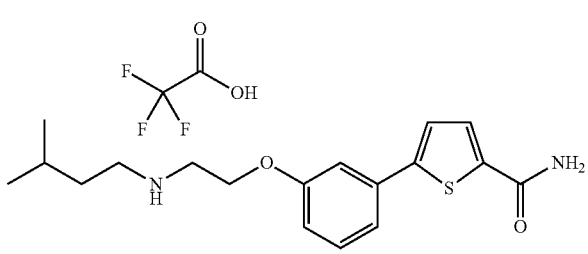<br>5-[3-({2-[(3-Methylbutyl)amino]ethyl}oxy)phenyl]-2-thiophenecarboxamide trifluoroacetic acid salt | (M + H) 332, $t_R$ 1.50 min (LC/MS method A) | Used II-15 chloride[1) |
| 100 | 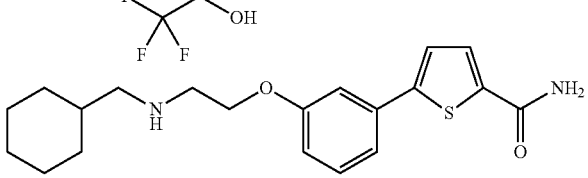<br>5-[3-({2-[(cyclohexylmethyl)amino]ethyl}oxy)phenyl]-2-thiophenecarboxamide trifluoroacetic acid salt | (M + H) 358, $t_R$ 1.65 min (LC/MS method A) | Used II-15 chloride[1) |

TABLE 1-continued

Compounds of Formula I Generated from Compounds of Formula II

| Ex. | Structure and Name | Characterization Data | Method/Comments |
|---|---|---|---|
| 101 | 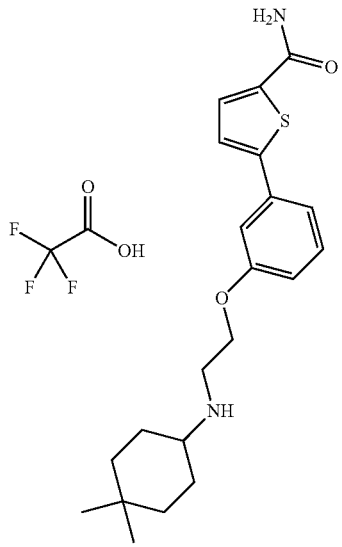<br>5-[3-({2-[(4,4-dimethylcyclohexyl)amino]ethyl}oxy)phenyl]-2-thiophenecarboxamide trifluoroacetic acid salt | (M+) 372, $t_R$ 1.73 min (LC/MS method A) | Used II-15 chloride and III-1 amine[1,2] |
| 102 | 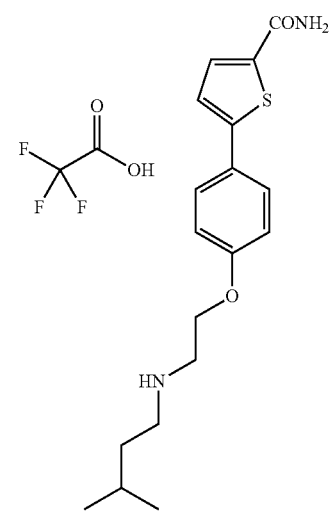<br>5-[4-({2-[(3-methylbutyl)amino]ethyl}oxy)phenyl]-2-thiophenecarboxamide trifluoroacetic acid salt | (M + H) 333, $t_R$ 1.51 min (LC/MS method A) | Used II-15 chloride[1] |

TABLE 1-continued

Compounds of Formula I Generated from Compounds of Formula II

| Ex. | Structure and Name | Characterization Data | Method/Comments |
| --- | --- | --- | --- |
| 103 | 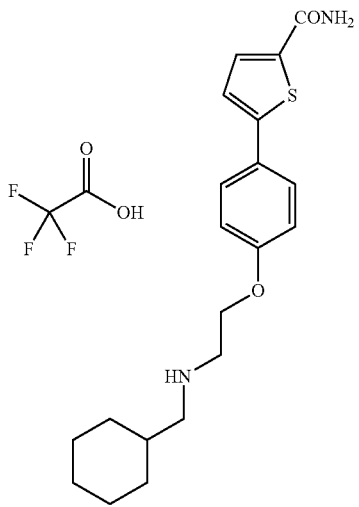<br>5-[4-({2-[(cyclohexylmethyl)amino]ethyl}oxy)phenyl]-2-thiophenecarboxamide trifluoroacetic acid salt | (M + H) 359, $t_R$ 1.68 min (LC/MS method A) | Used II-15 chloride[1] |
| 104 | 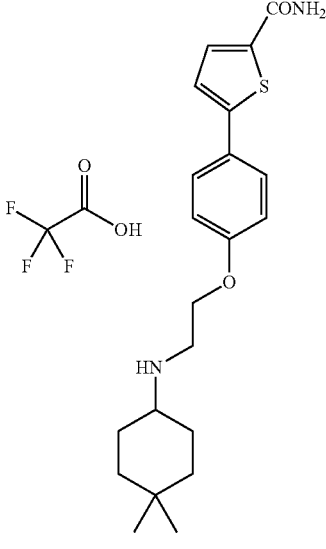<br>5-[4-({2-[(4,4-dimethylcyclohexyl)amino]ethyl}oxy)phenyl]-2-thiophenecarboxamide trifluoroacetic acid salt | (M + H) 373, $t_R$ 1.74 min (LC/MS method A) | Used II-15 chloride and III-1 amine[1] |

TABLE 1-continued

Compounds of Formula I Generated from Compounds of Formula II

| Ex. | Structure and Name | Characterization Data | Method/Comments |
|---|---|---|---|
| 105 | 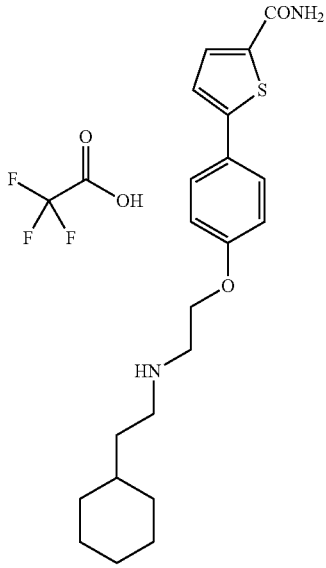<br>5-[4-({2-[(2-cyclohexylethyl)amino]ethyl}oxy)phenyl]-2-thiophenecarboxamide trifluoroacetic acid salt | (M + H) 372, $t_R$ 1.79 min (LC/MS method A) | Used II-15 chloride and III-7[1)] |
| 106 | 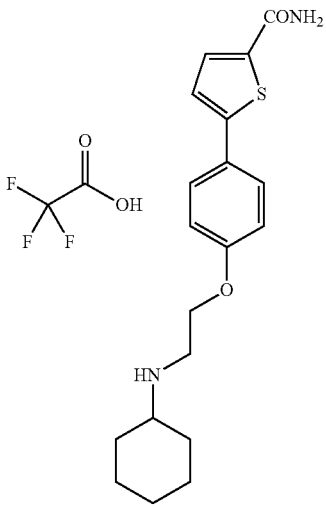<br>5-(4-{[2-(cyclohexylamino)ethyl]oxy}phenyl)-2-thiophenecarboxamide trifluoroacetic acid salt | (M + H) 344, $t_R$ 1.47 min (LC/MS method A) | Used II-15 chloride[1)] |
| 107 | 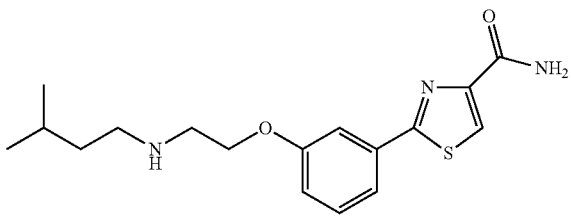<br>2-[3-({2-[(3-Methylbutyl)amino]ethyl}oxy)-phenyl]-1,3-thiazole-4-carboxamide | (M + H) 335, $t_R$ 1.51 min (LC/MS method A) | Used II-16 chloride |

TABLE 1-continued

Compounds of Formula I Generated from Compounds of Formula II

| Ex. | Structure and Name | Characterization Data | Method/Comments |
|---|---|---|---|
| 108 | 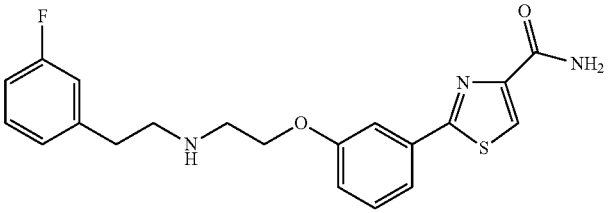<br>2-{3-[(2-{[2-(3-fluorophenyl)ethyl]amino}ethyl)oxy]phenyl}-1,3-thiazole-4-carboxamide | (M + H) 386, $t_R$ 1.63 min (LC/MS method A) | Used II-16 chloride |
| 109 | 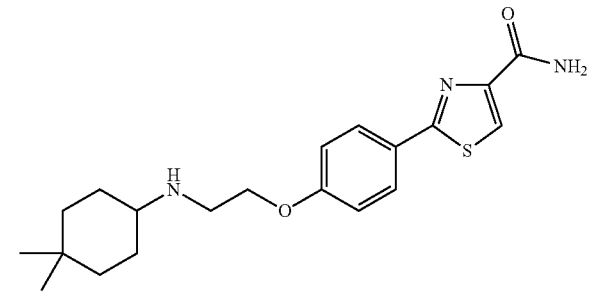<br>2-[4-({2-[(4,4-Dimethylcyclohexyl)amino]-ethyl}oxy)phenyl]-1,3-thiazole-4-carboxamide | (M + H) 374, $t_R$ 1.80 min (LC/MS method A) | Used II-17 chloride and III-1 amine |
| 110 | 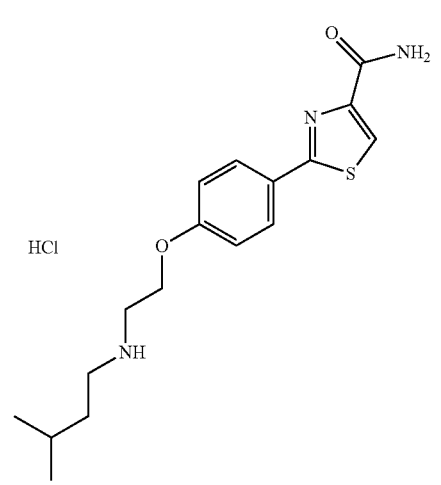<br>2-[4-({2-[(3-methylbutyl)amino]ethyl}oxy)phenyl]-1,3-thiazole-4-carboxamide hydrochloride | (M + H) 334, $t_R$ 1.39 min (LC/MS method A) | Used II-17 chloride |

TABLE 1-continued

Compounds of Formula I Generated from Compounds of Formula II

| Ex. | Structure and Name | Characterization Data | Method/Comments |
|---|---|---|---|
| 111 | 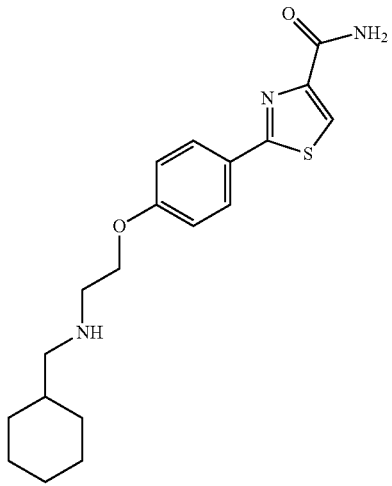<br>2-[4-({2-[(cyclohexylmethyl)amino]ethyl}oxy)phenyl]-1,3-thiazole-4-carboxamide | (M + H) 360, $t_R$ 1.54 min (LC/MS method A) | Used II-17 chloride |

Note 1: In some cases, final compounds prepared by this method required purification. There compounds were purified by RP-HPLC ($C_{18}$ column, MeCN/$H_2O$ gradient with TFA additive), yielding final compounds (as TFA salts).

Note 2: Free-based the resulting salt.

Note 3: Sometimes a promoter such as NaI, $Bu_4NI$ was used to facilitate the reaction.

Note 4: Reaction performed by microwave heating (90-100° C., 220 W, with air-cooling) in a septum-sealed tube for 30 min intervals until starting material consumed.

General Method 2 for Preparation of Compounds of Formula I

Example 112

4-[5-({[2-(3-fluorophenyl)ethyl]amino}methyl)-2-thienyl]benzamide

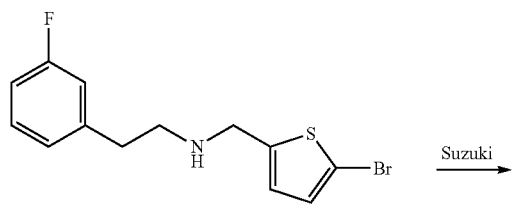

Suzuki ⟶

-continued

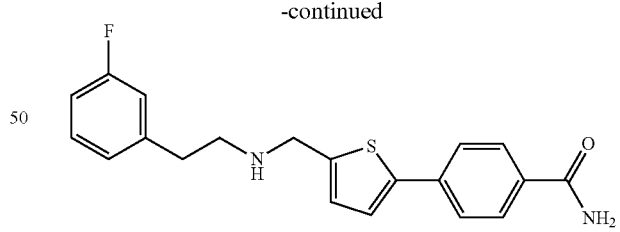

To a 5 ml conical vial was added [(5-bromo-2-thienyl)methyl][2-(3-fluorophenyl)ethyl]amine (210 mg, 0.67 mmol, Intermediate V-1), (4-aminocarbonylphenyl) boronic acid (110 mg, 0.67 mmol), $PdCl_2(PPh_3)_2$ (49 mg, 0.07 mmol), $K_3PO_4$ (426 mg, 2.0 mmol) and DME/$H_2O$ (3/1, 4 mL). The reaction mixture was placed in a microwave at 100° C. for 30 min. The mixture was filtered through a plug of silica gel and purified by RP-HPLC ($C_{18}$ column, MeCN/$H_2O$ gradient with TFA additive) to yield 23 mg of 4-[5-({[2-(3-fluorophenyl)ethyl]amino}methyl)-2-thienyl]benzamide trifluoroacetate. (M+H) 355, 1.43 min (LC/MS method A).

TABLE 2

Compounds of Formula I from Compounds of Formula V

| Ex. | Structure and Name | Characterization Data | Method/Comments |
|---|---|---|---|
| 113 | 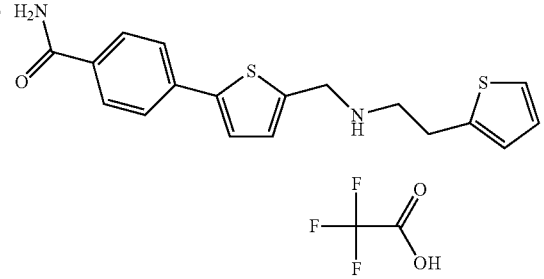<br>4-[5-({[2-(2-thienyl)ethyl]amino}methyl)-2-thienyl]benzamide trifluoroacetate | (M + H) 343, 1.14 min (LC/MS method A) | Used Intermediate V-2 and 4-bromobenzamide |
| 114 | 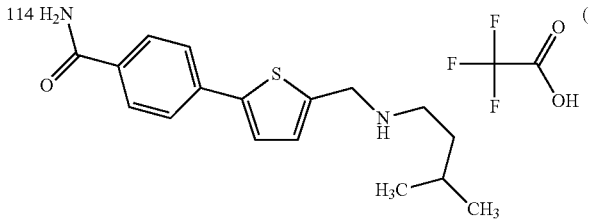<br>4-(5-{[(3-methylbutyl)amino] methyl}-2-thienyl)benzamide trifluoroacetate | (M + H) 303, 1.36 min (LC/MS method A) | Used Intermediate V-3 and 4-bromobenzamide |
| 115 | 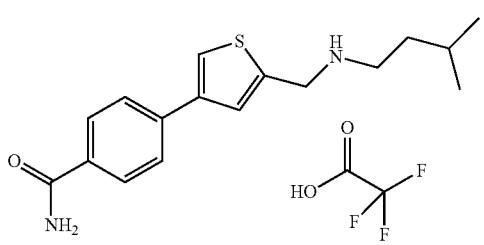<br>4-(5-{[(3-methylbutyl)amino] methyl}-3-thienyl)benzamide trifluoroacetate | (M + H) 303, 1.32 min (LC/MS method A) | Used Intermediate V-4 and 4-bromobenzamide |
| 116 | 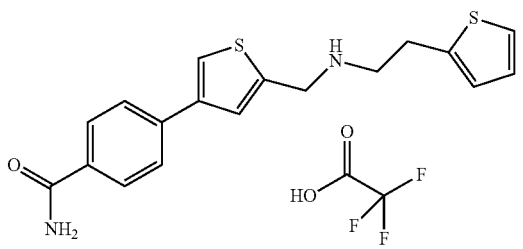<br>4-[5-({[2-(2-thienyl)ethyl]amino}methyl)-3-thienyl]benzamide trifluoroacetate | (M + 1) 343, 1.55 min (LC/MS method A) | Used Intermediate V-5 and 4-bromobenzamide |

TABLE 2-continued

Compounds of Formula I from Compounds of Formula V

| Ex. | Structure and Name | Characterization Data | Method/Comments |
|---|---|---|---|
| 117 | 4-[5-({[2-(3-fluorophenyl)ethyl]amino}methyl)-3-thienyl]benzamide trifluoroacetate | (M + 1) 355, 1.44 min (LC/MS method A) | Used Intermediate V-6 and 4-bromobenzamide |
| 118 | 4-(5-{[(4,4-dimethylcyclohexyl)amino]methyl}-3-thienyl)benzamide trifluoroacetate | (M + 1) 343, 1.58 min (LC/MS method A) | Used Intermediate V-7 and 4-bromobenzamide |
| 119 | 3-(5-{[(4,4-dimethylcyclohexyl)amino]methyl}-3-thienyl)benzamide trifluoroacetate | (M + 1) 343, 1.61 min (LC/MS method A) | Used Intermediate V-7 and IV-6 |
| 120 | 4'-{(1R)-1-[(4,4-dimethylcyclohexyl)amino]ethyl}-3-biphenylcarboxamide trifluoroacetate | (LC/MS Method A) 1.76 min, m/z 351 (M + H, freebase) | Used Intermediate V-9 and [3-(aminocarbonyl)phenyl]boronic acid[1] |

TABLE 2-continued

Compounds of Formula I from Compounds of Formula V

| Ex. | Structure and Name | Characterization Data | Method/Comments |
|---|---|---|---|
| 121 | 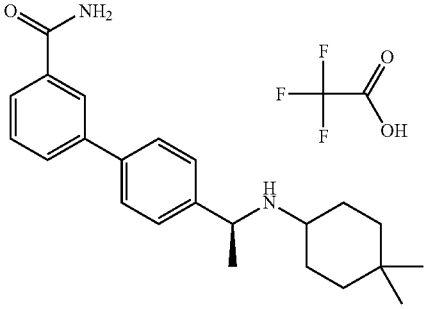<br>4'-{(1S)-1-[(4,4-dimethylcyclohexyl)amino]ethyl}-3-biphenylcarboxamide trifluoroacetate | (LC/MS Method A) 1.75 min, m/z 351 (M + 1, freebase) | Used Intermediate V-10 and [3-(aminocarbonyl)phenyl]boronic acid[1) |
| 122 | 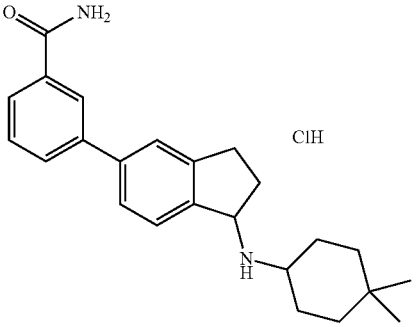<br>3-{1-[(4,4-dimethylcyclohexyl)amino]-2,3-dihydro-1H-inden-5-yl}benzamide hydrochloride | LC/MS (method A) 1.77 min; m/z 363(M + H) | Used Intermediate V-21 and [3-(aminocarbonyl)phenyl]boronic acid PhMe/EtOH (4:1) as organic cosolvent[1,2) |

Note 1:
Na$_2$CO$_3$ was used as the base in the coupling in place of K$_3$PO$_4$.

Note 2:
In lieu of the HPLC purification step, chromatography on ISCO amine-functionalized silica column using Hex/EtOAc eluted the compound. This was further subjected to HCl and concentrated to the HCl salt.

General Method 3 for Preparation of Compounds of Formula I

Example 123

N-[4'-({2-[(4,4-dimethylcyclohexyl)amino]ethyl}oxy)-4-biphenylyl]acetamide trifluoroacetate

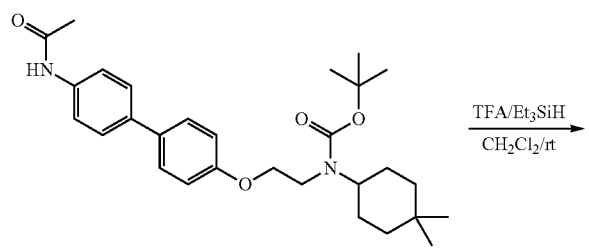

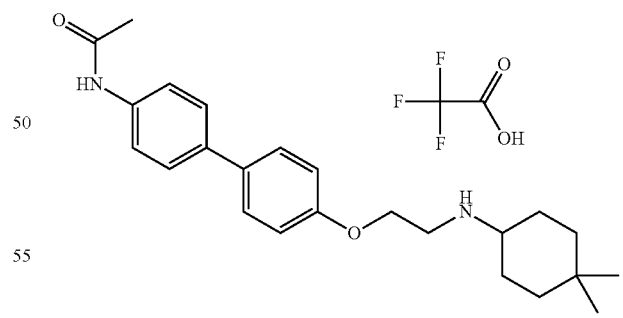

To a solution of 1,1-dimethylethyl (2-{[4'-(acetylamino)-4-biphenylyl]oxy}ethyl) (4,4-dimethylcyclohexyl)carbamate (0.0624 g; 0.13 mmol; Intermediate VI-1) and Et$_3$SiH (0.060 mL; 0.37 mmol; ≥2.5 equiv) in CH$_2$Cl$_2$ (2 mL) at rt was added TFA (1 mL). The mixture was aged 3 h and concentrated to dryness, affording the title compound as a colorless solid (see Note 1). (LC/MS Method A) 1.83 min, m/z 381 (M+H, freebase).

Note 1) In some cases, final compounds prepared by this method required purification. These compounds were purified by RP-HPLC ($C_{18}$ column, MeCN/$H_2O$ gradient with TFA additive), yielding final compounds (as TFA salts).

TABLE 3

Compounds of Formula I from Compounds of Formula VI

| Ex. | Structure and Name | Characterization Data | Method/Comments |
|---|---|---|---|
| 124 | 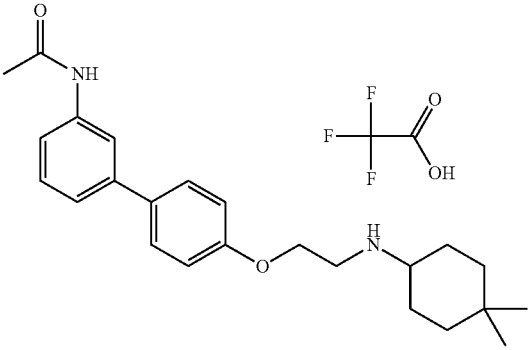<br>N-[4'-({2-[(4,4-dimethylcyclohexyl)amino]ethyl}oxy)-3-biphenylyl]acetamide trifluoroacetate | Note 2 | Used Intermediate VI-2 |
| 125 | 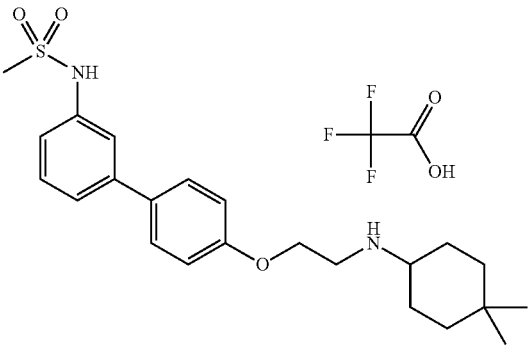<br>N-[4'-({2-[(4,4-dimethylcyclohexyl)amino]ethyl}oxy)-3-biphenylyl]methanesulfonamide trifluoroacetate | LC/MS (LC/MS Method A) 1.85 min, m/z 415 M − H, freebase). | Used Intermediate VI-3 |
| 126 | 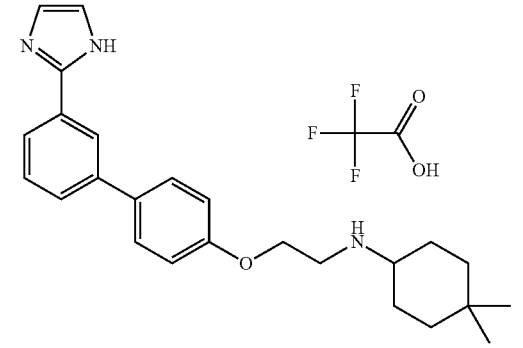<br>N-(2-{[3'-(1H-imidazol-2-yl)-4-biphenylyl]oxy}ethyl)-4,4-dimethyl cyclohexanamine trifluoroacetate | (LC/MS Method A) 1.43 min, m/z 390 (M + H, freebase) | Used Intermediate VI-4 |

TABLE 3-continued

Compounds of Formula I from Compounds of Formula VI

| Ex. | Structure and Name | Characterization Data | Method/Comments |
|---|---|---|---|
| 127 | 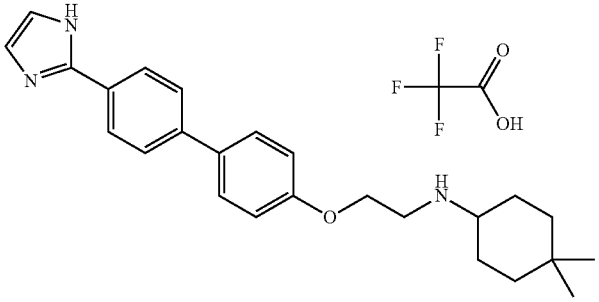<br>N-(2-{[4'-(1H-imadazol-2-yl)-4-biphenylyl]oxy}ethyl)-4,4-dimethylcyclohexanamine trifluoroacetate | (LC/MS Method A) 1.41 min, m/z 390 (M + 1, freebase) | Used Intermediate VI-5 |
| 128 | 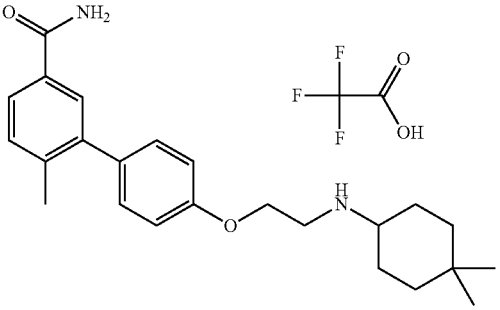<br>4'-({2-[(4,4-dimethylcyclohexyl)amino]ethyl}oxy)-6-methyl-3-biphenyl carboxamide trifluoroacetate | (LC/MS Method A) 1.75 min, m/z 381 (M + 1, freebase) | Used Intermediate VI-6 |
| 129 | 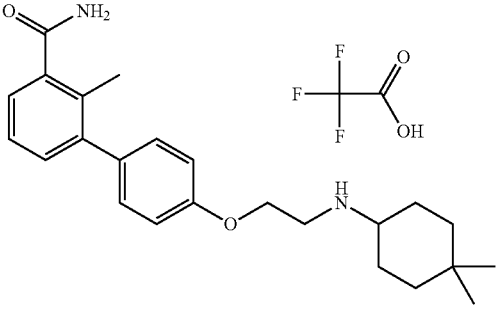<br>4'-({2-[(4,4-dimethylcyclohexyl)amino]ethyl}oxy)-2-methyl-3-biphenyl carboxamide trifluoroacetate | (LC/MS Method A) 1.87 min, m/z 381 (M + 1) | Used Intermediate VI-7 |

TABLE 3-continued

Compounds of Formula I from Compounds of Formula VI

| Ex. | Structure and Name | Characterization Data | Method/Comments |
|---|---|---|---|
| 130 | 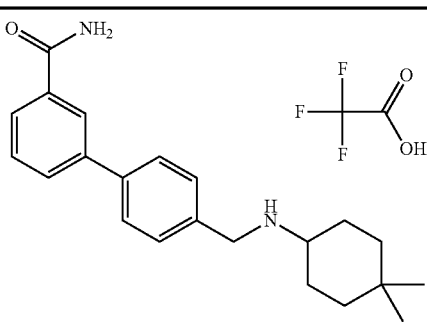  4′-{[(4,4-Dimethylcyclohexyl)amino] methyl}-3-biphenylcarboxamide trifluoroacetate | Need Data | Used Intermediate VI-8[1)] |
| 131 | 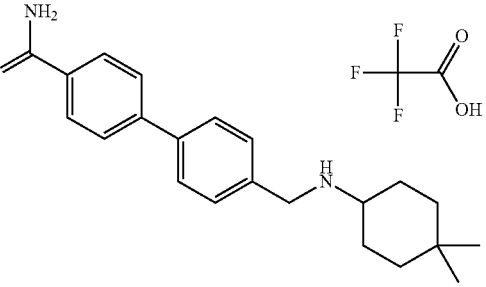  4′-{[(4,4-dimethylcyclohexyl)amino] methyl}-4-biphenylcarboxamide trifluoroacetate | LC/MS (LC/MS Method A) 1.63 min, m/z 337 (M + H, freebase) | Used Intermediate VI-9 |
| 132 | 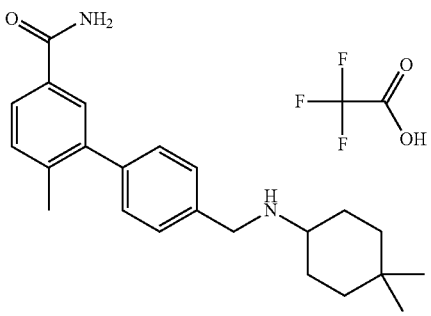  4′-{[(4,4-dimethylcyclohexyl)amino] methyl}-6-methyl-3-biphenylcarboxamide trifluoroacetate | (LC/MS Method A) 1.76 min, m/z 351 (M + H, freebase) | Used Intermediate VI-10 |
| 133 | 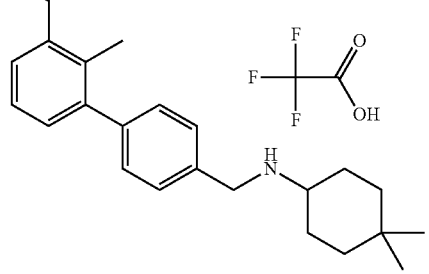  4′-{[(4,4-dimethylcyclohexyl)amino] methyl}-2-methyl-3-biphenylcarboxamide trifluoroacetate | (LC/MS Method A) 1.64 min, m/z 351 (M + H, freebase) | Used Intermediate VI-11 |

TABLE 3-continued

Compounds of Formula I from Compounds of Formula VI

| Ex. | Structure and Name | Characterization Data | Method/Comments |
|---|---|---|---|
| 134 | 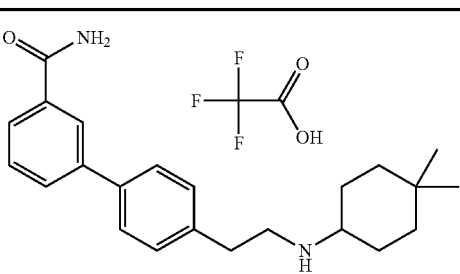<br>4'-{2-[(4,4-dimethylcyclohexyl)amino]ethyl}-3-biphenylcarboxamide trifluoroacetate | (LC/MS Method A) 1.72 min, m/z 351 (M + H, freebase) | Used Intermediate VI-12 |
| 135 | 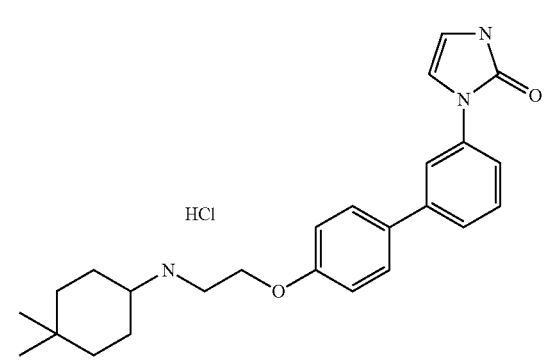<br>1-[4'-({2-[(4,4-dimethylcyclohexyl)amino]ethyl}oxy)-3-biphenylyl]-1,3-dihydro-2H-imidazol-2-one hydrochloride | LC/MS (LC/MS Method A) 0.75 min, m/z 406.3 (M + 1, freebase) | Used Intermediate VI-13, final compound was free-based, then treated with 1.0M HCl in Et$_2$O |
| 136 | 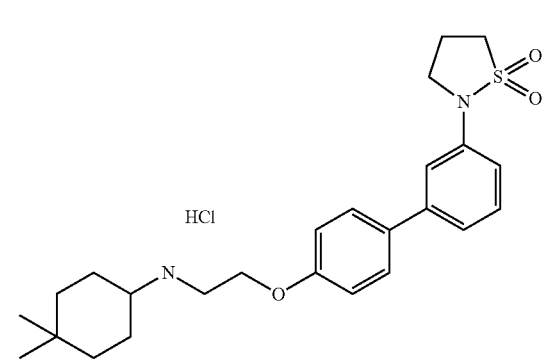<br>N-(2-{[3'-(1,1-dioxido-2-isothiazolidinyl)-4-biphenylyl]oxy}ethyl)-4,4-dimethyl cyclohexanamine hydrochloride | LC/MS (LC/MS Method A) 0.76 min, m/z 443.3 (M + 1, freebase) | Used Intermediate VI-14, final compound was free-based, then treated with 1.0M HCl in Et$_2$O |

TABLE 3-continued

Compounds of Formula I from Compounds of Formula VI

| Ex. | Structure and Name | Characterization Data | Method/ Comments |
|---|---|---|---|
| 137 | 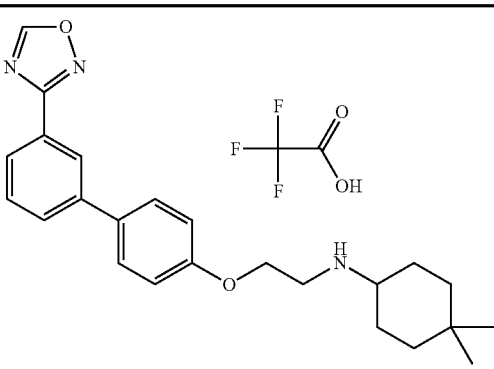<br>(4,4-Dimethylcyclohexyl)(2-{[3'-(1,2,4-oxadiazol-3-yl)-4-biphenyl]oxy} ethyl)amine trifluoroacetate | Note 3 | Used Intermediate VI-15 |
| 138 | 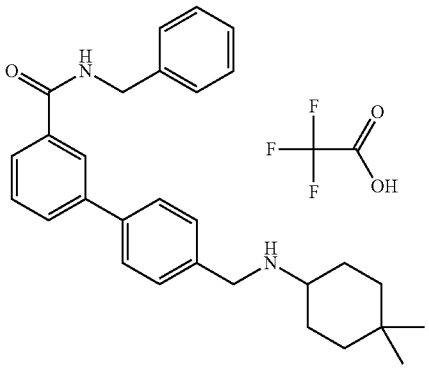<br>4'-{[(4,4-dimethylcyclohexyl)amino]methyl}-N-(phenylmethyl)-3-biphenylcarboxamide trifluoroacetate | LC/MS (method E) 0.67 min; m/z 427(M + H) | Used Intermediate VI-18 |
| 139 | 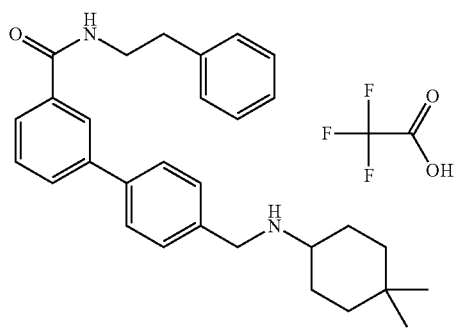<br>4'-{[(4,4-dimethylcyclohexyl)amino]methyl}-N-(2-phenylmethyl)-3-biphenylcarboxamide trifluoroacetate | LC/MS (method E) 0.69 min; m/z 441(M + H) | Used Intermediate VI-16 |

TABLE 3-continued

Compounds of Formula I from Compounds of Formula VI

| Ex. | Structure and Name | Characterization Data | Method/Comments |
|---|---|---|---|
| 140 | 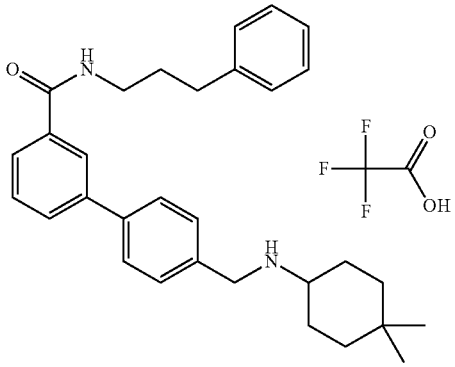<br>4'-{[(4,4-dimethylcyclohexyl)amino]methyl}-N-(3-phenylpropyl)-3-biphenylcarboxamide trifluoroacetate | LC/MS (method E) 0.71 min; m/z 455(M + H) | Used Intermediate VI-17 |
| 141 | 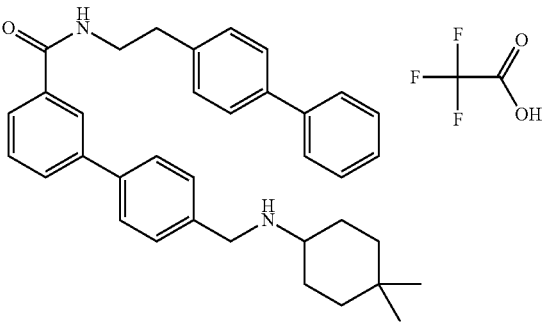<br>N-[2-(4-biphenylyl)ethyl]-4'-{[4,4-dimethylcyclohexyl)amino]methyl}-3-biphenylcarboxamide trifluoroacetate | LC/MS (method E) 0.75 min; m/z 517(M + H) | Used Intermediate VI-19 |
| 142 | 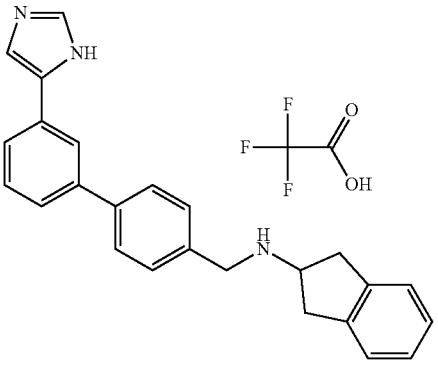<br>N-{[3'-(1H-imidazol-4-yl)-4-biphenyl]methyl}-2,3-dihydro-1H-inden-2-amine trifluoroacetate | LC/MS (method B) 1.72 min; m/z 364(M + H) | Used Intermediate VI-20 |

Note 1:
The title compound was also prepared as described in General Method X (TFA salt) and General Method Y (HCl salt).

Note 2:
$^1$H NMR (400 MHz, DMSO-$d_6$) δ 0.91 (s, 6H), 1.2 (app. T, J = 12.5 Hz, 2H), 1.43 (app. D, J = 13.1 Hz, 2H), 1.55 (app. D, J = 12.2 Hz, 2H), 1.88 (app. D, J = 11.1 Hz, 2H), 2.06 (s, 3H), 3.04 (br. s, 1H), 4.27 (br. s, 2H), 7.09 (m, 2H), 7.26 (d, J = 7.2 Hz, 1H), 7.34 (app. T, J = 7.6 Hz, 1H), 7.45 (d, J = 7.9 Hz, 1H), 7.57 (m, 2H), 7.90 (s, 1H), 8.66 (br. s, 1H), 10.03 (s, 1H). (N.B.: missing CH$_2$ signal assumed to be obscured by water peak).

Note 3:
$^1$H NMR (400 MHz, DMSO-$d_6$) δ 0.91 (s, 6H), 1.22 (app. t, J = 13.0 Hz, 2H), 1.44 (app. d, J = 13.0 Hz, 2H), 1.55 (app. q, J = 12.4 Hz, 2H), 1.88 (app. d, J = 11.2 Hz, 2H), 3.04 (m, 1H), 4.29 (unresolved t, 2H), 7.13 (m, 2H), 7.65 (app. t, J = 7.8 Hz, 1H), 7.72 (m, 2H), 7.86 (d, J = 7.6 Hz, 1H), 7.99 (d, J = 7.5 Hz, 1H), 8.23 (s, 1H), 8.52-8.84 (br. s, 2H), 9.73 (s, 1H) (N.B.: missing CH$_2$ signal assumed to be obscured by water peak).

General Method 4 for Preparation of Compounds of Formula I

Example 143

4'-({2-[(4,4-Dimethylcyclohexyl)amino]ethyl}oxy)-2'-methyl-3-biphenylcarboxamide trifluoroacetate

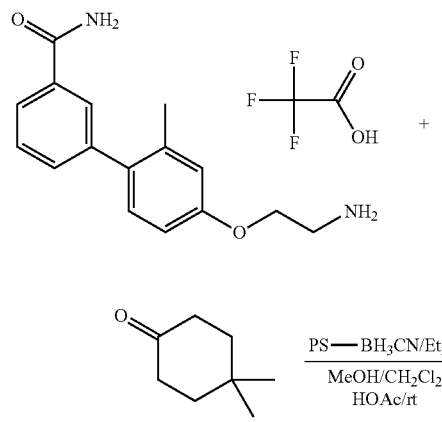

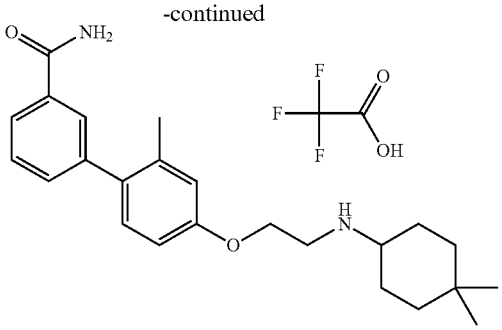

To a solution of 4'-[(2-aminoethyl)oxy]-2'-methyl-3-biphenylcarboxamide trifluoroacetate (0.105 g; 0.273 mmol; Intermediate VII-1) and 4,4-dimethylcyclohexanone (0.038 g; 0.30 mmol; Intermediate Step 1 of III-1) in MeOH/CH$_2$Cl$_2$/HOAc (3 mL; 1:1 MeOH/CH$_2$Cl$_2$ with 5% HOAc) was added Et$_3$N (0.040 mL; 0.27 mmol), followed by PS—BH$_3$CN (0.32 g; ca. 4.2 mmol/g; ca. 1.35 mmol BH$_3$CN). The mixture was agitated overnight at rt using an orbital shaker, and the resin was removed by filtration. The filtrate was concentrated in vacuo, and the residue was purified by RP-HPLC (C$_{18}$ column, MeCN/H$_2$O gradient with TFA additive) affording the title compound as a colorless foam. (LC/MS Method C) 2.24 min, m/z 381 (M+1, free-base).

The following were prepared in a manner similar to that described in the above example with notation and comment provided for the particular example below the table.

TABLE 4

Compounds of Formula I from Compounds of Formula VII

| Ex. | Structure and Name | Characterization Data | Method/Comments |
| --- | --- | --- | --- |
| 144 | 3'-{2-[(cyclohexylmethyl)amino]ethyl}-4-biphenyl carboxamide trifluoroacetate | (M + H) 381, 1.83 min. (LC/MS method A) | Used VII-2 and cyclohexane carboxaldehyde Note 5, 6 |
| 145 | 3'-{2-[(3-methylbutyl)amino]ethyl}-4-biphenylcarboxamide trifluoroacetate | (M + H) 311, 1.55 min. (LC/MS method A) | Used VII-2 Note 5, 6 |

TABLE 4-continued

Compounds of Formula I from Compounds of Formula VII

| Ex. | Structure and Name | Characterization Data | Method/Comments |
|---|---|---|---|
| 146 | 3'-[1-(3-methylbutyl)-4-piperidinyl]-4-biphenylcarboxamidehydrochloride | (M + H) 351, 1.49 min. (LC/MS method A) | Used VII-3 Note 6, 7 |
| 147 | 3-[2-(4,4-dimethylcyclohexyl)-1,2,3,4-tetrahydro-6-isoquinolinyl]benzamide hydrochloride | LC/MS (method A) 2.02 min; m/z 363 (M + H). | Used I-VII-9 (Boc'd) Note 3 and Ex III-1 Step 1 intermed. Note 2 |
| 148 | 3-[2-(3-methylbutyl)-1,2,3,4-tetrahydro-6-isoquinolinyl]benzamide trifluoroacetate | LC/MS (method C) 1.87 min, m/z 323 (M + H). | Used VII-4 |
| 149 | 4-[2-(4,4-dimethylcyclohexyl)-1,2,3,4-tetrahydro-7-isoquinolinyl]benzamide trifluoroacetate | LC/MS (method D) 1.93 min, m/z 363 (M + H). | Used I-VII-10 and Ex III-1 Step 1 intermed. Note 3 |

TABLE 4-continued

Compounds of Formula I from Compounds of Formula VII

| Ex. | Structure and Name | Characterization Data | Method/Comments |
|---|---|---|---|
| 150 | 3-(2-cyclohexyl-1,2,3,4-tetrahydro-6-isoquinolinyl)benzamide trifluoroacetate | LC/MS (method A) 1.8 min; m/z 335 (M + H) | Used VII-4<br>Note 4 |
| 151 | 3-[2-(3,3-dimethylcyclohexyl)-1,2,3,4-tetrahydro-6-isoquinolinyl]benzamide trifluoroacetate | LC/MS (method A) 2 min; m/z 363 (M + H) | Used VII-4<br>Note 4 |
| 152 | 3-[2-(cyclohexylmethyl)-1,2,3,4-tetrahydro-6-isoquinolinyl]benzamide trifluoroacetate | LC/MS (method A) 1.95 min; m/z 349 (M + H) | Used VII-4<br>Note 4 |
| 153 | 3-[2-(phenylmethyl)-1,2,3,4-tetrahydro-6-isoquinolinyl]benzamide hydrochloride | LC/MS (method A) 1.85 min; m/z 343 (M + H) | Used VII-4<br>Purified by flash chromatography, added HCl (4M in dioxane) to column fractions.<br>Note 4 |

TABLE 4-continued

Compounds of Formula I from Compounds of Formula VII

| Ex. | Structure and Name | Characterization Data | Method/Comments |
|---|---|---|---|
| 154 | 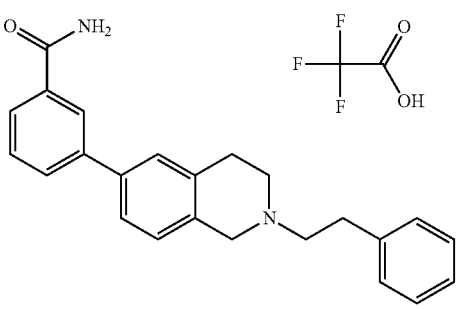<br>3-[2-(2-(phenylethyl)-1,2,3,4-tetrahydro-6-isoquinolinyl]benzamide trifluoroacetate | LC/MS (method A) 1.91 min; m/z 357 (M + H) | Used VII-4<br>Note 4 |
| 155 | 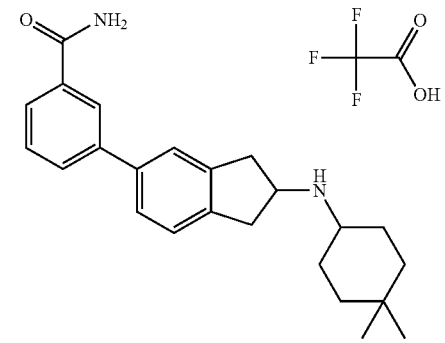<br>3-{2-[(4,4-dimethylcyclohexyl)amino]-2,3-dihydro-1H-inden-5-yl}benzamide trifluoroacetate | LC/MS (method A) 2.19 min; m/z 363 (M + H) | Used VII-5 and Ex III-1 Step 1 Intermed.<br>Note 4 |
| 156 | 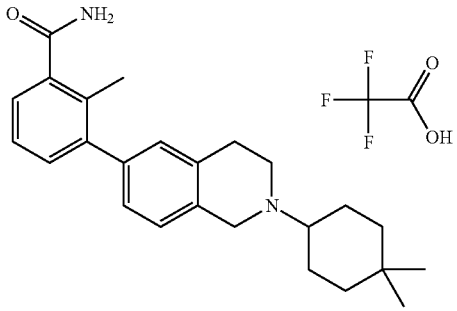<br>[2-(4,4-dimethylcyclohexyl)-1,2,3,4-tetrahydro-6-isoquinolinyl]-2-methylbenzamide trifluoroacetate | LC/MS (method A) 2.06 min; m/z 377 (M + H) | Used I-VII-5 and Ex III-1 Step 1 intermed.<br>Note 3, 4 |

TABLE 4-continued

Compounds of Formula I from Compounds of Formula VII

| Ex. | Structure and Name | Characterization Data | Method/Comments |
|---|---|---|---|
| 157 | 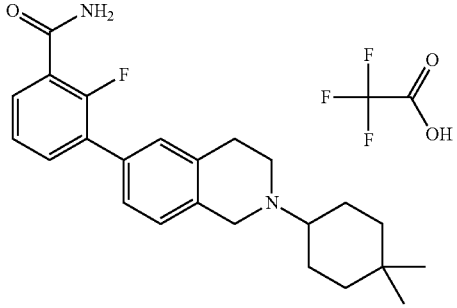<br>3-[2-(4,4-dimethylcyclohexyl)-1,2,3,4-tetrahydro-6-isoquinolinyl]-2-fluorobenzamide trifluoroacetate | LC/MS (method A) 2.06 min; m/z 382 (M + H) | Used I-VII-6 and Ex III-1 Step 1 intermed. Note 3, 4 |
| 158 | 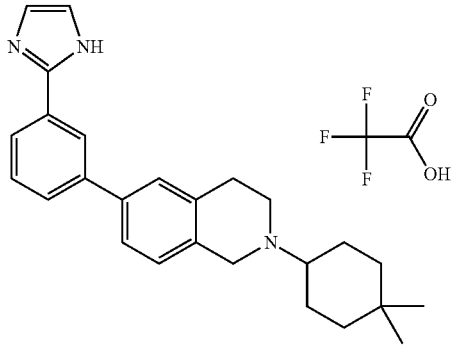<br>2-(4,4-dimethylcyclohexyl)-6-[3-(1H-imidazol-2-yl)phenyl]-1,2,3,4-tetrahydroisoquinoline trifluoroacetate | LC/MS (method A) 1.79 min; m/z 386 (M + H) | Used I-VII-7 and Ex III-1 Step 1 intermed. Note 3, 4 |
| 159 | 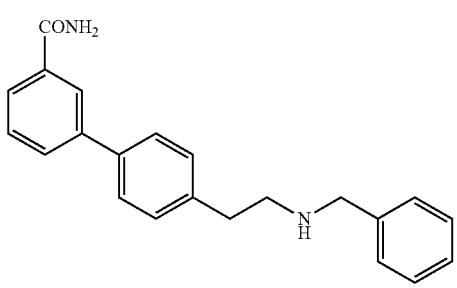<br>4'-{2-[(phenylmethyl)amino]ethyl}-3-biphenylcarboxamide | LC/MS (method E) 0.52 min; m/z 331 (M + H) | Used VII-7 Note 4, 8 |
| 160 | 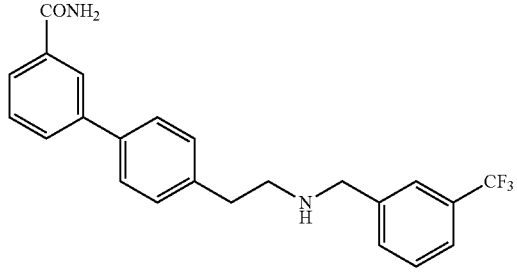<br>4'-{2-({[3-(trifluoromethyl)phenyl]methyl}amino)ethyl]-3-biphenyl carboxamide | LC/MS (method E) 0.57 min; m/z 399 (M + H) | Used VII-7 Note 4, 8 |

TABLE 4-continued

Compounds of Formula I from Compounds of Formula VII

| Ex. | Structure and Name | Characterization Data | Method/Comments |
|---|---|---|---|
| 161 | 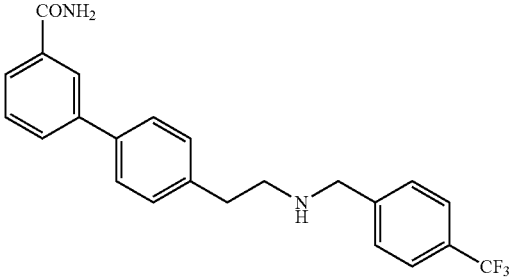<br>4'-[2-({[4-(trifluoromethyl)phenyl]methyl}amino)ethyl]-3-biphenyl carboxamide | LC/MS (method E) 0.57 min; m/z 399 (M + H) | Used VII-7<br>Note 4, 8 |
| 162 | 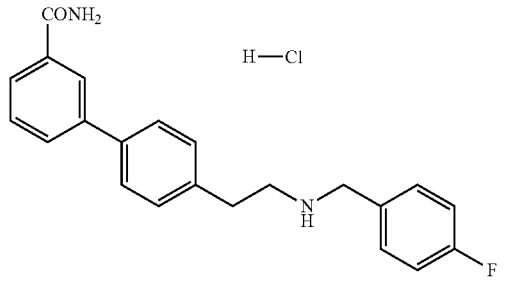<br>4'-(2-{[(4-fluorophenyl]methyl}amino)ethyl]-3-biphenylcarboxamide hydrochloride | LC/MS (method E) 0.53 min; m/z 349 (M + H) | Used VII-7<br>Note 4, 7(prior to HCl salt formation, the freebase was chromatographed on silica using EtOAc/MeOH) |
| 163 | 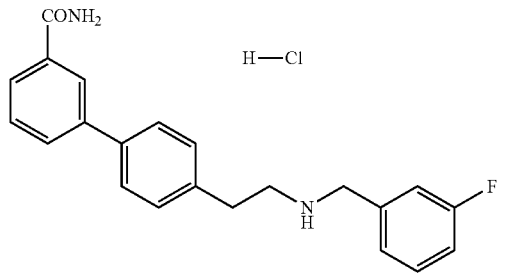<br>4'-{2-{[(3-fluorophenyl)methyl]amino}ethyl]-3-biphenylcarboxamide hydrochloride | LC/MS (method E) 0.52 min; m/z 349 (M + H) | Used VII-7<br>Note 6, 7(prior to HCl salt formation, the freebase was chromatographed on silica using EtOAc/MeOH) |
| 164 | 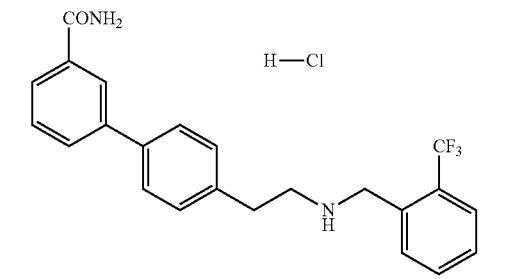<br>4'-[2-({[2-trifluoromethyl)phenyl]methyl}amino)ethyl]-3-biphenylcarboxamide hydrochloride | LC/MS (method E) 0.56 min; m/z 399 (M + H) | Used VII-7<br>Note 4, 7(prior to HCl salt formation, the freebase was chromatographed on silica using EtOAc/MeOH) |

TABLE 4-continued

Compounds of Formula I from Compounds of Formula VII

| Ex. | Structure and Name | Characterization Data | Method/Comments |
|-----|--------------------|-----------------------|-----------------|
| 165 | 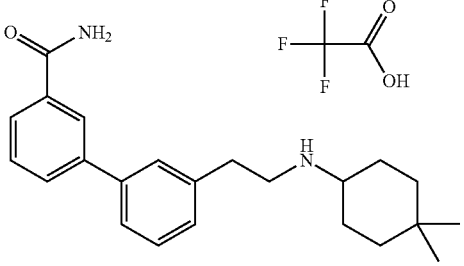<br>3'-{2-[(4,4-dimethylcyclohexyl)amino]ethyl}-3-biphenylcarboxamide trifluoroacetate | LC/MS (method B) 2.17 min; m/z 373 (M + H) | Used VII-7 and III-1 Step 1 intermed. Note 4 |
| 166 | 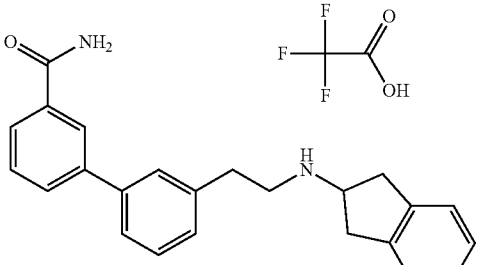<br>3'-[2-(2,3-dihydro-1H-inden-2-ylamino)ethyl]-3-biphenylcarboxamide trifluoroacetate | LC/MS (method B) 2.06 min; m/z 357 (M + H) | Used VII-7 Note 4 |
| 167 | 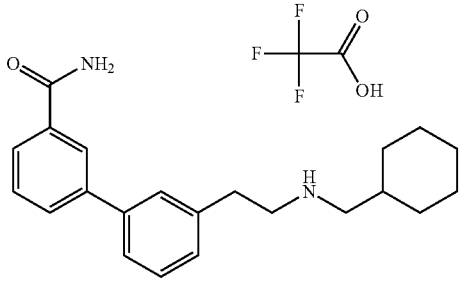<br>3'-{2-[(cyclohexylmethyl)amino]ethyl}-3-biphenylcarboxamide trifluoroacetate | LC/MS (method B) 2.09 min; m/z 337 (M + H) | Used VII-7 Note 4 |
| 168 | 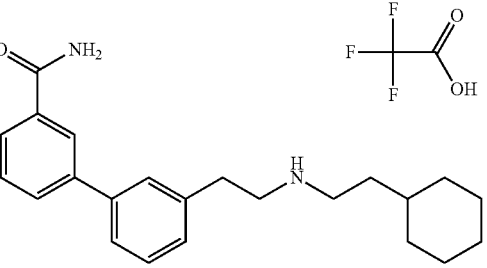<br>3'-{2-[(2-cyclohexylmethyl)amino]ethyl}-3-biphenylcarboxamide trifluoroacetate | LC/MS (method B) 2.23 min; m/z 351 (M + H) | Used VII-7 Note 4 |

TABLE 4-continued

Compounds of Formula I from Compounds of Formula VII

| Ex. | Structure and Name | Characterization Data | Method/Comments |
|---|---|---|---|
| 169 | 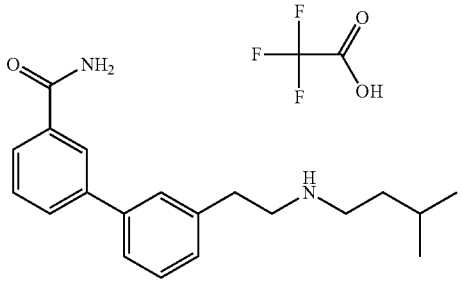<br><br>3'-{2-[(3-methylbutyl)amino]ethyl}-3-biphenylcarboxamide trifluoroacetate | LC/MS (method B) 2.17 min; m/z 373 (M + H) | Used VII-7<br>Note 4 |

Note 1
PS-H₃CN = polymer-supported trialkylammonium cyanoborohydride (novabiochem A30113).
Note 2
Prepared using a conventional reducing agent (1.1 equiv NaBH₃CN) in THF/MeOH/HOAc (5:2:0.5 respectively). After stirring 3 d, the mixture was concentrated in vacuo, and partitioned between CH₂Cl₂/1M NaOH. The layers were separated, the aqueous layer was extracted with CH₂Cl₂ (×2), combined organics were washed (water, brine), dried over Na₂SO₄ and concentrated in vacuo. The residue was purified by flash chromatography (EtOAc/hexanes). HCl (ca. 4 equiv of a 4M solution in dioxane) was added to column eluent containing the desired product, affording the title compound as a cream-colored solid. The corresponding TFA salt of the title compound has also been prepared from I-VII-9 without isolation of VII-4 (cf. Note 3).
Note 3
The deprotected form of Formula VII was not characterized. The crude TFA salt of VII obtained from acidolysis of a Boc protecting group (TFA/Et₃SiH/CH₂Cl₂) was either admixed with an equimolar amount of Et₃N, or subjected to a basic aqueous workup (CHCl₃/satd Na₂CO₃) to obtain crude Formula VII which was used directly for reductive alkylation.
Note 4
'MP-H₃CN' (Argonaut Technologies 800407) was used as reducing agent (instead of 'PS—BH₃CN'), and MeOH/THF containing ca. 5% HOAc was used as solvent (instead of MeOH/CH₂Cl₂/HOAc).
Note 5
Some dialkylated product was also produced in this reaction.
Note 6
Prepared using the standard reductive alkylation reagent sodium triacetoxyborohydride (1.5-3 eq) and (1-3 eq) of aldehyde to amine (VII-2).
Note 7
A base extractive workup was performed and the organics subjected to HCl in Et₂O or dioxane and the precipitate filtered to give the title compound as the HCl salt.
Note 8
Instead of HPLC purification the crude material was subjected to silica chromatography using EtOAc/MeOH followed by recrystallization from CH₂Cl₂/Hexane.

General Method 5 for Preparation of Compounds of Formula I

Compounds of Formula I Prepared According to General Method 5 Procedures

Example 170

3'-({[(4,4-dimethylcyclohexyl)methyl]amino}methyl)-2-methyl-4-biphenylcarboxamide hydrochloride

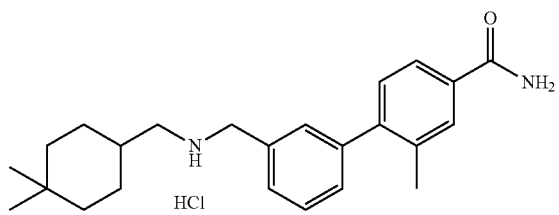 [SMILES: Cc1cc(C(N)=O)ccc1-c1cccc(CNCC2CCC(C)(C)CC2)c1 ; Cl]

A mixture of 3'-formyl-2-methyl-4-biphenylcarboxamide (0.15 g, 0.63 mmol; Ex. IX-23), 4,4-dimethylcyclohexylmethylamine hydrochloride (0.28 g, 1.6 mmol; Ex III-1) and acetic acid (4 drops) in methanol was stirred at room temperature for 30 min. Sodium triacetoxyborohydride (0.34 g, 1.6 mmol) was added in one portion and the mixture was stirred at room temperature for 72 hr. Water (10 mL) was added and the mixture was stirred at room temperature for 2 hr. The mixture was concentrated in vacuo to remove the methanol and the residue was taken up in a mixture of ethyl acetate and 5% Na₂CO₃ (aq). The aqueous phase was extracted with ethyl acetate. The combined organic phase was washed with brine, silica gel was added and the mixture was concentrated in vacuo.

The residue was purified by flash chromatography (CH₂Cl₂/MeOH). The freebase product obtained was dissolved in acetonitrile, filtered, and HCl was added (1M in Et₂O) until turbid, and allowed to stand at room temperature. Precipitated solid was collected by filtration, washed with (Et₂O) and air-dried to give the title compound as a white solid. LC/MS (method A) 1.90 min; m/z 365 (M+H).

Example 171

2: 4'-[(2,3-Dihydro-1H-inden-2-ylamino)methyl]-3-biphenyl-carboxamide trifluoroacetate

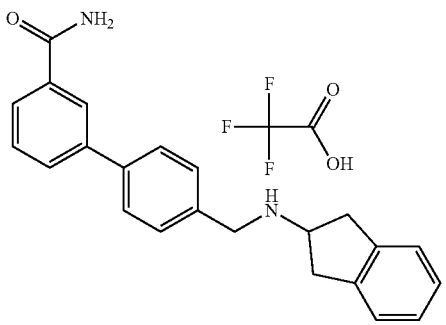

To a solution of 4'-formyl-3-biphenylcarboxamide (0.056 g; 0.25 mmol; Ex. IX-1) in MeOH/CH₂Cl₂/HOAc (5% v/v HOAc in 1:1 MeOH/CH₂Cl₂, 3 mL) at room temperature was added 2-aminoindane (0.375 mmol; Note 1), followed by PS—BH₃CN (0.30 g; see Note 2). The mixture was agitated overnight, resin was removed by filtration and the filtrate was concentrated in vacuo The residue was purified by preparative HPLC (C-18 column, MeCN/H₂O gradient with 0.1% TFA additive) affording the final compound as a colorless solid (Note 3). LC/MS (method A) 1.58 min, m/z 343 (M+H, 57%), 210 ([M-aminoindane]+H, 100%).

Note 1 2-aminoindane hydrochloride was admixed with an equimolar amount of Et₃N in CH₂Cl₂ before mixing with IX-1.

Note 2 'PS—BH₃CN'=polymer-supported trialkylammonium cyanoborohydride reagent (novabiochem A30113). An excess of PS—BH₃CN was used (est. 3-5 equiv BH₃CN based on benzaldehyde starting materials).

Note 3 The title compound (as HCl salt) was also prepared using solution-phase conditions similar to Example 172 below.

Example 172

4'-{[(4,4-dimethylcyclohexyl)amino]methyl}-3-biphenyl-carboxamide hydrochloride

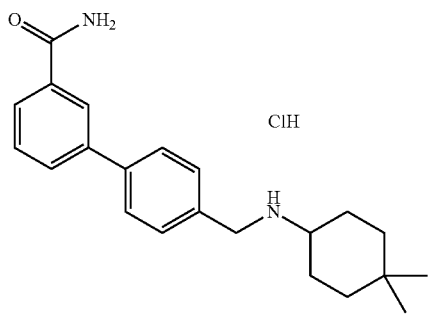 [SMILES: CC1(C)CCC(NCc2ccc(-c3cccc(C(N)=O)c3)cc2)CC1 ; Cl]

A mixture of 4'-formyl-3-biphenylcarboxamide (0.576 g; 2.56 mmol; Ex IX-1), 4,4-dimethylcyclohexylamine (0.390 g; 3.07 mmol; Note 1), and TsOH.H₂O (0.049 g; 0.26 mmol) in PhH (15 mL) was heated under reflux overnight, using a Dean-Stark trap to remove water. Upon cooling, volatiles were removed in vacuo, the residue was dissolved in 2.5% HOAc in MeOH (20 mL), and NaBH₃CN (0.17 g; 2.8 mmol) was added in one portion. The mixture was stirred at room ca. 1 h (Note 2). The mixture was concentrated in vacuo, the residue was partitioned between CH₂Cl₂/1M NaOH and the layers were separated. The organic layer was washed (H₂O, brine), dried over Na₂SO₄, filtered and concentrated in vacuo. The residue was purified by preparative HPLC(C-18 column, MeCN/H₂O gradient with 0.1% TFA additive); eluent containing desired product was poured into EtOAc/satd Na₂CO₃, layers were separated, the organic layer was washed with brine and dried over Na₂SO₄. HCl (1 mL of a 4M solution in dioxane) was added to the dried extract and the mixture was concentrated in vacuo, affording the title compound as a colorless solid (Note 3). LC/MS (method A) 2.06 min, m/z 337 (M+H).

Note 1 Ex III-1 was freebased before use by partitioning between Et₂O and satd Na₂CO₃, separating layers, drying the organic layer over Na₂SO₄ and concentrating in vacuo.

Note 2 An aliquot of the reaction mixture after 45 min indicated complete conversion.

Note 3 The title compound was also prepared as a TFA salt according to General Method 3.

Compounds of Formula I Prepared by General Method 5

The following examples were prepared from the appropriate compounds of Formula IX and III in a manner similar to one of the representative examples given above; any significant deviations are noted below table. Compounds of Formula III which are readily available from commercial sources are not listed in the table.

TABLE 5

Compounds of Formula I from Compounds of Formula IX

| Ex | Structure and Name | Characterization Data | Comments |
|---|---|---|---|
| 173 | 4'-{[(4,4-dimethylcyclohexyl)-amino]methyl}-6-methyl-3-biphenylcarboxamide trifluoroacetate | LC/MS (method A) 1.76 min, m/z 351 (M + H) | Used IX-3 and III-1 General Method: Example 171 |

TABLE 5-continued

Compounds of Formula I from Compounds of Formula IX

| Ex | Structure and Name | Characterization Data | Comments |
|---|---|---|---|
| 174 | 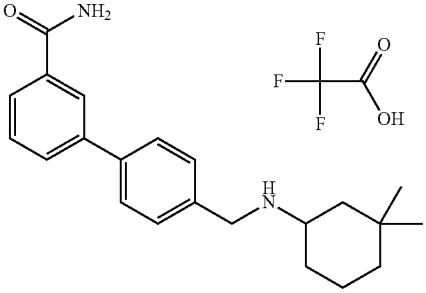<br>rac 4'-{[(3,3-dimethylcyclo-hexyl)amino] methyl}-3-biphenylcarboxamide trifluoroacetate | LC/MS (method A)<br>1.66 min, m/z 337<br>(M + H) | Used IX-1 and III-3<br>General Method:<br>Example 171 |
| 175 | 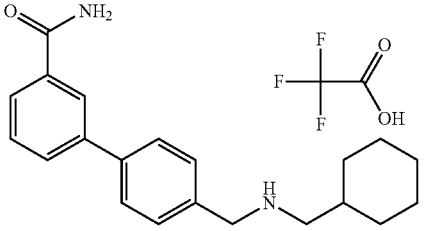<br>4'-{[(cyclohexylmethyl)amino]methyl}-3-biphenylcarboxamide trifluoroacetate | LC/MS (method A)<br>1.57 min, m/z 323<br>(M + H) | Used IX-1<br>General Method:<br>Example 171 |
| 176 | 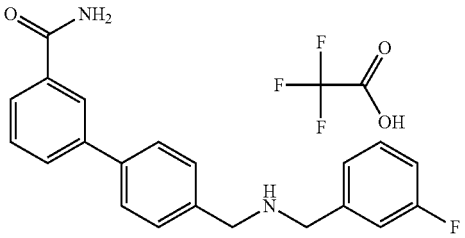<br>4'-({[(3-fluorophenyl)methyl]amino}methyl)-3-biphenylcarboxamide trifluoroacetate | LC/MS (method A)<br>1.45 min, m/z 335<br>(M + H) | Used IX-1<br>General Method:<br>Example 171 |
| 177 | 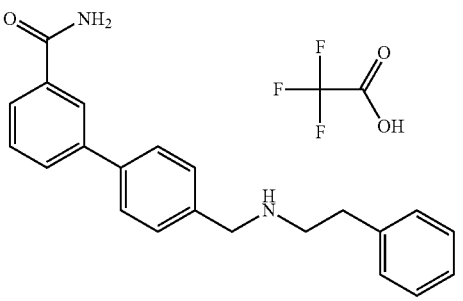<br>4'-{[(2-phenylethyl))amino]methyl}-3-biphenylcarboxamide trifluoroacetate | LC/MS (method A)<br>1.51 min, m/z 331<br>(M + H) | Used IX-1<br>General Method:<br>Example 171 |

TABLE 5-continued

Compounds of Formula I from Compounds of Formula IX

| Ex | Structure and Name | Characterization Data | Comments |
|---|---|---|---|
| 178 | 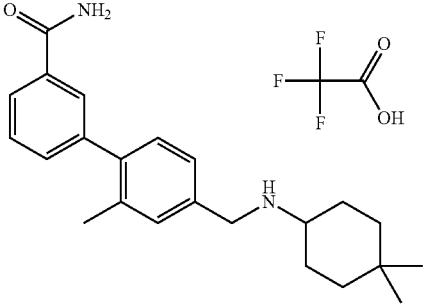<br>4'-{[(4,4-dimethylcyclohexyl)amino]methyl}-2'-methyl-3-biphenylcarboxamide trifluoroacetate | LC/MS (method A)<br>1.72 min, m/z 351<br>(M + H) | Used IX-4 and III-1<br>General Method:<br>Example 171 |
| 179 | 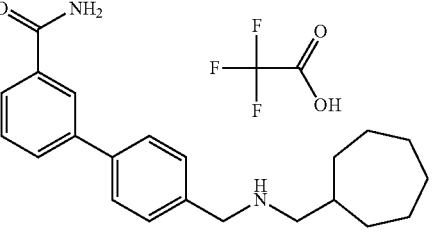<br>4'-{[(cycloheptylmethyl)amino]methyl}-3-biphenylcarboxamide trifluoroacetate | LC/MS (method C)<br>2.10 min, m/z 337<br>(M + H) | Used IX-1<br>General Method:<br>Example 171 |
| 180 | 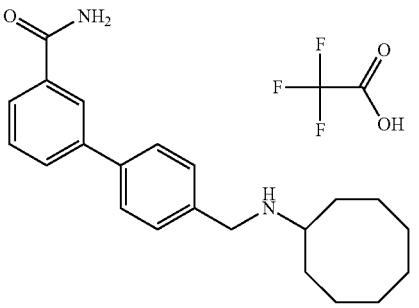<br>4'-[(cyclooctylamino)methyl]-3-biphenylcarboxamide trifluoroacetate | LC/MS (method C)<br>2.09 min, m/z 337<br>(M + H) | Used IX-1<br>General Method:<br>Example 171 |
| 181 | 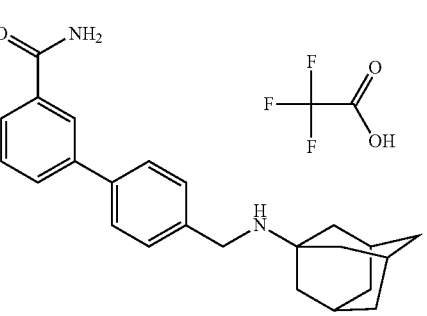<br>4'-[(tricyclo[3.3.1.13,7]dec-1-ylamino)methyl]-3-biphenyl-carboxamide trifluoroacetate | LC/MS (method C)<br>2.09 min, m/z 361<br>(M + H) | Used IX-1<br>General Method:<br>Example 171 |

TABLE 5-continued

Compounds of Formula I from Compounds of Formula IX

| Ex | Structure and Name | Characterization Data | Comments |
|---|---|---|---|
| 182 | 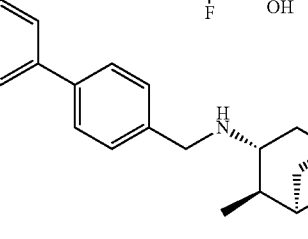<br>4'-({[(1R,2R,3R,5S)-2,6,6-trimethyl-bicyclo[3.1.1]hept-3-yl]amino}methyl)-3-biphenyl-carboxamide trifluoroacetate | LC/MS (method C)<br>2.22 min, m/z 363<br>(M + H) | Used IX-1<br>General Method:<br>Example 171 |
| 183 | 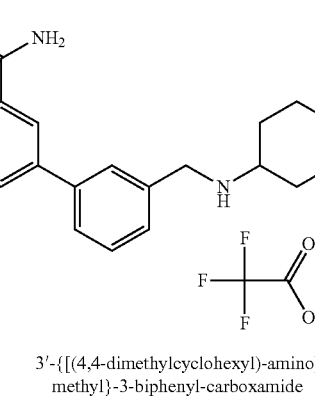<br>3'-{[(4,4-dimethylcyclohexyl)-amino]methyl}-3-biphenyl-carboxamide trifluoroacetate | LC/MS (method C)<br>2.11 min, m/z 337<br>(M + H) | Used IX-5 and III-1<br>General Method:<br>Example 171 |
| 184 | 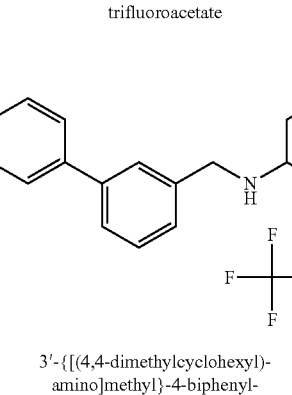<br>3'-{[(4,4-dimethylcyclohexyl)-amino]methyl}-4-biphenyl-carboxamide trifluoroacetate | LC/MS (method C)<br>2.10 min, m/z 337<br>(M + H) | Used IX-6 and III-1<br>General Method:<br>Example 171 |
| 185 | 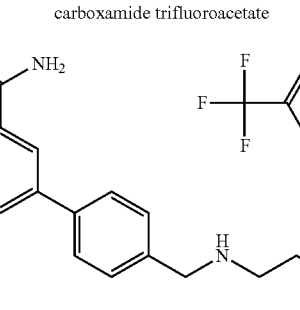<br>4'-{[(3-methylbutyl)amino]methyl}-3-biphenylcarboxamide trifluoroacetate | LC/MS (method C)<br>1.94 min, m/z 297<br>(M + H) | Used IX-1<br>General Method:<br>Example 171 |

TABLE 5-continued

Compounds of Formula I from Compounds of Formula IX

| Ex | Structure and Name | Characterization Data | Comments |
|----|---|---|---|
| 186 | 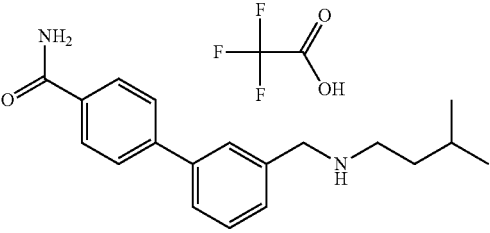<br>3'-{[(3-methylbutyl)amino]methyl}-4-biphenylcarboxamide trifluoroacetate | LC/MS (method C)<br>1.89 min, m/z 297<br>(M + H) | Used IX-6<br>General Method:<br>Example 171 |
| 187 | 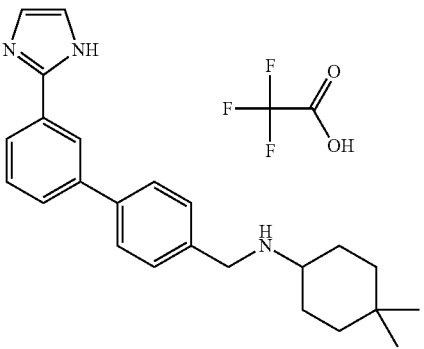<br>N-{[3'-(1H-imidazol-2-yl)-4-biphenylyl]methyl}-4,4-dimethylcyclohexanamine trifluoroacetate | LC/MS (method A)<br>1.37 min, m/z 360<br>(M + H) | Used IX-7 and III-1<br>General Method:<br>Example 171 |
| 188 | 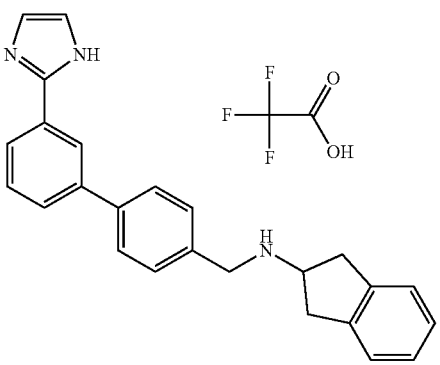<br>N-{[3'-(1H-imidazol-2-yl)-4-biphenylyl]methyl}-2,3-dihydro-1H-inden-2-amine trifluoroacetate | LC/MS (method A)<br>1.15 min, m/z 366<br>(M + H) | Used IX-7<br>General Method:<br>Example 171 |

TABLE 5-continued

Compounds of Formula I from Compounds of Formula IX

| Ex | Structure and Name | Characterization Data | Comments |
|---|---|---|---|
| 189 | 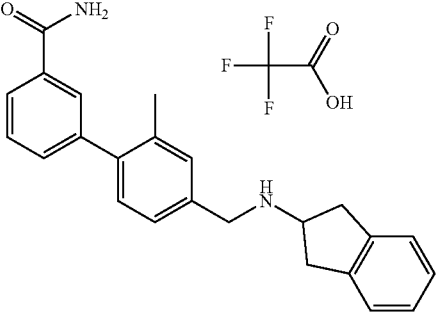  4′-[(2,3-dihydro-1H-inden-2-ylamino)methyl]-2′-methyl-3-biphenylcarboxamide trifluoroacetate | LC/MS (method A) 1.61 min, m/z 357 (M + H) | Used IX-4 General Method: Example 171 |
| 190 | 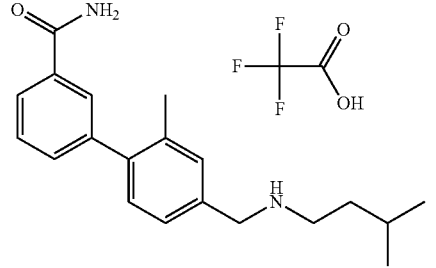  2′-methyl-4′-{[(3-methylbutyl)-amino]methyl}-3-biphenyl-carboxamide trifluoroacetate | LC/MS (method A) 1.49 min, m/z 311 (M + H) | Used IX-4 General Method: Example 171 |
| 191 | 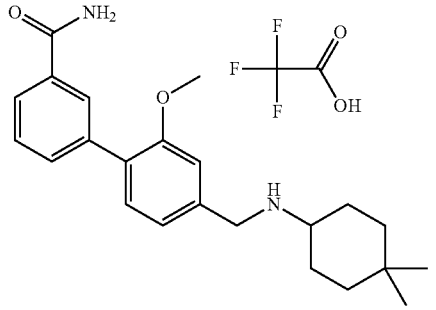  4′-{[(4,4-dimethylcyclohexyl)amino]methyl}-2′-(methyloxy)-3-biphenyl carboxamide trifluoroacetate | LC/MS (method C) 2.13 min, m/z 367 (M + H) | Used IX-8 and III-1 General Method: Example 171 |

TABLE 5-continued

Compounds of Formula I from Compounds of Formula IX

| Ex | Structure and Name | Characterization Data | Comments |
|---|---|---|---|
| 192 | 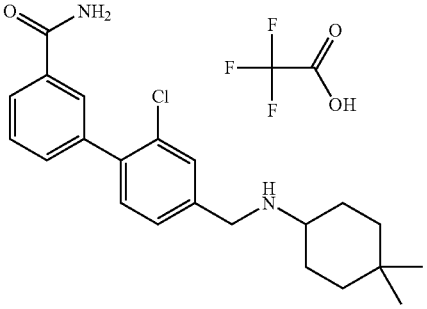<br>2'-chloro-4'-{[(4,4-dimethyl-cyclohexyl)amino]methyl}-3-biphenylcarboxamide trifluoroacetate | LC/MS (method C)<br>2.17 min, m/z 371<br>(M + H) | Used IX-9 and III-1<br>General Method:<br>Example 171 |
| 193 | 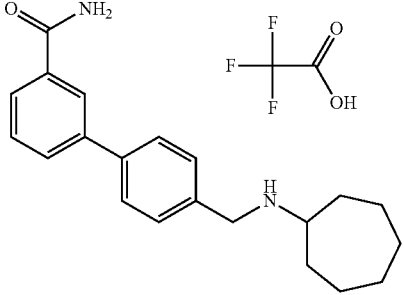<br>4'-[(cycloheptylamino)methyl]-3-biphenylcarboxamide trifluoroacetate | LC/MS (method C)<br>1.99 min, m/z 323<br>(M + H) | Used IX-1<br>General Method:<br>Example 171 |
| 194 | 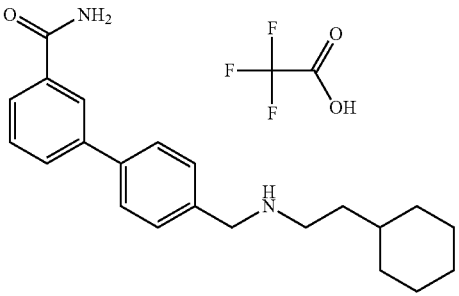<br>4'-{[(2-cyclohexylethyl)amino]methyl}-3-biphenylcarboxamide trifluoroacetate | LC/MS (method C)<br>2.18 min, m/z 337<br>(M + H) | Used IX-1 and III-7<br>General Method:<br>Example 171 |

TABLE 5-continued

Compounds of Formula I from Compounds of Formula IX

| Ex | Structure and Name | Characterization Data | Comments |
|---|---|---|---|
| 195 | 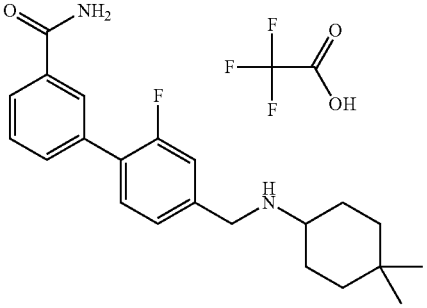4'-{[(4,4-dimethylcyclohexyl)amino]methyl}-2'-fluoro-3-biphenyl-carboxamide trifluoroacetate | LC/MS (method D) 2.05 min, m/z 355 (M + H) | Used IX-10 and III-1 General Method: Example 171 |
| 196 | 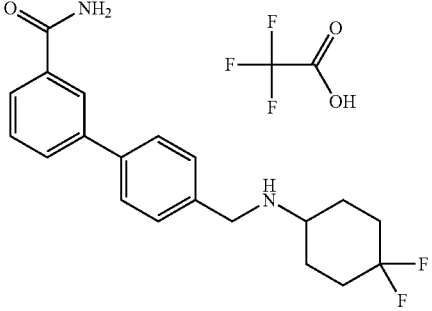4'-{[(4,4-dimethylcyclohexyl)amino]methyl}-3-biphenylcarboxamide trifluoroacetate | LC/MS (method D) 1.77 min, m/z 345 (M + H) | Used IX-1 and 4,4-difluorocyclohexylamine hydrochloride (commercial). General Method: Example 171 |
| 197 | 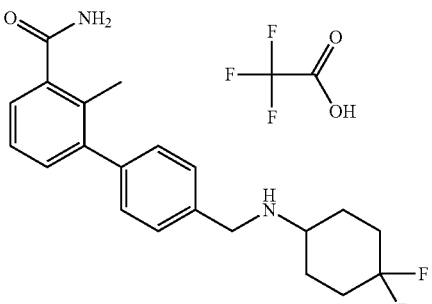4'-{[(4,4-difluorocyclohexyl)amino]methyl}-2-methyl-3-biphenyl-carboxamide trifluoroacetate | LC/MS (method D) 1.57 min, m/z 359 (M + H) | Used IX-2 and 4,4-difluorocyclohexylamine hydrochloride (commercial). General Method: Example 171 |

TABLE 5-continued

Compounds of Formula I from Compounds of Formula IX

| Ex | Structure and Name | Characterization Data | Comments |
|---|---|---|---|
| 198 | 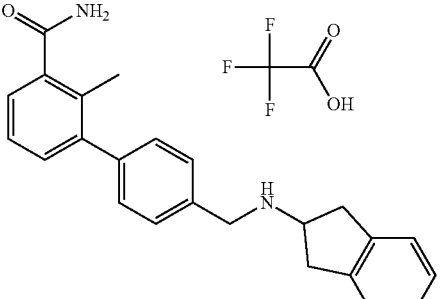<br>4'-[(2,3-dihydro-1H-inden-2-ylamino)methyl]-2-methyl-3-biphenylcarboxamide trifluoroacetate | LC/MS (method D)<br>1.87 min, m/z 357<br>(M + H) | Used IX-2<br>General Method:<br>Example 171 |
| 199 | 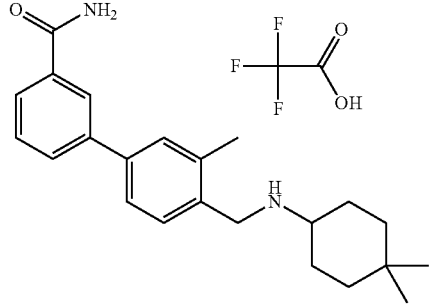<br>4'-{[(4,4-dimethylcyclohexyl)amino]methyl}-3'-methyl-3-biphenyl-carboxamide trifluoroacetate | LC/MS (method B)<br>2.16 min, m/z 351<br>(M + H) | Used IX-16 and III-1<br>General Method:<br>Example 171 |
| 200 | 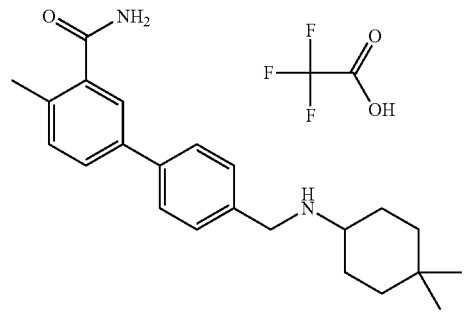<br>4'-{[(4,4-dimethylcyclohexyl)amino]methyl}-4-methyl-3-biphenyl-carboxamide trifluoroacetate | LC/MS (method B)<br>2.15 min, m/z 351<br>(M + H) | Used IX-17 and III-1<br>General Method:<br>Example 171 |

TABLE 5-continued

Compounds of Formula I from Compounds of Formula IX

| Ex | Structure and Name | Characterization Data | Comments |
|---|---|---|---|
| 201 | 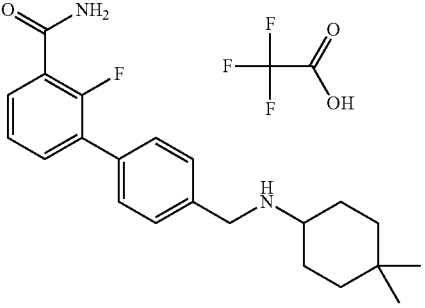<br>4'-{[(4,4-dimethylcyclohexyl)amino]methyl}-2-fluoro-3-biphenyl-carboxamide trifluoroacetate | LC/MS (method B) 2.08 min, m/z 355 (M + H) | Used IX-12 and III-1<br>General Method:<br>Example 171 |
| 202 | 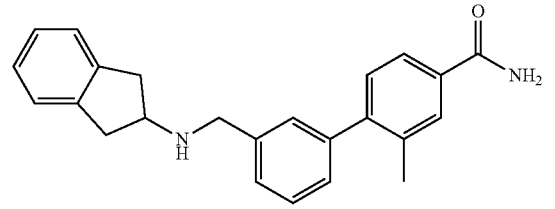<br>3'-[(2,3-dihydro-1H-inden-2-ylamino)methyl]-2-methyl-4-biphenyl-carboxamide hydrochloride | LC/MS (method B). 1.63 min, m/z 357 (M + H). | Used IX-23<br>General Method:<br>Example 170 |
| 203 | 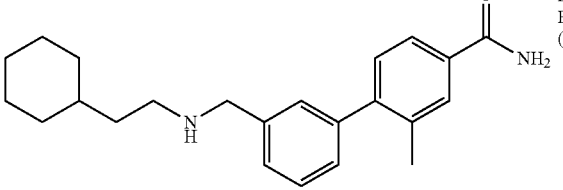<br>3'-{[(2-cyclohexylethyl) amino] methyl}-2-methyl-4-biphenyl carboxamide hydrochloride | LC/MS (method B). 1.82 min, m/z 351 (M + H). | Used IX-23 and III-7<br>General Method:<br>Example 170 |
| 204 | 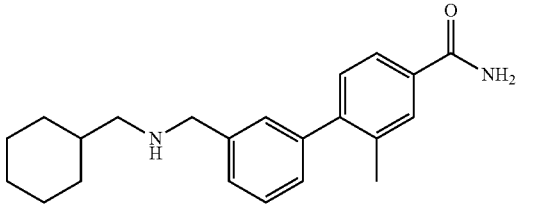<br>3'-{[(cyclohexylethyl) amino] methyl}-2-methyl-4-biphenyl carboxamide hydrochloride | LC/MS (method B). 1.61 min, m/z 337 (M + H). | Used IX-23<br>General Method:<br>Example 170 |

TABLE 5-continued

Compounds of Formula I from Compounds of Formula IX

| Ex | Structure and Name | Characterization Data | Comments |
|---|---|---|---|
| 205 | 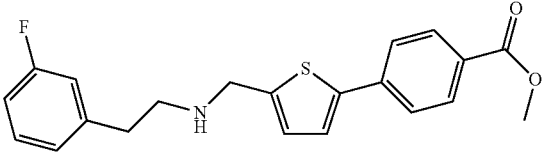<br>methyl 4-[5-({[2-(3-fluorophenyl)ethyl]amino}methyl)-2-thienyl]-benzoate | LC/MS (method A) 1.89 min; m/z 370 | Used methyl 4-(5-formyl-2-thienyl)-benzoate (commercial) General Method: Example 170 Used DCE as solvent. |
| 206 | 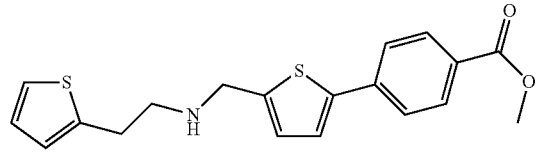<br>methyl 4-[5-({[2-(2-thienyl)ethyl]amino}methyl)-2-thienyl]-benzoate | LC/MS (method A) 1.81 min; m/z 318 | Used methyl 4-(5-formyl-2-thienyl)bezoate (commercial) General Method: Example 170 Used DCE as solvent. |
| 207 | 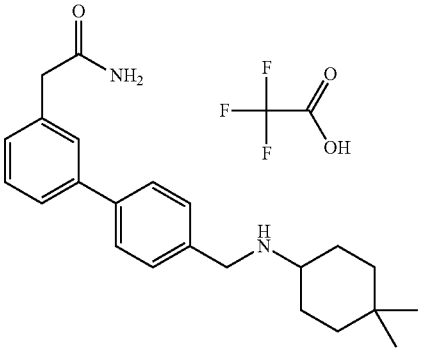<br>2-(4'-{[(4,4-dimethyl-cyclohexyl)amino]methyl}-3-biphenylyl)acetamide trifluoroacetate | LC/MS (method D) 2.08 min, m/z 351 (M + H). | Used IX-20 and III-1 General Method: Example 171 |
| 208 | 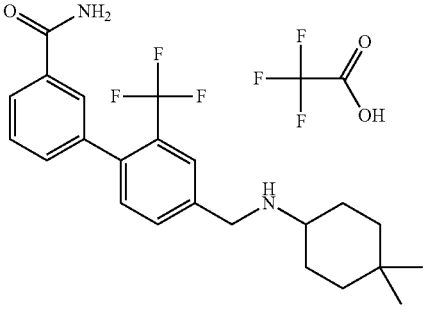<br>4'-{[(4,4-dimethylcyclohexyl)-amino]methyl}-2'-(trifluoro-methyl)-3-biphenylcarboxamide trifluoroacetate | LC/MS (method D) 2.14 min, m/z 405 (M + H). | Used IX-54 and III-1 General Method: Example 171 |

TABLE 5-continued

Compounds of Formula I from Compounds of Formula IX

| Ex | Structure and Name | Characterization Data | Comments |
|---|---|---|---|
| 209 | 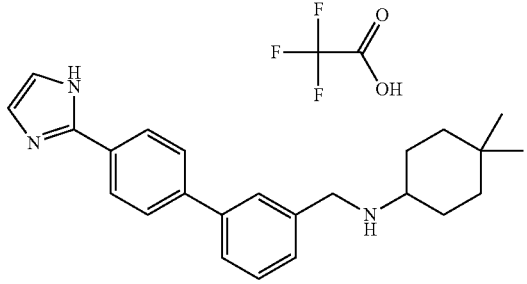<br>N-{[4'-(1H-imidazol-2-yl)-3-biphenylyl]methyl}-4,4-dimethylcyclohexanamine trifluoroacetate | LC/MS (method A) 1.77 min; m/z 360(M + H). | Used IX-18 and III-1 General Method: Example 171 |
| 210 | 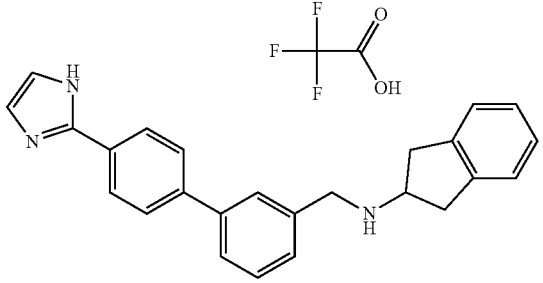<br>N-{[4'-(1H-imidazol-2-yl)-3-biphenylyl]methyl}-2,3-dihydro-1H-inden-2-amine trifluoroacetate | LC/MS (method A) 1.65 min; m/z 366(M + H). | Used IX-18 General Method: Example 171 |
| 211 | 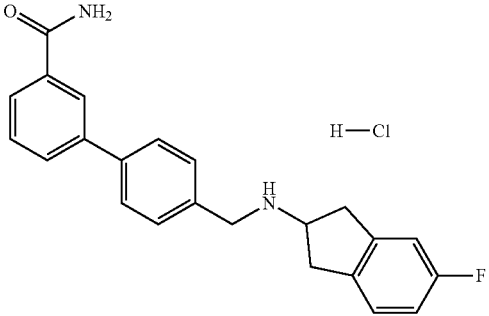<br>4'-{[(5-fluoro-2,3-dihydro-1H-inden-2-yl)amino]methyl}-3-biphenylcarboxamide hydrochloride | LC/MS (method A) 2.05 min; m/z 361(M + H). | Used IX-1 and III-10 General Method: Example 171 |

TABLE 5-continued

Compounds of Formula I from Compounds of Formula IX

| Ex | Structure and Name | Characterization Data | Comments |
|---|---|---|---|
| 212 | 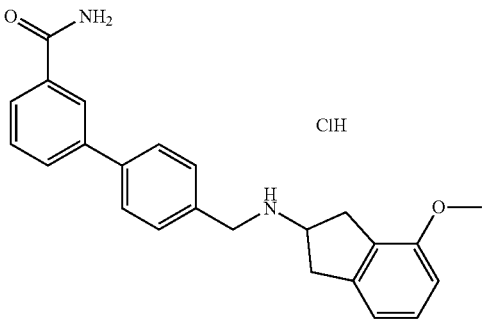<br>4'-{([4-(methyloxy)-2,3-dihydro-1H-inden-2-yl]amino}methyl)-3-biphenylcarboxamide hydrochloride | LC/MS (method A) 2.03 min; m/z 373(M + H). | Used IX-1 and III-14 General Method: Example 171 |
| 213 | 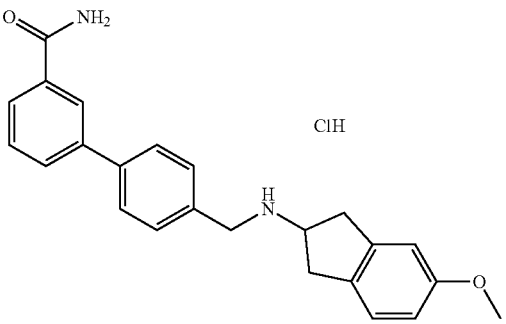<br>4'-{([5-(methyloxy)-2,3-dihydro-1H-inden-2-yl]amino}methyl)-3-biphenylcarboxamide hydrochloride | LC/MS (method A) 1.99 min; m/z 372(M + H). | Used IX-1 and III-13 General Method: Example 171 |
| 214 | 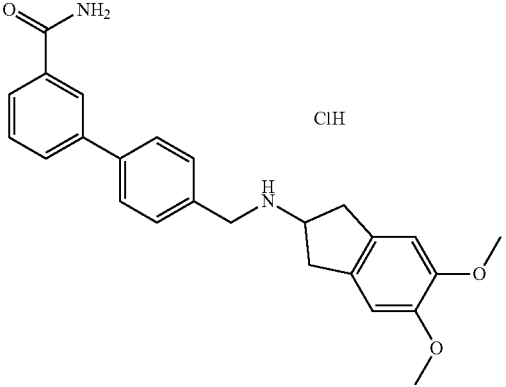<br>4'-({[5,6-bis(methyloxy)-2,3-dihydro-1H-inden-2-yl]amino}methyl)-3-biphenylcarboxamide hydrochloride | LC/MS (method A) 1.9 min; m/z 403(M + H). | Used IX-1 and III-15 General Method: Example 171 |

TABLE 5-continued

Compounds of Formula I from Compounds of Formula IX

| Ex | Structure and Name | Characterization Data | Comments |
| --- | --- | --- | --- |
| 215 | 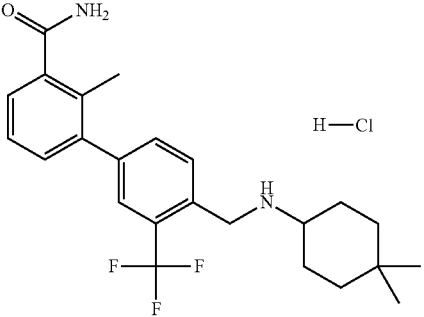<br>4'-{[(4,4-dimethylcyclohexyl)amino]methyl)-2-methyl-3'-(trifluoromethyl)-3-biphenylcarboxamide hydrochloride | LC/MS (method A)<br>2.28 min; m/z<br>419(M + H). | Used IX-56 and III-1<br>General Method:<br>Example 171<br>Note 1, 2 |
| 216 | 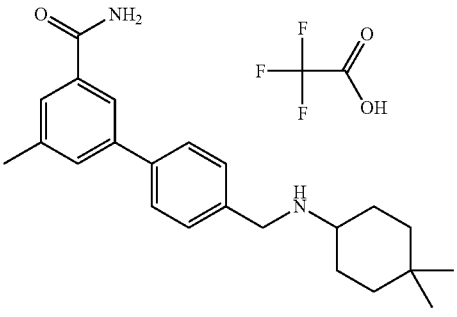<br>4'-{[(4,4-dimethylcyclohexyl)amino]methyl}-5 methyl-3-biphenyl-carboxamide trifluoroacetate | LC/MS (method B)<br>2.22 min; m/z<br>351(M + H). | Used IX-11 and III-1<br>General Method:<br>Example 171<br>Note 1 |
| 217 | 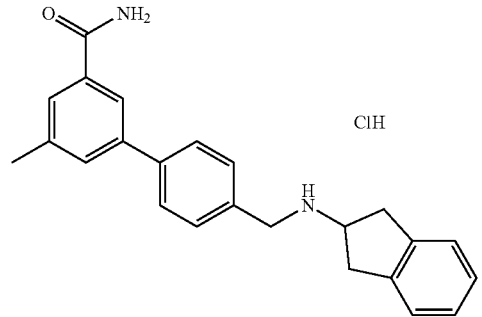<br>4'-[(2,3-dihydro-1H-inden-2-ylamino)methyl]-5-methyl-3-biphenylcarboxamide hydrochloride | LC/MS (method B)<br>2.14 min; m/z<br>357(M + H). | Used IX-11<br>General Method:<br>Example 171<br>Note 1, 2 |

TABLE 5-continued

Compounds of Formula I from Compounds of Formula IX

| Ex | Structure and Name | Characterization Data | Comments |
|----|-------------------|----------------------|----------|
| 218 | 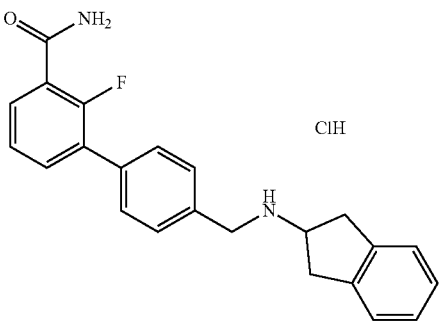<br>4'-[(2,3-dihydro-1H-inden-2-ylamino)methyl]-2-fluoro-3-biphenylcarboxamide hydrochloride | LC/MS (method B)<br>1.99 min; m/z<br>361(M + H). | Used IX-12<br>General Method:<br>Example 171<br>Note 1, 2 |
| 219 | 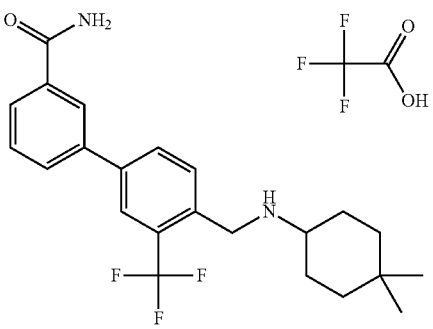<br>4'-{[(4,4-dimethylcyclohexyl)amino]methyl}-3'-(trifluoromethyl)-3-biphenylacetamide trifluoroacetate | LC/MS (method B)<br>2.33 min; m/z<br>405(M + H). | Used IX-55 and III-1<br>General Method:<br>Example 171<br>Note 1 |
| 220 | 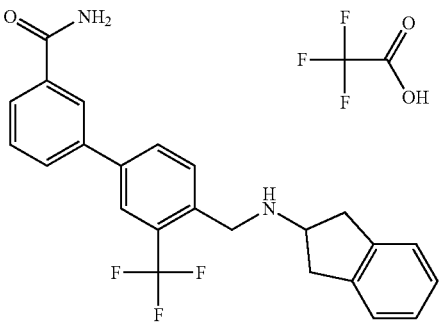<br>4'-[(2,3-dihydro-1H-inden-2-ylamino)methyl]-3'-(trifluoro-methyl)-3-biphenylcarboxamide trifluoroacetate | LC/MS (method B)<br>2.23 min; m/z<br>411(M + H). | Used IX-55<br>General Method:<br>Note 1<br>Example 171 |

TABLE 5-continued

Compounds of Formula I from Compounds of Formula IX

| Ex | Structure and Name | Characterization Data | Comments |
|---|---|---|---|
| 221 | 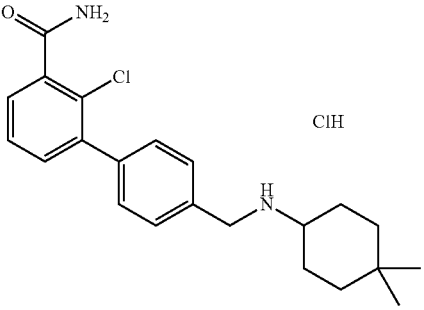<br>2-chloro-4'-{[(4,4-dimethyl-cyclohexyl)amino]methyl}-3-biphenylcarboxamide hydrochloride | LC/MS (method B) 2.06 min; m/z 371(M + H). | Used IX-13 and III-1<br>General Method:<br>Example 171<br>Note 1, 2<br>Also 170 (Note 3) |
| 222 | 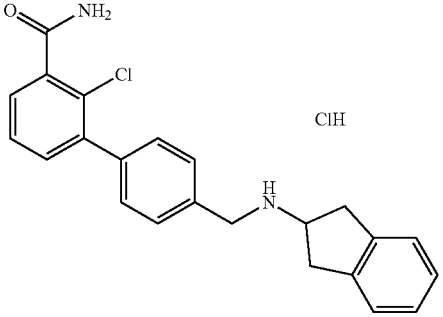<br>2-chloro-4'-[(2,3-dihydro-1H-inden-2-ylamino)methyl]-3-biphenylcarboxamide hydrochloride | LC/MS (method B) 1.94 min; m/z 377(M + H). | Used IX-13<br>General Method:<br>Example 171<br>Note 1, 2 |
| 223 | 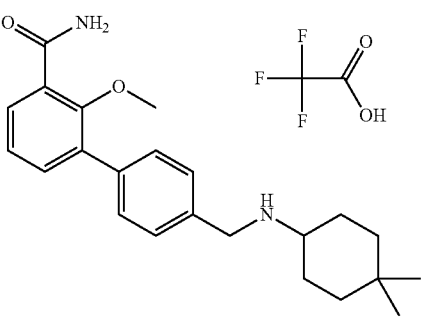<br>4'-{[(4,4-dimethylcyclohexyl)-amino]methyl}-2-(methyloxy)-3-biphenylcarboxamide trifluoroacetate | LC/MS (method A) 2.1 min; m/z 367(M + H). | Used IX-14 and III-1<br>General Method:<br>Example 171<br>Note 1 |

TABLE 5-continued

Compounds of Formula I from Compounds of Formula IX

| Ex | Structure and Name | Characterization Data | Comments |
|----|--------------------|-----------------------|----------|
| 224 | 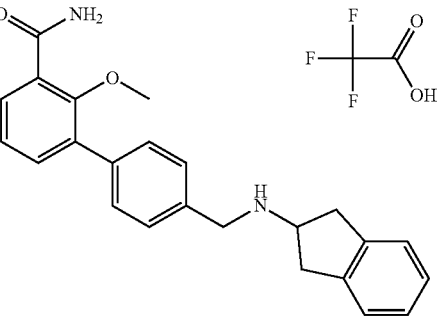  4′-[(2,3-dihydro-1H-inden-2-ylamino)methyl]-2-(methyloxy)-3-biphenylcarboxamide trifluoroacetate | LC/MS (method A) 2.01 min; m/z 373(M + H). | Used IX-14 General Method: Example 171 Note 1 |
| 225 | 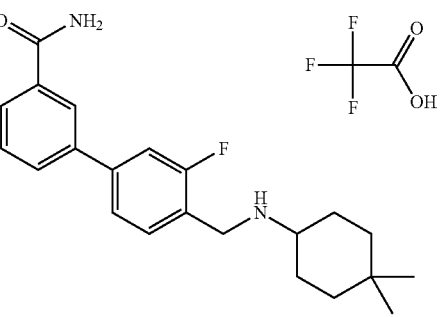  4′-{[(4,4-dimethylcyclohexyl)-amino]methyl}-3′-fluoro-3-biphenylcarboxamide trifluoroacetate | LC/MS (method A) 2.13 min; m/z 355(M + H). | Used IX-1 and III-1 General Method: Example 171 Note 1, 2 Also 170 (Note 3) |
| 226 | 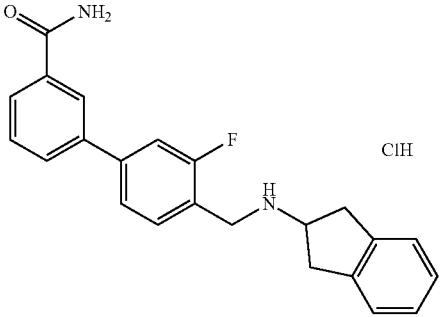  4′-[(2,3-dihydro-1H-inden-2-ylamino)methyl]-3′-methyl-3-biphenylcarboxamide hydrochloride | LC/MS (method A) 2.02 min; m/z 361(M + H). | Used IX-1 General Method: Example 171 Note 1, 2 |

TABLE 5-continued

Compounds of Formula I from Compounds of Formula IX

| Ex | Structure and Name | Characterization Data | Comments |
|----|--------------------|----------------------|----------|
| 227 | 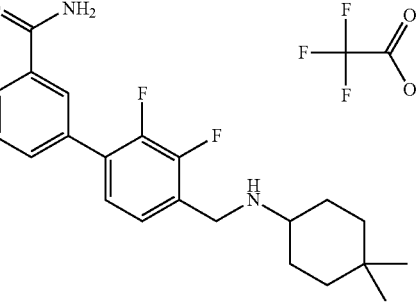<br>4'-{[(4,4-dimethylcyclohexyl)-amino]methyl}-2',3'-difluoro-3-biphenylcarboxamide trifluoroacetate | LC/MS (method A) 2.21 min; m/z 373(M + H). | Used IX-47 and III-1<br>General Method:<br>Example 171<br>Note 1 |
| 228 | 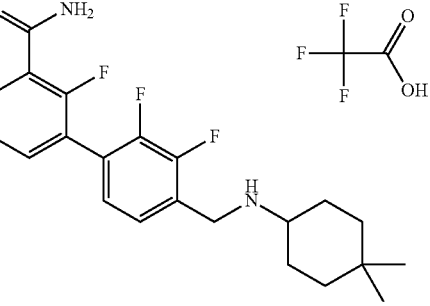<br>4'-{[(4,4-dimethylcyclohexyl)amino)methyl}-2,2',3'-trifluoro-3-biphenyl-carboxamide trifluoroacetate | LC/MS (method A) 2.15 min; m/z 391(M + H). | Used IX-46 and III-1<br>General Method:<br>Example 171<br>Note 1 |
| 229 | 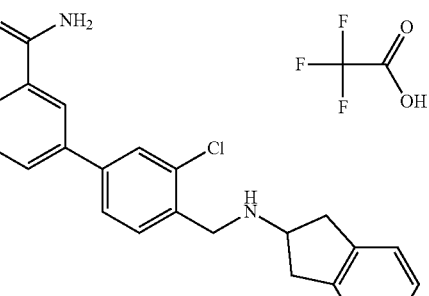<br>3'-chloro-4'-[(2,3-dihydro-1H-inden-2-ylamino)methyl]-3-biphenylcarboxamide trifluoroacetate | LC/MS (method A) 2.1 min; m/z 377(M + H). | Used IX-44<br>General Method:<br>Example 171<br>Note 1 |

TABLE 5-continued

Compounds of Formula I from Compounds of Formula IX

| Ex | Structure and Name | Characterization Data | Comments |
|---|---|---|---|
| 230 | 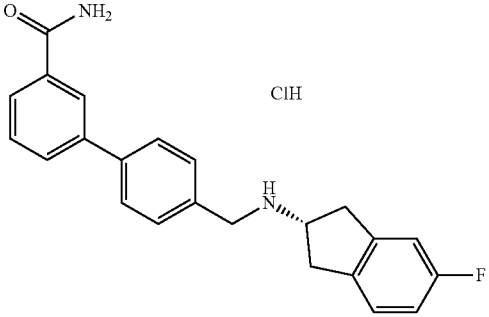<br>4'-({[(2S)-5-fluoro-2,3-dihydro-1H-inden-2-yl]amino}methyl)-3-biphenylcarboxamide hydrochloride | LC/MS (method B) 2.05 min; m/z 361(M + H). | Used IX-1 and (S)-III-11<br>General Method:<br>Example 170<br>Note 4 |
| 231 | 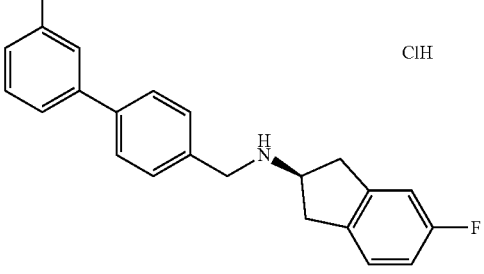<br>4'-({[(2R)-5-fluoro-2,3-dihydro-1H-inden-2-yl]amino}methyl)-3-biphenylcarboxamide hydrochloride | LC/MS (method B) 2.01 min; m/z 361(M + H). | Used IX-1 and (R)-III-11<br>General Method:<br>Example 170<br>Note 4 |
| 232 | 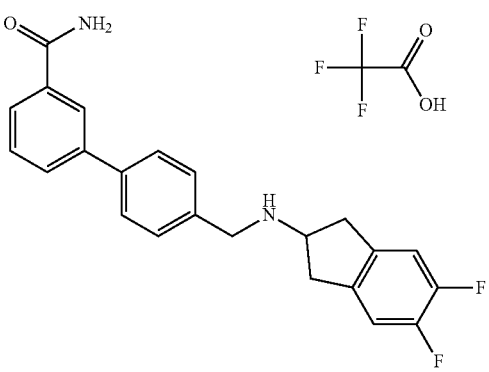<br>4'-{[(5,6-difluoro-2,3-dihydro-1H-inden-2-yl)amino]methyl}-3-biphenylcarboxamide trifluoroacetate | LC/MS (method A) 2.01 min; m/z 379(M + H). | Used IX-1 and III-9<br>General Method:<br>Example 171<br>Note 1 |

TABLE 5-continued

Compounds of Formula I from Compounds of Formula IX

| Ex | Structure and Name | Characterization Data | Comments |
|---|---|---|---|
| 233 | 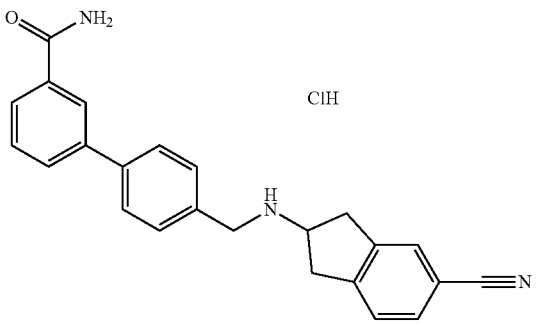<br>4'-{[(5-cyano-2,3-dihydro-1H-inden-2-yl)amino]methyl}-3-biphenylcarboxamide trifluoroacetate | LC/MS (method A)<br>1.84 min; m/z<br>368(M + H). | Used IX-1 and III-12<br>General Method:<br>Example 171<br>Note 1, 2 |
| 234 | 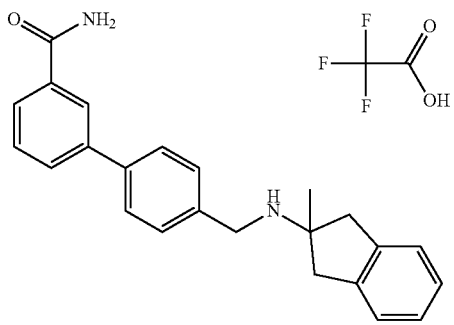<br>4'-{[(2-methyl-2,3-dihydro-1H-inden-2-yl)amino]methyl}-3-biphenylcarboxamide trifluoroacetate | LC/MS (method A)<br>2.01 min; m/z<br>357(M + H). | Used IX-1 and III-16<br>General Method:<br>Example 171<br>Note 1 |
| 235 | 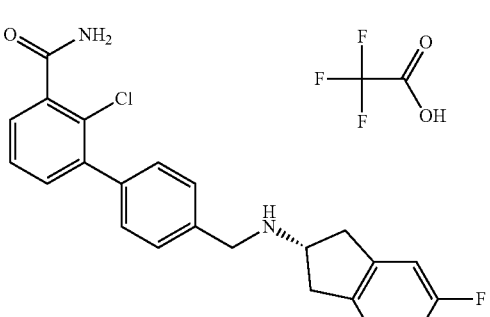<br>2-chloro-4'-({[(2S)-5-fluoro-2,3-dihydro-1H-inden-2-yl]amino}-methyl)-3-biphenylcarboxamide trifluoroacetate | LC/MS (method A)<br>1.88 min; m/z<br>395(M + H). | Used IX-13 and (S)-III-11<br>General Method:<br>Example 171<br>Note 1 |

TABLE 5-continued

Compounds of Formula I from Compounds of Formula IX

| Ex | Structure and Name | Characterization Data | Comments |
|---|---|---|---|
| 236 | 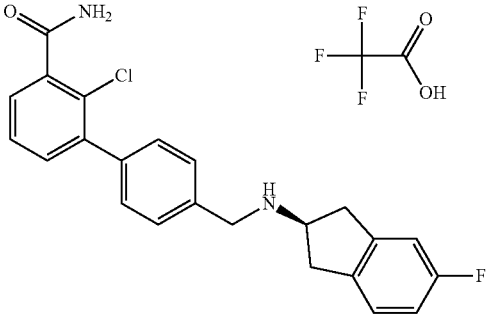<br>2-chloro-4'-({[(2R)-5-fluoro-2,3-dihydro-1H-inden-2-yl]amino}-methyl)-3-biphenyl-carboxamide trifluoroacetate | LC/MS (method A) 1.88 min; m/z 395(M + H). | Used IX-13 and (R)-III-11 General Method: Example 171 Note 1 |
| 237 | 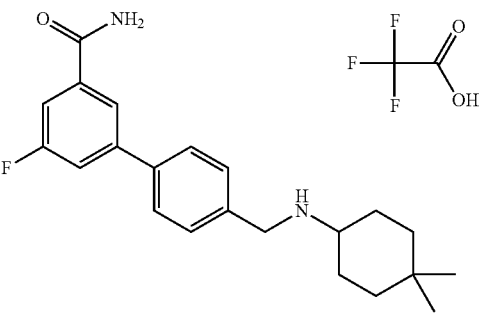<br>4'-{[(4,4-dimethylcyclohexyl)amino]methyl}-5-fluoro-3-biphenyl-carboxamide trifluoroacetate | LC/MS (method A) 2.14 min; m/z 355(M + H). | Used IX-48 and III-1 General Method: Example 171 Note 1 |
| 238 | 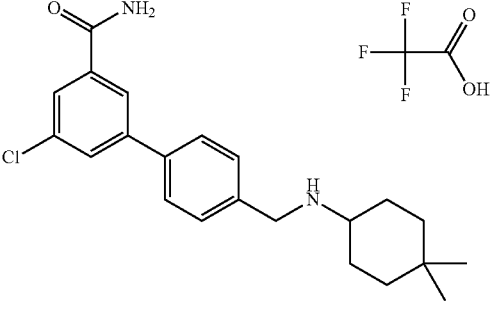<br>5-chloro-4'-{[(4,4-dimethyl-cyclohexyl)amino]methyl}-3-biphenylcarboxamide trifluoroacetate | LC/MS (method A) 2.24 min; m/z 371(M + H). | Used IX-49 and III-1 General Method: Example 171 Note 1 |

TABLE 5-continued

Compounds of Formula I from Compounds of Formula IX

| Ex | Structure and Name | Characterization Data | Comments |
|---|---|---|---|
| 239 | 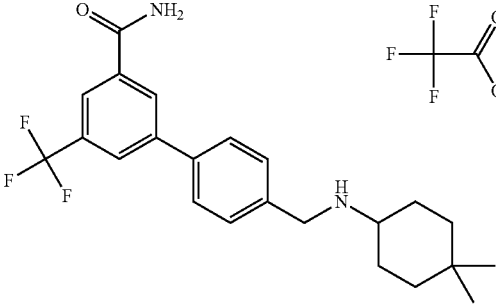<br>4'-{[(4,4-dimethylcyclohexyl)-amino]methyl}-5-(trifluoro-methyl)-3-biphenyl-carboxamide trifluoroacetate | LC/MS (method A) 2.3 min; m/z 405(M + H). | Used IX-50 and III-1<br>General Method:<br>Example 171<br>Note 1 |
| 240 | 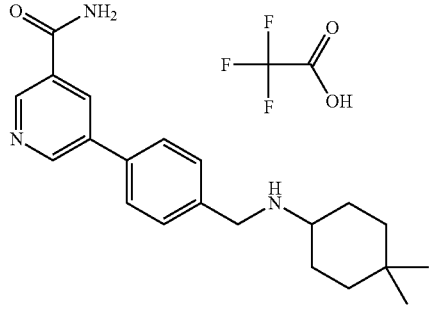<br>5-(4-{[(4,4-dimethylcyclohexyl)-amino]methyl}phenyl)-3-pyridinecarboxamide trifluoroacetate | LC/MS (method A) 1.9 min; m/z 338(M + H). | Used IX-45 and III-1<br>General Method:<br>Example 171<br>Note 1 |
| 241 | 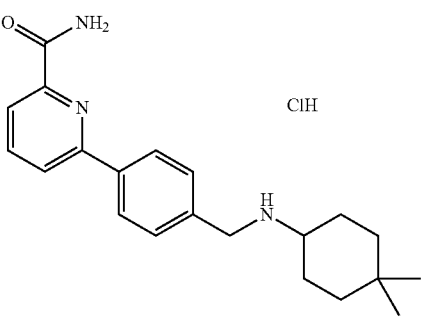<br>6-(4-{[(4,4-dimethylcyclohexyl)-amino]methyl}phenyl)-2-pyridinecarboxamide hydrochloride | LC/MS (method A) 2.04 min; m/z 338(M + H). | Used IX-51 and III-1<br>General Method:<br>Example 171<br>Note 1, 2 |

TABLE 5-continued

Compounds of Formula I from Compounds of Formula IX

| Ex | Structure and Name | Characterization Data | Comments |
|---|---|---|---|
| 242 | 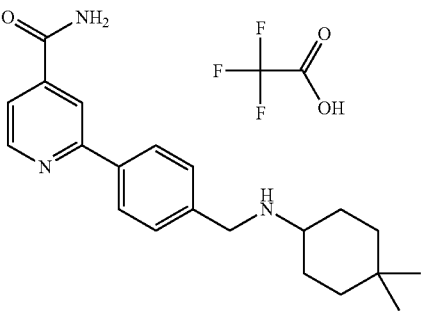<br>2-(4-{[(4,4-dimethylcyclohexyl)-amino]methyl}phenyl)-4-pyridinecarboxamide trifluoroacetate | LC/MS (method A) 1.95 min; m/z 338(M + H). | Used IX-52 and III-1 General Method: Example 171 Note 1 |
| 243 | 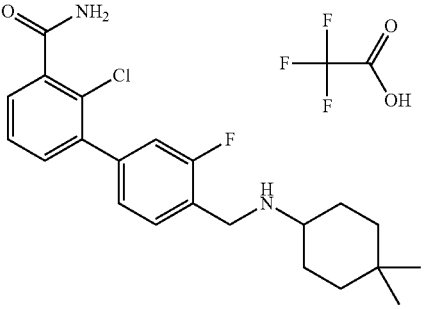<br>2-chloro-4'-{[(4,4-dimethyl-cyclohexyl)-amino]methyl}-3'-fluoro-3-biphenylcarboxamide trifluoroacetate | LC/MS (method A) 2.03 min; m/z 389(M + H). | Used IX-38 and III-1 General Method: Example 171 Note 1 |
| 244 | 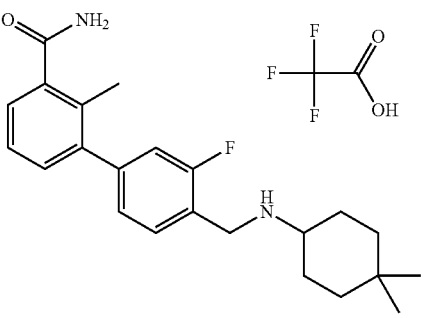<br>4'-{[(4,4-dimethylcyclohexyl)amino]methyl}-3'-fluoro-2-methyl-3-biphenylcarboxamide trifluoroacetate | LC/MS (method A) 2.11 min; m/z 369(M + H). | Used IX-53 and III-1 General Method: Example 171 Note 1 |

TABLE 5-continued

Compounds of Formula I from Compounds of Formula IX

| Ex | Structure and Name | Characterization Data | Comments |
|---|---|---|---|
| 245 | 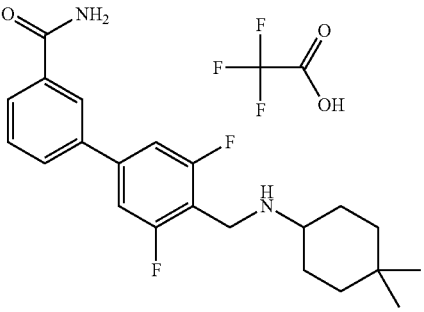<br>4'-{[(4,4-dimethylcyclohexyl)-amino]methyl}-3',5'-difluoro-3-biphenylcarboxamide trifluoroacetate | LC/MS (method A)<br>2.13 min; m/z<br>373(M + H). | Used IX-41 and III-1<br>General Method:<br>Example 171<br>Note 1<br>Also 170 (Note 4) |
| 246 | 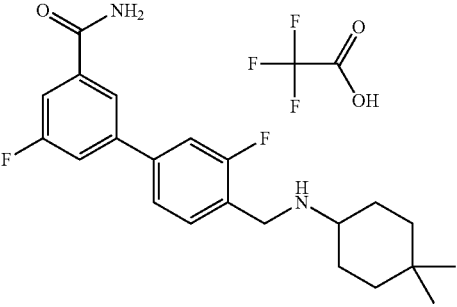<br>4'-{[(4,4-dimethylcyclohexyl)-amino]methyl}-3',5'-difluoro-3-biphenyl-carboxamide trifluoroacetate | LC/MS (method A)<br>2.21 min; m/z<br>373(M + H). | Used IX-42 and III-1<br>General Method:<br>Example 171<br>Note 1 |
| 247 | 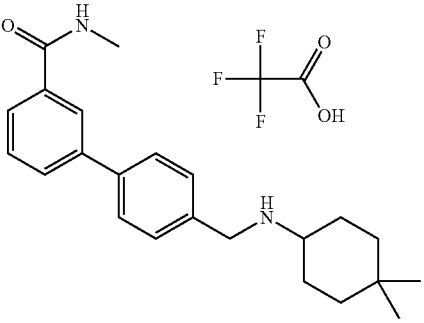<br>4'-{[(4,4-dimethylcyclohexyl)-amino]methyl}-N-methyl-3-biphenylcarboxamide trifluoroacetate | LC/MS (method A)<br>2.13 min; m/z<br>351(M + H). | Used IX-43 and III-1<br>General Method:<br>Example 171<br>Note 1 |

TABLE 5-continued

Compounds of Formula I from Compounds of Formula IX

| Ex | Structure and Name | Characterization Data | Comments |
|---|---|---|---|
| 248 | 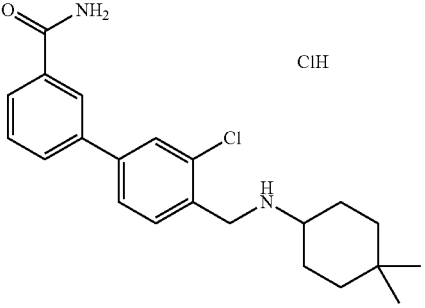<br>3'-chloro-4'-{[(4,4-dimethyl-cyclohexyl)amino]methyl}-3-biphenylcarboxamide hydrochloride | LC/MS (method A) 2.21 min; m/z 371 (79%), 373 (100%)(M + H). | Used IX-44 and III-1<br>General Method:<br>Example 171<br>Note 1, 2 |
| 249 | 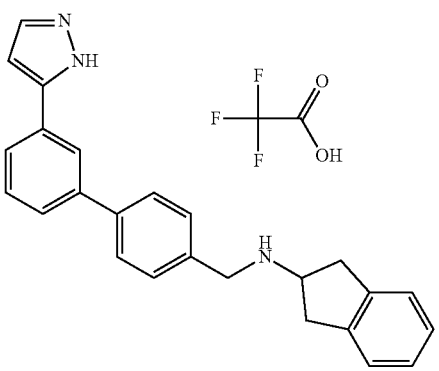<br>N-{[3'-(1H-pyrazol-5-yl)-4-biphenylyl]methyl}-2,3-dihydro-1H-inden-2-amine trifluoroacetate | LC/MS (method A) 1.9 min; m/z 366(M + H). | Used IX-57<br>General Method:<br>Example 171<br>Note 1 |
| 250 | 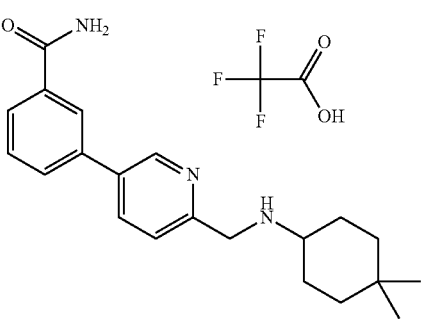<br>3-(6-{[(4,4-dimethylcyclohexyl)-amino]methyl}-3-pyridinyl)-benzamide trifluoroacetate | LC/MS (method B) 2 min; m/z 338(M + H). | Used IX-40 and III-1<br>General Method:<br>Example 171<br>Note 1 |

TABLE 5-continued

Compounds of Formula I from Compounds of Formula IX

| Ex | Structure and Name | Characterization Data | Comments |
| --- | --- | --- | --- |
| 251 | 3-(5-{[(4,4-dimethylcyclohexyl)-amino]methyl}-2-pyridinyl)-benzamide trifluoroacetate | LC/MS (method B) 1.9 min; m/z 338(M + H). | Used IX-19 and III-1 General Method: Example 171 Note 1 |
| 252 | 4'-[(2,3-dihydro-1H-inden-2-ylamino)methyl]-5-fluoro-3-biphenylcarboxamide trifluoroacetate | LC/MS (method B) 2.06 min; m/z 361(M + H). | Used IX-48 and III-1 General Method: Example 171 Note 1 |
| 253 | 4'-[(2,3-dihydro-1H-inden-2-ylamino)methyl]-3',5-difluoro-3-biphenylcarboxamide trifluoroacetate | LC/MS (method B) 2.09 min; m/z 379(M + H). | Used IX-42 General Method: Example 171 Note 1, 2 |

TABLE 5-continued

Compounds of Formula I from Compounds of Formula IX

| Ex | Structure and Name | Characterization Data | Comments |
|---|---|---|---|
| 254 | 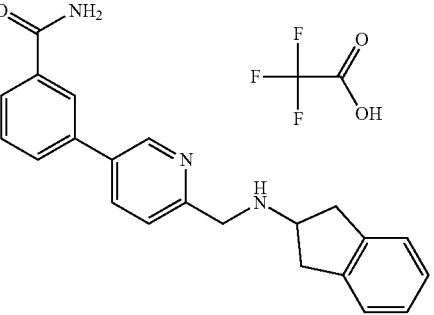<br>3-{6-[(2,3-dihydro-1H-inden-2-ylamino)methyl]-3-pyridinyl}-benzamide trifluoroacetate | LC/MS (method B)<br>1.88 min; m/z<br>344(M + H). | Used IX-40<br>General Method:<br>Example 171<br>Note 1 |
| 255 | 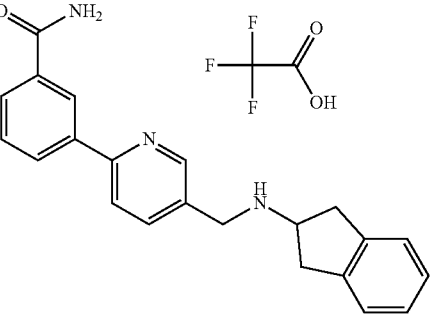<br>3-{5-[(2,3-dihydro-1H-inden-2-ylamino)methyl]-2-pyridinyl}-benzamide trifluoroacetate | LC/MS (method B)<br>1.77 min; m/z<br>344(M + H). | Used IX-19<br>General Method:<br>Example 171<br>Note 1 |
| 256 | 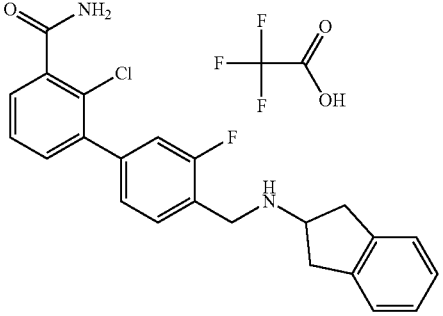<br>2-chloro-4'-[(2,3-dihydro-1H-inden-2-ylamino)methyl]-3'-fluoro-3-biphenylcarboxamide trifluoroacetate | LC/MS (method B)<br>1.92 min; m/z<br>395(M + H). | Used IX-39<br>General Method:<br>Example 171<br>Note 1 |

TABLE 5-continued

Compounds of Formula I from Compounds of Formula IX

| Ex | Structure and Name | Characterization Data | Comments |
|----|---|---|---|
| 257 | 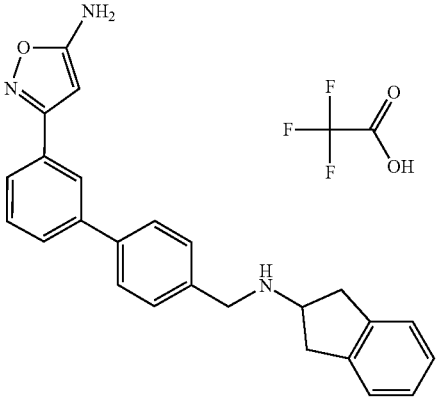<br>3-{4'-[(2,3-dihydro-1H-inden-2-ylamino)methyl]-3-biphenylyl}-5-isoxazolamine trifluoroacetate | LC/MS (method A) 1.77 min; m/z 383(M + H). | Used IX-21<br>General Method: Example 171<br>Note 1 |
| 258 | 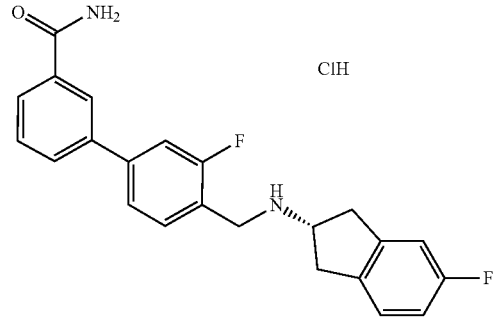<br>3'-fluoro-4'-({[(2S)-5-fluoro-2,3-dihydro-1H-inden-2-yl]amino}-methyl)-3-biphenylcarboxamide hydrochloride | LC/MS (method A) 1.62 min; m/z 379(M + H). | Used IX-15 and (S)-III-11<br>General Method: Example 171<br>Note 1, 2<br>Also 170 (Note 3) |
| 259 | 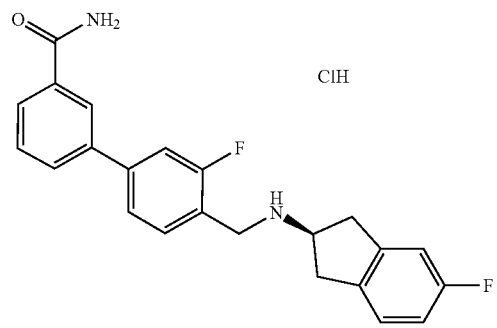<br>3'-fluoro-4'-({[(2R)-5-fluoro-2,3-dihydro-1H-inden-2-yl]amino}-methyl)-3-biphenylcarboxamide hydrochloride | LC/MS (method A) 1.62 min; m/z 379(M + H). | Used IX-15 and (R)-III-11<br>General Method: Example 171<br>Note 1, 2<br>Also 170 (Note 3) |

TABLE 5-continued

Compounds of Formula I from Compounds of Formula IX

| Ex | Structure and Name | Characterization Data | Comments |
|---|---|---|---|
| 260 | 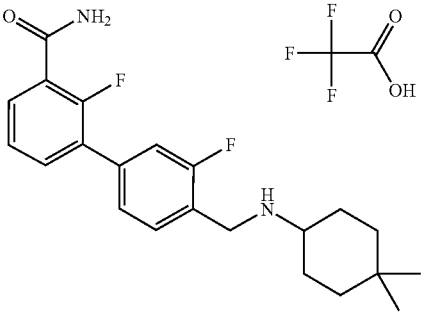<br>4'-{[(4,4-dimethylcyclohexyl)amino]methyl}-2,3'-difluoro-3-biphenyl-carboxamide trifluoroacetate | LC/MS (method E) 1.02 min; m/z 373(M + H). | Used IX-22 and III-1<br>General Method: Example 171<br>Note 1 |
| 261 | 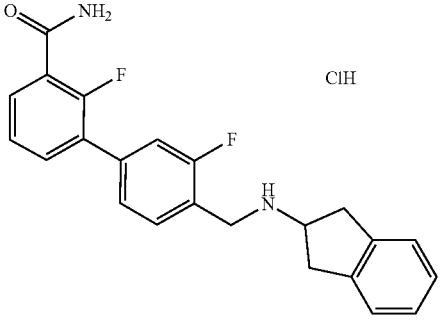<br>4'-[(2,3-dihydro-1H-inden-2-ylamino)methyl]-2,3'-difluoro-3-biphenylcarboxamide hydrochloride | LC/MS (method E) 0.94 min; m/z 379(M + H). | Used IX-22<br>General Method: Example 171<br>Note 1, 2 |
| 262 | 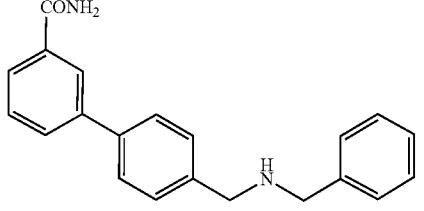<br>4'-{[(phenylmethyl)amino]methyl}-3-biphenylcarboxamide | LC/MS (method E) 0.63 min; m/z 317 (M + 1) | Used IX-1<br>General Method: Example 171<br>Note 1, 4 |
| 263 | 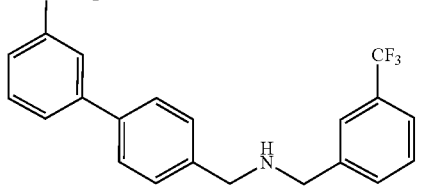<br>4'-[({[3-trifluoromethyl)-phenyl]methyl}amino)methyl]-3-biphenyl-carboxamide | LC/MS (method E) 0.69 min; m/z 385 (M + 1) | Used IX-1<br>General Method: Example 171<br>Note 1, 4 |

TABLE 5-continued

Compounds of Formula I from Compounds of Formula IX

| Ex | Structure and Name | Characterization Data | Comments |
|---|---|---|---|
| 264 | 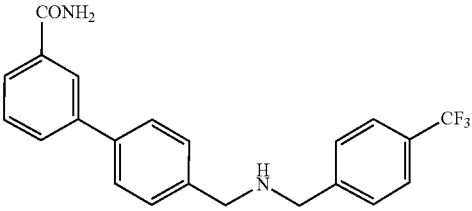<br>4'-[({[4-(trifluoromethyl)-phenyl]methyl}amino)methyl]-3-biphenyl-carboxamide | LC/MS (method E) 0.7 min; m/z 385 (M + 1) | Used IX-1<br>General Method:<br>Example 171<br>Note 1, 4 |
| 265 | 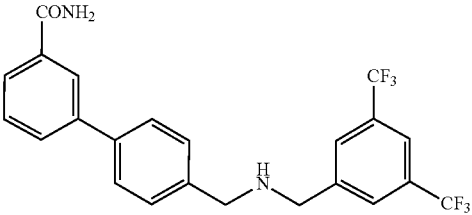<br>4'-[({[3,5-bis(trifluoromethyl)-phenyl]methyl}amino)methyl]-3-biphenyl-carboxamide | LC/MS (method E) 0.61 min; m/z 453 (M + 1) | Used IX-1<br>General Method:<br>Example 171<br>Note 1, 4 |
| 266 | 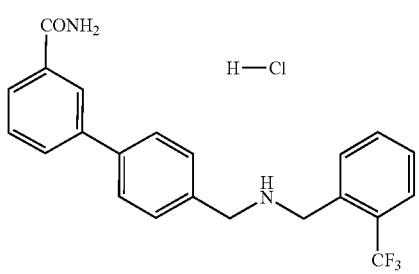<br>4'-[({[2-(trifluoromethyl)-phenyl]methyl}amino)methyl]-3-biphenylcarboxamide hydrochloride | LC/MS (method E) 0.55 min; m/z 385 (M + 1) | Used IX-1<br>General Method:<br>Example 171<br>Note 1, 5 |
| 267 | 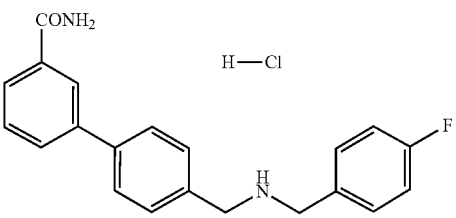<br>4'-({[(4-fluorophenyl)methyl]-amino}methyl)-3-biphenyl-carboxamide hydrochloride | LC/MS (method E) 0.56 min; m/z 335 (M + 1) | Used IX-1<br>General Method:<br>Example 171<br>Note 1, 5 |

TABLE 5-continued

Compounds of Formula I from Compounds of Formula IX

| Ex | Structure and Name | Characterization Data | Comments |
|---|---|---|---|
| 268 | 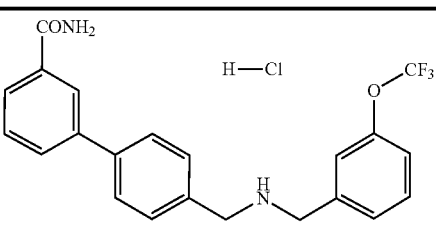<br>4'-{[({3-[(trifluoromethyl)oxy]phenyl}methyl)amino]-methyl}-3-biphenylcarboxamide hydrochloride | LC/MS (method E) 0.63 min; m/z 401 (M + 1) | Used IX-1<br>General Method:<br>Example 171<br>Note 1, 5 |
| 269 | 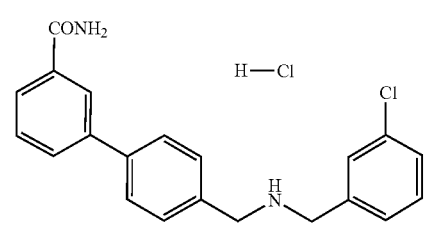<br>4'-({[(3-chlorophenyl)methyl]-amino}methyl)-3-biphenyl-carboxamide hydrochloride | LC/MS (method E) 0.58 min; m/z 351 (M + 1) | Used IX-1<br>General Method:<br>Example 171<br>Note 1, 5 |
| 270 | 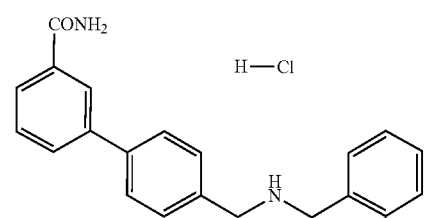<br>4'-({[(2-fluorophenyl)methyl]-amino}methyl)-3-biphenyl-carboxamide hydrochloride | LC/MS (method E) 0.52 min; m/z 335 (M + 1) | Used IX-1<br>General Method:<br>Example 171<br>Note 1, 5 |
| 271 | 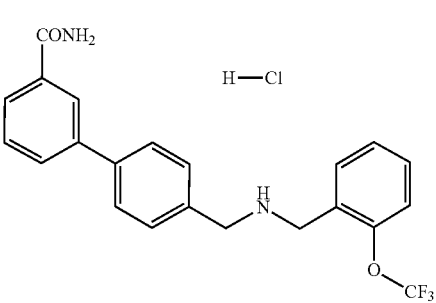<br>4'-{[({2-[(trifluoromethyl)oxy]-phenyl}methyl)amino]methyl}-3-biphenylcarboxamide hydrochloride | LC/MS (method E) 0.59 min; m/zz 401 (M + 1 | Used IX-1<br>General Method:<br>Example 171<br>Note 1, 5 |

TABLE 5-continued

Compounds of Formula I from Compounds of Formula IX

| Ex | Structure and Name | Characterization Data | Comments |
| --- | --- | --- | --- |
| 272 | 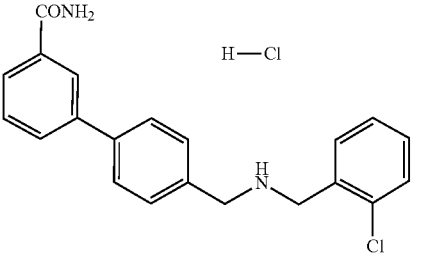<br>4'-({[(2-chlorophenyl)methyl]-amino}methyl)-3-biphenyl-carboxamide hydrochloride | LC/MS (method E) 0.54 min; m/z 351 (M + 1) | Used IX-1<br>General Method:<br>Example 171<br>Note 1, 5 |
| 273 | 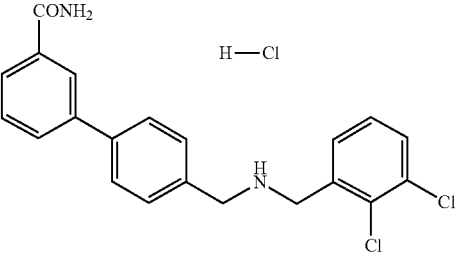<br>4'-({[(2,3-dichlorophenyl)-methyl]amino}methyl)-3-biphenylcarboxamide hydrochloride | LC/MS (method E) 0.59 min; m/z 385 and 387 (M + 1 Cl isotopes) | Used IX-1<br>General Method:<br>Example 171<br>Note 1, 5 |
| 274 | 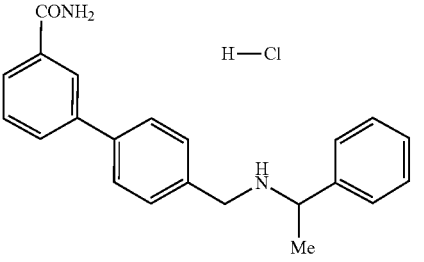<br>4'-{[(1-phenylethyl)amino]-methyl}-3-biphenylcarboxamide | LC/MS (method E) 0.66 min; m/z 331 (M + 1) | Used IX-1<br>General Method:<br>Example 171<br>Note 1, 4 |
| 275 | 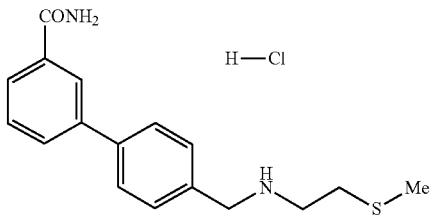<br>4'-({[2-(methylthio)ethyl]-amino}methyl)-3-biphenyl-carboxamide hydrochloride | LC/MS (method E) 0.49 min; m/z 301 (M + 1) | Used IX-1<br>General Method:<br>Example 171<br>Note 1, 5 |

TABLE 5-continued

Compounds of Formula I from Compounds of Formula IX

| Ex | Structure and Name | Characterization Data | Comments |
|---|---|---|---|
| 276 | 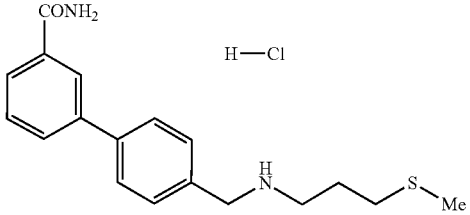<br>4'-({[3-(methylthio)propyl]-amino}methyl)-3-biphenyl-carboxamide hydrochloride (U24649-165) | LC/MS (method E) (0.51) min; m/z 315 (M + 1) | Used IX-1<br>General Method: Example 171<br>Note 1, 5 |
| 277 | 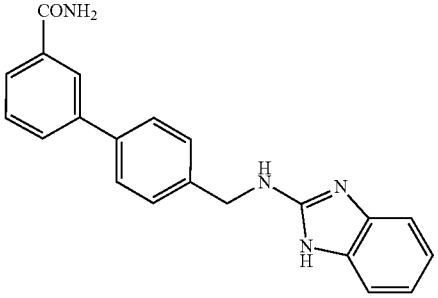<br>4'-[(1H-benzimidazol-2-yl-amino)methyl]-3-biphenyl-carboxamide | LC/MS (method E) 0.65 min; m/z 343 (M + 1) | Used IX-1<br>General Method: Example 172<br>Note 6 |
| 278 | 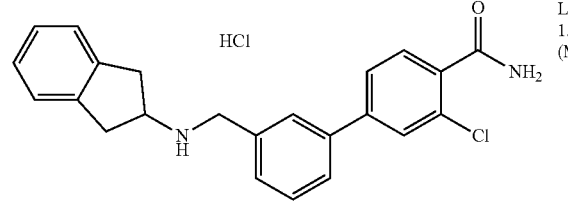<br>3-chloro-3'-[(2,3-dihydro-1H-inden-2-ylamino) methyl]-4-biphenyl carboxamide hydrochloride. | LC/MS (method A) 1.52 min; m/z 377 (M + H). | Used IX-24<br>General Method: Example 170 |
| 279 | 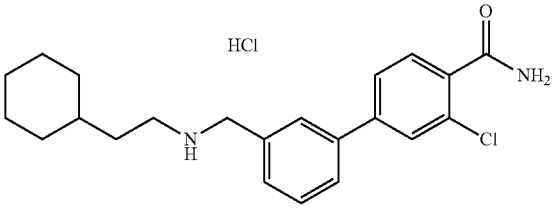<br>3-chloro-3'-{[(2-cyclo hexyl ethyl)-amino]methyl}-4-biphenyl carboxamide hydrochloride. | LC/MS (method A) 1.72 min; m/z 371 (M + H). | Used IX-24 and III-7<br>General Method: Example 170 |

TABLE 5-continued

Compounds of Formula I from Compounds of Formula IX

| Ex | Structure and Name | Characterization Data | Comments |
|---|---|---|---|
| 280 | 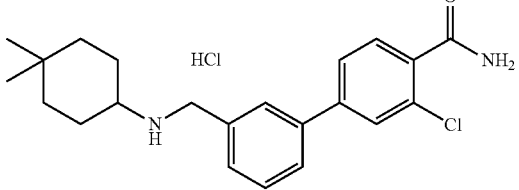<br>3-chloro-3'-{[(4,4-dimethyl cyclohexyl)amino]methyl}-4-biphenylcarboxamide hydrochloride. | LC/MS (method A) 1.71 min; m/z 371 (M + H). | Used IX-24 and III-1 General Method: Example 170 |
| 281 | 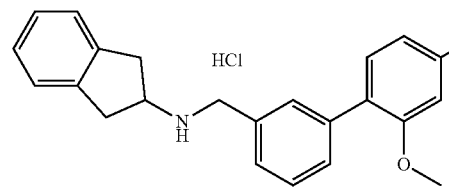<br>3'-[(2,3-dihydro-1H-inden-2-ylamino)methyl]-2-(methyloxy)-4-biphenyl carboxamide hydrochloride. | LC/MS (method B) 1.53 min; m/z 373 (M + H). | Used IX-25 General Method: Example 170 |
| 282 | 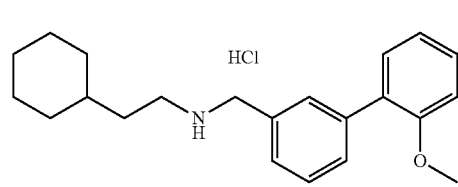<br>3'-{[(2-cyclohexyl ethyl) amino]methyl}-2-(methyl oxy)-4-biphenyl carboxamide hydrochloride | LC/MS (method A) 1.79 min; m/z 367 (M + H). | Used IX-25 and III-7 General Method: Example 170 |
| 283 | 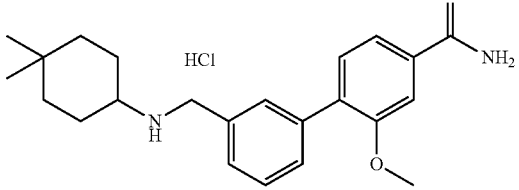<br>3'-{[(4,4-dimethylcyclo hexyl)-amino]methyl}-2-(methyloxy)-4-biphenylcarboxamide hydrochloride. | LC/MS (method A) 1.68 min; m/z 367 (M + H). | Used IX-25 and III-1 General Method: Example 170 |
| 284 | 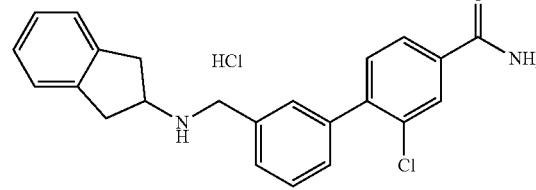<br>2-chloro-3'-[(2,3-dihydro-1H-inden-2-ylamino)methyl]-4-biphenylcarboxamide hydrochloride. | LC/MS (method A) 1.65 min; m/z 377 (M + H). | Used IX-26 General Method: Example 170 |

TABLE 5-continued

Compounds of Formula I from Compounds of Formula IX

| Ex | Structure and Name | Characterization Data | Comments |
|---|---|---|---|
| 285 | 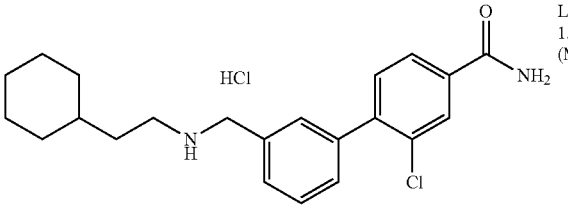<br>2-chloro-3'-{[(2-cyclohexyl ethyl)amino]methyl}-4-biphenylcarboxamide hydrochloride. | LC/MS (method A) 1.88 min; m/z 371 (M + H). | Used IX-26 and III-7 General Method: Example 170 |
| 286 | 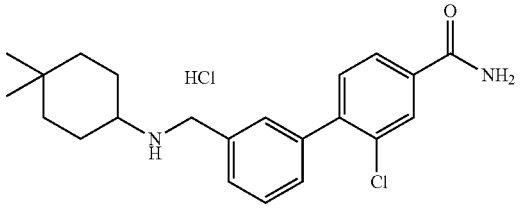<br>2-chloro-3'-{[(4,4-dimethylcyclohexyl)amino]methyl}-4-biphenyl-carboxamide hydrochloride. | LC/MS (method B) 1.76 min; m/z 371 (M + H). | Used IX-26 and III-1 General Method: Example 170 |
| 287 | 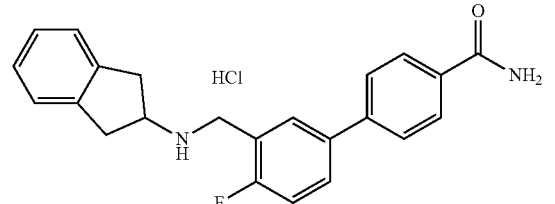<br>3'-[(2,3-dihydro-1H-inden-2-ylamino)methyl]-4'-fluoro-4-biphenylcarboxamide hydrochloride. | LC/MS (method A) 1.59 min; m/z 361(M + H). | Used IX-27 General Method: Example 170 |
| 288 | 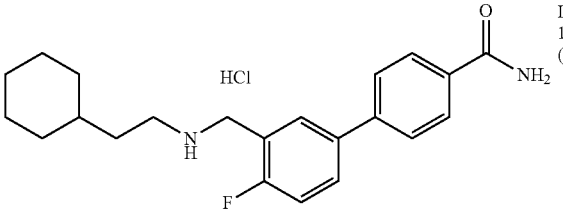<br>3'-{[(2-cyclohexylethyl)amino]-methyl}-4'-fluoro-4-biphenyl-carboxamide hydrochloride. | LC/MS (method A) 1.80 min; m/z 355 (M + H). | Used IX-27 and III-7 General Method: Example 170 |

TABLE 5-continued

Compounds of Formula I from Compounds of Formula IX

| Ex | Structure and Name | Characterization Data | Comments |
|---|---|---|---|
| 289 | 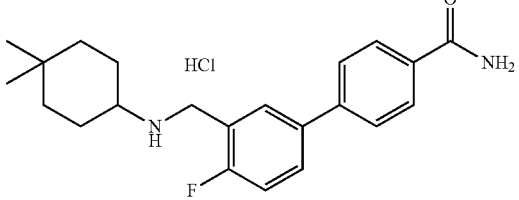<br>3'-{[(4,4-dimethylcyclohexyl)-amino]methyl}-4'-fluoro-4-biphenylcarboxamide hydrochloride | LC/MS (method A) 1.72 min; m/z 355 (M + H). | Used IX-27 and III-1<br>General Method: Example 170 |
| 290 | 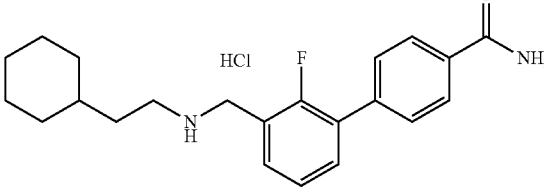<br>3'-{[(2-cyclohexylethyl)amino]-methyl}-2'-fluoro-4-biphenyl carboxamide hydrochloride | 355 1.71 LC/MS (method A) min; m/z (M + H). | Used IX-28 and III-7<br>General Method: Example 170 |
| 291 | 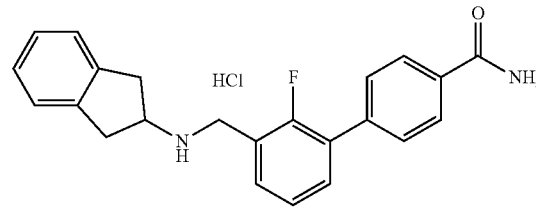<br>3'-[(2,3-dihydro-1H-inden-2-ylamino)methyl]-2'-fluoro-4-biphenyl carboxamide hydrochloride | LC/MS (method A) 1.48 min; m/z 361 (M + H). | Used IX-28<br>General Method: Example 170 |
| 292 | 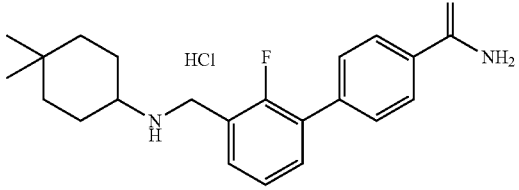<br>3'-{[(4,4-dimethylcyclohexyl)-amino]methyl}-2'-fluoro-4-biphenyl carboxamide hydrochloride | LC/MS (method A) 1.63 min; m/z 355 (M + H). | Used IX-28 and III-1<br>General Method: Example 170 |

TABLE 5-continued

Compounds of Formula I from Compounds of Formula IX

| Ex | Structure and Name | Characterization Data | Comments |
|---|---|---|---|
| 293 | 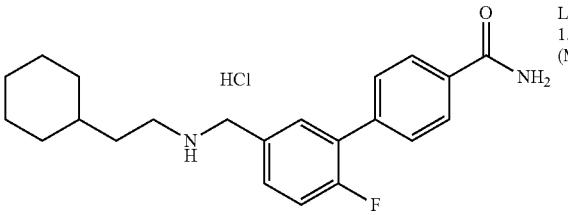<br>5'-{[(2-cyclohexylethyl)-amino]methyl}-2'-fluoro-4-biphenylcarboxamide hydrochloride | LC/MS (method A) 1.75 min; m/z 355 (M + H). | Used IX-29 and III-7<br>General Method: Example 170 |
| 294 | 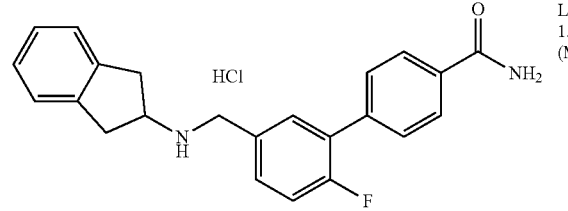<br>5'-[(2,3-dihydro-1H-inden-2-ylamino)methyl]-2'-fluoro-4-biphenylcarboxamide hydrochloride | LC/MS (method A) 1.53 min; m/z 361 (M + H). | Used IX-29<br>General Method: Example 170 |
| 295 | 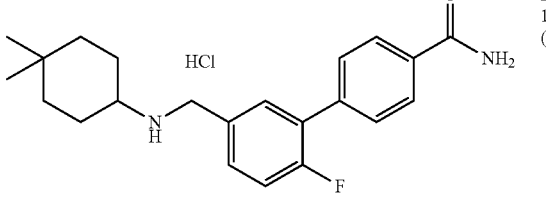<br>5'-{[4,4-dimethylcyclohexyl)-amino]methyl}-2'-fluoro-4-biphenylcarboxamide hydrochloride | LC/MS (method A) 1.72 min; m/z 355 (M + H). | Used IX-29 and III-1<br>General Method: Example 170<br>Note 6 |
| 296 | 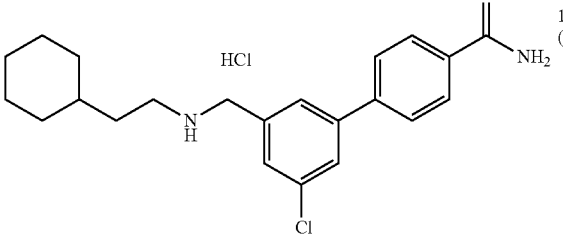<br>3'-chloro-5'-{[(2-cyclohexyl-ethyl)amino]methyl}-4-biphenyl-carboxamide hydrochloride. | LC/MS (method A) 1.89 min; m/z 371 (M + H). | Used IX-30 and III-7<br>General Method: Example 170 |

TABLE 5-continued

Compounds of Formula I from Compounds of Formula IX

| Ex | Structure and Name | Characterization Data | Comments |
|---|---|---|---|
| 297 | 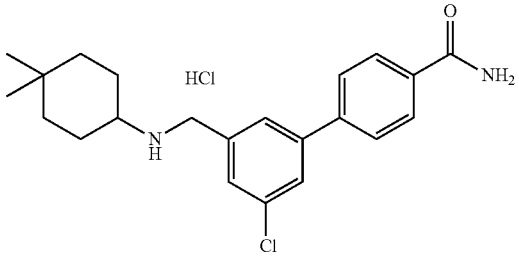<br>3'-chloro-5'-{[(4,4-dimethyl-cyclohexyl)amino]methyl}-4-biphenylcarboxamide hydrochloride. | LC/MS (method A) 1.80 min; m/z 371 (M + H). | Used IX-30 and III-1<br>General Method: Example 170<br>Note 6 |
| 298 | 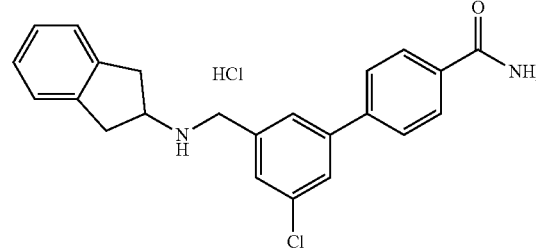<br>3'-chloro-5'-[(2,3-dihydro-1H-inden-2-ylamino)methyl]-4-biphenyl carboxamide hydrochloride. | LC/MS (method A) 1.69 min; m/z 377 (M + H). | Used IX-30<br>General Method: Example 170 |
| 299 | 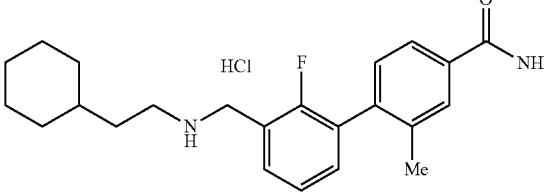<br>3'-{[(2-cyclohexyl-ethyl)amino]-methyl}-2'-fluoro-2-methyl-4-biphenylcarboxamide hydrochloride. | LC/MS (method A) 1.80 min; m/z 369 (M + H). | Used IX-31 and III-7<br>General Method: Example 170 |
| 300 | 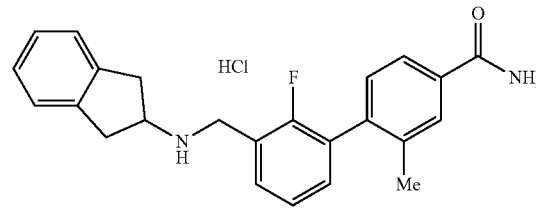<br>3'-[(2,3-dihydro-1H-inden-2-ylamino)methyl]-2'-fluoro-2-methyl-4-biphenyl carboxamide hydrochloride. | LC/MS (method A) 1.62 min; m/z 375 (M + H). | Used IX-31<br>General Method: Example 170 |

TABLE 5-continued

Compounds of Formula I from Compounds of Formula IX

| Ex | Structure and Name | Characterization Data | Comments |
|---|---|---|---|
| 301 | 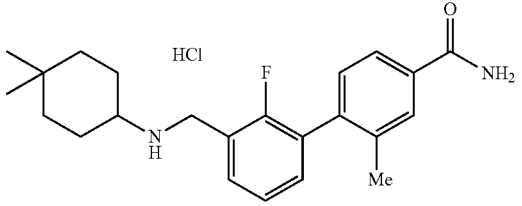<br>3'-{[(4,4-dimethylcyclohexyl)-amino]methyl}-2'-fluoro-2-methyl-4-biphenyl carboxamide hydrochloride. | LC/MS (method A) 1.69 min; m/z 369 (M + H). | Used IX-31 and III-1<br>General Method: Example 170<br>Note 6 |
| 302 | 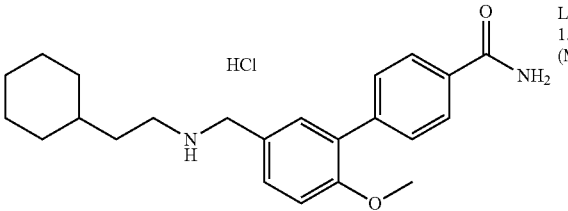<br>5'-{[(2-cyclohexylethyl)-amino]methyl}-2'-(methyloxy)-4-biphenylcarboxamide hydrochloride. | LC/MS (method A) 1.74 min; m/z 367 (M + H). | Used IX-32 and III-7<br>General Method: Example 170 |
| 303 | 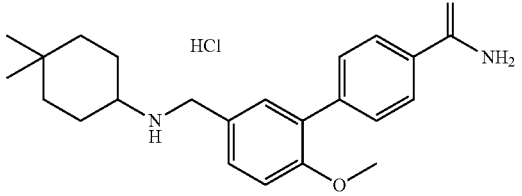<br>5'-{[(4,4-dimethylcyclohexyl)-amino]methyl}-2'-(methyloxy)-4-biphenyl carboxamide hydrochloride. | LC/MS (method A) 1.70 min; m/z 367 (M + H). | Used IX-32 and III-1<br>General Method: Example 170<br>Note 6 |
| 304 | 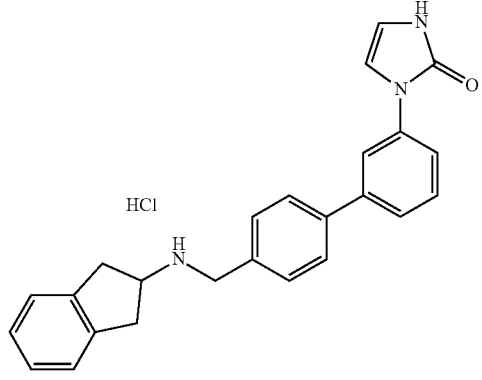<br>1-{4'-[(2,3-dihydro-1H-inden-2-ylamino)methyl]-3-biphenylyl}-1,3-dihydro-2H-imidazol-2-one hydrochloride | LC/MS (method A) 0.69 min; m/z 382 (M + H). | Used IX-34<br>General Method: Example 170<br>Note 7 |

TABLE 5-continued

Compounds of Formula I from Compounds of Formula IX

| Ex | Structure and Name | Characterization Data | Comments |
|----|---|---|---|
| 305 | 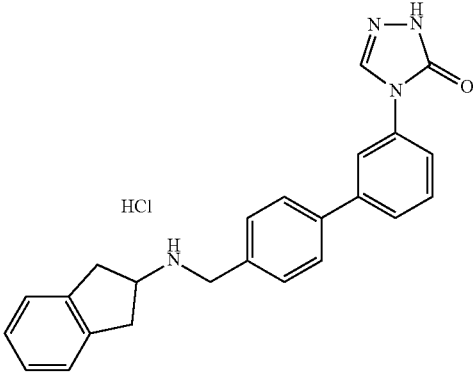<br>4-{4'-[(2,3-dihydro-1H-inden-2-ylamino)methyl]-3-biphenylyl}-2,4-dihydro-3H-1,2,4-triazol-3-one hydrochloride | LC/MS (method A)<br>0.66 min, m/z 383<br>(M + H). | Used IX-35<br>General Method:<br>Example 170<br>Note 7 |
| 306 | 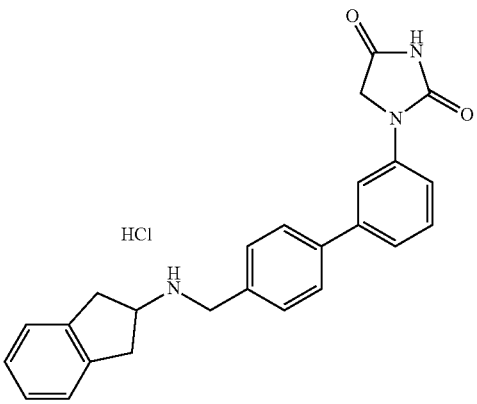<br>1-{4'-[(2,3-dihydro-1H-inden-2-ylamino)methyl]-3-biphenyl}-2,4-imidazolidinedione hydrochloride | LC/MS (method A)<br>0.66 min, m/z 398<br>(M + H). | Used IX-36<br>General Method:<br>Example 170<br>Note 7 |
| 307 | 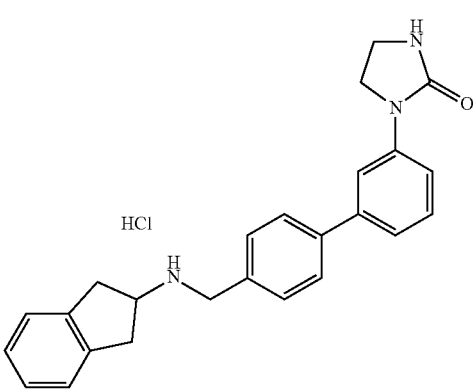<br>1-{4'-[(2,3-dihydro-1H-inden-2-ylamino)methyl]-3-biphenylyl}-2-imidazolidinone hydrochloride | LC/MS (method A)<br>0.71 min, m/z 338<br>(M + H). | Used IX-37<br>General Method:<br>Example 170<br>Note 7 |

TABLE 5-continued

Compounds of Formula I from Compounds of Formula IX

| Ex | Structure and Name | Characterization Data | Comments |
|----|---------------------|----------------------|----------|
| 308 | 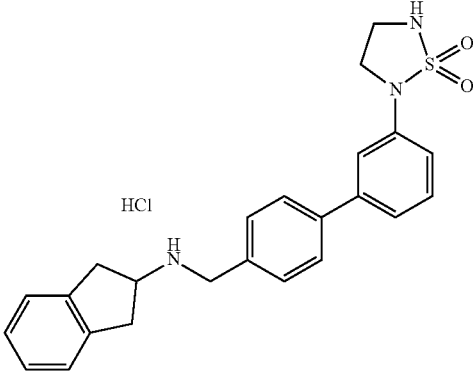<br>N-{[3'-(1,1-dioxido-1,2,5-thiadiazolidin-2-yl)-4-biphenyl-yl]methyl}-2,3-dihydro-1H-inden-2-amine hydrochloride | LC/MS (method A) 0.58 min, m/z 420 (M + H). | Used IX-38<br>General Method: Example 170<br>Note 7 |
| 309 | 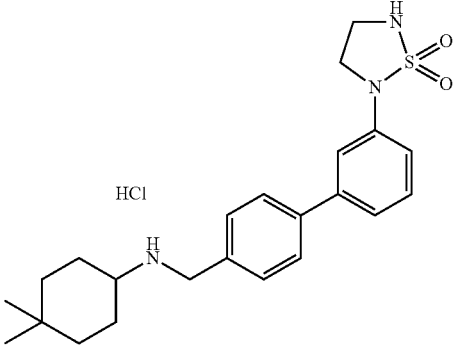<br>N-{[3'-(1,1-dioxido-1,2,5-thia-diazolidin-2-yl)-4-biphenylyl]-methyl}-4,4-dimethylcyclo-hexanamine hydrochloride | LC/MS (method A) 0.61 min, m/z 414 (M + H). | Used IX-38 and III-1<br>General Method: Example 170<br>Note 7 |

| Ex | Structure and Name | Characterization Data | Comments |
|---|---|---|---|
| 310 | 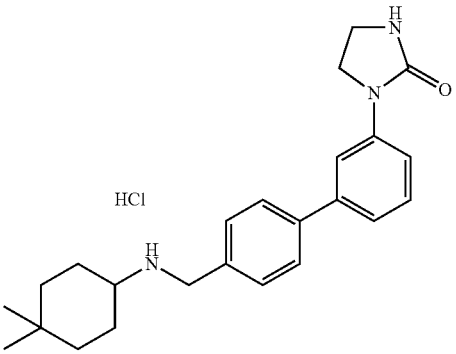<br>1-(4'-{[(4,4-dimethylcyclohexyl)-amino]methyl}-3-biphenylyl]-2-imidazolidinone hydrochloride | LC/MS (method A) 0.74 min, m/z 378 (M + H). | Used IX-37 and III-1 General Method: Example 170 Note 7 |

Note 1
'MP-H$_3$CN' polymer-supported cyanoborohydride (Argonaut Technologies p/n 800407) was used as reducing agent (ca. 3 equiv BH$_3$CN), THF/MeOH/HOAc mixture (ca. 5% HOAc in 1:1 THF/MeOH) was used as solvent.
Note 2
Product was purified by flash chromatography (EtOAc/hexanes) using amine-functionalized silica gel (Teledyne-Isco p/n 68-2203-102). HCl solution (4M in dioxane) was added to column eluent containing the desired product and the whole was concentrated in vacuo, affording an HCl salt.
Note 3
NaBH$_3$CN (1.2 equiv) was used as reducing agent, and THF/MeOH/HOAc (ca. 5% HOAc in 1:1 THF/MeOH) was used as solvent.
Note 4
Title compounds were obtained as freebases from the crude reaction filtrates, after concentration, by triturating with CH$_2$Cl$_2$, and drying in vacuo at 60° C. overnight.
Note 5
In those cases where the reaction products could not be resolved from impurities by chromatography, the crude residues were subjected to standard N-Boc protection conditions (Boc$_2$O/Et$_3$N/CH$_2$Cl$_2$). The resulting carbamate was then purified by flash chromatography (EtOAc/hexanes), dissolved in CH$_2$Cl$_2$ and treated with HCl in dioxane, effecting deprotection and affording the title compound as an HCl salt.
Note 6
Amine hydrochloride salt used was admixed with Et$_3$N before use.
Note 7
Crude residues obtained after aqueous workup (Na$_2$CO$_3$/EtOAc) were taken up in dioxane and treated with HCl in Et$_2$O. Supernatant liquid was decanted away, and the precipitated solids were air-dried, affording the title compounds as HCl salts.

General Method 6 for Preparation of Compounds of Formula I

General Method 6

Preparation of 2,5-Substituted Furans

Example 311

Preparation of 4-[5-({[2-(3-fluorophenyl)ethyl]amino}methyl)-2-furanyl]benzamide

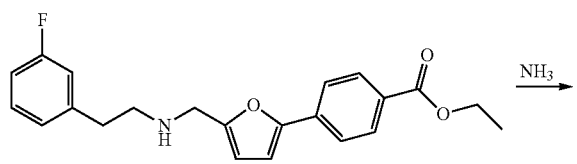

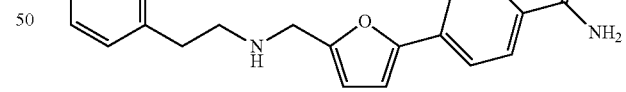

To a 50 mL sealed tube was added ethyl 4-[5-({[2-(3-fluorophenyl)ethyl]amino}methyl)-2-furanyl]benzoate (100 mg, 0.27 mmol, Example X-1), 2.0 M MeOH/NH$_3$ (20 mL), and KCN (30 mg). The reaction mixture was stirred at 125° C. overnight. The crude mixture was purified on RP-preparative HPLC to give 3 mg of 4-[5-({[2-(3-fluorophenyl)ethyl]amino}methyl)-2-furanyl]benzamide. (M+1) 339.23, 1.42 min (LC/MS method A)

The following were prepared in a manner similar to that described in General Method 6 Example using the corresponding amine

TABLE 6

Compounds of Formula I from Compounds of Formula X via Aminolysis

| Ex. | Structure and Name | Characterization Data | Method/Comments |
|---|---|---|---|
| 312 | 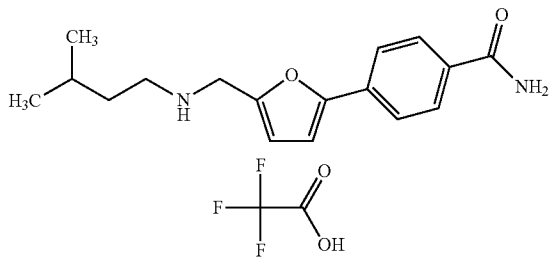<br>4-(5-{[(3-methylbutyl)amino] methyl}-2-furanyl)benzamide trifluoroacetate | (M + H) 287, 1.24 min (LC/MS method A) | Used Example X-2 |

General Method 7

Deprotection of Compounds of Formula X to Compounds of Formula I

Example 313

N-{[4'-(1H-1,2,4-triazol-3-yl)-3-biphenylyl]methyl}-2,3-dihydro-1H-inden-2-amine hydrochloride

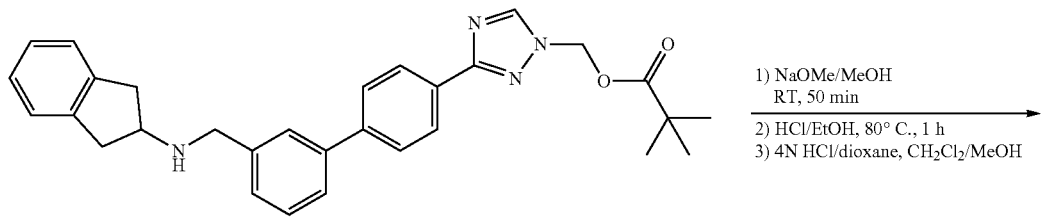

1) NaOMe/MeOH
   RT, 50 min
2) HCl/EtOH, 80° C., 1 h
3) 4N HCl/dioxane, CH₂Cl₂/MeOH

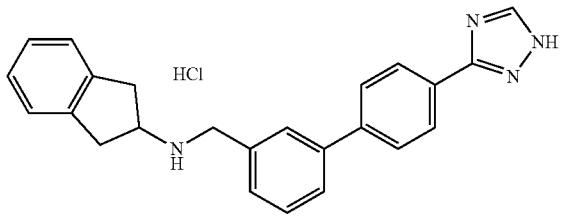

To a solution of (3-{3'-[(2,3-dihydro-1H-inden-2-ylamino)methyl]-4-biphenylyl}-1H-1,2,4-triazol-1-yl)methyl 2,2-dimethylpropanoate (0.084 g, 0.17 mmol, Example X-3) in EtOH (1.5 mL) was added a 4.37 M solution of NaOMe in MeOH (0.08 mL, 0.35 mmol). The mixture was stirred for 50 min at RT. A 1.2M solution of concentrated HCl in EtOH was added (1.2 mL), and the mixture was heated at 80° C. for 1 h. The reaction mixture was cooled, diluted with water, and basified to a pH of 10 with addition of saturated Na₂CO₃ (aq). The mixture was extracted with EtOAc. The combined organic extracts were washed with water and brine, dried with anhydrous Na₂SO₄, and concentrated in vacuo. The residue was dissolved in CH₂Cl₂ and MeOH, and 4N HCl in dioxane was added (0.2 mL). After stirring for 15 min, the precipitate was filtered, washed with CH₂Cl₂, and dried, affording the title compound as a colorless solid (0.057 g, 89%). (M+H) 367, 1.74 min (LC/MS Method B).

TABLE 7

Compounds of Formula I from Compounds of Formula X via N-deprotection

| Ex. | Structure and Name | Characterization Data | Method/Comments |
|---|---|---|---|
| 314 | 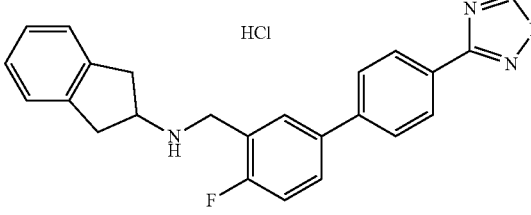<br>N-{[4-fluoro-4'-(1H-1,2,4-triazol-3-yl)-3-biphenylyl]methyl}-2,3-dihydro-1H-inden-2-amine hydrochloride | (M + H) 385, 1.79 min (LC/MS Method B) | Synthesized from X-4. |
| 315 | 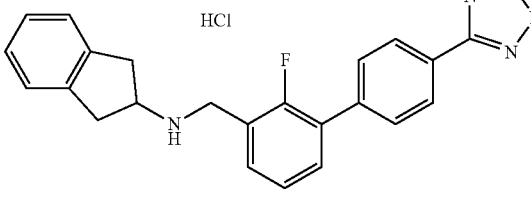<br>N-{[2-fluoro-4'-(1H-1,2,4-triazol-3-yl)-3-biphenylyl]methyl}-2,3-dihydro-1H-inden-2-amine hydrochloride | (M + H) 385, 1.74 min (LC/MS Method B) | Synthesized from X-5. |
| 316 | 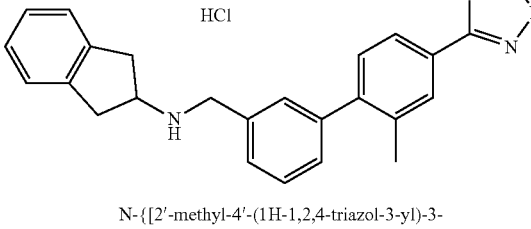<br>N-{[2'-methyl-4'-(1H-1,2,4-triazol-3-yl)-3-biphenylyl]methyl}-2,3-dihydro-1H-inden-2-amine hydrochloride | (M + H) 381, 1.77 min (LC/MS Method B) | Synthesized from X-6. Eliminated MeOH for salt formation. |
| 317 | 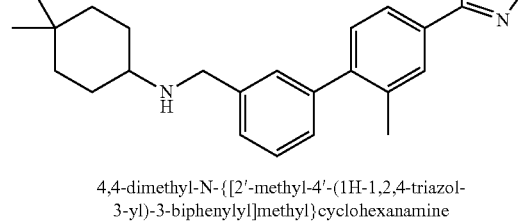<br>4,4-dimethyl-N-{[2'-methyl-4'-(1H-1,2,4-triazol-3-yl)-3-biphenylyl]methyl}cyclohexanamine hydrochloride | (M + H) 375, 0.60 min (LC/MS Method F) | Synthesized from X-7. |
| 318 | 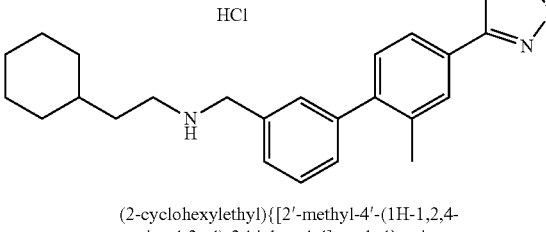<br>(2-cyclohexylethyl){[2'-methyl-4'-(1H-1,2,4-triazol-3-yl)-3-biphenylyl] methyl}amine hydrochloride | (M + H) 375, 0.62 min (LC/MS Method F) | Synthesized from X-8. |

TABLE 7-continued

Compounds of Formula I from Compounds of Formula X via N-deprotection

| Ex. | Structure and Name | Characterization Data | Method/Comments |
|---|---|---|---|
| 319 | 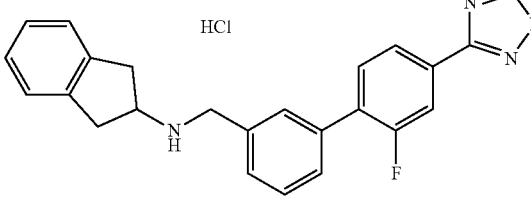><br>N-{[2'-fluoro-4'-(1H-1,2,4-triazol-3-yl)-3-biphenylyl]methyl}-2,3-dihydro-1H-inden-2-amine hydrochloride | (M + H) 385, 1.78 min (LC/MS Method B) | Synthesized from X-9. |
| 320 | 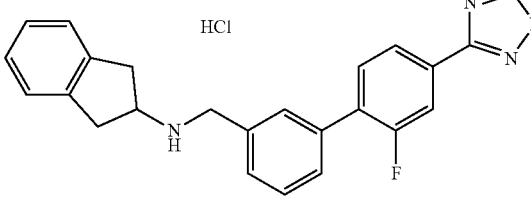<br>N-{[2'-fluoro-4'-(1H-1,2,4-triazol-3-yl)-3-biphenylyl]methyl}-4,4-dimethylcyclohexanamine hydrochloride | (M + H) 379, 0.61 min (LC/MS Method F) | Synthesized from X-10. |
| 321 | 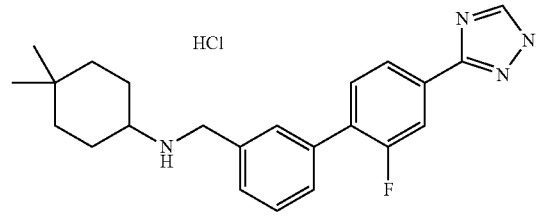<br>(2-cyclohexylethyl){[2'-fluoro-4'-(1H-1,2,4-triazol-3-yl)-3-biphenylyl] methyl}amine hydrochloride | (M + H) 379, 0.61 min (LC/MS Method F) | Synthesized from X-11. Eliminated MeOH for salt formation. |
| 322 | 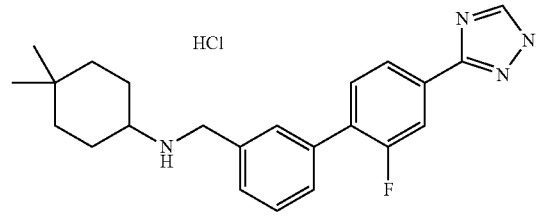<br>N-{[2,2'-difluoro-4'-(1H-1,2,4-triazol-3-yl)-3-biphenylyl]methyl}-2,3-dihydro-1H-inden-2-amine hydrochloride | (M + H) 403, 0.56 min (LC/MS Method F) | Synthesized from X-12. |
| 323 | 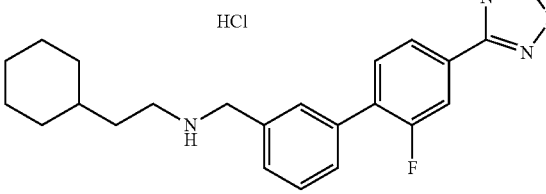<br>4,4-dimethyl-N-{[4'-(1H-1,2,4-triazol-3-yl)-3-biphenylyl]methyl}cyclohexanamine hydrochloride | (M + H) 361, 0.59 min (LC/MS Method F) | Synthesized from X-13. |

TABLE 7-continued

Compounds of Formula I from Compounds of Formula X via N-deprotection

| Ex. | Structure and Name | Characterization Data | Method/Comments |
|---|---|---|---|
| 324 | 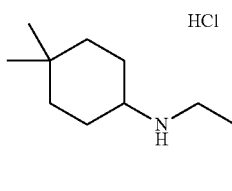<br>N-{[2-fluoro-4'-(1H-1,2,4-triazol-3-yl)-3-biphenylyl]methyl}-4,4-dimethylcyclohexanamine hydrochloride | (M + H) 379, 0.58 min (LC/MS Method F) | Synthesized from X-14. Eliminated MeOH for salt formation. |
| 325 | 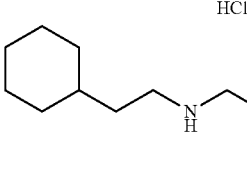<br>(2-cyclohexylethyl){[2-fluoro-4'-(1H-1,2,4-triazol-3-yl)-3-biphenylyl]methyl}amine hydrochloride | (M + H) 379, 0.60 min (LC/MS Method F) | Synthesized from X-15. Eliminated MeOH for salt formation. |
| 326 | 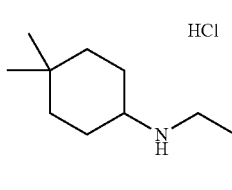<br>N-{[2,2'-difluoro-4'-(1H-1,2,4-triazol-3-yl)-3-biphenylyl]methyl}-4,4-dimethylcyclohexanamine hydrochloride | (M + H) 397, 0.59 min (LC/MS Method F) | Synthesized from X-16. Eliminated MeOH for salt formation. |
| 327 | 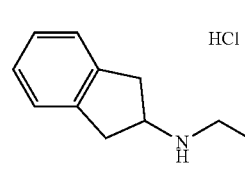<br>N-{[2-fluoro-2'-methyl-4'-(1H-1,2,4-triazol-3-yl)-3-biphenylyl]methyl}-2,3-dihydro-1H-inden-2-amine hydrochloride | (M + H) 399, 0.56 min (LC/MS Method F) | Synthesized from X-17. Eliminated MeOH for salt formation. |
| 328 | 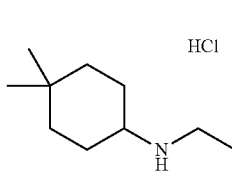<br>N-{[2-fluoro-2'-methyl-4'-(1H-1,2,4-triazol-3-yl)-3-biphenylyl]methyl}-4,4-dimethylcyclohexanamine hydrochloride | (M + H) 393, 0.59 min (LC/MS Method F) | Synthesized from X-18. Eliminated MeOH for salt formation. |

TABLE 7-continued

Compounds of Formula I from Compounds of Formula X via N-deprotection

| Ex. | Structure and Name | Characterization Data | Method/Comments |
|---|---|---|---|
| 329 | 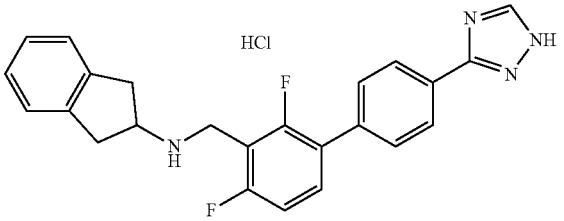<br>N-{[2,4-difluoro-4'-(1H-1,2,4-triazol-3-yl)-3-biphenylyl]methyl}-2,3-dihydro-1H-inden-2-amine hydrochloride | (M + H) 403, 0.56 min (LC/MS Method F) | Synthesized from X-19. Eliminated MeOH for salt formation. |
| 330 | 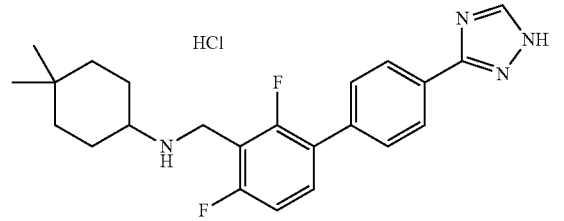<br>N-{[2,4-difluoro-4'-(1H-1,2,4-triazol-3-yl)-3-biphenylyl]methyl}-4,4-dimethylcyclohexanamine hydrochloride | (M + H) 397, 0.60 min (LC/MS Method F) | Synthesized from X-20. Eliminated MeOH for salt formation. |
| 331 | 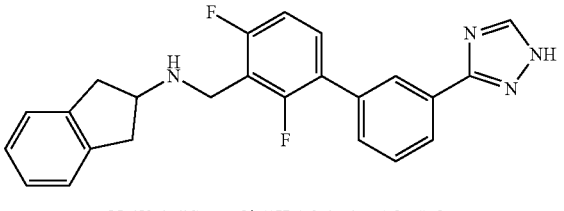<br>N-{[2,4-difluoro-3'-(1H-1,2,4-triazol-3-yl)-3-biphenylyl]methyl}-2,3-dihydro-1H-inden-2-amine hydrochloride | (M + H) 403, 0.71 min (LC/MS Method F) | Synthesized from X-21. Eliminated MeOH for salt formation. |
| 332 | 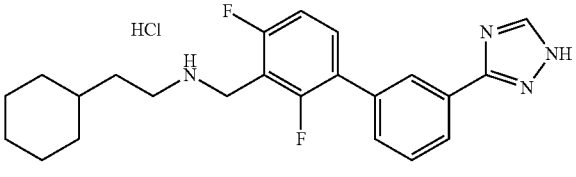<br>(2-cyclohexylethyl){[2,4-difluoro-3'-(1H-1,2,4-triazol-3-yl)-3-biphenylyl]methyl}amine hydrochloride | (M + H) 397, 0.76 min (LC/MS Method F) | Synthesized from X-23. Eliminated MeOH for salt formation. |
| 333 | 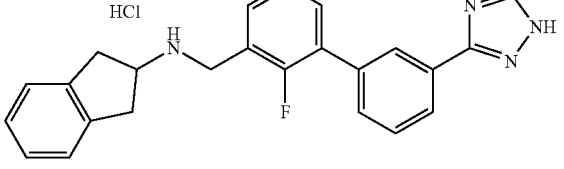<br>N-{[2-fluoro-3'-(1H-1,2,4-triazol-3-yl)-3-biphenylyl]methyl}-2,3-dihydro-1H-inden-2-amine hydrochloride | (M + H) 385, 0.70 min (LC/MS Method F) | Synthesized from X-24. |

TABLE 7-continued

Compounds of Formula I from Compounds of Formula X via N-deprotection

| Ex. | Structure and Name | Characterization Data | Method/Comments |
|---|---|---|---|
| 334 | 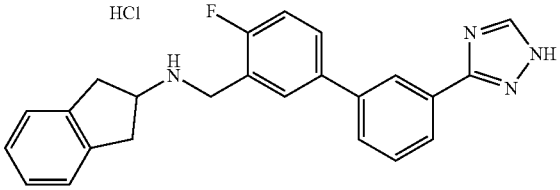<br>N-{[4-fluoro-3'-(1H-1,2,4-triazol-3-yl)-3-biphenylyl]methyl}-2,3-dihydro-1H-inden-2-amine hydrochloride | (M + H) 385, 1.81 min (LC/MS Method A) | Synthesized from X-25. Eliminated MeOH for salt formation. |
| 335 | 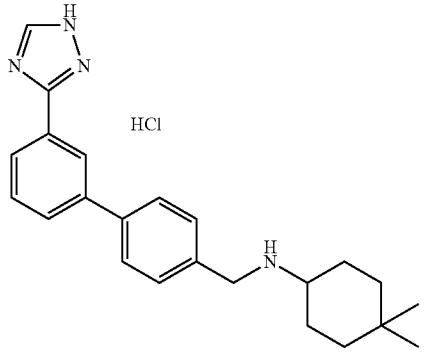<br>(4,4-dimethylcyclohexyl){[3'-(1H-1,2,4-triazol-3-yl)-4-biphenylyl]methyl}amine hydrochloride | LC/MS (method B) 2.26 min; m/z 361 (M + H) | Synthesized from X-26 |
| 336 | 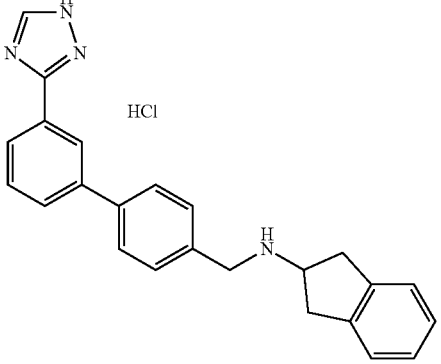<br>N-{[3'-(1H-1,2,4-triazol-3-yl)-4-biphenylyl]methyl}-2,3-dihydro-1H-inden-2-amine hydrochloride | LC/MS (method B) 2.17 min; m/z 367 (M + H) | Synthesized from X-27 |
| 337 | 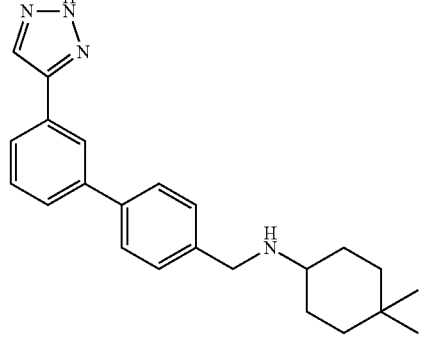<br>(4,4-dimethylcyclohexyl){[3'-(2H-1,2,3-triazol-4-yl)-4-biphenylyl]methyl}amine trifluoroacetate | LC/MS (method A) 2.31 min; m/z 361 (M + H) | Synthesized from X-28 |

TABLE 7-continued

Compounds of Formula I from Compounds of Formula X via N-deprotection

| Ex. | Structure and Name | Characterization Data | Method/Comments |
|---|---|---|---|
| 338 | 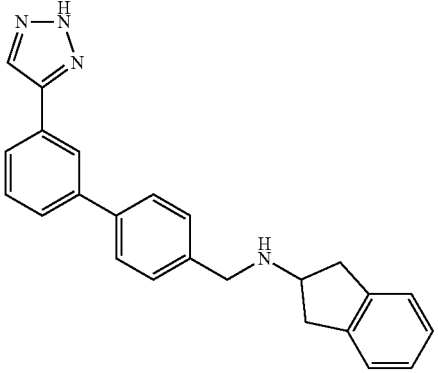<br>N-{[3'-(2H-1,2,3-triazol-4-yl)-4-biphenylyl]methyl}-2,3-dihydro-1H-inden-2-amine trifluoroacetate | LC/MS (method A) 2.21 min; m/z 367 (M + H) | Synthesized from X-29 |
| 339 | 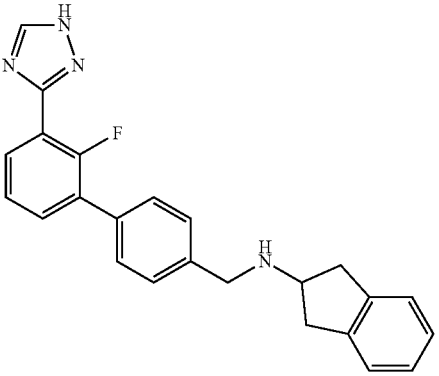<br>N-{[2'-fluoro-3'-(1H-1,2,4-triazol-3-yl)-4-biphenylyl]methyl}-2,3-dihydro-1H-inden-2-amine | LC/MS (method A) 1.66 min; m/z 386 (M + H) | Synthesized from X-30 |
| 340 | 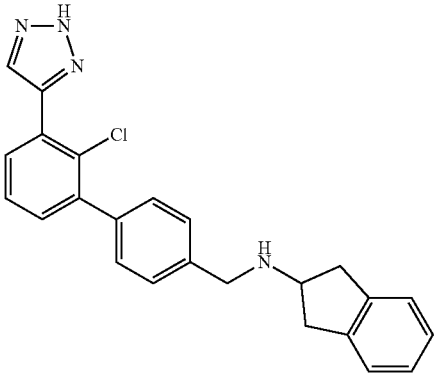<br>N-{[2'-chloro-3'-(1H-1,2,4-triazol-3-yl)-4-biphenylyl]methyl}-2,3-dihydro-1H-inden-2-amine | LC/MS (method A) 1.61 min; m/z 399 (100%), 400 (21%), 402 (37%) (M + H) | Synthesized from X-31 |

TABLE 7-continued

Compounds of Formula I from Compounds of Formula X via N-deprotection

| Ex. | Structure and Name | Characterization Data | Method/Comments |
|---|---|---|---|
| 341 | 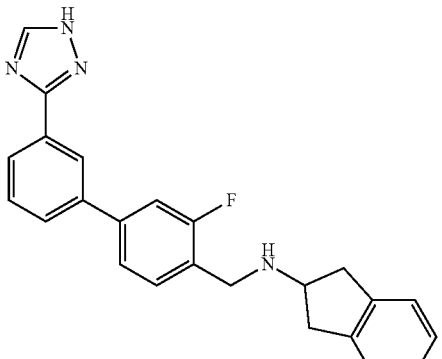<br>N-{[3-fluoro-3'-(1H-1,2,4-triazol-3-yl)-4-biphenylyl]methyl}-2,3-dihydro-1H-inden-2-amine | LC/MS (method A) 1.76 min; m/z 385 (M + H) | Synthesized from X-32 |
| 342 | 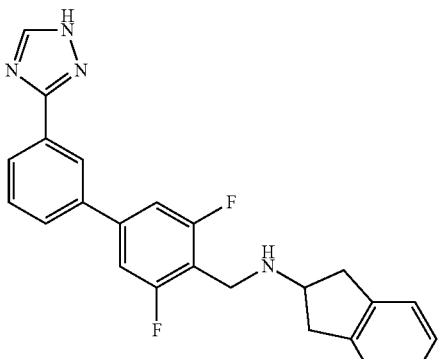<br>N-{[3,5-difluoro-3'-(1H-1,2,4-triazol-3-yl)-4-biphenylyl]methyl}-2,3-dihydro-1H-inden-2-amine hydrochloride | 0.71 min; m/z 403 (M + H) | Synthesized from X-33<br>Note 2 |
| 343 | 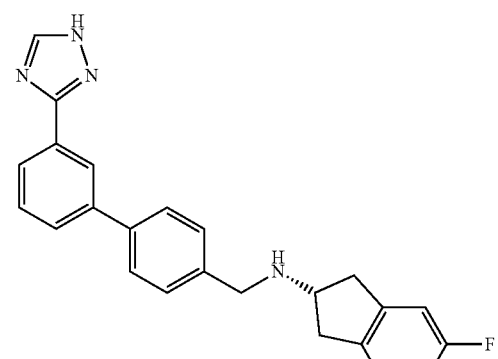<br>[(2S)-5-fluoro-2,3-dihydro-1H-inden-2-yl]{[3'-(1H-1,2,4-triazol-3-yl)-4-biphenylyl]methyl}amine hydrochloride | LC/MS (method A) 1.76 min; m/z 385 (M + H) | Synthesized from X-34 |

TABLE 7-continued

Compounds of Formula I from Compounds of Formula X via N-deprotection

| Ex. | Structure and Name | Characterization Data | Method/Comments |
|---|---|---|---|
| 344 | 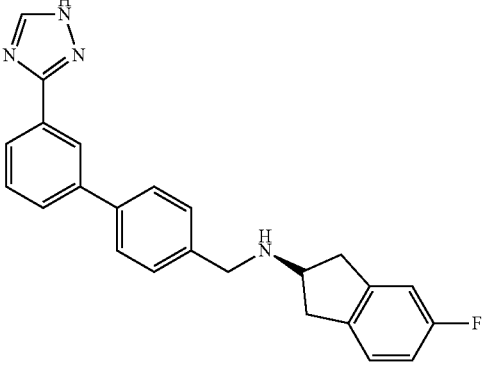[(2R)-5-fluoro-2,3-dihydro-1H-inden-2-yl]{[3'-(1H-1,2,4-triazol-3-yl)-4-biphenylyl]methyl}amine hydrochloride | LC/MS (method A) 1.74 min; m/z 385 (M + H) | Synthesized from X-35 |
| 345 | 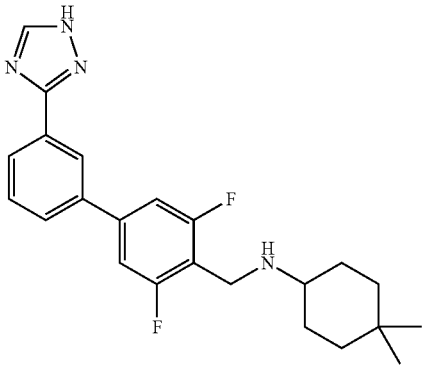N-{[3,5-difluoro-3'-(1H-1,2,4-triazol-3-yl)-4-biphenylyl]methyl}-4,4-dimethylcyclohexanamine trifluoroacetate | LC/MS (method E) 0.59 min; m/z 397 (M + H) | Synthesized from X-36 |
| 346 | 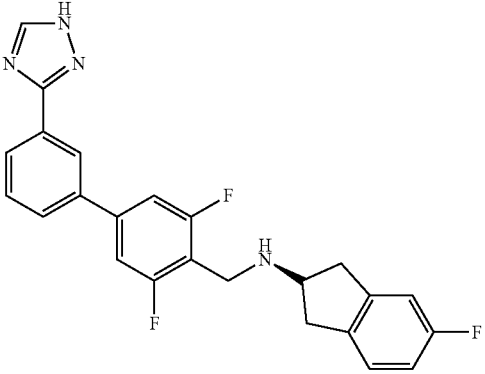{[3,5-difluoro-3'-(1H-1,2,4-triazol-3-yl)-4-biphenylyl]methyl}[(2R)-5-fluoro-2,3-dihydro-1H-inden-2-yl]amine hydrochloride | LC/MS (method E) 0.72 min; m/z 421 (M + H) | Synthesized from X-37 |

TABLE 7-continued

Compounds of Formula I from Compounds of Formula X via N-deprotection

| Ex. | Structure and Name | Characterization Data | Method/Comments |
|---|---|---|---|
| 347 | {[3,5-difluoro-3'-(1H-1,2,4-triazol-3-yl)-4-biphenylyl]methyl}[(2S)-5-fluoro-2,3-dihydro-1H-inden-2-yl]amine trifluoroacetate | LC/MS (method E) 0.56 min; m/z 421 (M + H) | Synthesized from X-38 |
| 348 | (2-cyclohexyl-2,2-difluoroethyl){[3,5-difluoro-3'-(1H-1,2,4-triazol-3-yl)-4-biphenylyl]methyl}amine hydrochloride | LC/MS (method E) 0.85 min; m/z 433 (M + H) | Synthesized from X-39 |
| 349 | (2-cyclohexylethyl){[3,5-difluoro-3'-(1H-1,2,4-triazol-3-yl)-4-biphenylyl]methyl}amine trifluoroacetate | LC/MS (method E) 0.6 min; m/z 397 (M + H) | Synthesized from X-40 |

TABLE 7-continued

Compounds of Formula I from Compounds of Formula X via N-deprotection

| Ex. | Structure and Name | Characterization Data | Method/Comments |
|---|---|---|---|
| 350 | 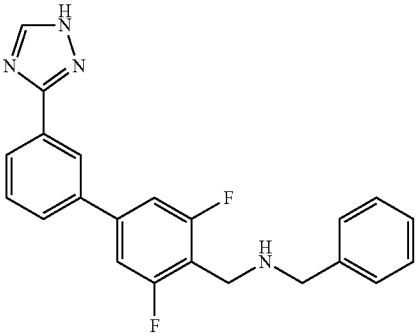<br>{[3,5-difluoro-3'-(1H-1,2,4-triazol-3-yl)-4-biphenylyl]methyl}(phenylmethyl)amine trifluoroacetate | LC/MS (method E) 0.54 min; m/z 377 (M + H) | Synthesized from X-41 |
| 351 | 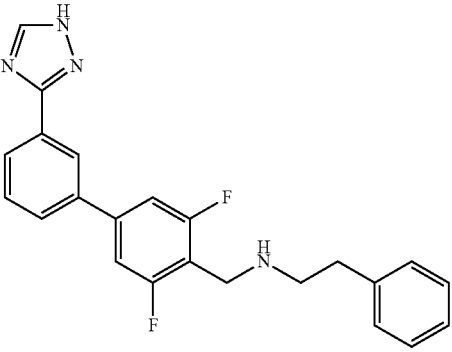<br>N-{[3,5-difluoro-3'-(1H-1,2,4-triazol-3-yl)-4-biphenylyl]methyl}-2-phenylethanamine hydrochloride | LC/MS (method E) 0.71 min; m/z 391 (M + H) | Synthesized from X-42 |
| 352 | 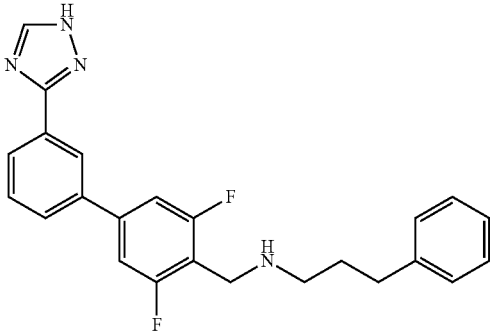<br>N-{[3,5-difluoro-3'-(1H-1,2,4-triazol-3-yl)-4-biphenylyl]methyl}-3-phenyl-1-propanamine trifluoroacetate | LC/MS (method E) 0.57 min; m/z 405 (M + H) | Synthesized from X-43 |

TABLE 7-continued

Compounds of Formula I from Compounds of Formula X via N-deprotection

| Ex. | Structure and Name | Characterization Data | Method/Comments |
|---|---|---|---|
| 353 | 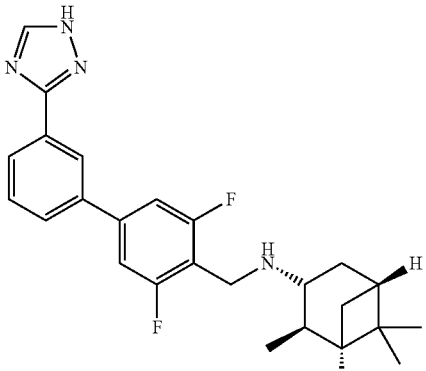<br>{[3,5-difluoro-3'-(1H-1,2,4-triazol-3-yl)-4-biphenylyl]methyl}[(1R,2R,3R,5R)-2,6,6-trimethylbicyclo[3.1.1]hept-3-yl]amine trifluoroacetate | LC/MS (method E)<br>0.62 min; m/z 423<br>(M + H) | Synthesized from X-44 |

Note 1:
Purified by reverse phase chromatography (CH$_3$CN/H$_2$O/TFA).

Note 2:
The crude product can also be isolated as diHCl salt straight from the reaction after one hour of stirring. Then recrystallized from EtOH/HCl(aq).

LC/MS Method A (Standard Electrospry Method): Mass Spectrometry is used to confirm peak identity with electrospray+/−ionization scanning from 100-1000 m/z and DAD from 220-400 nm. Phenomenex Luna column 4.6 mm by 2 cm, particle size 3 um, ambient temperature. Solvent flow at 2 ml/min. Gradient begins at 10% MeOH and goes linearly to 100% MeOH in 3 minutes, holds 100% MeOH for 1 minute, making total chromatogram time 4 minutes. 2 ul sample injection. Aqueous mobile phase contains 0.1% v/v Formic Acid and MeOH contains 0.075% v/v Formic Acid.

LC/MS Method B (Standard APCI Method): Mass Spectrometry is used to confirm peak identity with APCI+/−ionization scanning from 100-1000 m/z and DAD from 220-400 nm. Phenomenex Luna column 4.6 mm by 2 cm, particle size 3 um, ambient temperature. Solvent flow at 2 ml/min. Gradient begins at 10% MeOH and goes linearly to 100% MeOH in 3 minutes, holds 100% MeOH for 1 minute, making total chromatogram time 4 minutes. 2 ul sample injection. Aqueous mobile phase contains 0.1% v/v Formic Acid and MeOH contains 0.075% v/v Formic Acid.

LC/MS Method C (Polar APCI Method): Mass Spectrometry is used to confirm peak identity with APCI+/−ionization scanning from 100-1000 m/z and DAD from 220-400 nm. Phenomenex Luna column 4.6 mm by 2 cm, particle size 3 um, ambient temperature. Solvent flow at 2 ml/min. Gradient begins at 2% MeOH and goes linearly to 26% MeOH in 1 minute, then goes linearly from 26% MeOH to 100% MeOH in 2 min., then holds 100% MeOH for 1 minute, making total chromatogram time 4 minutes. 2 ul sample injection. Aqueous mobile phase contains 0.1% v/v Formic Acid and MeOH contains 0.075% v/v Formic Acid.

LC/MS Method D (Polar Electrospray Method): Mass Spectrometry is used to confirm peak identity with electrospray+/−ionization scanning from 100-1000 m/z and DAD from 220-400 nm. Phenomenex Luna column 4.6 mm by 2 cm, particle size 3 um, ambient temperature. Solvent flow at 2 ml/min. Gradient begins at 2% MeOH and goes linearly to 26% MeOH in 1 minute, then goes linearly from 26% MeOH to 100% MeOH in 2 min., then holds 100% MeOH for 1 minute, making total chromatogram time 4 minutes. 2 ul sample injection. Aqueous mobile phase contains 0.1% v/v Formic Acid and MeOH contains 0.075% v/v Formic Acid.

LC-MS Method E (Standard Electrospray Fast Mass Spec Method): Electrospray+ionization scanning from 100-800 m/z with DAD sum from 220-400 nm. Waters Acquity UPLC column 2.1 mm by 5 cm, particle size 1.7 um, temperature at 40 degrees C. Solvent flow at 1 ml/min. Gradient begins at 6% ACN and goes linearly to 70% ACN in 0.57 minute; gradient then goes linearly to 99% ACN from 0.57 minute to 1.06 minute, holds 99% ACN until 1.5 minute, making total chromatogram time 1.5 minutes. 1.5 ul sample injection. Aqueous mobile phase contains 0.1% v/v Formic Acid and ACN contains trace v/v Formic Acid.

LC-MS Method F (Standard APCI Fast Mass Spec Method): Mass Spectrometry is used to confirm peak identity with APCI+/−ionization scanning from 100-1000 m/z and DAD from 220-400 nm. Column is Waters Acquity BEH UPLC column 2.1 mm by 5 cm, particle size 1.7 um, temperature at 25 degrees C. Solvent flow at 1 ml/min. Gradient begins at 6% ACN and goes linearly to 70% ACN in 0.57 minute; gradient then goes linearly to 99% ACN from 0.57 minute to 1.06 minute, holds 99% ACN until 1.5 minute, making total chromatogram time 1.5 minutes. 1.5 ul sample injection. Aqueous mobile phase contains 0.1% v/v Formic Acid and ACN contains trace v/v Formic Acid.

Abbreviations
anhyd anhydrous
APCI atmospheric pressure chemical ionization
app. apparent
BH$_3$.DMS borane-dimethyl sulfide complex
(Boc)$_2$O di-tert-butyl dicarbonate
BOC tert-Butoxycarbonyl
br. broad
ca. approximately
cf. compare to
conc concentrated
Cbz benzyloxycarbonyl DCE dichloroethane
DIBAL-H diisobutylaluminum hydride
DIPEA diisopropylethylamine
DMAP 4-dimethylaminopyridine
DME 1,2-dimethoxyethane
DMF dimethylformamide
DMSO dimethylsulfoxide
dppf 1,1'-Bis(diphenylphosphino)ferrocene
ESI electrospray ionization
$Et_2O$ diethyl ether
$Et_3N$ triethylamine
$Et_3SiH$ triethylsilane
EtOAc ethyl acetate
EtOH ethanol
h hour
HOAc acetic acid
in vacuo under reduced pressure
KOAc potassium acetate
LC/MS liquid chromatography-mass spectrometry
MeCN acetonitrile
MeOH methanol
min minute
μwave microwave
N.B. note bene (attention)
PhH benzene
PhMe toluene
POM pivaloyloxymethyl
PPA polyphosphoric acid
PS—$BH_3CN$ (polystyrylmethyl)trimethylammonium cyanoborohydride
PTFE (poly)tetrafluoroethylene polymer
Ra—Ni Raney Nickel
Rochelle's salt potassium sodium tartrate
RP-HPLC reverse phase high pressure liquid chromatography
rt room temperature
sat'd saturated
SEM 2-(trimethylsilyl)ethoxymethyl
S-Phos 2-(2',6'-dimethoxybiphenyl)di-cyclohexylphosphine
t-Bu tert-butyl
$t_R$ retention time on the LC/MS instrument
$Tf_2O$ trifluoromethanesulfonic anhydride
TFA trifluoroacetic acid
THF tetrahydrofuran
TLC thin layer chromatography
TsOH p-toluenesulfonic acid Method of Testing Compounds of the Invention Materials LEADSeeker WGA™ beads and GTPgS35 were purchased from Amersham Bioscience (Piscataway, N.J.). GDP, Saponin™ DAMGO™, Met-Enkephalin, Dynorphin A, NaCl and HEPES™ were purchased from SIGMA (St Louis, Mo.). MgCl2 was purchased from J. T. Baker (Pillipsburg, N.J.). Opioid membranes, hOPRD, hOPRK and hOPRM were prepared at GlaxoSmithkline (Harlow, UK). Cells expressing opioid receptors were prepared as membranes using standard methodologies. Collected cell pellets were homogenized with a blender followed by a low speed centrifugation to remove nuclei and unbroken cells. This was followed by two high speed spins and washes homogenized with a dounce homogenizer. Membranes were stored at −70 C and are stable for at least six months.

Assay buffer; 20 mM HEPES, 10 mM MgCL2, and 100 mM NaCl dissolved in labgrade water, pH 7.4 with KOH.

[35S]GTPgammaS Binding Assay Measured by LEADseeker SPA (384 Well)

Dilute GTPgS35 1:900 in assay buffer in half of required final assay volume (volume A). Add the corresponding standard agonist, Met-Enkephalin (hOPRD), Dynorphin A (hOPRK) or DAMGO (hOPRM) to give a solution concentration of 8×[EC50], for a final assay concentration of 4×[EC50] to volume A. Resuspend LEADSeeker beads in assay buffer in order to generate a 40 mg/mL stock solution. GDP is dissolved in assay buffer at 1 mM. Add beads (100 microgram/well final) to assay buffer containing saponin (60 microgram/mL) in half of final assay volume (volume B). Mix well by vortexing. Add opioid membranes to each respective volume B, for a final assay concentration of 1.5 microgram/well (hOPRD), 1.0 microgram/well (hOPRK), and 1.5 microgram/well (hOPRM). Continuously mix the bead/membrane solution (volume B) for 30 min prior to adding to the GTPgS35 solution (volume A) in a 1:1 ratio using a stir plate. Just prior to adding bead/membrane solution to the GTPgS35 solution, add GDP to volume B at 20 microMolar (10 microMolar final assay concentration). Add the bead/membrane solution to the GTPgS35 solution in a 1:1 ratio. Add 10 microLiters of the bead/membrane/GTPgS35 mix to the assay plate using a Multidrop (Titertek™). Agitation of the solution is needed to prevent the beads/membrane from settling at the bottom. Plates are sealed, spun at 1000 rpm for 2 mins, tapped on side to agitate and incubated at room temperature for 5 hours. Plates are then imaged using a Viewlux Plus™ Imager (Perkin Elmer).

Acceptable compounds of the invention have an activity of less than 30 micromolar using this test method.

What is claimed is:

1. A method of treatment comprising administering a compound which is N-{[3,5-difluoro-3'-(1H-1,2,4-triazol-3-yl)-4-biphenylyl]methyl}-2,3-dihydro-1H-inden-2-amine or a salt thereof to a human suffering from drug addiction, substance addiction, or a combination thereof.

2. The method of claim 1 wherein said compound is a citrate, phosphate or mono- or di-hydrochloride salt of N-{[3,5-difluoro-3'-(1H-1,2,4-triazol-3-yl)-4-biphenylyl]methyl}-2,3-dihydro-1H-inden-2-amine.

3. The method of claim 2 wherein said compound is the citrate salt.

4. The method of claim 2 wherein said compound is the phosphate salt.

5. The method of claim 2 wherein said compound is the mono- or di-hydrochloride salt.

6. A method of treatment comprising administering a pharmaceutical composition comprising (i) a compound which is N-{[3,5-difluoro-3'-(1H-1,2,4-triazol-3-yl)-4-biphenylyl]methyl}-2,3-dihydro-1H-inden-2-amine or a salt thereof and (ii) at least one carrier or excipient to a human suffering from drug addiction, substance addiction, or a combination thereof.

7. The method of claim 6 wherein said compound is a citrate, phosphate or mono- or di-hydrochloride salt of N-{[3,5-difluoro-3'-(1H-1,2,4-triazol-3-yl)-4-biphenylyl]methyl}-2,3-dihydro-1H-inden-2-amine.

8. The method of claim 6 wherein said compound is the citrate salt.

9. The method of claim 6 wherein said compound is the phosphate salt.

10. The method of claim 6 wherein said compound is the mono- or di-hydrochloride salt.

* * * * *